United States Patent
Tohnishi et al.

(10) Patent No.: US 6,362,369 B2
(45) Date of Patent: *Mar. 26, 2002

(54) PHTHALIC ACID DIAMIDE DERIVATIVES FLUORINE-CONTAINING ANILINE COMPOUNDS AS STARTING MATERIAL, AGRICULTURAL AND HORTICULTURAL INSECTICIDES, AND A METHOD FOR APPLICATION OF THE INSECTICIDES

(75) Inventors: Masanori Tohnishi, Sakai; Hayami Nakao, Kawachinagano; Eiji Kohno, Habikino; Tateki Nishida, Tondabayashi; Takashi Furuya, Izumisano; Toshiaki Shimizu, Kawachinagano; Akira Seo, Hashimoto; Kazuyuki Sakata; Shinsuke Fujioka, both of Kawachinagano; Hideo Kanno, Ibaraki, all of (JP)

(73) Assignee: Nihon Nohyaku Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,261

(22) Filed: Feb. 16, 1999

Related U.S. Application Data

(63) Continuation-in-part of application No. 09/198,391, filed on Nov. 24, 1998, now abandoned.

(30) Foreign Application Priority Data

Nov. 25, 1997 (JP) ............................................. 9-339393
Feb. 17, 1998 (JP) ............................................ 10-051351

(51) Int. Cl.[7] ........................ A01N 37/18; C07C 233/05
(52) U.S. Cl. ....................... 564/156; 514/351; 514/365; 514/372; 514/374; 514/378; 514/535; 514/616; 546/329; 548/198; 548/214; 548/215; 548/240; 560/46
(58) Field of Search ........................... 564/156; 514/616, 514/351, 365, 372, 374, 378, 525; 546/329; 548/215, 240, 198, 214; 560/46

(56) References Cited

U.S. PATENT DOCUMENTS

| | | |
|---|---|---|
| 3,502,685 A | 3/1970 | Gevirtz et al. |
| 4,120,863 A | 10/1978 | Tamborski |
| 4,694,016 A | 9/1987 | Lu et al. |
| 4,732,845 A | 3/1988 | Keiji et al. |
| 5,248,781 A | 9/1993 | McKillop |

FOREIGN PATENT DOCUMENTS

| | | |
|---|---|---|
| DE | 3305569 | 8/1989 |
| DE | 3802175 | 8/1989 |
| DE | 3802175 A | 8/1989 |
| EP | 0119428 A | 9/1984 |
| EP | 0119428 | 9/1984 |
| EP | 61180753 | 8/1986 |
| EP | 0 246 061 B1 | 5/1987 |
| EP | 0 246 061 | 11/1987 |
| EP | 0 298 803 | 1/1989 |
| EP | 0 325 983 | 8/1989 |
| EP | 03198049 | 8/1991 |
| GB | 1 535 234 | 12/1978 |
| JP | A-59-163353 | 9/1984 |
| JP | 60-008247 | 5/1985 |
| JP | A-61-180753 | 8/1986 |
| JP | 61-180753 A | 8/1986 |
| JP | A-63-99046 | 4/1988 |
| JP | 03-198049 | 8/1991 |
| JP | A-61-84065 | 7/1994 |

OTHER PUBLICATIONS

Boyd et al., *Synthesis and Reactions of Cyclic Isoimidium Salts*, J.C.S. Perkin I, (1978), pp. 1338–1350.

*Primary Examiner*—Shailendra Kumar
(74) *Attorney, Agent, or Firm*—Manelli Denison & Selter PLLC; Paul E. White, Jr.

(57) ABSTRACT

The present invention provides a phthalic acid diamide derivative represented by the general formula (I)

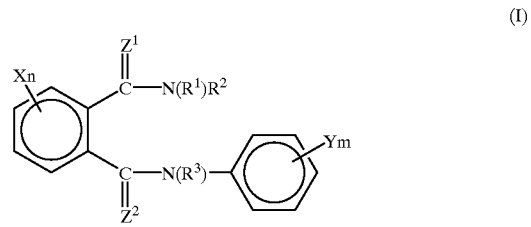

(I)

(wherein $R^1$, $R^2$ and $R^3$ are each H, $C_3$–$C_6$ cycloalkyl group, group of the formula —$A^1$—$Q_l$ or the like; X may be the same or different and are each halogen atom, nitro group, phenyl group, group of the formula —$A^2$—$R^7$ or the like; n is 1 to 4; Y may be same or different and are each halogen atom, cyano group, phenyl group, group of the formula —$A^2$—$R^7$ or the like; m is 1 to 5; $Z^1$ and $Z^2$ are each O or S), fluorine-containing aniline compound represented by the general formula (ST-I) as starting material for said phthalic acid diamide derivative

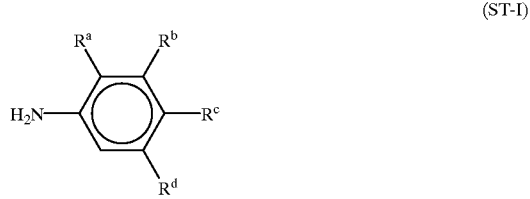

(ST-I)

(wherein $R^a$ is halogen atom, $C_1$–$C_6$ alkyl group or the like and $R^b$, $R^c$ and $R^d$ is H or $C_2$–$C_6$ perfluoroalkyl group), and an agricultural and horticultural insecticide containing said phthaldiamide derivative, as well as to provide a method for use of said insecticide. The agricultural and horticultural insecticides of the present invention show excellent activities for controlling injurious insects.

19 Claims, No Drawings

OTHER PUBLICATIONS

Boyd et al., *Synthesis and Reactions of Cyclic Isoimidium Salts*, J.C.S. Perkin I, (1978), pp. 1338–1350.
Takada, Patent Abstracts of Japan, vol. 018, No. 528, Oct. 6, 1994.
Qilin et al., "A facile method for fluoalkylation of aniline and its derivatives", Chemical Abstracts, vol. 109, No. 25, Dec. 19, 1988, p. 803.
Derwent Abstract 86–011629/02 & JP 60/237055, Showa Denko KK, published Nov. 25, 1985.
Derwent Abstract 85–052337/09 & JP 60/008257, Showa Denko KK, published Jan. 17, 1985.
XP002128158, Oct. 1962, Chemical Abstract.
XP002095529, Jan. 1968, Chemical Abstract.
XP002095530, Apr. 1969, Chemical Abstract.
XP002128157, Dec. 1973, Chemical Abstract.
XP002095528, Aug. 1979, Chemical Abstract.
XP002128156, Feb. 1988, Chemical Abstract.
XP002095527, Aug. 1988, Chemical Abstract.
XP002095526, Nov. 1990, Chemical Abstract.
XP002095525, May 1994, Chemical Abstract.
XP002128155, May 1995, Chemical Abstract.
XP002095524, Dec. 1995, Chemical Abstract.
XP002128154, Jan. 1996, Chemical Abstract.
XP002095523, Feb. 1996, Chemical Abstract.
XP002128153, May 1997, Chemical Abstract.
Perry, Robert J., et al., "Polyimide formation through the palladium–mediated carbonylation. . . ", Chemical Abstracts, Feb. 5, 1996, vol. 124, No. 6, p. 12.
Hall, Nigel, "Monoazo dyes containing a fluorosulfonyl group and their use", Chemical Abstracts, Dec. 25, 1995, vol. 123, No. 26, p. 180.
Beely, Nigel, et al., "Preparation of trisbustituted phenyl derivatives as selective phosphodiesterase IV inhibitors", Chemical Abstracts, May 23, 1994, Vo. 120, No. 21, p. 1012, 1994.
Ismail, M. Fekry et al., "Reacton of N–arylphthalisoimidium perchlorates with amines and aromatic hydrocarbons under Friedel–Crafts. . . ", Chemical Abstracts, vol. 113, No. 19, p. 686, 1990.
Ganin, E. V., et al., "N–substituted isophthalimide formation", Chemical Abstracts, vol. 109, No. 5, p. 604, 1988.
De Silva, S. Osmund et al., "Directed lithiation of N,N–diethylbenzamides", Chemical Abstracts, vol. 91, No. 9, p. 569, 1979.
De Toranzo et al., "Syntheses of unsymmetric o–phthalic acid diamides", Chemical Abstracts, vol. 68, No. 3, p. 1198, 1968.
Resplandy et al., "Synthesis of 6–phenanthridone–7–carboxylic acids from N–arylphthalamic acids", Chemical Abstracts, vol. 70, No. 15, p. 353, 1969.

PHTHALIC ACID DIAMIDE DERIVATIVES FLUORINE-CONTAINING ANILINE COMPOUNDS AS STARTING MATERIAL, AGRICULTURAL AND HORTICULTURAL INSECTICIDES, AND A METHOD FOR APPLICATION OF THE INSECTICIDES

CROSS-REFERENCE TO RELATED APPLICATION

This application is a continuation-in-part application of earlier U.S. application Ser. No. 09/198,391 filed Nov. 24, 1998 now abandoned, of which contents are all incorporated herein by reference.

BACKGROUND OF THE INVENTION

1. Field of the Invention

The present invention relates to phthalic acid diamide derivatives, fluorine-containing aniline compounds as starting material for said derivative, agricultural and horticultural insecticides containing said derivative as an active ingredient, and a method for application of the insecticides.

2. Related Art

Japanese Patent Application Nos. 59-163353 and 61-180753 and J. C. S. Perkin I, 1338–1350, (1978), etc. disclose some of the phthalic acid diamide derivatives of the present invention but neither describe nor suggest their usefulness as agricultural and horticultural insecticides. JP-A-63-99046 and JP-A-6-184065 describe the fact that anilines similar to the fluorine-containing aniline compound of the present invention are useful as intermediates of benzoylurea type insecticides.

SUMMARY OF THE INVENTION

The present inventors earnestly studied in order to develop a novel agricultural and horticultural insecticide, and consequently found that the phthalic acid diamide derivatives represented by the general formula (I) of the present invention are novel compounds not known as agricultural and horticultural insecticides in any literature and that said derivatives including the compounds disclosed in the above references can be used for a new purpose as agricultural and horticultural insecticides. Further, the present inventors found that the fluorine-containing aniline compounds represented by the general formula (ST-I) of the present invention are novel compounds which have not been known in any literature and is useful as an intermediate of a medicine, agrochemical, chemical product etc. In particular, they found that the fluorine-containing aniline compound of the general formula (ST-I) is useful as a starting material for the agricultural and horticultural insecticide containing the phthalic acid diamide derivative of the general formula (I) as an active ingredient. Thus, the present invention has been accomplished.

DETAILED DESCRIPTION OF THE INVENTION

The present invention relates to phthalic acid diamide derivatives of the general formula (I),

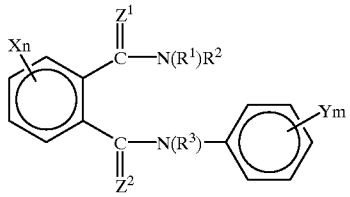

(I)

wherein $R^1$, $R^2$ and $R^3$ may be the same or different, and are each a hydrogen atom, a cyano group, a $C_3-C_6$ cycloalkyl group, a halo-$C_3-C_6$ cycloalkyl group, a $C_3-C_6$ cycloalkenyl group, a halo-$C_3-C_6$ cycloalkenyl group or a group of the formula —$A^1$—$Q_l$ (wherein $A^1$ is —O—, —S—, —$SO_2$—, —C(=O)—, a group of the formula —N($R^4$)— (wherein $R^4$ is a $C_1-C_6$ alkyl-carbonyl group, a halo-$C_1-C_6$ alkylcarbonyl group, a $C_1-C_6$ alkoxycarbonyl group, a phenylcarbonyl group, or a substituted phenylcarbonyl group having at least one substituent which may be the same or different, and is selected from the group consisting of a halogen atom, a cyano group, a nitro group, a $C_1-C_6$ alkyl group, a halo-$C_1-C_6$ alkyl group, a $C_2-C_6$ alkenyl group, a halo-$C_2-C_6$ alkenyl group, a $C_2-C_6$ alkynyl group, a halo-$C_2-C_6$ alkynyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group, a halo-$C_1-C_6$ alkylsulfonyl group, a mono-$C_1-C_6$ alkylamino group and a di-$C_1-C_6$ alkylamino group which may be the same or different), a $C_1-C_8$ alkylene group, a $C_3-C_6$ alkenylene group or a $C_3-C_6$ alkynylene group;

(1) when $A^1$ is —O— or a group of the formula —N($R^4$)— (wherein $R^4$ is the same as defined above), then Q is a hydrogen atom, a $C_1-C_6$ alkyl group, a halo-$C_1-C_6$ alkyl group, a $C_3-C_6$ alkenyl group, a halo-$C_3-C_6$ alkenyl group, a $C_3-C_6$ alkynyl group, a phenyl group, a substituted phenyl group having at least one substituent which may be the same or different and is selected from the group consisting of a halogen atom, a cyano group, a nitro group, a $C_1-C_6$ alkyl group, a halo-$C_1-C_6$ alkyl group, a $C_2-C_6$ alkenyl group, a halo-$C_2-C_6$ alkenyl group, a $C_2-C_6$ alkynyl group, a halo-$C_2-C_6$ alkynyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group, a halo-$C_1-C_6$ alkyl sulfonyl group, a mono-$C_1-C_6$ alkylamino group and a di-$C_1-C_6$ alkylamino group which may be the same or different, a phenyl-$C_1-C_4$ alkyl group or a substituted phenyl-$C_1-C_4$ alkyl group having at least one substituent, in the phenyl ring, which may be the same or different and is selected from the group consisting of a halogen atom, a cyano group, a nitro group, a $C_1-C_6$ alkyl group, a halo-$C_1-C_6$ alkyl group, a $C_2-C_6$ alkenyl group, a halo-$C_2-C_6$ alkenyl group, a $C_2-C_6$ alkynyl group, a halo-$C_2-C_6$ alkynyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

(2) when $A^1$ is —S—, —$SO_2$— or —C(=O)—, then Q is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_1$–$C_6$ alkoxy group, a mono-$C_1$–$C_6$ alkylamino group, a di-$C_1$–$C_6$ alkylamino group which may be the same or different, a $C_1$–$C_6$ alkoxycarbonylamino group, a $C_1$–$C_6$ alkoxycarbonyl-$C_1$–$C_6$ alkylamino group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylamino group, a substituted phenylamino group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or a pyrazolyl group), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (3) when $A^1$ is a $C_1$–$C_8$ alkylene group, a $C_3$–$C_6$ alkenylene group or a $C_3$–$C_6$ alkynylene group, then Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkyl-sulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$Z^3$—$R^5$ (wherein $Z^3$ is —O—, —S—, —SO—, —$SO_2$— or a group of the formula —N($R^6$)— (wherein $R^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^5$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkyl-thio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a Cl–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different);

l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

X may be the same or different, and is a hydrogen atom, a halogen atom, a cyano group, a nitro group, a $C_3$–$C_6$ cycloalkyl group, a halo-$C_3$–$C_6$ cycloalkyl group, a phenyl group, a substituted phenyl group having at least one substituents which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^2$—$R^7$ (wherein $A^2$ is —O—, —S—, —SO—, —$SO_2$—, —C(=O)—, —C(=$NOR^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl-$C_1$–$C_4$ alkyl group, or a substituted phenyl-$C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkyl-sulfonyl group, a mono-$C_1$–$C_6$ alkylamino group and a di-$C_1$–$C_6$ alkylamino group which may be the same or different), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —$SO_2$—, then $R^7$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group, a di-$C_1$–$C_6$ alkoxyphosphoryl group which may be the same or different, a di-$C_1$–$C_6$ alkoxythiophosphoryl group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ a alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^3$—$R^9$ (wherein $A^3$ is —C(=O)—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_3$–$C_6$ alkynylene group or a halo-$C_3$–$C_6$ alkynylene group, (i) when $A^3$ is —C(=O)— or —$SO_2$—, then $R^9$ is a $C_1$–$C_6$ alkyl group, a halo-$C_1$–$C_6$ alkyl group, a $C_1$–$C_6$ alkoxy group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (ii) when $A^3$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_3$–$C_6$ alkynylene group or a halo-$C_3$–$C_6$ alkynylene group, then $R^9$ is a hydrogen atom, a halogen atom, a cyano group, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^4$—$R^{10}$ (wherein $A^4$ is —O—, —S—, —SO—, —$SO_2$—, —C(=O)—, or a group of the formula —N($R^{11}$)— (wherein $R^{11}$ is a hydrogen atom, a $C_1$–$C_6$ alkyl group, a halo-$C_1$–$C_6$ alkyl group, a $C_3$–$C_6$ alkenyl group, a $C_3$–$C_6$ alkynyl group, a $C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^{10}$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different));

(2) when $A^2$ is —C(=O)— or a group of the formula —C(=NOR$^8$)— (wherein R$^8$ is the same as defined above), then R$^7$ is a $C_1$–$C_6$ alkyl group, a halo $C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylamino group, a substituted phenylamino group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having one or more substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then R$^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^5$—$R^{12}$ (wherein $A^5$ is —O—, —S—, —SO—, —SO$_2$— or a group of the formula —N(R$^{13}$)— (wherein R$^{13}$ is a hydrogen atom, a $C_1$–$C_6$ alkyl group, a halo-$C_1$–$C_6$ alkyl group, a $C_2$–$C_6$ alkenyl group, a $C_2$–$C_6$ alkynyl group, a $C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^{12}$ is a hydrogen atom, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituents which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^6$—$R^{14}$ (wherein $A^6$ is —C(=O)—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(i) when $A^6$ is —C(=O)— or —$SO_2$—, then $R^{14}$ is a $C_1$–$C_6$ alkyl group, a halo-$C_1$–$C_6$ alkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

(ii) when $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^{14}$ is a hydrogen atom, a halogen atom, a cyano group, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a $C_1$–$C_6$ alkylcarbonyl group, a halo-$C_1$–$C_6$ alkylcarbonyl group, a $C_1$–$C_6$ alkoxycarbonyl group, a phenyl group, a substituted phenyl group having at least one substituent which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenoxy group, a substituted phenoxy group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylthio group, a substituted phenylthio group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$-alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different)));

n is an integer of 1 to 4;

further, X may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), by combining together with the adjacent carbon atoms in the phenyl ring, and said condensed ring may have at least one substituents, which may be the same or different, and selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a $C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo- $C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), and a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

Y is the same or different, and is a hydrogen atom, a halogen atom, a cyano group, a nitro group, a $C_3$–$C_6$ cycloalkyl group, a halo-$C_3$–$C_6$ cycloalkyl group, a di-$C_1$–$C_6$ alkoxyphosphoryl group which may be the same or different, a di-$C_1$–$C_6$ alkoxythiophosphoryl group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same as defined the above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^2$—$R^7$ (wherein $A^2$ and $R^7$ are the same as defined above);

m is an integer of 1 to 5;

further, Y may form a condensed ring (the condensed ring is the same as defined above), by combining together with the adjacent carbon atoms in the phenyl ring, said condensed ring may have at least one substituents, which may be the same or different, and selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), and a substituted heterocyclic group (wherein said heterocyclic group is the same as defined above) having at lease one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

$Z^1$ and $Z^2$ are each represents an oxygen atom or a sulfur atom; provided that, (1) when X, $R^1$ and $R^3$ are hydrogen atoms at the same time; m is an integer of 2; Y at 2-position is a fluorine atom and Y at 3-position is a chlorine atom; then $R^2$ is not ethyl group, isopropyl group, cyclohexyl group, 2-propenyl group, methylthiopropyl group and a-methylbenzyl group, (2) when X and $R^3$ are hydrogen atoms at the same time; m is an integer of 2; Y at 2-position is a fluorine atom and Y at 3-position is a chlorine atom; then the 4 to 7 membered ring by combining $R^1$ and $R^2$ to each other, in which the ring may contain the same or different 1 to 3 hetero atoms selected from the group consisting of oxygen atom, sulfur atom and nitrogen atom is not morpholino group, (3) when X, $R^1$ and $R^3$ are hydrogen atoms at the same time; and $R^2$ is 1,2,2-trimethylpropyl group; then Y is not a hydrogen atom, (4) when X, $R^1$ and $R^3$ are hydrogen atoms at the same time; $R^2$ is 2,2-dimethylpropyl group; and m is an integer of 1; then Y is not 2-ethoxy group, and (5) when X, $R^1$ and $R^3$ are hydrogen atoms at the same time; and $R^2$ is tert-butyl group group; and m is an integer of 1; then Y is not 4-Chlorine atom, 2-nitro group, 4-nitro group, 3-methoxy group, 4-methoxy group and 2,6-dimethyl groups;

fluorine-containing aniline compounds represented by the general formula (ST-I) as starting material for the phthalic acid diamide derivatives:

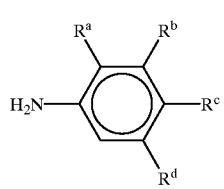

(ST-I)

(wherein $R^a$ is a halogen atom, a $C_1$–$C_6$ alkyl group, a $C_1$–$C_6$ alkoxy group or a trifluoromethyl group, and each of $R^b$, $R^c$ and $R^d$ is a hydrogen atom or a $C_2$–$C_6$ perfluoroalkyl group, provided that at least one of $R^b$, $R^c$ and $R^d$ is not a hydrogen atom and that $R^c$ is neither a pentafluoroethyl group nor a n-heptafluoropropyl group when $R^a$ is a fluorine atom and each of $R^b$ and $R^d$ is a hydrogen atom); agricultural and horticultural insecticides containing as an active ingredient any of the phthalic acid diamide derivatives of the general formula (I) including known compounds; and a method for application of the insecticides.

In the definition of the general formula (I) representing the phthalic acid diamide derivative of the present invention, the halogen atom includes chlorine atom, bromine atom, iodine atom and fluorine atom. The term "$C_1$–$C_6$ alkyl" means a linear or branched alkyl group of 1 to 6 carbon atoms, such as methyl, ethyl, n-propyl, i-propyl, n-butyl, i-butyl, s-butyl, t-butyl, n-pentyl, n-hexyl, or the like. The term "$C_1$–$C_8$ alkylene" means a linear or branched alkylene group of 1 to 8 carbon atoms, such as methylene, ethylene, propylene, trimethylene, dimethylmethylene, tetramethylene, i-butylene, dimethylethylene, pentamethylene, hexamethylene, heptamethylene, octamethylene or the like. The term "halo-$C_1$–$C_6$ alkyl" means a substituted and linear or branched alkyl group of 1 to 6 carbon atoms having as the substituent(s) one or more halogen atoms which may be the same or different.

As the ring which $R^1$ and $R^2$ form by combining to each other, i.e., the 4- to 7-membered ring by combining to each other, in which the ring may contain the same or different 1 to 3 hetero atoms selected from the group consisting of oxygen atom, sulfur atom and nitrogen atom, there can be exemplified azetidine ring, pyrrolidine ring, pyrroline ring, piperidine ring, imidazolidine ring, imidazoline ring, oxazolidine ring, thiazolidine ring, isoxazolidine ring, isothiazolidine ring, tetrahydropyridine ring, piperazine ring, morpholine ring, thiomorpholine ring, dioxazine ring, dithiazine ring, etc.

The phthalic acid diamide derivative of the general formula (I) of the present invention contains an asymmetric carbon atom or some asymmetric center in the structural formula in some cases or has two optical isomers in some cases. The present invention includes these optical isomers and all mixtures containing the optical isomers in arbitrary proportions.

Preferable examples of each substituent of the phthalic acid diamide derivative of the general formula (I) of the present invention are as follows. Preferable examples of each of $R^1$ and $R^2$ which may be the same or different are hydrogen atom, $C_1$–$C_6$ alkyl groups such as methyl, ethyl, i-propyl, etc. Preferable examples of $R^3$ are hydrogen atom, and $C_1$–$C_6$ alkyl groups such as methyl, ethyl, n-propyl, i-propyl, n-butyl, etc. Preferable examples of X are halogen atoms, nitro group, halo-$C_1$–$C_6$ alkyl groups, halo-$C_1$–$C_6$ alkoxy groups, halo-$C_1$–$C_6$ alkylthio groups, etc. Preferable examples of Y are halo-$C_1$–$C_6$ alkyl groups, halo-$C_1$–$C_6$ alkoxy groups, halo-$C_1$–$C_6$ alkylthio groups, etc.

The phthalic acid diamide derivative of the general formula (I) of the present invention can be produced, for example, by any of the processes illustrated below.

Production process 1

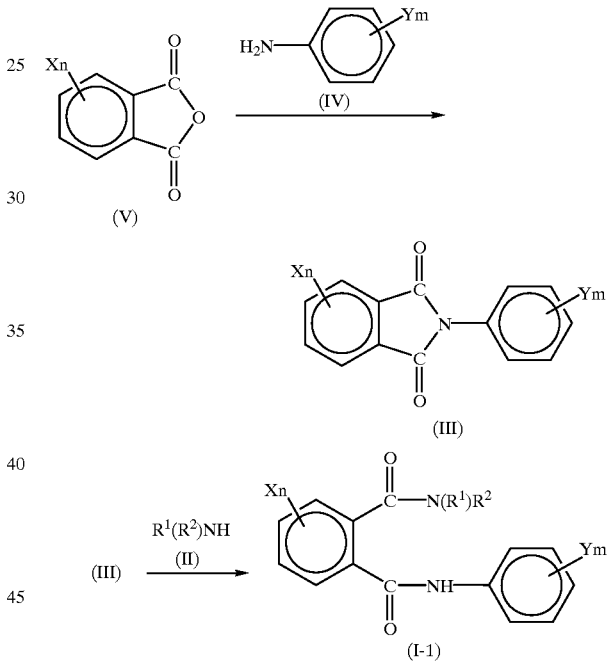

wherein $R^1$, $R^2$, X, n, Y and m are as defined above.

A phthalic anhydride derivative of the general formula (V) is reacted with an aniline of the general formula (IV) in the presence of an inert solvent to obtain a phthalimide derivative of the general formula (III). The phthalimide derivative (III) is reacted with an amine of the general formula (II) after or without being isolated, whereby a phthalic acid diamide derivative of the general formula (I-1) can be produced.

(1) General formula (V)→general formula (III)

As the inert solvent used in this reaction, any solvent may be used so long as it does not markedly inhibit the progress of the reaction. There can be exemplified aromatic hydrocarbons such as benzene, toluene, xylene, etc.; halogenated hydrocarbons such as dichloromethane, chloroform, carbon tetrachloride, etc., chlorinated aromatic hydrocarbons such as chlorobenzene, dichlorobenzene, etc.; a cyclic or cyclic ethers such as diethyl ether, dioxane, tetrahydrofuran, etc., esters such as ethyl acetate, etc.; amides such as dimethylformamide, dimethylacetamide, etc.; acids such as acetic acid, etc.; dimethyl sulfoxide; and 1,3-dimethyl-2-imidazolidinone. These inert solvents may be used alone or as a mixture thereof.

Since the reaction is an equimolar reaction, it is sufficient that the reactants are used in equimolar amounts, though either of them may be used in excess. If necessary, the reaction may be carried out under dehydrating conditions.

As to the reaction temperature, the reaction can be carried out in a temperature range of room temperature to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced. The desired compound can be subjected to the subsequent reaction without isolation from the reaction solution.

The phthalic anhydride derivative of the general formula (V) can be produced by the process described in J. Org. Chem., 52, 129 (1987), J. Am. Chem. Soc., 51, 1865 (1929), J. Am. Chem. Soc., 63, 1542 (1941), etc. The aniline of the general formula (IV) can be produced by the process described in J. org. Chem., 29, 1 (1964), Angew. Chem. Int. Ed. Engl., 24, 871 (1985), Synthesis, 1984, 667, Bulletin of the Chemical Society of Japan, 1973, 2351, DE-2606982, JP-A-1-90163, etc.

(2) General formula (III)→general formula (I-1)

In this reaction, there can be used the inert solvents exemplified above as the inert solvent used in the reaction (1).

Since the reaction is an equimolar reaction, it is sufficient that the reactants are used in equimolar amounts, though the amine of the general formula (II) may be used in excess.

As to the reaction temperature, the reaction can be carried out in a temperature range of room temperature to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced.

Production process 2

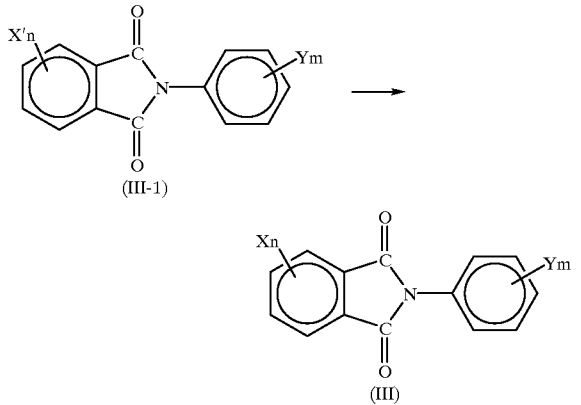

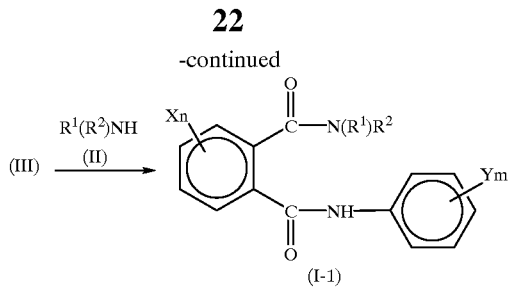

wherein $R^1$, $R^2$, n, X, Y and m are as defined above, and X' is a halogen atom or a nitro group, provided that X is other than a hydrogen atom or a nitro group.

A phthalimide derivative of the general formula (III-1) is reacted with a reactant corresponding to X in the presence of an inert solvent to obtain a phthalimide derivative of the general formula (III). The phthalimide derivative (III) is reacted with an amine of the general formula (II) after or without being isolated, whereby a phthalic acid diamide derivative of the general formula (I-1) can be produced.

(1) General formula (III-1)→general formula (III)

This reaction can be carried out according to the methods described in J. Org. Chem., 42, 3415 (1977), Tetrahedron, 25, 5921 (1969), Synthesis, 1984, 667, Chem. Lett., 1973, 471, J. Org. Chem., 39, 3318 (1974), J. Org. Chem., 39, 3327 (1974), etc.

(2) General formula (III)→general formula (I-1)

This reaction can be carried out according to production process 1-(2).

Production process 3

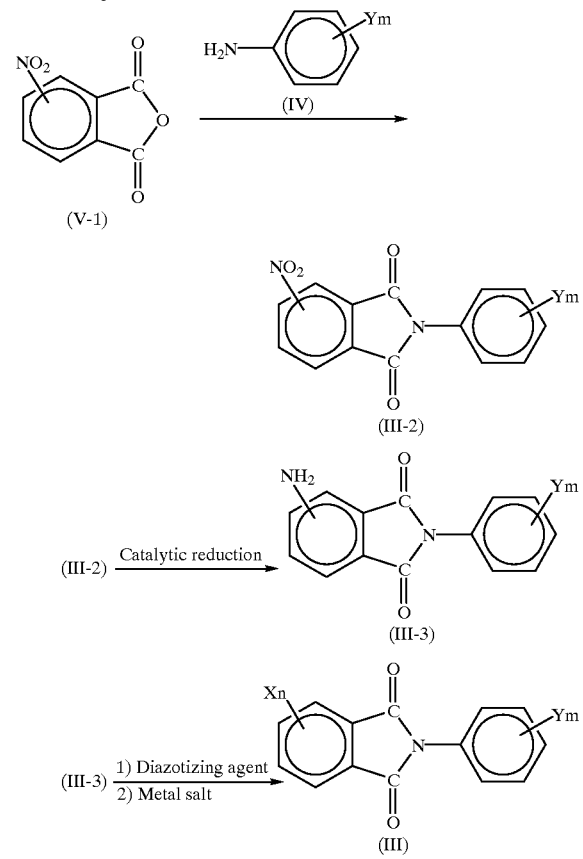

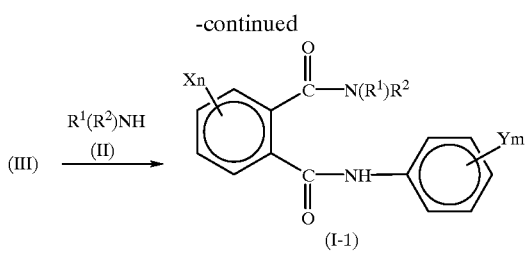

wherein $R^1$, $R^2$, X, Y, m and n are as defined above.

A phthalic anhydride of the general formula (V-1) is reacted with an aniline of the general formula (IV) in the presence of an inert solvent to obtain a phthalimide derivative of the general formula (III-2). The phthalimide derivative (III-2) is subjected to catalytic reduction with hydrogen after or without isolation to obtain a phthalimide derivative of the general formula (III-3). The phthalimide derivative (III-3) is converted to a phthalimide derivative of the general formula (III) by adding a diazotizing agent and then a metal salt after or without isolation of the phthalimide derivative (III-3). The phthalimide derivative (III) is reacted with an amine of the general formula (II) after or without being isolated, whereby a phthalic acid diamide derivative of the general formula (I-1) can be produced.

(1) General formula (V-1)→general formula (III-2)

The desired compound can be produced by this reaction in the same manner as in production process 1-(1).

(2) General formula (III-2)→general formula (III-3)

Any solvent may be used in this reaction so long as it does not markedly inhibit the progress of the reaction. There can be exemplified alcohols such as methanol, ethanol, propanol, etc.; acyclic or cyclic ethers such as diethyl ether, dioxane, tetrahydrofuran, etc., and acids such as acetic acid, etc. These inert solvents may be used alone or as a mixture thereof.

As the catalyst for catalytic reduction used in this reaction, there can be exemplified palladium carbon, Raney nickel, palladium black, platinum black, etc. The amount of the catalyst used may be properly chosen in a range of 0.1 to 10% by weight based on the weight of the phthalimide derivative of the general formula (III-2). This reaction is carried out under a hydrogen atmosphere and the hydrogen pressure may be properly chosen in a range of 1 to 10 atmospheric pressure.

As to the reaction temperature, the reaction can be carried out in a temperature range of room temperature to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction mixture containing the desired compound by a conventional method, and if necessary, purified by recrystallization, column chromatography, etc., whereby the desired compound can be produced. The desired compound can be subjected to the subsequent reaction without isolation from the reaction mixture. (3) General formula (III-3)→general formula (III)

In this reaction, an acidic solvent can be used as an inert solvent. The acidic solvent includes, for example, an aqueous hydrochloric acid solution, an aqueous hydrobromic acid solution, an aqueous hydroiodic acid solution, an aqueous sulfuric acid solution, acetic acid and trifluoroacetic acid. These acidic solvents may be used alone or as a mixture thereof. In addition, these acidic solvents may be used in admixture with ethers such as tetrahydrofuran, dioxane, etc.

The diazotizing agent includes, for example, sodium nitrite, nitrosyl hydrogensulfate and alkyl nitrites. The amount of the diazotizing agent used may be properly chosen in a range of equal amount to excess amount relative to the amount of the phthalimide derivative of the general formula (III-3).

As to the reaction temperature, the reaction can be carried out in a temperature range of $-50°$ C. to the reflux temperature of the inert solvent used. Although the reaction time is varied depending on the scale of reaction, the reaction temperature, etc., it may be properly chosen in a range of several minutes to 48 hours.

As the metal salt added after the production of a diazonium salt, there can be used, for example, cuprous chloride, cuprous bromide, potassium iodide, copper cyanide, potassium xanthate and sodium thiorate. The amount of the metal salt used may be properly chosen in a range of 1 equivalent to excess equivalents per equivalent of the phthalimide derivative of the general formula (III-3).

After completion of the reaction, the desired compound is isolated from the reaction mixture containing the desired compound by a conventional method, and if necessary, purified by recrystallization, column chromatography, etc., whereby the desired compound can be produced. The desired compound can be subjected to the subsequent reaction without isolation from the reaction mixture.

The reaction can be carried out according to the method described in Org. Synth., IV, 160 (1963), Org. Synth., III, 809 (1959), J. Am. Chem. Soc., 92, 3520 (1970), etc.

(4) General formula (III)→general formula (I-1)

The desired compound can be produced by this reaction in the same manner as in production process 1-(2).

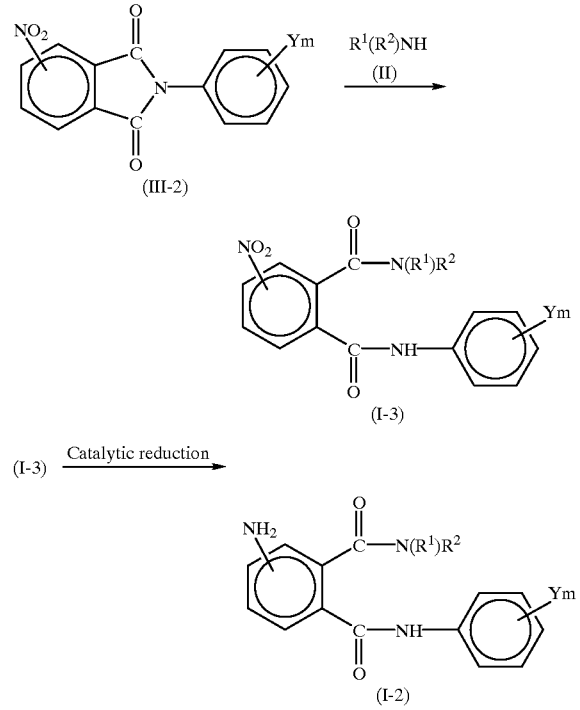

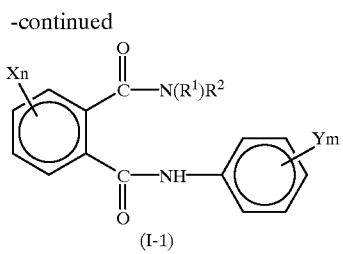

wherein $R^1$, $R^2$, X, Y, m and n are as defined above.

A phthalimide derivative of the general formula (III-2) is reacted with an amine of the general formula (II) in the presence of an inert solvent to obtain a phthalic acid diamide derivative of the general formula (I-3). The phthalic acid diamide derivative (I-3) is subjected to catalytic reduction with hydrogen after or without isolation to obtain a phthalic acid diamide derivative of the general formula (I-2). A phthalic acid diamide derivative of the general formula (I-1) can be produced from the phthalic acid diamide derivative (I-2) by adding a diazotizing agent and then a metal salt after or without isolating the phthalic acid diamide derivative (I-2).

(1) General formula (III-2)→general formula (I-3)

The desired compound can be produced by this reaction in the same manner as in production process 1-(2).

(2) General formula (I-3)→general formula (I-2)

The desired compound can be produced by this reaction in the same manner as in production process 3-(2).

(3) General formula (I-2)→general formula (I-1)

The desired compound can be produced by this reaction in the same manner as in production process 3-(3).

Production process 5

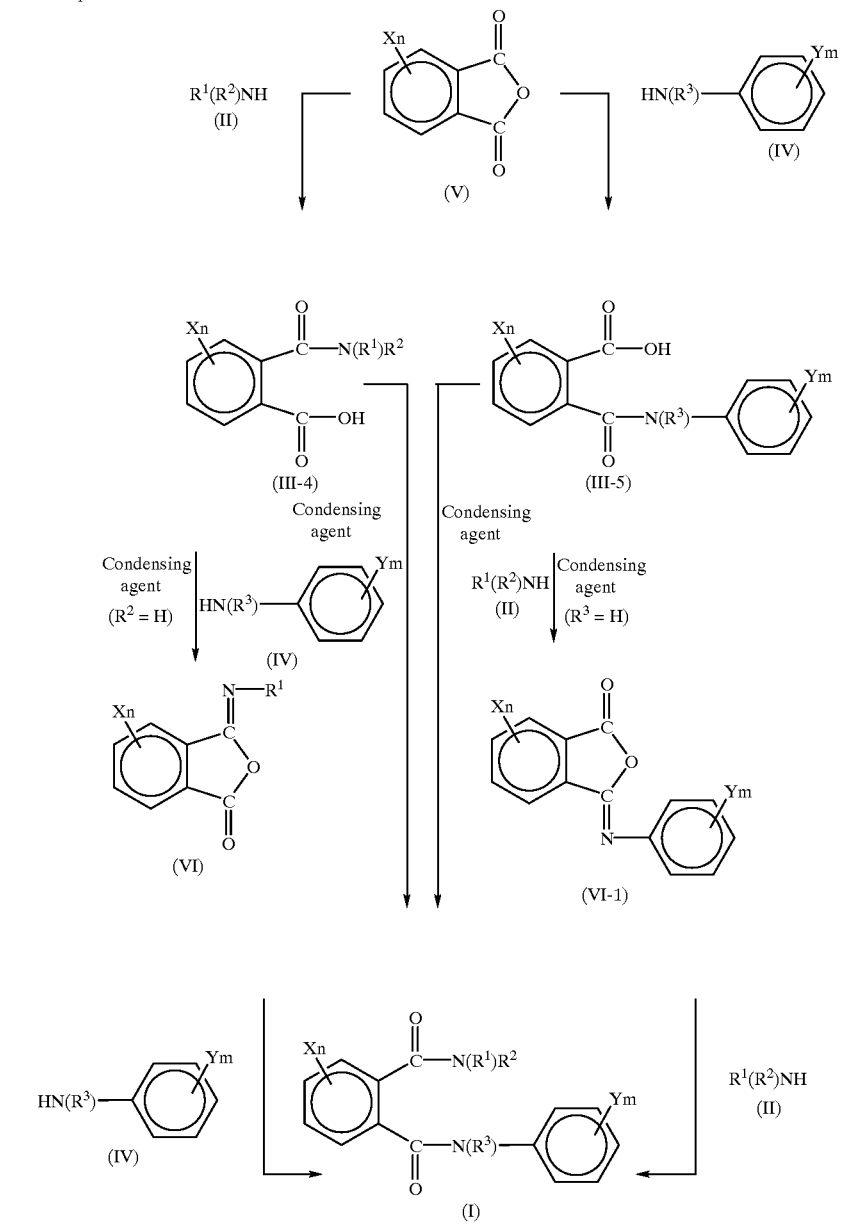

wherein $R^1$, $R^2$, $R^3$, X, n, Y and m are as defined above.

A phthalic anhydride derivative of the general formula (V) is reacted with an amine of the general formula (II) in the presence of an inert solvent to obtain a phthalamide of the general formula (III-4). The phthalamide (III-4) is treated as follows after or without isolation. When $R^2$ of the phthalamide (III-4) is a hydrogen atom, the phthalamide (III-4) is condensed into a compound of the general formula (VI) in the presence of a condensing agent, and the compound (VI) is reacted with an aniline of the general formula (IV) in the presence of an inert solvent after or without being isolated. When $R^2$ of the phthalamide (III-4) is other than a hydrogen atom, the phthalamide (III-4) is condensed with an aniline of the general formula (IV) in the presence of a condensing agent. Thus, a phthalic acid diamide derivative of the general formula (I) can be produced.

Alternatively, a phthalic anhydride derivative of the general formula (V) is reacted with an aniline of the general formula (IV) in the presence of an inert solvent to obtain a phthalanilide of the general formula (III-5). The phthalanilide (III-5) is treated as follows after or without isolation. When $R^3$ of the phthalanilide (III-5) is a hydrogen atom, the phthalanilide (III-5) is condensed into a compound of the general formula (VI-1) in the presence of a condensing agent, and the compound (VI-1) is reacted with an amine of the general formula (II) in the presence of an inert solvent after or without being isolated. When $R^3$ of the phthalanilide (III-5) is other than a hydrogen atom, the phthalanilide (III-5) is condensed with an amine of the general formula (II) in the presence of a condensing agent. Thus, a phthalic acid diamide derivative of the general formula (I) can be produced.

(1) General formula (V) or general formula (VI-1)→general formula (III-4) or general formula (I), respectively The desired compound can be produced by this reaction in the same manner as in production process 1-(2).

(2) General formula (III-4) or general formula (III-5) →general formula (VI) or general formula (VI-1), respectively The desired compound can be produced by this reaction according to the method described in J. Med. Chem., 10, 982 (1967).

(3) General formula (VI) or general formula (V)→general formula (I) or general formula (III-5), respectively The desired compound can be produced by this reaction in the same manner as in production process 1-(2).

(4) General formula (III-4) or general formula (III-5) →general formula (I)

The desired compound can be produced by reacting the phthalamide derivative of the general formula (III-4) or the general formula (III-5) with the aniline of the general formula (IV) or the amine of the general formula (II), respectively, in the presence of a condensing agent and an inert solvent. If necessary, the reaction can be carried out in the presence of a base.

The inert solvent used in the reaction includes, for example, tetrahydrofuran, diethyl ether, dioxane, chloroform and dichloromethane. As the condensing agent used in the reaction, any condensing agent may be used so long as it is used in usual amide synthesis. The condensing agent includes, for example, Mukaiyama reagent (e.g. 2-chloro-N-methylpyridinium iodide), 1,3-dicyclohexylcarbodiimide (DCC), carbonyldiimidazole (CDI) and diethyl phosphorocyanidate (DEPC). The amount of the condensing agent used may be properly chosen in a range of 1 mole to excess moles per mole of the phthalamide derivative of the general formula (III-4) or the general formula (III-5).

As the base usable in the reaction, there can be exemplified organic bases such as triethylamine, pyridine, etc. and inorganic bases such as potassium carbonate, etc. The amount of the base used may be properly chosen in a range of 1 mole to excess moles per mole of the phthalamide derivative of the general formula (III-4) or the general formula (III-5).

As to the reaction temperature, the reaction can be carried out in a temperature range of 0° C. to the boiling point of the inert solvent used. Although the reaction time is varied depending on the scale of reaction, the reaction temperature, etc., it ranges from several minutes to 48 hours.

After completion of the reaction, the desired compound is isolated from the reaction solution containing the desired compound by a conventional method, and if necessary, purified by recrystallization, column chromatography, etc., whereby the desired compound can be produced.

Production process 6

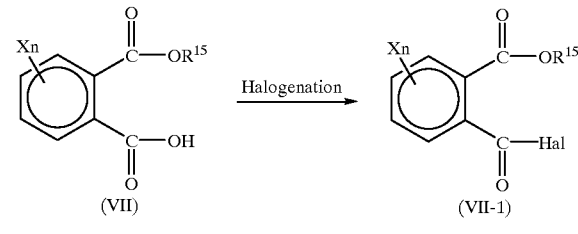

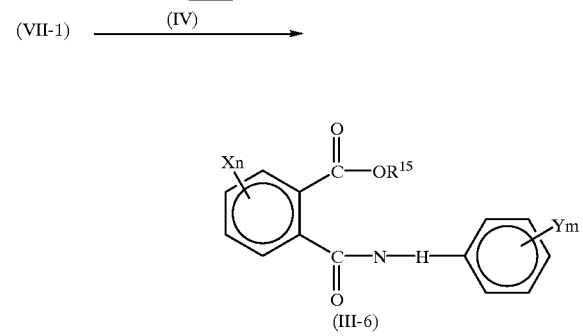

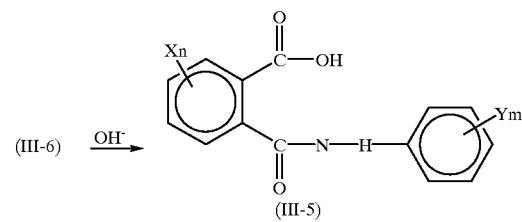

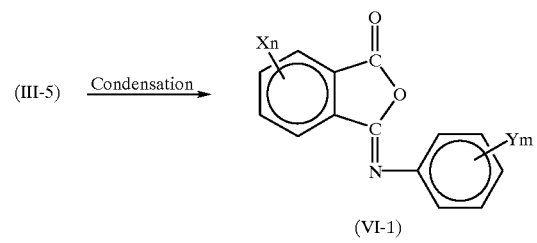

-continued

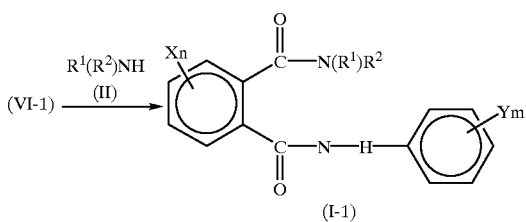

wherein $R^1$, $R^2_1$ X, n, Y and m are as defined above, Hal is a halogen atom, and $R^{15}$ is a $(C_1-C_3)$alkyl group.

A phthalic acid ester derivative of the general formula (VII) is halogenated into a phthaloyl halide of the general formula (VII-1) in the presence or absence of an inert solvent. The phthaloyl halide (VII-1) is reacted with an aniline of the general formula (IV) in the presence of an inert solvent and a base after or without being isolated, to obtain a phthalanilide of the general formula (III-6). The phthalanilide (III-6) is hydrolyzed into a phthalanilide of the general formula (III-5) in the presence or absence of an inert solvent after or without being isolated. The phthalanilide (III-5) is condensed into a phthalic anhydride derivative of the general formula (VI-1) after or without being isolated. The phthalic anhydride derivative (VI-1) is reacted with an amine of the general formula (II), whereby a phthalic acid diamide derivative of the general formula (I-1) can be produced.

(1) General formula (VII)→general formula (VII-1)

As the inert solvent usable in this reaction, any solvent may be used so long as it does not markedly inhibit the progress of the reaction. There can be exemplified aromatic hydrocarbons such as benzene, toluene, xylene, etc.; halogenated hydrocarbons such as dichloromethane, chloroform, carbon tetrachloride, etc., chlorinated aromatic hydrocarbons such as chlorobenzene, dichlorobenzene, etc.; acyclic or cyclic ethers such as diethyl ether, dioxane, tetrahydrofuran, etc., and esters such as ethyl acetate, etc. These inert solvents may be used alone or as a mixture thereof.

As the halogenating agents, there can be used, for example, thionyl chloride, phosphoryl chloride, and phosphorus trichloride. The amount of the halogenating agent used may be properly chosen in a range of 1 to 10 equivalents per equivalent of the phthalic acid ester of the general formula (VII).

As to the reaction temperature, the reaction can be carried out in a temperature range of 0° C. to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced. The desired compound can be subjected to the subsequent reaction without isolation from the reaction solution.

The phthalic acid ester of the general formula (VII) can be produced, for example, by the process described in J. Med. Chem., 31, 1466 (1988).

(2) General formula (VII-1)→general formula (III-6)

As the inert solvent used in this reaction, there may be used, for example, the inert solvents exemplified in production process 1-(1).

As the base, an inorganic base or an organic base may be used. As the inorganic base, there may be used, for example, hydroxides of alkali metals, such as sodium hydroxide, potassium hydroxide, etc. As the organic base, there may be used triethylamine, pyridine, etc. The amount of the base used may be properly chosen in a range of 0.5 to 3 equivalents per equivalent of the phthaloyl halide of the general formula (VII-1).

Since the reaction is an equimolar reaction, it is sufficient that the reactants are used in equimolar amounts, though the amount of the aniline of the general formula (IV) used may be properly chosen in a range of 0.5 to 2 equivalents per equivalent of the phthaloyl halide of the general formula (VII-1).

As to the reaction temperature, the reaction can be carried out in a temperature range of 0° C. to the ref lux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced. The desired compound can be subjected to the subsequent reaction without isolation from the reaction solution.

(3) General formula (III-6)→general formula (III-5)

As the inert solvent usable in this reaction, there may be used water, alcohols (e.g. methanol, ethanol and propanol) as water-soluble solvents, and mixed solvents of water and a water-soluble solvent.

As the base used for the hydrolysis, there may be used, for example, hydroxides of alkali metals, such as sodium hydroxide, potassium hydroxide, etc. The amount of the base used may be properly chosen in a range of 1 to 10 equivalents per equivalent of the phthalanilide of the general formula (III-6).

As to the reaction temperature, the reaction can be carried out in a temperature range of 0° C. to the reflux temperature of the inert solvent used. Although the reaction time is varied depending on the scale of reaction, the reaction temperature, etc., it may be properly chosen in a range of several minutes to 48 hours.

After completion of the reaction, the desired compound is isolated from the reaction solution containing the desired compound by a conventional method, and if necessary, purified by recrystallization, column chromatography, etc., whereby the desired compound can be produced. The desired compound can be subjected to the subsequent reaction without isolation from the reaction solution.

(4) General formula (III-5)→general formula (VI-1)

The desired compound can be produced by this reaction according to production process 5-(2).

(5) General formula (VI-1)→general formula (I-1)

The desired compound can be produced by this reaction according to production process 1-(2).

Production process 7
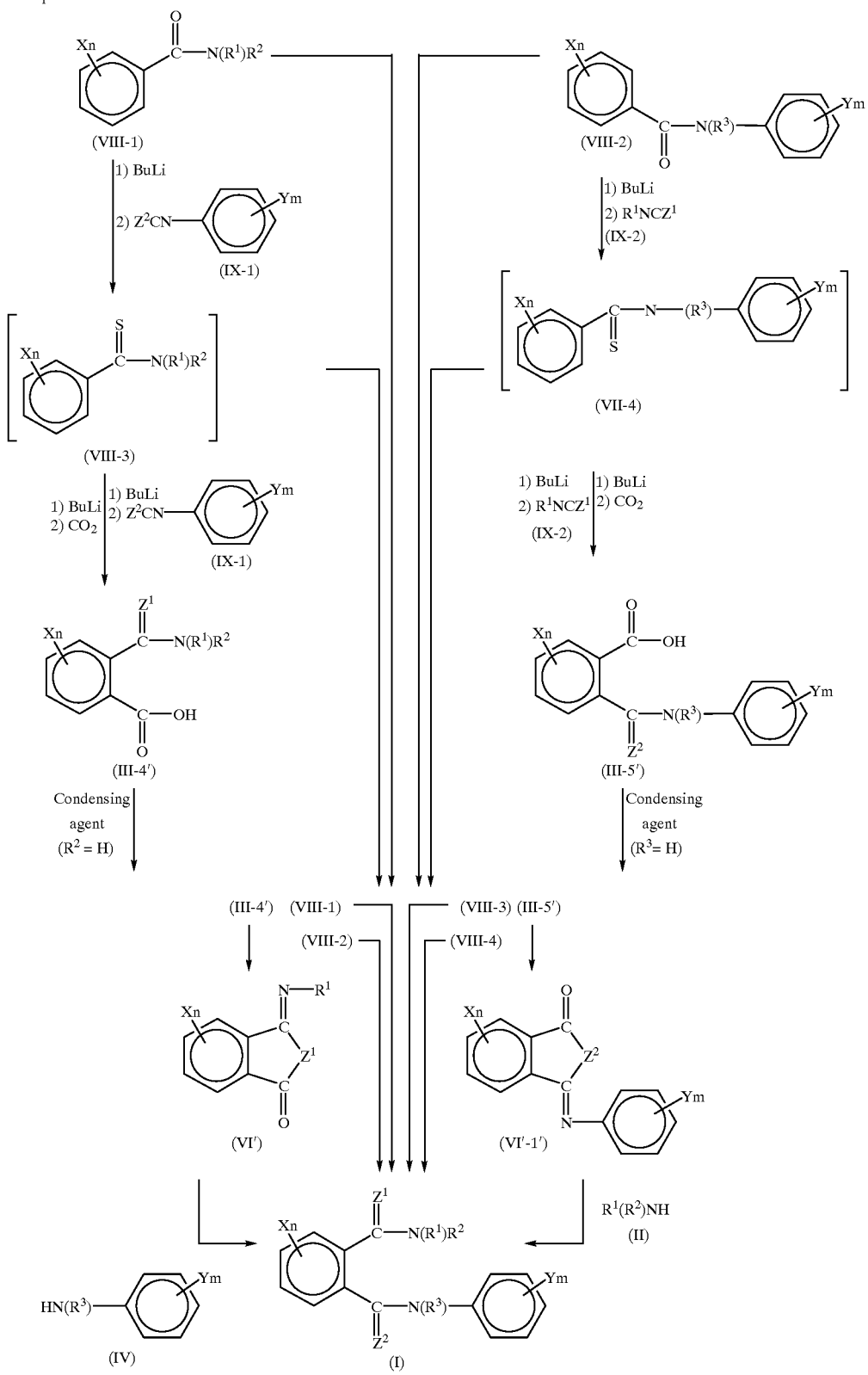
wherein $R^1$, $R^2$, R, X, Y, m, n, $Z^1$ and $Z^2$ are as defined above.
A benzamide derivative of the general formula (VIII-1) or the general formula (VIII-2) or a thiobenzamide derivative of the general formula (VIII-3) or the general formula (VIII-4) obtained by thiocarbonylation of the benzamide derivative of the general formula (VIII-1) or the general formula (VIII-2), respectively, is subjected to ortho-metallation by using a metal reagent such as butyllithium. The compound thus obtained is directly reacted with an isocyanate or isothiocyanate derivative of the general formula (IX-1) or (IX-2), or the compound is reacted with carbon dioxide to obtain a phthalamide derivative of the general formula (III-4') or the general formula (III-5'), which is treated in the same manner as in production processes 5-(1) to 5-(4). Thus, a phthalic acid diamide derivative of the general formula (I) can be produced.

(1) General formula (VIII-1) or general formula (VIII-2) →general formula (VIII-3) or general formula (VIII-4), respectively The desired compound can be produced by this reaction according to the method described in J. Org. Chem., 46, 3558 (1981).

(2) General formula (VIII-1), general formula (VIII-2), general formula (VIII-3) or general formula (VIII-4) →general formula (I)

In this step, the benzamide derivative of the general formula (VIII-1) or the general formula (VIII-2) or the thiobenzamide derivative of the general formula (VIII-3) or the general formula (VIII-4) obtained by thiocarbonylation of the benzamide derivative of the general formula (VIII-1) or the general formula (VIII-2), respectively, is subjected to ortho-lithiation according to the method described in J. Org. Chem., 29, 853 (1964). The compound thus obtained is reacted with the isocyanate or isothiocyanate derivative of the general formula (IX-1) or (IX-2) at −80°C. to room temperature, whereby the desired compound can be produced.

After completion of the reaction, the desired compound is isolated from the reaction solution containing the desired compound by a conventional method, and if necessary, purified by recrystallization, column chromatography, etc., whereby the desired compound can be obtained.

(3) General formula (VIII-1), general formula (VIII-2), general formula (VIII-3) or general formula (VIII-4) →general formula (III-4') or the general formula (III-5')

In this step, the desired compound can be produced by carrying out the same ortho-lithiation as in the above step (2) and introducing carbon dioxide into the ortho-lithiation product at −80° C. to room temperature.

After completion of the reaction, the desired compound is isolated from the reaction solution containing the desired compound by a conventional method, and if necessary, purified by recrystallization, column chromatography, etc., whereby the desired compound can be obtained. (4) General formula (III-4') or general formula (III-5')→general formula (I)

In this step, the desired compound can be produced in the same manner as in production process 1-(2) or 5-(4).

Tables 1 and 2 show typical examples of the phthalic acid diamide derivative of the general formula (I) used as the active ingredient of the agricultural and horticultural insecticide of the present invention, but the examples are not intended in any way to limit the scope of the present invention.

General formula (I)

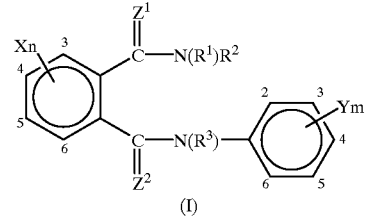

(I)

TABLE 1

($Z^1$, $Z^2$ = O)

| No | $R^1$ | $R^2$ | $R^3$ | Xn | Ym | Physical Properties (melting point: ° C. |
|---|---|---|---|---|---|---|
| 1 | H | H | H | 3-$NO_2$ | 2-$CH_3$-5-Cl | 173–175 |
| 2 | $CH_3$ | H | H | H | 4-$CF_3$ | 129–131 |
| 3 | $CH_3$ | H | H | 3-$NO_2$ | 2-$CH_3$-5-Cl | 169–171 |
| 4 | $CH_3$ | H | H | 3-$NO_2$ | 2-$CH_3$-4-$OCHF_2$ | 167–169 |
| 5 | $CH_3$ | $CH_3$ | H | 6-$NO_2$ | 2-$CH_3$-5-Cl | 171–173 |
| 6 | $CH_3$ | $CH_3$ | H | 6-$NO_2$ | 2-$CH_3$-4-$OCHF_2$ | 167–169 |
| 7 | $C_2H_5$ | H | H | H | 4-$CF_3$ | 134–136 |
| 8 | $C_2H_5$ | H | H | 3-Cl | 2-$CH_3$-4-$OCHF_2$ | 179–180 |
| 9 | $C_2H_5$ | H | H | 6-Cl | 2-$CH_3$-4-$OCHF_2$ | 189–190 |
| 10 | $C_2H_5$ | H | H | 3-$NO_2$ | 2-$CH_3$-5-Cl | 175–177 |
| 11 | $C_2H_5$ | H | H | 3-$NO_2$ | 2-$CH_3$-4-$OCHF_2$ | 207–208 |
| 12 | $C_2H_5$ | $C_2H_5$ | H | H | 4-$CF_3$ | 148–150 |
| 13 | $C_2H_5$ | $C_2H_5$ | H | 3-$NO_2$ | 2-$CH_3$-5-Cl | 175–177 |
| 14 | n-$C_3H_7$ | H | H | H | 4-$CF_3$ | 138–140 |
| 15 | n-$C_3H_7$ | H | H | 3-Cl | 2-$CH_3$-4-$OCHF_2$ | 171–173 |
| 16 | n-$C_3H_7$ | H | H | 6-Cl | 2-$CH_3$-4-$OCHF_2$ | 189–191 |
| 17 | n-$C_3H_7$ | H | H | 3-$NO_2$ | 2-$CH_3$-4-$OCHF_2$ | 184–186 |
| 18 | n-$C_3H_7$ | H | H | 3-$NO_2$ | 2-$CH_3$-5-Cl | 187–189 |
| 19 | n-$C_3H_7$ | H | H | 5-$CF_3$ | 2,6-$(C_2H_5)_2$ | 230–232 |
| 20 | i-$C_3H_7$ | H | H | H | H | 192–194 |
| 21 | i-$C_3H_7$ | H | H | H | 2-$NO_2$ | 198–200 |
| 22 | i-$C_3H_7$ | H | H | H | 4-$NO_2$ | 139–141 |
| 23 | i-$C_3H_7$ | H | H | H | 4-F | 199–201 |
| 24 | i-$C_3H_7$ | H | H | H | 2-$CH_3$ | 191–193 |
| 25 | i-$C_3H_7$ | H | H | H | 4-$CF_3$ | 198–200 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 26 | i-$C_3H_7$ | H | H | H | 3-$CF_3$ | 174–176 |
| 27 | i-$C_3H_7$ | H | H | H | 4-$CF_2CF_2CF_3$ | 237–238 |
| 28 | i-$C_3H_7$ | H | H | H | 4-$(CF_2)_3CF_3$ | 137–139 |
| 29 | i-$C_3H_7$ | H | H | H | 4-$OCF_3$ | 155–157 |
| 30 | i-$C_3H_7$ | H | H | H | 4-$OCF_2CHFOC_3F_7$-n | 220–222 |
| 31 | i-$C_3H_7$ | H | H | H | 3-$SCF_3$ | 176–178 |
| 32 | i-$C_3H_7$ | H | H | H | 4-$SCHF_2$ | 169–170 |
| 33 | i-$C_3H_7$ | H | H | H | 4-$SCH_2CF_3$ | 166–167 |
| 34 | i-$C_3H_7$ | H | H | H | 4-$SCF_2CHF_2$ | 169–170 |
| 35 | i-$C_3H_7$ | H | H | H | 4-$S(CF_2)_3CF_3$ | 159–161 |
| 36 | i-$C_3H_7$ | H | H | H | 4-$SCF(CF_3)_2$ | 145–147 |
| 37 | i-$C_3H_7$ | H | H | H | 4-$SCF_2CBrF_2$ | 158–160 |
| 38 | i-$C_3H_7$ | H | H | H | 4-$SOCF_2CBrF_2$ | 180–182 |
| 39 | i-$C_3H_7$ | H | H | H | 4-$SO(CF_2)_3CF_3$ | 192–193 |
| 40 | i-$C_3H_7$ | H | H | H | 4-$SO_2CH_2CF_3$ | 169–170 |
| 41 | i-$C_3H_7$ | H | H | H | 2,3-$Cl_2$ | 151–153 |
| 42 | i-$C_3H_7$ | H | H | H | 2,4-$Cl_2$ | 162–164 |
| 43 | i-$C_3H_7$ | H | H | H | 3,4-$F_2$ | 172–174 |
| 44 | i-$C_3H_7$ | H | H | H | 2,4-$(CH_3)_2$ | 162–163 |
| 45 | i-$C_3H_7$ | H | H | H | 2-Cl-4-$CF_3$ | 197–199 |
| 46 | i-$C_3H_7$ | H | H | H | 2-Cl-4-$CF(CF_3)_2$ | 201–202 |
| 47 | i-$C_3H_7$ | H | H | H | 2-Cl-4-$OCF_3$ | 151–153 |
| 48 | i-$C_3H_7$ | H | H | H | 2-Br-4-$OCF_3$ | 146–147 |
| 49 | i-$C_3H_7$ | H | H | H | 2-$CH_3$-3-Cl | 196–198 |
| 50 | i-$C_3H_7$ | H | H | H | 2-$CH_3$-4-Cl | 180–182 |
| 51 | i-$C_3H_7$ | H | H | H | 2-$CH_3$-5-Cl | 161–162 |
| 52 | i-$C_3H_7$ | H | H | H | 2-$CH_3$-4-Br | 159–261 |
| 53 | i-$C_3H_7$ | H | H | H | 2-$CH_3$-5-F | 168–170 |
| 54 | i-$C_3H_7$ | H | H | H | 2-$CH_3$-5-$C_4H_9$-t | 203–204 |
| 55 | i-$C_3H_7$ | H | H | H | 2-$CH_3$-4-$CF_2CF_3$ | 157–159 |
| 56 | i-$C_3H_7$ | H | H | H | 2-$CH_3$-4-$CF_2CF_2CF_3$ | 177–178 |
| 57 | i-$C_3H_7$ | H | H | H | 2-$CH_3$-4-$CF(CF_3)_2$ | 230–231 |
| 58 | i-$C_3H_7$ | H | H | H | 2-$CH_3$-4-$OCHF_2$ | 135–137 |
| 59 | i-$C_3H_7$ | H | H | H | 2-$CH_3$-4-$OCF_3$ | 172–173 |
| 60 | i-$C_3H_7$ | H | H | H | 2-$CH_3$-4-$OCF_2CHF_2$ | 145–146 |
| 61 | i-$C_3H_7$ | H | H | H | 2-$CH_3$-3-$OCF_2CHClF$ | 172–174 |
| 62 | i-$C_3H_7$ | H | H | H | 2-$CH_3$-4-$OCF_2CHClF$ | 142–144 |
| 63 | i-$C_3H_7$ | H | H | H | 2-$CH_3$-4-$CF_2CBrF_2$ | 164–166 |
| 64 | i-$C_3H_7$ | H | H | H | 2-$CH_3$-4-$CF_2CCl_2F$ | 172–173 |
| 65 | i-$C_3H_7$ | H | H | H | 2-$CH_3$-4-$OCF_2CHFCF_3$ | 151–152 |
| 66 | i-$C_3H_7$ | H | H | H | 2-$CH_3$-4-$OCF_2CBrFCF_3$ | 163–164 |
| 67 | i-$C_3H_7$ | H | H | H | 2-$CH_3$-4-$OCF_2CHFOCF_3$ | 146–148 |
| 68 | i-$C_3H_7$ | H | H | H | 2-$CH_3$-4-$SC_3H_7$-i | 178–180 |
| 69 | i-$C_3H_7$ | H | H | H | 2-$CH_3$-4-$OCH_2OCH_3$ | 165–166 |
| 70 | i-$C_3H_7$ | H | H | H | 2-$CH_3$-4-$OCH_2SCH_3$ | 160–162 |
| 71 | i-$C_3H_7$ | H | H | H | 2-$CH_3$-4-$COOCH_3$ | 163–165 |
| 72 | i-$C_3H_7$ | H | H | H | 2-$CH_3$-4-$OCH_2COOCH_3$ | 121–122 |
| 73 | i-$C_3H_7$ | H | H | H | 2-$CH_3$-4-($F_5$-PhO) | 185–187 |
| 74 | i-$C_3H_7$ | H | H | H | 2-$CH_3$-4-(3-$CF_3$-PhO) | 150–152 |
| 75 | i-$C_3H_7$ | H | H | H | 2-$CH_3$-4-(2-Cl-4-$CF_3$-PhO) | 183–185 |
| 76 | i-$C_3H_7$ | H | H | H | 2-$CH_3$-4-(4-Cl-Ph-$CH_2$O) | 188–189 |
| 77 | i-$C_3H_7$ | H | H | H | 2-$CH_3$-4-(4-Cl-PhS) | 181–182 |
| 78 | i-$C_3H_7$ | H | H | H | 2-$CH_3$-4-(5-$CF_3$-2-Pyi-O) | 165–167 |
| 79 | i-$C_3H_7$ | H | H | H | 2-$CH_3$-4-(3-Cl-5-$CF_3$-2-Pyi-O) | 184–185 |
| 80 | i-$C_3H_7$ | H | H | H | 4-(3-Cl-5-$CF_3$-2-Pyi-S) | 173–175 |
| 81 | i-$C_3H_7$ | H | H | H | 2-$CH_3$-4-P=O($OC_2H_5$)$_2$ | 134–136 |
| 82 | i-$C_3H_7$ | H | H | H | 2-$CH_3$-4-OP=S($OCH_3$)$_2$ | 132–134 |
| 83 | i-$C_3H_7$ | H | H | H | 2-$CF_3$-4-$OCHF_2$ | 147–149 |
| 84 | i-$C_3H_7$ | H | H | H | 3,5-$Cl_2$-4-$OCHF_2$ | 183–185 |
| 85 | i-$C_3H_7$ | H | H | H | 3-N=C($CF_3$)—NH-4 | 217–218 |
| 86 | i-$C_3H_7$ | H | H | H | 3-N=C($CF_3$)—N($CH_3$)-4 | 171–173 |
| 87 | i-$C_3H_7$ | H | H | 3-Cl | 4-$C_4H_9$-n | 169–171 |
| 88 | i-$C_3H_7$ | H | H | 3-Cl | 4-$C_4H_9$-t | 224–226 |
| 89 | i-$C_3H_7$ | H | H | 3-Cl | 4-$CF(CF_3)_2$ | 198–200 |
| 90 | i-$C_3H_7$ | H | H | 3-Cl | 4-$CF_2CF_2CF_3$ | 203–204 |
| 91 | i-$C_3H_7$ | H | H | 3-Cl | 4-$(CF_2)_3CF_3$ | 176–178 |
| 92 | i-$C_3H_7$ | H | H | 3-Cl | 4-$OCHF_2$ | 205–207 |
| 93 | i-$C_3H_7$ | H | H | 3-Cl | 4-$OCF_2CHFOC_3F_7$-n | 169–171 |
| 94 | i-$C_3H_7$ | H | H | 3-Cl | 4-$SCH_3$ | 231–232 |
| 95 | i-$C_3H_7$ | H | H | 6-Cl | 4-$SCH_3$ | 193–195 |
| 96 | i-$C_3H_7$ | H | H | 3-Cl | 4-$SOCH_3$ | 178–182 |
| 97 | i-$C_3H_7$ | H | H | 3-Cl | 4-$SO_2CH_3$ | 208–210 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 98 | i-$C_3H_7$ | H | H | 3-Cl | 4-$SCHF_2$ | 220–222 |
| 99 | i-$C_3H_7$ | H | H | 3-Cl | 3-$SCF_3$ | 189–191 |
| 100 | i-$C_3H_7$ | H | H | 3-Cl | 3-$SOCF_3$ | 183–187 |
| 101 | i-$C_3H_7$ | H | H | 3-Cl | 4-$SCH_2CF_3$ | 191–193 |
| 102 | i-$C_3H_7$ | H | H | 3-Cl | 4-$SCF_2CHF_2$ | 198–200 |
| 103 | i-$C_3H_7$ | H | H | 3-Cl | 4-$SCF_2CBrF_2$ | 201–203 |
| 104 | i-$C_3H_7$ | H | H | 3-Cl | 4-$SCF(CF_3)_2$ | 221–223 |
| 105 | i-$C_3H_7$ | H | H | 3-Cl | 4-$S(CF_2)_3CF_3$ | 199–200 |
| 106 | i-$C_3H_7$ | H | H | 3-Cl | 4-$SOCF(CF_3)_2$ | 204–206 |
| 107 | i-$C_3H_7$ | H | H | 3-Cl | 4-$SO_2CH_2CF_3$ | 202–204 |
| 108 | i-$C_3H_7$ | H | H | 3-Cl | 4-$SO_2CF_2CHF_2$ | 227–230 |
| 109 | i-$C_3H_7$ | H | H | 3-Cl | 4-$COCH_3$ | 217–219 |
| 110 | i-$C_3H_7$ | H | H | 3-Cl | 4-Ph | 215–217 |
| 111 | i-$C_3H_7$ | H | H | 3-Cl | 2,3-$Cl_2$ | 168–169 |
| 112 | i-$C_3H_7$ | H | H | 3-Cl | 2,4-$Cl_2$ | 190–192 |
| 113 | i-$C_3H_7$ | H | H | 3-Cl | 2,4-$F_2$ | 188–190 |
| 114 | i-$C_3H_7$ | H | H | 3-Cl | 2-Cl-4-F | 172–173 |
| 115 | i-$C_3H_7$ | H | H | 3-Cl | 2-F-4-Cl | 181–182 |
| 116 | i-$C_3H_7$ | H | H | 3-Cl | 2,3,4-$F_3$ | 174–176 |
| 117 | i-$C_3H_7$ | H | H | 3-Cl | 2,3-$(CH_3)_2$ | 187–189 |
| 118 | i-$C_3H_7$ | H | H | 3-Cl | 2-$CH_3$-3-Cl | 200–202 |
| 119 | i-$C_3H_7$ | H | H | 3-Cl | 2-$CH_3$-4-Cl | 213–215 |
| 120 | i-$C_3H_7$ | H | H | 3-Cl | 2-$CH_3$-5-Cl | 183–185 |
| 121 | i-$C_3H_7$ | H | H | 3-Cl | 2-$CH_3$-4-Br | 210–212 |
| 122 | i-$C_3H_7$ | H | H | 3-Cl | 2-$CH_3$-4-I | 206–208 |
| 123 | i-$C_3H_7$ | H | H | 3-Cl | 2-$CH_3$-4-$OCH_3$ | 191–192 |
| 124 | i-$C_3H_7$ | H | H | 3-Cl | 2,3-$(CH_3)_2$-4-$OCH_3$ | 208–210 |
| 125 | i-$C_3H_7$ | H | H | 3-Cl | 2-Cl-4-$CF_3$ | 156–157 |
| 126 | i-$C_3H_7$ | H | H | 3-Cl | 2-Cl-4-$CF(CF_3)_2$ | 204–206 |
| 127 | i-$C_3H_7$ | H | H | 3-Cl | 2-$CH_3$-4-$CF_3$ | 219–220 |
| 128 | i-$C_3H_7$ | H | H | 3-Cl | 2-$CH_3$-4-$CF_2CF_3$ | 199–200 |
| 129 | i-$C_3H_7$ | H | H | 3-Cl | 2-$CH_3$-4-$OCF_2CCl_3$ | 169–171 |
| 130 | i-$C_3H_7$ | H | H | 3-Cl | 2-$CH_3$-4-$CF_2CF_2CF_3$ | 214–215 |
| 131 | i-$C_3H_7$ | H | H | 3-Cl | 2-$CH_3$-4-$CF(CF_3)_2$ | 220–222 |
| 132 | i-$C_3H_7$ | H | H | 3-Cl | 2-$CH_3$-4-$(CF_2)_3CF_3$ | 188–189 |
| 133 | i-$C_3H_7$ | H | H | 3-Cl | 2-$CH_3$-4-$(CF_2)_5CF_3$ | 161–163 |
| 134 | i-$C_3H_7$ | H | H | 3-Cl | 3-Cl-4-$OCHF_2$ | 197–199 |
| 135 | i-$C_3H_7$ | H | H | 3-Cl | 2-Cl-4-$OCF_3$ | 158–159 |
| 136 | i-$C_3H_7$ | H | H | 3-Cl | 2-Br-4-$OCF_3$ | 169–170 |
| 137 | i-$C_3H_7$ | H | H | 3-Cl | 3-F-4-$OCHF_2$ | 211–212 |
| 138 | i-$C_3H_7$ | H | H | 3-Cl | 2-$CH_3$-4-$OCHF_2$ | 193–195 |
| 139 | i-$C_3H_7$ | H | H | 3-Cl | 2-$CH_3$-4-$OCF_3$ | 199–201 |
| 140 | i-$C_3H_7$ | H | H | 3-Cl | 2-$CH_3$-4-$OCBrF_2$ | 181–182 |
| 141 | i-$C_3H_7$ | H | H | 3-Cl | 2-$CH_3$-4-$OCF_2CHF_2$ | 202–204 |
| 142 | i-$C_3H_7$ | H | H | 3-Cl | 2-$CH_3$-3-$OCF_2CHClF$ | 169–171 |
| 143 | i-$C_3H_7$ | H | H | 3-Cl | 2-$CH_3$-4-$OCF_2CHClF$ | 194–196 |
| 144 | i-$C_3H_7$ | H | H | 3-Cl | 2-$CH_3$-4-$OCF_2CBrF_2$ | 193–194 |
| 145 | i-$C_3H_7$ | H | H | 3-Cl | 2-$CH_3$-4-$OCF_2CCl_2F$ | 202–203 |
| 146 | i-$C_3H_7$ | H | H | 3-Cl | 2-$CH_3$-4-$OCF_2CHFCF_3$ | 186–187 |
| 147 | i-$C_3H_7$ | H | H | 3-Cl | 2-$CH_3$-4-$OCH_2CF_2CHF_2$ | 207–208 |
| 148 | i-$C_3H_7$ | H | H | 3-Cl | 2-$CH_3$-4-$OCF_2CBrFCF_3$ | 205–206 |
| 149 | i-$C_3H_7$ | H | H | 3-Cl | 2-$CH_3$-4-$OCF_2CHFOCF_3$ | 179–181 |
| 150 | i-$C_3H_7$ | H | H | 3-Cl | 2-$CH_3$-4-$OCHF_2$-5-Cl | 191–192 |
| 151 | i-$C_3H_7$ | H | H | 3-Cl | 3,5-$Cl_2$-4-$OCHF_2$ | 205–207 |
| 152 | i-$C_3H_7$ | H | H | 3-Cl | 2-$CH_3$-4-$OCF_2CHF_2$-5-Cl | 211–212 |
| 153 | i-$C_3H_7$ | H | H | 3-Cl | 2-$CH_3$-4-$SC_3H_7$-i | 189–191 |
| 154 | i-$C_3H_7$ | H | H | 3-Cl | 2-$CH_3$-4-$SCHF_2$ | 189–191 |
| 155 | i-$C_3H_7$ | H | H | 3-Cl | 2-$CH_3$-4-$SOCHF_2$ | 173–176 |
| 156 | i-$C_3H_7$ | H | H | 3-Cl | 2-$CH_3$-4-$SO_2CHF_2$ | 168–170 |
| 157 | i-$C_3H_7$ | H | H | 3-Cl | 2-$CH_3$-4-($F_5$-PhO) | 224–226 |
| 158 | i-$C_3H_7$ | H | H | 3-Cl | 2-$CH_3$-4-(5-$CF_3$-2-Pyi-O) | 189–191 |
| 159 | i-$C_3H_7$ | H | H | 3-Cl | 2-$CH_3$-4-(3-Cl-5-$CF_3$-2-Pyi-O) | 204–205 |
| 160 | i-$C_3H_7$ | H | H | 3-Cl | 4-(3-Cl-5-$CF_3$-2-Pyi-S) | 213–215 |
| 161 | i-$C_3H_7$ | H | H | 3-Cl | 2-$CH_3$-4-$P=O(OC_2H_5)_2$ | 71–73 |
| 162 | i-$C_3H_7$ | H | H | 3-Cl | 2-$CH_3$-4-$OP=S(OCH_3)_2$ | 168–170 |
| 163 | i-$C_3H_7$ | H | H | 3-Cl | 2-$CF_3$-4-$OCHF_2$ | 194–196 |
| 164 | i-$C_3H_7$ | H | H | 3-Cl | 3-$CF_3$-4-$OCHF_2$ | 208–209 |
| 165 | i-$C_3H_7$ | H | H | 3-Cl | 3-N=C($CF_3$)—O-4 | 248–250 |
| 166 | i-$C_3H_7$ | H | H | 3-Cl | 3-N=C($CF_3$)—NH-4 | 194–196 |
| 167 | i-$C_3H_7$ | H | H | 3-Cl | 3-N=C($CF_3$)—N($CH_3$)-4 | 225–227 |
| 168 | i-$C_3H_7$ | H | H | 4-Cl | H | 190–192 |
| 169 | i-$C_3H_7$ | H | H | 4-Cl | 4-F | 213–215 |

TABLE 1-continued ($Z^1$, $Z^2$ = O)

| No | $R^1$ | $R^2$ | $R^3$ | Xn | Ym | Physical Properties (melting point: °C. |
|---|---|---|---|---|---|---|
| 170 | i-$C_3H_7$ | H | H | 4-Cl | 2-$CH_3$ | 208–210 |
| 171 | i-$C_3H_7$ | H | H | 4-Cl | 3-$CF_3$ | 196–198 |
| 172 | i-$C_3H_7$ | H | H | 4-Cl | 4-$OCF_3$ | 192–194 |
| 173 | i-$C_3H_7$ | H | H | 4-Cl | 2,4-$Cl_2$ | 174–176 |
| 174 | i-$C_3H_7$ | H | H | 4-Cl | 3,4-$F_2$ | 231–233 |
| 175 | i-$C_3H_7$ | H | H | 4-Cl | 2,3-$Cl_2$ | 186–188 |
| 176 | i-$C_3H_7$ | H | H | 4-Cl | 2-$CH_3$-3-Cl | 203–205 |
| 177 | i-$C_3H_7$ | H | H | 4-Cl | 2-$CH_3$-4-Cl | 206–208 |
| 178 | i-$C_3H_7$ | H | H | 4-Cl | 2-$CH_3$-5-Cl | 207–208 |
| 179 | i-$C_3H_7$ | H | H | 4-Cl | 2-$CH_3$-5-F | 229–231 |
| 180 | i-$C_3H_7$ | H | H | 4-Cl | 2-$CH_3$-4-$OCHF_2$ | 223–224 |
| 181 | i-$C_3H_7$ | H | H | 5-Cl | H | 186–188 |
| 182 | i-$C_3H_7$ | H | H | 5-Cl | 4-F | 209–211 |
| 183 | i-$C_3H_7$ | H | H | 5-Cl | 2-$CH_3$ | 187–189 |
| 184 | i-$C_3H_7$ | H | H | 5-Cl | 3-$CF_3$ | 198–200 |
| 185 | i-$C_3H_7$ | H | H | 5-Cl | 4-$OCF_3$ | 180–182 |
| 186 | i-$C_3H_7$ | H | H | 5-Cl | 2,3-$Cl_2$ | 167–169 |
| 187 | i-$C_3H_7$ | H | H | 5-Cl | 2,4-$Cl_2$ | 165–167 |
| 188 | i-$C_3H_7$ | H | H | 5-Cl | 3,4-$F_2$ | 207–209 |
| 189 | i-$C_3H_7$ | H | H | 5-Cl | 2-$CH_3$-3-Cl | 204–206 |
| 190 | i-$C_3H_7$ | H | H | 5-Cl | 2-$CH_3$-4-Cl | 202–204 |
| 191 | i-$C_3H_7$ | H | H | 5-Cl | 2-$CH_3$-5-Cl | 209–210 |
| 192 | i-$C_3H_7$ | H | H | 5-Cl | 2-$CH_3$-5-F | 192–194 |
| 193 | i-$C_3H_7$ | H | H | 5-Cl | 2-$CH_3$-4-$OCHF_2$ | 188–189 |
| 194 | i-$C_3H_7$ | H | H | 5-Cl | 2,3,4-$F_3$ | 224–226 |
| 195 | i-$C_3H_7$ | H | H | 6-Cl | 4-$C_4H_9$-n | 194–196 |
| 196 | i-$C_3H_7$ | H | H | 6-Cl | 4-$C_4H_9$-t | 235–237 |
| 197 | i-$C_3H_7$ | H | H | 6-Cl | 4-$CF_2CF_2CF_3$ | 216–217 |
| 198 | i-$C_3H_7$ | H | H | 6-Cl | 4-$CF(CF_3)_2$ | 209–211 |
| 199 | i-$C_3H_7$ | H | H | 6-Cl | 4-$(CF_2)_3CF_3$ | 196–198 |
| 200 | i-$C_3H_7$ | H | H | 6-Cl | 4-$OCHF_2$ | 223–225 |
| 201 | i-$C_3H_7$ | H | H | 6-Cl | 4-$OCF_2CHFOC_3F_7$-n | 205–207 |
| 202 | i-$C_3H_7$ | H | H | 6-Cl | 4-$SCH_2CF_3$ | 189–190 |
| 203 | i-$C_3H_7$ | H | H | 6-Cl | 4-$SCF_2CHF_2$ | 211–213 |
| 204 | i-$C_3H_7$ | H | H | 6-Cl | 4-$SCF(CF_3)_2$ | 250–252 |
| 205 | i-$C_3H_7$ | H | H | 6-Cl | 4-$S(CF_2)_3CF_3$ | 210–212 |
| 206 | i-$C_3H_7$ | H | H | 6-Cl | 3-$SOCF_3$ | 212–215 |
| 207 | i-$C_3H_7$ | H | H | 6-Cl | 4-$COCH_3$ | 230–232 |
| 208 | i-$C_3H_7$ | H | H | 6-Cl | 2,3-$Cl_2$ | 179–180 |
| 209 | i-$C_3H_7$ | H | H | 6-Cl | 2,4-$Cl_2$ | 199–200 |
| 210 | i-$C_3H_7$ | H | H | 6-Cl | 2,4-$F_2$ | 196–198 |
| 211 | i-$C_3H_7$ | H | H | 6-Cl | 2-Cl-4-F | 196–197 |
| 212 | i-$C_3H_7$ | H | H | 6-Cl | 2-F-4-Cl | 184–186 |
| 213 | i-$C_3H_7$ | H | H | 6-Cl | 2,3-$(CH_3)_2$ | 214–216 |
| 214 | i-$C_3H_7$ | H | H | 6-Cl | 2-$CH_3$-4-Cl | 233–235 |
| 215 | i-$C_3H_7$ | H | H | 6-Cl | 2-$CH_3$-5-Cl | 204–206 |
| 216 | i-$C_3H_7$ | H | H | 6-Cl | 2-$CH_3$-4-Br | 242–244 |
| 217 | i-$C_3H_7$ | H | H | 6-Cl | 2-$CH_3$-4-I | 236–238 |
| 218 | i-$C_3H_7$ | H | H | 6-Cl | 2-$CH_3$-4-$OCH_3$ | 195–197 |
| 219 | i-$C_3H_7$ | H | H | 6-Cl | 2,3-$(CH_3)_2$-4-$OCH_3$ | 242–244 |
| 220 | i-$C_3H_7$ | H | H | 6-Cl | 2-Cl-4-$CF_3$ | 171–172 |
| 221 | i-$C_3H_7$ | H | H | 6-Cl | 2-$CH_3$-4-$CF_3$ | 234–236 |
| 222 | i-$C_3H_7$ | H | H | 6-Cl | 2-$CH_3$-4-$OCF_2CCl_3$ | 169–171 |
| 223 | i-$C_3H_7$ | H | H | 6-Cl | 2-$CH_3$-4-$CF_2CF_3$ | 215–217 |
| 224 | i-$C_3H_7$ | H | H | 6-Cl | 2-$CH_3$-4-$CF(CF_3)_2$ | 238–240 |
| 225 | i-$C_3H_7$ | H | H | 6-Cl | 2-$CH_3$-4-$(CF_2)_3CF_3$ | 177–178 |
| 226 | i-$C_3H_7$ | H | H | 6-Cl | 2-$CH_3$-4-$(CF_2)_5CF_3$ | 167–169 |
| 227 | i-$C_3H_7$ | H | H | 6-Cl | 3,5-$Cl_2$-4-$OCHF_2$ | 196–198 |
| 228 | i-$C_3H_7$ | H | H | 6-Cl | 2-$CH_3$-4-$OCF_2CCl_2F$ | 218–220 |
| 229 | i-$C_3H_7$ | H | H | 6-Cl | 2-$CH_3$-4-$OCF_2CBrF_2$ | 214–215 |
| 230 | i-$C_3H_7$ | H | H | 6-Cl | 2-$CH_3$-4-$OCH_2CF_2CHF_2$ | 212–213 |
| 231 | i-$C_3H_7$ | H | H | 6-Cl | 2-Cl-4-$CF(CF_2)_2$ | 212–214 |
| 232 | i-$C_3H_7$ | H | W | 6-Cl | 3-Cl-4-$OCHF_2$ | 204–206 |
| 233 | i-$C_3H_7$ | H | H | 6-Cl | 3-F-4-$OCHF_2$ | 225–227 |
| 234 | i-$C_3H_7$ | H | H | 6-Cl | 2-Cl-4-$OCF_3$ | 161–162 |
| 235 | i-$C_3H_7$ | H | H | 6-Cl | 2-Br-4-$OCF_3$ | 188–189 |
| 236 | i-$C_3H_7$ | H | H | 6-Cl | 2-$CH_3$-4-$OCHF_2$ | 213–215 |
| 237 | i-$C_3H_7$ | H | H | 6-Cl | 2-$CH_3$-4-$OCF_3$ | 212–214 |
| 238 | i-$C_3H_7$ | H | H | 6-Cl | 2-$CH_3$-4-$OCBrF_2$ | 195–196 |
| 239 | i-$C_3H_7$ | H | H | 6-Cl | 2-$CH_3$-4-$OCF_2CHF_2$ | 199–201 |
| 240 | i-$C_3H_7$ | H | H | 6-Cl | 2-$CH_3$-3-$OCF_2CHClF$ | 195–197 |
| 241 | i-$C_3H_7$ | H | H | 6-Cl | 2-$CH_3$-4-$OCF_2CHClF$ | 204–213 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 242 | i-$C_3H_7$ | H | H | 6-Cl | 2-$CH_3$-4-$OCF_2CHFCF_3$ | 199–200 |
| 243 | i-$C_3H_7$ | H | H | 6-Cl | 2-$CH_3$-4-$OCF_2CBrFCF_3$ | 226–227 |
| 244 | i-$C_3H_7$ | H | H | 6-Cl | 2-$CH_3$-4-$OCF_2CHFOCF_3$ | 210–212 |
| 245 | i-$C_3H_7$ | H | H | 6-Cl | 2-$CH_3$-4-$OCHF_2$-5-Cl | 234–235 |
| 246 | i-$C_3H_7$ | H | H | 6-Cl | 2-$CH_3$-4-$OCF_2CHF_2$-5-Cl | 230–232 |
| 247 | i-$C_3H_7$ | H | H | 6-Cl | 2-$CH_3$-4-$SCHF_2$ | 199–201 |
| 248 | i-$C_3H_7$ | H | H | 6-Cl | 2-$CH_3$-4-($F_5$-PhO) | 243–245 |
| 249 | i-$C_3H_7$ | H | H | 6-Cl | 2-$CH_3$-4-(5-$CF_3$-2-Pyi-O) | 116–120 |
| 250 | i-$C_3H_7$ | H | H | 6-Cl | 2-$CH_3$-4-(3-Cl-5-$CF_3$-2-Pyi-O) | 219–221 |
| 251 | i-$C_3H_7$ | H | H | 6-Cl | 2-$CH_3$-4-P=O($OC_2H_5$)$_2$ | 146–147 |
| 252 | i-$C_3H_7$ | H | H | 6-Cl | 2-$CH_3$-4-OP=S($OCH_3$)$_2$ | 183–185 |
| 253 | i-$C_3H_7$ | H | H | 6-Cl | 2-$CF_3$-4-$OCHF_2$ | 234–236 |
| 254 | i-$C_3H_7$ | H | H | 6-Cl | 3-$CF_3$-4-$OCHF_2$ | 204–205 |
| 255 | i-$C_3H_7$ | H | H | 6-Cl | 3-N=C($CF_3$)—O-4 | 270–272 |
| 256 | i-$C_3H_7$ | H | H | 6-Cl | 3-N=C($CF_3$)—NH-4 | 213–215 |
| 257 | i-$C_3H_7$ | H | H | 6-Cl | 3-N=C($CF_3$)—N($CH_3$)-4 | 239–241 |
| 258 | i-$C_3H_7$ | H | H | 3,6-$Cl_2$ | 2-$CH_3$-4-$OCHF_2$ | 221–222 |
| 259 | i-$C_3H_7$ | H | H | 3,6-$Cl_2$ | 2-$CH_3$-4-Cl | 234–235 |
| 260 | i-$C_3H_7$ | H | H | 3,4,5,6-$Cl_4$ | 2-$CH_3$-4-Cl | 265–266 |
| 261 | i-$C_3H_7$ | H | H | 3-Br | 4-$CF_3$ | 221–223 |
| 262 | i-$C_3H_7$ | H | H | 3-Br | 4-$OCF_3$ | 208–210 |
| 263 | i-$C_3H_7$ | H | H | 3-Br | 2,3-($CH_3$)$_2$ | 248–250 |
| 264 | i-$C_3H_7$ | H | H | 3-Br | 2,4-($CH_3$)$_2$ | 223–224 |
| 265 | i-$C_3H_7$ | H | H | 3-Br | 2,4,6-($CH_3$)$_3$ | 254–255 |
| 266 | i-$C_3H_7$ | H | H | 3-Br | 2-$CH_3$-3-Cl | 215–217 |
| 267 | i-$C_3H_7$ | H | H | 3-Br | 2-$CH_3$-4-Cl | 176–178 |
| 268 | i-$C_3H_7$ | H | H | 3-Br | 2-$CH_3$-5-Cl | 196–198 |
| 269 | i-$C_3H_7$ | H | H | 3-Br | 2,3-($CH_3$)$_2$-4-Cl | 222–224 |
| 270 | i-$C_3H_7$ | H | H | 3-Br | 2,4-($CH_3$)$_2$-3-Cl | 236–238 |
| 271 | i-$C_3H_7$ | H | H | 3-Br | 2-$C_2H_5$-4-Cl | 205–207 |
| 272 | i-$C_3H_7$ | H | H | 3-Br | 2-$CH_3$-4-Br | 220–222 |
| 273 | i-$C_3H_7$ | H | H | 3-Br | 2,3-($CH_3$)$_2$-4-Br | 200–202 |
| 274 | i-$C_3H_7$ | H | H | 3-Br | 2-$CH_3$-4-I | 203–205 |
| 275 | i-$C_3H_7$ | H | H | 3-Br | 2-$CH_3$-4-F | 223–224 |
| 276 | i-$C_3H_7$ | H | H | 3-Br | 2-Cl-4-$CF_3$ | 156–157 |
| 277 | i-$C_3H_7$ | H | H | 3-Br | 2-$CH_3$-4-$CF_3$ | 227–228 |
| 278 | i-$C_3H_7$ | H | H | 3-Br | 2-$CH_3$-4-$CF_2CF_3$ | 201–202 |
| 279 | i-$C_3H_7$ | H | H | 3-Br | 2-$CH_3$-4-$CF_2CF_2CF_3$ | 199–200 |
| 280 | i-$C_3H_7$ | H | H | 3-Br | 2-$CH_3$-4-CF($CF_3$)$_2$ | 222–224 |
| 281 | i-$C_3H_7$ | H | H | 3-Br | 2-$CH_3$-4-($CF_2$)$_3CF_3$ | 190–191 |
| 282 | i-$C_3H_7$ | H | H | 3-Br | 2-$CH_3$-4-$OCH_3$ | 199–200 |
| 283 | i-$C_3H_7$ | H | H | 3-Br | 2-$CH_3$-4-$OCH_2CF_2CHF_2$ | 206–207 |
| 284 | i-$C_3H_7$ | H | H | 3-Br | 2,4-($CH_3$)$_2$-3-$OCHF_2$ | 187–189 |
| 285 | i-$C_3H_7$ | H | H | 3-Br | 2,3-($CH_3$)$_2$-4-$OCH_3$ | 206–208 |
| 286 | i-$C_3H_7$ | H | H | 3-Br | 2-Cl-4-$OCF_3$ | 165–167 |
| 287 | i-$C_3H_7$ | H | H | 3-Br | 2-Br-4-$OCF_3$ | 179–180 |
| 288 | i-$C_3H_7$ | H | H | 3-Br | 2-$CH_3$-4-$OCHF_2$ | 205–207 |
| 289 | i-$C_3H_7$ | H | H | 3-Br | 2-$CH_3$-4-$OCF_3$ | 211–213 |
| 290 | i-$C_3H_7$ | H | H | 3-Br | 2-$CH_3$-4-$OCBrF_2$ | 178–180 |
| 291 | i-$C_3H_7$ | H | H | 3-Br | 2-$CH_3$-4-$OCF_2CHFCF_3$ | 196–197 |
| 292 | i-$C_3H_7$ | H | H | 3-Br | 2-$CH_3$-4-$OCF_2CHClF$ | 194–195 |
| 293 | i-$C_3H_7$ | H | H | 3-Br | 2-$CH_3$-4-$OCF_2CHF_2$ | 205–207 |
| 294 | i-$C_3H_7$ | H | H | 3-Br | 2-$CH_3$-3-Cl-4-$OCHF_2$ | 229–230 |
| 295 | i-$C_3H_7$ | H | H | 3-Br | 2,3-($CH_3$)$_2$-4-$OCHF_2$ | 219–220 |
| 296 | i-$C_3H_7$ | H | H | 3-Br | 2-$CH_3$-4-$SCH_3$ | 215–217 |
| 297 | i-$C_3H_7$ | H | H | 3-Br | 2-$CH_3$-4-(3-$CF_3$-PhO) | 156–158 |
| 298 | i-$C_3H_7$ | H | H | 3-Br | 2-$CH_3$-4-(3-Cl-5-$CF_3$-2-Pyi-O) | 206–208 |
| 299 | i-$C_3H_7$ | H | H | 3-Br | 2-$CH_3$-4-(5-$CF_3$-2-Pyi-O) | 182–184 |
| 300 | i-$C_3H_7$ | H | H | 3-Br | -3-$OCH_2$O-4- | 195–198 |
| 301 | i-$C_3H_7$ | H | H | 6-Br | 4-$CF_3$ | 190–192 |
| 302 | i-$C_3H_7$ | H | H | 6-Br | 4-$OCF_3$ | 210–212 |
| 303 | i-$C_3H_7$ | H | H | 6-Br | 2,3-($CH_3$)$_2$ | 250–252 |
| 304 | i-$C_3H_7$ | H | H | 6-Br | 2,4,6-($CH_3$)$_3$ | 272–274 |
| 305 | i-$C_3H_7$ | H | H | 6-Br | 2-$CH_3$-3-Cl | 214–216 |
| 306 | i-$C_3H_7$ | H | H | 6-Br | 2-$CH_3$-4-Cl | 198–200 |
| 307 | i-$C_3H_7$ | H | H | 6-Br | 2-$CH_3$-5-Cl | 194–196 |
| 308 | i-$C_3H_7$ | H | H | 6-Br | 2,3-($CH_3$)$_2$-4-Cl | 227–229 |
| 309 | i-$C_3H_7$ | H | H | 6-Br | 2,4-($CH_3$)$_2$-3-Cl | 249–251 |
| 310 | i-$C_3H_7$ | H | H | 6-Br | 2-$C_2H_5$-4-Cl | 243–245 |
| 311 | i-$C_3H_7$ | H | H | 6-Br | 2-$CH_3$-4-Br | 227–228 |
| 312 | i-$C_3H_7$ | H | H | 6-Br | 2,3-($CH_3$)$_2$-4-Br | 209–211 |
| 313 | i-$C_3H_7$ | H | H | 6-Br | 2-$CH_3$-4-I | 227–229 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 314 | i-$C_3H_7$ | H | H | 6-Br | 2-$CH_3$-4-F | 231–232 |
| 315 | i-$C_3H_7$ | H | H | 6-Br | 2-Cl-4-$CF_3$ | 169–170 |
| 316 | i-$C_3H_7$ | H | H | 6-Br | 2-$CH_3$-4-$CF_3$ | 232–234 |
| 317 | i-$C_3H_7$ | H | H | 6-Br | 2-$CH_3$-4-$CF(CF_3)_2$ | 236–238 |
| 318 | i-$C_3H_7$ | H | H | 6-Br | 2-$CH_3$-4-$(CF_2)_3CF_3$ | 208–210 |
| 319 | i-$C_3H_7$ | H | H | 6-Br | 2-$CH_3$-4-$OCH_2CF_2CHF_2$ | 209–211 |
| 320 | i-$C_3H_7$ | H | H | 6-Br | 2,4-$(CH_3)_2$-3-$OCHF_2$ | 247–249 |
| 321 | i-$C_3H_7$ | H | H | 6-Br | 2,3-$(CH_3)_2$-4-$OCH_3$ | 250–252 |
| 322 | i-$C_3H_7$ | H | H | 6-Br | 2-$CH_3$-4-$OCH_3$ | 220–222 |
| 323 | i-$C_3H_7$ | H | H | 6-Br | 2-Cl-4-$OCF_3$ | 182–183 |
| 324 | i-$C_3H_7$ | H | H | 6-Br | 2-Br-4-$OCF_3$ | 195–196 |
| 325 | i-$C_3H_7$ | H | H | 6-Br | 2-$CH_3$-4-$OCHF_2$ | 225–226 |
| 326 | i-$C_3H_7$ | H | H | 6-Br | 2-$CH_3$-4-$OCF_3$ | 223–225 |
| 327 | i-$C_3H_7$ | H | H | 6-Br | 2-$CH_3$-4-$OCBrF_2$ | 194–196 |
| 328 | i-$C_3H_7$ | H | H | 6-Br | 2-$CH_3$-4-$OCF_2CHFCF_3$ | 212–213 |
| 329 | i-$C_3H_7$ | H | H | 6-Br | 2-$CH_3$-4-$OCF_2CHClF$ | 211–213 |
| 330 | i-$C_3H_7$ | H | H | 6-Br | 2-$CH_3$-4-$OCF_2CHF_2$ | 214–215 |
| 331 | i-$C_3H_7$ | H | H | 6-Br | 2,3-$(CH_3)_2$-4-$OCHF_2$ | 228–229 |
| 332 | i-$C_3H_7$ | H | H | 6-Br | 2-$CH_3$-3-Cl-4-$OCHF_2$ | 224–225 |
| 333 | i-$C_3H_7$ | H | H | 6-Br | 2-$CH_3$-4-$SCH_3$ | 215–217 |
| 334 | i-$C_3H_7$ | H | H | 6-Br | 2-$CH_3$-4-(3-$CF_3$-PhO) | 194–195 |
| 335 | i-$C_3H_7$ | H | H | 6-Br | 2-$CH_3$-4-(5-$CF_3$-2-Pyi-O) | 201–203 |
| 336 | i-$C_3H_7$ | H | H | 6-Br | 2-$CH_3$-4-(3-Cl-5-$CF_3$-2-Pyi-O) | 234–236 |
| 337 | i-$C_3H_7$ | H | H | 6-Br | -3-$OCH_2O$-4- | 205–207 |
| 338 | i-$C_3H_7$ | H | H | 3,4-$Br_2$ | 2-$CH_3$-4-$OCHF_2$ | 196–197 |
| 339 | i-$C_3H_7$ | H | H | 3,4-$Br_2$ | 2-$CH_3$-4-Cl | 199–201 |
| 340 | i-$C_3H_7$ | H | H | 3,6-Br | 2-$CH_3$-4-$OCHF_2$ | 233–234 |
| 341 | i-$C_3H_7$ | H | H | 3,6-$Br_2$ | 2-$CH_3$-4-Cl | 245–247 |
| 342 | i-$C_3H_7$ | H | H | 5,6-$Br_2$ | 2-$CH_3$-4-$OCHF_2$ | 208–210 |
| 343 | i-$C_3H_7$ | H | H | 5,6-$Br_2$ | 2-$CH_3$-4-Cl | 259–261 |
| 344 | i-$C_3H_7$ | H | H | 3,4,5,6-$Br_4$ | 2-$CH_3$-4-Cl | 270–272 |
| 345 | i-$C_3H_7$ | H | H | 3-I | 4-Cl | 230–232 |
| 346 | i-$C_3H_7$ | H | H | 3-I | 4-Br | 251–253 |
| 347 | i-$C_3H_7$ | H | H | 3-I | 4-I | 231–233 |
| 348 | i-$C_3H_7$ | H | H | 3-I | 3-$CF_3$ | 194–197 |
| 349 | i-$C_3H_7$ | H | H | 3-I | 4-$CF_3$ | 223–224 |
| 350 | i-$C_3H_7$ | H | H | 3-I | 4-$CF_2CF_2CF_3$ | 217–219 |
| 351 | i-$C_3H_7$ | H | H | 3-I | 4-$CF(CF_3)_2$ | 209–211 |
| 352 | i-$C_3H_7$ | H | H | 3-I | 4-$OCF_3$ | 222–223 |
| 353 | i-$C_3H_7$ | H | H | 3-I | 4-$OCF_2CHFOCF_3$ | 192–194 |
| 354 | i-$C_3H_7$ | H | H | 3-I | 4-$SCHF_2$ | 204–206 |
| 355 | i-$C_3H_7$ | H | H | 3-I | 4-$SCH_2CF_3$ | 195–197 |
| 356 | i-$C_3H_7$ | H | H | 3-I | 4-$SCF_2CHF_2$ | 196–198 |
| 357 | i-$C_3H_7$ | H | H | 3-I | 4-$SCF_2CBrF_2$ | 203–205 |
| 358 | i-$C_3H_7$ | H | H | 3-I | 4-$SCF(CF_3)_2$ | 170–172 |
| 359 | i-$C_3H_7$ | H | H | 3-I | 4-$S(CF_2)_3CF_3$ | 185–187 |
| 360 | i-$C_3H_7$ | H | H | 3-I | 3,4-$F_2$ | 227–229 |
| 361 | i-$C_3H_7$ | H | H | 3-I | 2-$CH_3$-3-Cl | 222–224 |
| 362 | i-$C_3H_7$ | H | H | 3-I | 2-$CH_3$-4-Cl | 215–217 |
| 363 | i-$C_3H_7$ | H | H | 3-I | 2-$CH_3$-5-Cl | 210–212 |
| 364 | i-$C_3H_7$ | H | H | 3-I | 2,4-$(CH_3)_2$-3-Cl | 226–228 |
| 365 | i-$C_3H_7$ | H | H | 3-I | 2,3-$(CH_3)_2$-4-Cl | 235–237 |
| 366 | i-$C_3H_7$ | H | H | 3-I | 2-$CH_3$-4-Br | 227–229 |
| 367 | i-$C_3H_7$ | H | H | 3-I | 2-$CH_3$-4-I | 201–203 |
| 368 | i-$C_3H_7$ | H | H | 3-I | 2-$CH_3$-4-F | 227–228 |
| 369 | i-$C_3H_7$ | H | H | 3-I | 2-Cl-4-$CF_3$ | 170–171 |
| 370 | i-$C_3H_7$ | H | H | 3-I | 2-$CH_3$-3-$CF_3$ | 179–181 |
| 371 | i-$C_3H_7$ | H | H | 3-I | 2-$CH_3$-4-$CF_3$ | 202–203 |
| 372 | i-$C_3H_7$ | H | H | 3-I | 2-$CH_3$-4-$CF_2CF_3$ | 195–196 |
| 373 | i-$C_3H_7$ | H | H | 3-I | 2-$CH_3$-4-$CF_2CF_2CF_3$ | 193–195 |
| 374 | i-$C_3H_7$ | H | H | 3-I | 2-$CH_3$-4-$CF(CF_3)_2$ | 211–213 |
| 375 | i-$C_3H_7$ | H | H | 3-I | 2-$CH_3$-4-$(CF_2)_3CF_3$ | 203–204 |
| 376 | i-$C_3H_7$ | H | H | 3-I | 2-$CH_3$-4-$OCH_3$ | 204–206 |
| 377 | i-$C_3H_7$ | H | H | 3-I | 2-$CH_3$-4-O-$C_3H_7$-i | 209–211 |
| 378 | i-$C_3H_7$ | H | H | 3-I | 2,3-$(CH_3)_2$-4-$OCH_3$ | 220–222 |
| 379 | i-$C_3H_7$ | H | H | 3-I | 2-$CH_3$-4-$OCH_2CF_3$ | 223–224 |
| 380 | i-$C_3H_7$ | H | H | 3-I | 2-$CH_3$-4-$OCF_2CBrF_2$ | 228–230 |
| 381 | i-$C_3H_7$ | H | H | 3-I | 2-$CH_3$-4-$OCF_2CCl_2F$ | 230–231 |
| 382 | i-$C_3H_7$ | H | H | 3-I | 3-F-4-$OCHF_2$ | 208–210 |
| 383 | i-$C_3H_7$ | H | H | 3-I | 3,5-$Cl_2$-4-$OCHF_2$ | 234–236 |
| 384 | i-$C_3H_7$ | H | H | 3-I | 3-$OCH_3$-4-$OCHF_2$ | 196–198 |
| 385 | i-$C_3H_7$ | H | H | 3-I | 3,4-$(OCHF_2)_2$ | 171–172 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 386 | i-$C_3H_7$ | H | H | 3-I | 2-$CH_3$-4-$OCF_3$ | 214–216 |
| 387 | i-$C_3H_7$ | H | H | 3-I | 2-$CH_3$-4-$OCHF_2$ | 207–209 |
| 388 | i-$C_3H_7$ | H | H | 3-I | 2-$CH_3$-4-$OCH_2CF_2CHF_2$ | 229–231 |
| 389 | i-$C_3H_7$ | H | H | 3-I | 2-$CH_3$-4-$OCBrF_2$ | 181–182 |
| 390 | i-$C_3H_7$ | H | H | 3-I | 2-$CH_3$-4-$OCF_2CHF_2$ | 197–199 |
| 391 | i-$C_3H_7$ | H | H | 3-I | 2-$CH_3$-4-$OCF_2CHF_2$-5-Cl | 198–200 |
| 392 | i-$C_3H_7$ | H | H | 3-I | 2-$CH_3$-4-$OCF_2CHClF$ | 200–201 |
| 393 | i-$C_3H_7$ | H | H | 3-I | 2-$CH_3$-4-$OCF_2CHFCF_3$ | 213–214 |
| 394 | i-$C_3H_7$ | H | H | 3-I | 2-$CH_3$-4-$OCF_2CBrFCF_3$ | 233–234 |
| 395 | i-$C_3H_7$ | H | H | 3-I | 2-$CH_3$-4-$OCF_2CHFOCF_3$ | 213–215 |
| 396 | i-$C_3H_7$ | H | H | 3-I | 2-$CH_3$-4-$OCHF_2$-5-Cl | 230–232 |
| 397 | i-$C_3H_7$ | H | H | 3-I | 2-$CH_3$-4-($F_5$-PhO) | 245–247 |
| 398 | i-$C_3H_7$ | H | H | 3-I | 2-$CH_3$-4-(3-$CF_3$-PhO) | 168–170 |
| 399 | i-$C_3H_7$ | H | H | 3-I | 2-$CH_3$-4-(5-$CF_3$-2-Pyi-O) | 186–188 |
| 400 | i-$C_3H_7$ | H | H | 3-I | 2-$CH_3$-4-(3-Cl-5-$CF_3$-2-Pyi-O) | 212–214 |
| 401 | i-$C_3H_7$ | H | H | 3-I | 2-$CH_3$-4-$SO_2CH_3$ | 172–175 |
| 402 | i-$C_3H_7$ | H | H | 3-I | 2-$CH_3$-4-$SC_3H_7$-i | 190–192 |
| 403 | i-$C_3H_7$ | H | H | 3-I | 2-$CH_3$-4-$SCF_2CF_2CF_3$ | 227–228 |
| 404 | i-$C_3H_7$ | H | H | 3-I | 2-$CH_3$-4-(4-Cl-PhS) | 191–192 |
| 405 | i-$C_3H_7$ | H | H | 3-I | 4-(3-Cl-5-$CF_3$-2-Pyi-S) | 198–200 |
| 406 | i-$C_3H_7$ | H | H | 3-I | 2-Br-4-$OCF_3$ | 196–198 |
| 407 | i-$C_3H_7$ | H | H | 3-I | 2-Cl-4-$CF_2CF_2CF_3$ | 162–164 |
| 408 | i-$C_3H_7$ | H | H | 3-I | 2-Cl-4-$OCF_3$ | 173–175 |
| 409 | i-$C_3H_7$ | H | H | 3-I | 2-$CF_3$-4-$OCHF_2$ | 219–220 |
| 410 | i-$C_3H_7$ | H | H | 3-I | 3-$CF_3$-4-$OCHF_2$ | 128–130 |
| 411 | i-$C_3H_7$ | H | H | 6-I | 4-Cl | 251–253 |
| 412 | i-$C_3H_7$ | H | H | 6-I | 4-Br | 270–272 |
| 413 | i-$C_3H_7$ | H | H | 6-I | 4-I | 242–244 |
| 414 | i-$C_3H_7$ | H | H | 6-I | 3-$CF_3$ | 210–212 |
| 415 | i-$C_3H_7$ | H | H | 6-I | 4-$CF_3$ | 201–202 |
| 416 | i-$C_3H_7$ | H | H | 6-I | 4-$CF(CF_3)_2$ | 238–240 |
| 417 | i-$C_3H_7$ | H | H | 6-I | 4-$CF_2CF_2CF_3$ | 238–240 |
| 418 | i-$C_3H_7$ | H | H | 6-I | 4-$OCF_3$ | 193–194 |
| 419 | i-$C_3H_7$ | H | H | 6-I | 4-$OCF_2CHFOC_3F_7$-n | 213–214 |
| 420 | i-$C_3H_7$ | H | H | 6-I | 4-$SCH_2CF_3$ | 217–219 |
| 421 | i-$C_3H_7$ | H | H | 6-I | 4-$SCHF_2$ | 224–226 |
| 422 | i-$C_3H_7$ | H | H | 6-I | 4-$SCF_2CHF_2$ | 213–215 |
| 423 | i-$C_3H_7$ | H | H | 6-I | 4-$SCF_2CBrF_2$ | 220–222 |
| 424 | i-$C_3H_7$ | H | H | 6-I | 4-$SCF_2CF_2CF_3$ | 196–197 |
| 425 | i-$C_3H_7$ | H | H | 6-I | 4-$SCF(CF_3)_2$ | 216–218 |
| 426 | i-$C_3H_7$ | H | H | 6-I | 4-$S(CF_2)_3CF_3$ | 201–203 |
| 427 | i-$C_3H_7$ | H | H | 6-I | 2-$CH_3$-3-Cl | 252–254 |
| 428 | i-$C_3H_7$ | H | H | 6-I | 2-$CH_3$-4-Cl | 244–246 |
| 429 | i-$C_3H_7$ | H | H | 6-I | 2,4-$(CH_3)_2$-3-Cl | 260–262 |
| 430 | i-$C_3H_7$ | H | H | 6-I | 2-$CH_3$-4-Br | 241–243 |
| 431 | i-$C_3H_7$ | H | H | 6-I | 2-$CH_3$-4-I | 213–215 |
| 432 | i-$C_3H_7$ | H | H | 6-I | 2-$CH_3$-4-F | 251–252 |
| 433 | i-$C_3H_7$ | H | H | 6-I | 2-Cl-4-$CF_3$ | 195–196 |
| 434 | i-$C_3H_7$ | H | H | 6-I | 2,3-$(CH_3)_2$-4-Cl | 253–255 |
| 435 | i-$C_3H_7$ | H | H | 6-I | 2-$CH_3$-3-$CF_3$ | 245–251 |
| 436 | i-$C_3H_7$ | H | H | 6-I | 2-$CH_3$-4-$CF_3$ | 220–221 |
| 437 | i-$C_3H_7$ | H | H | 6-I | 2-$CH_3$-4-$CF_2CF_3$ | 203–205 |
| 438 | i-$C_3H_7$ | H | H | 6-I | 2-$CH_3$-4-$CF_2CF_2CF_3$ | 154–156 |
| 439 | i-$C_3H_7$ | H | H | 6-I | 2-$CH_3$-4-$CF(CF_3)_2$ | 237–239 |
| 440 | i-$C_3H_7$ | H | H | 6-I | 2-$CH_3$-4-$(CF_2)_3CF_3$ | 168–170 |
| 441 | i-$C_3H_7$ | H | H | 6-I | 2-$CH_3$-4-$OCH_3$ | 215–217 |
| 442 | i-$C_3H_7$ | H | H | 6-I | 2-$CH_3$-4-O-$C_3H_7$-i | 212–214 |
| 443 | i-$C_3H_7$ | H | H | 6-I | 2-$CH_3$-4-$OCH_2CF_3$ | 233–234 |
| 444 | i-$C_3H_7$ | H | H | 6-I | 2-$CH_3$-4-$OCF_2CBrF_2$ | 242–244 |
| 445 | i-$C_3H_7$ | H | H | 6-I | 2-$CH_3$-4-$OCF_2CCl_2F$ | 251–253 |
| 446 | i-$C_3H_7$ | H | H | 6-I | 2-$CH_3$-4-$OCF_2CBrFCF_3$ | 251–253 |
| 447 | i-$C_3H_7$ | H | H | 6-I | 2-$CH_3$-4-$OCH_2CF_2CHF_2$ | 235–237 |
| 448 | i-$C_3H_7$ | H | H | 6-I | 3-F-4-$OCHF_2$ | 214–216 |
| 449 | i-$C_3H_7$ | H | H | 6-I | 3,5-$Cl_2$-4-$OCHF_2$ | 211–213 |
| 450 | i-$C_3H_7$ | H | H | 6-I | 3-$OCH_3$-4-$OCHF_2$ | 215–217 |
| 451 | i-$C_3H_7$ | H | H | 6-I | 2,3-$(CH_3)_2$-4-$OCH_3$ | 253–254 |
| 452 | i-$C_3H_7$ | H | H | 6-I | 2-$CH_3$-4-$OCBrF_2$ | 192–194 |
| 453 | i-$C_3H_7$ | H | H | 6-I | 2-$CH_3$-4-$OCF_2CHF_2$ | 216–218 |
| 454 | i-$C_3H_7$ | H | H | 6-I | 2-$CH_3$-4-$OCF_2CHF_2$-5-Cl | 230–232 |
| 455 | i-$C_3H_7$ | H | H | 6-I | 2-$CH_3$-4-$OCF_2CHClF$ | 205–207 |
| 456 | i-$C_3H_7$ | H | H | 6-I | 2-$CH_3$-4-$OCF_2CHFCF_3$ | 222–223 |
| 457 | i-$C_3H_7$ | H | H | 6-I | 2-$CH_3$-4-$OCF_2CHFOCF_3$ | 258–260 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 458 | i-$C_3H_7$ | H | H | 6-I | 2-$CH_3$-4-(3-$CF_3$-PhO) | 198–199 |
| 459 | i-$C_3H_7$ | H | H | 6-I | 2-$CH_3$-4-($F_5$-PhO) | 262–264 |
| 460 | i-$C_3H_7$ | H | H | 6-I | 2-$CH_3$-4-(5-$CF_3$-2-Pyi-O) | 245–246 |
| 461 | i-$C_3H_7$ | H | H | 6-I | 2-$CH_3$-4-(3-Cl-5-$CF_3$-2-Pyi-O) | 231–232 |
| 462 | i-$C_3H_7$ | H | H | 6-I | 2-$CH_3$-4-$SC_3H_7$-i | 197–199 |
| 463 | i-$C_3H_7$ | H | H | 6-I | 2-$CH_3$-4-(4-Cl-PhS) | 211–213 |
| 464 | i-$C_3H_7$ | H | H | 6-I | 2-$CH_3$-4-$OCF_3$ | 230–232 |
| 465 | i-$C_3H_7$ | H | H | 6-I | 2-$CF_3$-4-$OCHF_2$ | 238–239 |
| 466 | i-$C_3H_7$ | H | H | 6-I | 2-Br-4-$OCF_3$ | 215–217 |
| 467 | i-$C_3H_7$ | H | H | 6-I | 2-Cl-4-$OCF_3$ | 186–188 |
| 468 | i-$C_3H_7$ | H | H | 6-I | 2-Cl-4-$CF_2CF_2CF_3$ | 199–200 |
| 469 | i-$C_3H_7$ | H | H | 6-I | 2-$CH_3$-4-$OCHF_2$ | 226–228 |
| 470 | i-$C_3H_7$ | H | H | 6-I | 2-$CH_3$-4-$OCHF_2$-5-Cl | 239–240 |
| 471 | i-$C_3H_7$ | H | H | 6-I | 3-$CF_3$-4-$OCHF_2$ | 238–239 |
| 472 | i-$C_3H_7$ | H | H | 3-F | 4-$(CF_2)_3CF_3$ | 187–188 |
| 473 | i-$C_3H_7$ | H | H | 3-F | 4-$CF_2CF_2CF_3$ | 182–183 |
| 474 | i-$C_3H_7$ | H | H | 3-F | 4-$CF(CF_3)_2$ | 206–208 |
| 475 | i-$C_3H_7$ | H | H | 3-F | 4-$OCF_3$ | 197–199 |
| 476 | i-$C_3H_7$ | H | H | 3-F | 4-$OCF_2CHFOC_3F_7$-n | 142–144 |
| 477 | i-$C_3H_7$ | H | H | 3-F | 4-$SCHF_2$ | 190–192 |
| 478 | i-$C_3H_7$ | H | H | 3-F | 4-$SCH_2CF_3$ | 157–158 |
| 479 | i-$C_3H_7$ | H | H | 3-F | 4-$SCF_2CHF_2$ | 177–178 |
| 480 | i-$C_3H_7$ | H | H | 3-F | 4-$SCF_2CBrF_2$ | 197–199 |
| 481 | i-$C_3H_7$ | H | H | 3-F | 4-$SCF(CF_3)_2$ | 206–208 |
| 482 | i-$C_3H_7$ | H | H | 3-F | 4-$S(CF_2)_3CF_3$ | 173–174 |
| 483 | i-$C_3H_7$ | H | H | 3-F | 4-$SOCH_2CF_3$ | 115–119 |
| 484 | i-$C_3H_7$ | H | H | 3-F | 4-$SOCF_2CBrF_2$ | 181–182 |
| 485 | i-$C_3H_7$ | H | H | 3-F | 4-$SOCF(CF_3)_2$ | 195–197 |
| 486 | i-$C_3H_7$ | H | H | 3-F | 4-$SO(CF_2)_3CF_3$ | 175–176 |
| 487 | i-$C_3H_7$ | H | H | 3-F | 4-$SO_2CH_2CF_3$ | 199–202 |
| 488 | i-$C_3H_7$ | H | H | 3-F | 2,3-$Cl_2$ | 175–177 |
| 489 | i-$C_3H_7$ | H | H | 3-F | 2-$CH_3$-3-Cl | 193–194 |
| 490 | i-$C_3H_7$ | H | H | 3-F | 2-$CH_3$-4-Cl | 192–194 |
| 491 | i-$C_3H_7$ | H | H | 3-F | 2-$CH_3$-5-Cl | 191–193 |
| 492 | i-$C_3H_7$ | H | H | 3-F | 2-$CH_3$-4-I | 192–194 |
| 493 | i-$C_3H_7$ | H | H | 3-F | 2-$CH_3$-5-F | 175–177 |
| 494 | i-$C_3H_7$ | H | H | 3-F | 2-$CH_3$-3-F | 187–189 |
| 495 | i-$C_3H_7$ | H | H | 3-F | 2-$CH_3$-4-$CF_2CF_3$ | 213–214 |
| 496 | i-$C_3H_7$ | H | H | 3-F | 2-$CH_3$-4-$CF_2CF_2CF_3$ | 191–192 |
| 497 | i-$C_3H_7$ | H | H | 3-F | 2-$CH_3$-4-$CF(CF_3)_2$ | 241–243 |
| 498 | i-$C_3H_7$ | H | H | 3-F | 2-$CH_3$-4-$(CF_2)_3CF_3$ | 138–139 |
| 499 | i-$C_3H_7$ | H | H | 3-F | 2-$CH_3$-3-$OCHF_2$ | 172–174 |
| 500 | i-$C_3H_7$ | H | H | 3-F | 2-$CH_3$-4-$OCHF_2$ | 160–162 |
| 501 | i-$C_3H_7$ | H | H | 3-F | 2-$CH_3$-4-$OCF_2CCl_3$ | 162–163 |
| 502 | i-$C_3H_7$ | H | H | 3-F | 2-$CH_3$-4-$OCF_2CCl_2F$ | 207–208 |
| 503 | i-$C_3H_7$ | H | H | 3-F | 2-$CH_3$-4-$OCF_2CBrF_2$ | 196–197 |
| 504 | i-$C_3H_7$ | H | H | 3-F | 2-Cl-4-$CF_3$ | 169–170 |
| 505 | i-$C_3H_7$ | H | H | 3-F | 2-Cl-4-$CF_2CF_2CF_3$ | 169–170 |
| 506 | i-$C_3H_7$ | H | H | 3-F | 3,5-$Cl_2$-4-$OCHF_2$ | 201–202 |
| 507 | i-$C_3H_7$ | H | H | 3-F | 2-Cl-4-$CF(CF_3)_2$ | 223–225 |
| 508 | i-$C_3H_7$ | H | H | 3-F | 2-Cl-4-$OCF_3$ | 169–170 |
| 509 | i-$C_3H_7$ | H | H | 3-F | 2-Br-4-$OCF_3$ | 164–165 |
| 510 | i-$C_3H_7$ | H | H | 3-F | 2-$CH_3$-4-$OCF_3$ | 183–184 |
| 511 | i-$C_3H_7$ | H | H | 3-F | 2-$CH_3$-4-$OCBrF_2$ | 177–178 |
| 512 | i-$C_3H_7$ | H | H | 3-F | 2-$CH_3$-4-$OCF_2CHF_2$ | 172–173 |
| 513 | i-$C_3H_7$ | H | H | 3-F | 2-$CH_3$-4-$OCF_2CHClF$ | 168–169 |
| 514 | i-$C_3H_7$ | H | H | 3-F | 2-$CH_3$-4-$OCF_2CHFCF_3$ | 160–162 |
| 515 | i-$C_3H_7$ | H | H | 3-F | 2-$CH_3$-4-$OCF_2CHFOCF_3$ | 148–150 |
| 516 | i-$C_3H_7$ | H | H | 3-F | 2-$CH_3$-4-$OCF_2CBrFCF_3$ | 148–150 |
| 517 | i-$C_3H_7$ | H | H | 3-F | 2-$CH_3$-4-$OCHF_2$-5-Cl | 187–188 |
| 518 | i-$C_3H_7$ | H | H | 3-F | 2-$CH_3$-4-$SC_3H_7$-i | 165–167 |
| 519 | i-$C_3H_7$ | H | H | 3-F | 2-$CH_3$-4-(3-$CF_3$-PhO) | 135–136 |
| 520 | i-$C_3H_7$ | H | H | 3-F | 2-$CH_3$-4-($F_5$-PhO) | 206–207 |
| 521 | i-$C_3H_7$ | H | H | 3-F | 2-$CH_3$-4-(2-Cl-4-$CF_3$-PhO) | 215–217 |
| 522 | i-$C_3H_7$ | H | H | 3-F | 2-$CH_3$-4-(4-Cl-PhS) | 176–178 |
| 523 | i-$C_3H_7$ | H | H | 3-F | 2-$CH_3$-4-(5-$CF_3$-2-Pyi-O) | 175–176 |
| 524 | i-$C_3H_7$ | H | H | 3-F | 2-$CH_3$-4-(3-Cl-5-$CF_3$-2-Pyi-O) | 188–190 |
| 525 | i-$C_3H_7$ | H | H | 3-F | 4-(3-Cl-5-$CF_3$-2-Pyi-S) | 213–215 |
| 526 | i-$C_3H_7$ | H | H | 3-F | 2-$CH_3$-4-OP=S$(OCH_3)_2$ | 175–177 |
| 527 | i-$C_3H_7$ | H | H | 3-F | 2-$CF_3$-4-$OCHF_2$ | 180–182 |
| 528 | i-$C_3H_7$ | H | H | 3-F | -3-$OCH_2$O-4- | 197–199 |
| 529 | i-$C_3H_7$ | H | H | 4-F | 2-$CH_3$-4-Cl | 217–218 |

TABLE 1-continued ($Z^1$, $Z^2$ = O)

| No | $R^1$ | $R^2$ | $R^3$ | Xn | Ym | Physical Properties (melting point: °C. |
|---|---|---|---|---|---|---|
| 530 | i-$C_3H_7$ | H | H | 4-F | 2-$CH_3$-5-Cl | 202–203 |
| 531 | i-$C_3H_7$ | H | H | 4-F | 2-$CH_3$-4-$OCHF_2$ | 191–193 |
| 532 | i-$C_3H_7$ | H | H | 5-F | 2-$CH_3$-4-Cl | 197–198 |
| 533 | i-$C_3H_7$ | H | H | 5-F | 2-$CH_3$-4-$CF_2CF_2CF_3$ | 213–215 |
| 534 | i-$C_3H_7$ | H | H | 5-F | 2-$CH_3$-4-$OCHF_2$ | 181–182 |
| 535 | i-$C_3H_7$ | H | H | 6-F | 4-$CF_2CF_2CF_3$ | 201–202 |
| 536 | i-$C_3H_7$ | H | H | 6-F | 4-$(CF_2)_3CF_3$ | 156–158 |
| 537 | i-$C_3H_7$ | H | H | 6-F | 4-$OCF_3$ | 212–214 |
| 538 | i-$C_3H_7$ | H | H | 6-F | 4-$OCF_2CHFOC_3F_7$-n | 178–180 |
| 539 | i-$C_3H_7$ | H | H | 6-F | 4-$SCH_2CF_3$ | 176–178 |
| 540 | i-$C_3H_7$ | H | H | 6-F | 4-$SCF_2CHF_2$ | 230–232 |
| 541 | i-$C_3H_7$ | H | H | 6-F | 4-$SCF(CF_3)_2$ | 218–220 |
| 542 | i-$C_3H_7$ | H | H | 6-F | 4-$S(CF_2)_3CF_3$ | 178–181 |
| 543 | i-$C_3H_7$ | H | H | 6-F | 2,3-$Cl_2$ | 158–160 |
| 544 | i-$C_3H_7$ | H | H | 6-F | 2-$CH_3$-3-Cl | 182–184 |
| 545 | i-$C_3H_7$ | H | H | 6-F | 2-$CH_3$-4-Cl | 204–206 |
| 546 | i-$C_3H_7$ | H | H | 6-F | 2-$CH_3$-5-Cl | 196–199 |
| 547 | i-$C_3H_7$ | H | H | 6-F | 2-$CH_3$-4-I | 213–215 |
| 548 | i-$C_3H_7$ | H | H | 6-F | 2-$CH_3$-3-F | 165–167 |
| 549 | i-$C_3H_7$ | H | H | 6-F | 2-$CH_3$-5-F | 181–183 |
| 550 | i-$C_3H_7$ | H | H | 6-F | 2-Cl-4-$CF_3$ | 190–191 |
| 551 | i-$C_3H_7$ | H | H | 6-F | 2-$CH_3$-4-$CF_2CF_3$ | 222–223 |
| 552 | i-$C_3H_7$ | H | H | 6-F | 2-$CH_3$-4-$OCF_2CCl_3$ | 184–185 |
| 553 | i-$C_3H_7$ | H | H | 6-F | 2-$CH_3$-4-$OCF_2CCl_2F$ | 214–215 |
| 554 | i-$C_3H_7$ | H | H | 6-F | 2-$CH_3$-4-$OCF_2CBrF_2$ | 208–210 |
| 555 | i-$C_3H_7$ | H | H | 6-F | 2-$CH_3$-4-$CF_2CF_2CF_3$ | 168–170 |
| 556 | i-$C_3H_7$ | H | H | 6-F | 2-$CH_3$-4-$CF(CF_3)_2$ | 255–257 |
| 557 | i-$C_3H_7$ | H | H | 6-F | 2-$CH_3$-4-$(CF_2)_3CF_3$ | 157–159 |
| 558 | i-$C_3H_7$ | H | H | 6-F | 2-$CH_3$-3-$OCHF_2$ | 177–179 |
| 559 | i-$C_3H_7$ | H | H | 6-F | 2-$CH_3$-4-$OCHF_2$ | 176–178 |
| 560 | i-$C_3H_7$ | H | H | 6-F | 3,5-$Cl_2$-4-$OCHF_2$ | 198–200 |
| 561 | i-$C_3H_7$ | H | H | 6-F | 2-Cl-4-$CF(CF_3)_2$ | 241–243 |
| 562 | i-$C_3H_7$ | H | H | 6-F | 2-Cl-4-$OCF_3$ | 171–172 |
| 563 | i-$C_3H_7$ | H | H | 6-F | 2-Br-4-$OCF_3$ | 181–182 |
| 564 | i-$C_3H_7$ | H | H | 6-F | 2-$CH_3$-4-$OCF_3$ | 193–195 |
| 565 | i-$C_3H_7$ | H | H | 6-F | 2-$CH_3$-4-$OCBrF_2$ | 181–183 |
| 566 | i-$C_3H_7$ | H | H | 6-F | 2-$CH_3$-4-$OCF_2CHF_2$ | 185–187 |
| 567 | i-$C_3H_7$ | H | H | 6-F | 2-$CH_3$-4-$OCF_2CHClF$ | 175–176 |
| 568 | i-$C_3H_7$ | H | H | 6-F | 2-$CH_3$-4-$OCF_2CHFCF_3$ | 176–178 |
| 569 | i-$C_3H_7$ | H | H | 6-F | 2-$CH_3$-4-$OCF_2CBrFCF_3$ | 217–219 |
| 570 | i-$C_3H_7$ | H | H | 6-F | 2-$CH_3$-4-$OCF_2CHFOCF_3$ | 183–185 |
| 571 | i-$C_3H_7$ | H | H | 6-F | 2-$CH_3$-4-$OCHF_2$-5-Cl | 209–211 |
| 572 | i-$C_3H_7$ | H | H | 6-F | 2-$CH_3$-4-(3-$CF_3$-PhO) | 184–185 |
| 573 | i-$C_3H_7$ | H | H | 6-F | 2-$CH_3$-4-($F_5$-PhO) | 227–228 |
| 574 | i-$C_3H_7$ | H | H | 6-F | 2-$CH_3$-4-(2-Cl-4-$CF_3$-PhO) | 220–222 |
| 575 | i-$C_3H_7$ | H | H | 6-F | 2-$CH_3$-4-(4-Cl-PhS) | 190–193 |
| 576 | i-$C_3H_7$ | H | H | 6-F | 2-$CH_3$-4-(5-$CF_3$-2-Pyi-O) | 206–207 |
| 577 | i-$C_3H_7$ | H | H | 6-F | 2-$CH_3$-4-(3-Cl-5-$CF_3$-2-Pyi-O) | 177–179 |
| 578 | i-$C_3H_7$ | H | H | 6-F | 2-$CH_3$-4-OP=S($OCH_3$)$_2$ | 188–190 |
| 579 | i-$C_3H_7$ | H | H | 6-F | 2-$CF_3$-4-$OCHF_2$ | 223–225 |
| 580 | i-$C_3H_7$ | H | H | 6-F | -3-$OCH_2$O-4- | 201–203 |
| 581 | i-$C_3H_7$ | H | H | 3,6-$F_2$ | 2-$CH_3$-4-$OCHF_2$ | 203–204 |
| 582 | i-$C_3H_7$ | H | H | 3,6-$F_2$ | 2-$CH_3$-4-Cl | 221–222 |
| 583 | i-$C_3H_7$ | H | H | 3,4,5,6-F4 | 2-$CH_3$-5-Cl | 189–191 |
| 584 | i-$C_3H_7$ | H | H | 3-$NO_2$ | 2,3-$Cl_2$ | 201–203 |
| 585 | i-$C_3H_7$ | H | H | 3-$NO_2$ | H | 236–238 |
| 586 | i-$C_3H_7$ | H | H | 3-$NO_2$ | 2-Cl | 190–192 |
| 587 | i-$C_3H_7$ | H | H | 3-$NO_2$ | 3-Cl | 227–229 |
| 588 | i-$C_3H_7$ | H | H | 3-$NO_2$ | 4-Cl | 238–240 |
| 589 | i-$C_3H_7$ | H | H | 3-$NO_2$ | 2-Br | 170–172 |
| 590 | i-$C_3H_7$ | H | H | 3-$NO_2$ | 3-Br | 196–198 |
| 591 | i-$C_3H_7$ | H | H | 3-$NO_2$ | 4-Br | 205–207 |
| 592 | i-$C_3H_7$ | H | H | 3-$NO_2$ | 2-F | 199–201 |
| 593 | i-$C_3H_7$ | H | H | 3-$NO_2$ | 3-F | 228–230 |
| 594 | i-$C_3H_7$ | H | H | 3-$NO_2$ | 4-F | 250–252 |
| 595 | i-$C_3H_7$ | H | H | 3-$NO_2$ | 4-I | 187–189 |
| 596 | i-$C_3H_7$ | H | H | 3-$NO_2$ | 4-$NO_2$ | 201–203 |
| 597 | i-$C_3H_7$ | H | H | 3-$NO_2$ | 3-CN | 220–222 |
| 598 | i-$C_3H_7$ | H | H | 3-$NO_2$ | 4-CN | 226–228 |
| 599 | i-$C_3H_7$ | H | H | 3-$NO_2$ | 2-$CH_3$ | 227–228 |
| 600 | i-$C_3H_7$ | H | H | 3-$NO_2$ | 3-$CH_3$ | 195–197 |
| 601 | i-$C_3H_7$ | H | H | 3-$NO_2$ | 4-$CH_3$ | 196–198 |

TABLE 1-continued ($Z^1$, $Z^2$ = O)

| No | $R^1$ | $R^2$ | $R^3$ | Xn | Ym | Physical Properties (melting point: °C. |
|---|---|---|---|---|---|---|
| 602 | i-$C_3H_7$ | H | H | 3-$NO_2$ | 2-$C_2H_5$ | 189–191 |
| 603 | i-$C_3H_7$ | H | H | 3-$NO_2$ | 2-$C_3H_7$-i | 190–192 |
| 604 | i-$C_3H_7$ | H | H | 3-$NO_2$ | 4-$C_3H_7$-i | 221–223 |
| 605 | i-$C_3H_7$ | H | H | 3-$NO_2$ | 4-$C_4H_9$-n | 193–195 |
| 606 | i-$C_3H_7$ | H | H | 3-$NO_2$ | 4-$CF_3$ | 192–194 |
| 607 | i-$C_3H_7$ | H | H | 3-$NO_2$ | 3-$CF_3$ | 220–222 |
| 608 | i-$C_3H_7$ | H | H | 3-$NO_2$ | 2-$CF_3$ | 215–217 |
| 609 | i-$C_3H_7$ | H | H | 3-$NO_2$ | 4-$CF_2CF_2CF_3$ | 184–185 |
| 610 | i-$C_3H_7$ | H | H | 3-$NO_2$ | 4-$CF(CF_3)_2$ | 243–244 |
| 611 | i-$C_3H_7$ | H | H | 3-$NO_2$ | 4-$(CF_2)_3CF_3$ | 220–221 |
| 612 | i-$C_3H_7$ | H | H | 3-$NO_2$ | 2-$OCH_3$ | 172–174 |
| 613 | i-$C_3H_7$ | H | H | 3-$NO_2$ | 3-$OCH_3$ | 201–203 |
| 614 | i-$C_3H_7$ | H | H | 3-$NO_2$ | 4-$OCH_3$ | 221–223 |
| 615 | i-$C_3H_7$ | H | H | 3-$NO_2$ | 3-O-$C_3H_7$-i | 198–200 |
| 616 | i-$C_3H_7$ | H | H | 3-$NO_2$ | 3-$OCHF_2$ | 188–190 |
| 617 | i-$C_3H_7$ | H | H | 3-$NO_2$ | 4-$OCHF_2$ | 222–224 |
| 618 | i-$C_3H_7$ | H | H | 3-$NO_2$ | 4-$OCF_3$ | 234–236 |
| 619 | i-$C_3H_7$ | H | H | 3-$NO_2$ | 4-$OCF_2CHFOC_3F_7$-n | 138–140 |
| 620 | i-$C_3H_7$ | H | H | 3-$NO_2$ | 4-$COOCH_3$ | 192–194 |
| 621 | i-$C_3H_7$ | H | H | 3-$NO_2$ | 3-$SCH_3$ | 205–207 |
| 622 | i-$C_3H_7$ | H | H | 3-$NO_2$ | 2-$SCH_3$ | 201–203 |
| 623 | i-$C_3H_7$ | H | H | 3-$NO_2$ | 3-$SCF_3$ | 203–205 |
| 624 | i-$C_3H_7$ | H | H | 3-$NO_2$ | 4-$SCH_2CF_3$ | 155–156 |
| 625 | i-$C_3H_7$ | H | H | 3-$NO_2$ | 4-$SCHF_2$ | 183–185 |
| 626 | i-$C_3H_7$ | H | H | 3-$NO_2$ | 4-$SCF_2CHF_2$ | 235–237 |
| 627 | i-$C_3H_7$ | H | H | 3-$NO_2$ | 4-$SCF_2CF_3$ | 190–192 |
| 628 | i-$C_3H_7$ | H | H | 3-$NO_2$ | 4-$SCF_2CBrF_2$ | 228–230 |
| 629 | i-$C_3H_7$ | H | H | 3-$NO_2$ | 4-$SCF(CF_3)_2$ | 242–243 |
| 630 | i-$C_3H_7$ | H | H | 3-$NO_2$ | 4-$S(CF_2)_3CF_3$ | 229–230 |
| 631 | i-$C_3H_7$ | H | H | 3-$NO_2$ | 4-$SO(CF_2)_3CF_3$ | 190–193 |
| 632 | i-$C_3H_7$ | H | H | 3-$NO_2$ | 4-O-Ph | 228–230 |
| 633 | i-$C_3H_7$ | H | H | 3-$NO_2$ | 2,4-$Cl_2$ | 202–204 |
| 634 | i-$C_3H_7$ | H | H | 3-$NO_2$ | 2,5-$Cl_2$ | 230–232 |
| 635 | i-$C_3H_7$ | H | H | 3-$NO_2$ | 2,6-$Cl_2$ | 210–212 |
| 636 | i-$C_3H_7$ | H | H | 3-$NO_2$ | 3,4-$Cl_2$ | 227–229 |
| 637 | i-$C_3H_7$ | H | H | 3-$NO_2$ | 3,5-$Cl_2$ | 194–196 |
| 638 | i-$C_3H_7$ | H | H | 3-$NO_2$ | 2,3-$F_2$ | 184–186 |
| 639 | i-$C_3H_7$ | H | H | 3-$NO_2$ | 2,4-$F_2$ | 210–212 |
| 640 | i-$C_3H_7$ | H | H | 3-$NO_2$ | 2,5-$F_2$ | 191–193 |
| 641 | i-$C_3H_7$ | H | H | 3-$NO_2$ | 2,6-$F_2$ | 173–175 |
| 642 | i-$C_3H_7$ | H | H | 3-$NO_2$ | 3,4-$F_2$ | 241–243 |
| 643 | i-$C_3H_7$ | H | H | 3-$NO_2$ | 3-Cl-4-F | 203–205 |
| 644 | i-$C_3H_7$ | H | H | 3-$NO_2$ | 2,3,4-$Cl_3$ | 203–205 |
| 645 | i-$C_3H_7$ | H | H | 3-$NO_2$ | 2,3,4-$F_3$ | 202–204 |
| 646 | i-$C_3H_7$ | H | H | 3-$NO_2$ | 2,3,4,5,6-$F_5$ | 192–194 |
| 647 | i-$C_3H_7$ | H | H | 3-$NO_2$ | 2,3-$(CH_3)_2$ | 200–202 |
| 648 | i-$C_3H_7$ | H | H | 3-$NO_2$ | 2,4-$(CH_3)_2$ | 201–203 |
| 649 | i-$C_3H_7$ | H | H | 3-$NO_2$ | 2,5-$(CH_3)_2$ | 221–223 |
| 650 | i-$C_3H_7$ | H | H | 3-$NO_2$ | 2,6-$(CH_3)_2$ | 234–236 |
| 651 | i-$C_3H_7$ | H | H | 3-$NO_2$ | 3,4-$(CH_3)_2$ | 195–197 |
| 652 | i-$C_3H_7$ | H | H | 3-$NO_2$ | 2,4,6-$(CH_3)_3$ | 229–231 |
| 653 | i-$C_3H_7$ | H | H | 3-$NO_2$ | 2,6-$(C_2H_5)_2$ | 258–260 |
| 654 | i-$C_3H_7$ | H | H | 3-$NO_2$ | 3,5-$(CF_3)_2$ | 225–227 |
| 655 | i-$C_3H_7$ | H | H | 3-$NO_2$ | 3-Cl-4-$CH_3$ | 208–210 |
| 656 | i-$C_3H_7$ | H | H | 3-$NO_2$ | 2-Cl-4-$CH_3$ | 195–197 |
| 657 | i-$C_3H_7$ | H | H | 3-$NO_2$ | 2-F-4-Cl-5-$CH_3$ | 193–195 |
| 658 | i-$C_3H_7$ | H | H | 3-$NO_2$ | 3-Cl-4-$OCHF_2$ | 222–224 |
| 659 | i-$C_3H_7$ | H | H | 3-$NO_2$ | 3,5-$Cl_2$-4-$OCHF_2$ | 218–220 |
| 660 | i-$C_3H_7$ | H | H | 3-$NO_2$ | 2-Cl-4-$CF_3$ | 217–219 |
| 661 | i-$C_3H_7$ | H | H | 3-$NO_2$ | 2-Cl-5-$CF_3$ | 193–195 |
| 662 | i-$C_3H_7$ | H | H | 3-$NO_2$ | 2,6-$Cl_2$-4-$CF_3$ | 226–228 |
| 663 | i-$C_3H_7$ | H | H | 3-$NO_2$ | 2-$CH_3$-3-Cl | 198–200 |
| 664 | i-$C_3H_7$ | H | H | 3-$NO_2$ | 2-$CH_3$-4-Cl | 235–237 |
| 665 | i-$C_3H_7$ | H | H | 3-$NO_2$ | 2-$CH_3$-5-Cl | 218–219 |
| 666 | i-$C_3H_7$ | H | H | 3-$NO_2$ | 2-$CH_3$-6-Cl | 248–250 |
| 667 | i-$C_3H_7$ | H | H | 3-$NO_2$ | 2-$C_2H_5$-4-Cl | 235–237 |
| 668 | i-$C_3H_7$ | H | H | 3-$NO_2$ | 2-$CH_3$-4,5-$Cl_2$ | 196–198 |
| 669 | i-$C_3H_7$ | H | H | 3-$NO_2$ | 2,3-$(CH_3)_2$-4-Cl | 226–228 |
| 670 | i-$C_3H_7$ | H | H | 3-$NO_2$ | 2,4-$(CH_3)_2$-3-Cl | 203–205 |
| 671 | i-$C_3H_7$ | H | H | 3-$NO_2$ | 2-$CH_3$-4-Br | 214–216 |
| 672 | i-$C_3H_7$ | H | H | 3-$NO_2$ | 2-$CH_3$-5-Br | 191–193 |
| 673 | i-$C_3H_7$ | H | H | 3-$NO_2$ | 2-$CH_3$-4-I | 227–227 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 674 | i-$C_3H_7$ | H | H | 3-$NO_2$ | 2-$CH_3$-3-F | 199–201 |
| 675 | i-$C_3H_7$ | H | H | 3-$NO_2$ | 2-$CH_3$-4-F | 226–228 |
| 676 | i-$C_3H_7$ | H | H | 3-$NO_2$ | 2-$CH_3$-5-F | 213–215 |
| 677 | i-$C_3H_7$ | H | H | 3-$NO_2$ | 2-$C_2H_5$-5-F | 191–193 |
| 678 | i-$C_3H_7$ | H | H | 3-$NO_2$ | 3-$CF_3$-4-Cl | 215–217 |
| 679 | i-$C_3H_7$ | H | H | 3-$NO_2$ | 2-$CF_3$-4-Cl | 208–210 |
| 680 | i-$C_3H_7$ | H | H | 3-$NO_2$ | 3-$CH_3$-4-Br | 199–201 |
| 681 | i-$C_3H_7$ | H | H | 3-$NO_2$ | 2-$CH_3$-3-$CF_3$ | 221–222 |
| 682 | i-$C_3H_7$ | H | H | 3-$NO_2$ | 2-$CH_3$-4-$CF_3$ | 236–237 |
| 683 | i-$C_3H_7$ | H | H | 3-$NO_2$ | 2-$CH_3$-4-$CF_2CF_3$ | 218–219 |
| 684 | i-$C_3H_7$ | H | H | 3-$NO_2$ | 2-$CH_3$-4-$CF_2CF_2CF_3$ | 188–189 |
| 685 | i-$C_3H_7$ | H | H | 3-$NO_2$ | 2-$CH_3$-4-$CF(CF_3)_2$ | 248–250 |
| 686 | i-$C_3H_7$ | H | H | 3-$NO_2$ | 2-$CH_3$-4-$(CF_2)_3CF_3$ | 225–226 |
| 687 | i-$C_3H_7$ | H | H | 3-$NO_2$ | 2-$CH_3$-3-$OCH_3$ | 198–200 |
| 688 | i-$C_3H_7$ | H | H | 3-$NO_2$ | 2-$CH_3$-4-$OCH_3$ | 208–210 |
| 689 | i-$C_3H_7$ | H | H | 3-$NO_2$ | 2,3-$(CH_3)_2$-4-$OCH_3$ | 253–255 |
| 690 | i-$C_3H_7$ | H | H | 3-$NO_2$ | 2-$CH_3$-4-O-$C_3H_7$-i | 233–234 |
| 691 | i-$C_3H_7$ | H | H | 3-$NO_2$ | 3-$CF_3$-5-$OCH_3$ | 214–216 |
| 692 | i-$C_3H_7$ | H | H | 3-$NO_2$ | 2-$CF_3$-4-$OCHF_2$ | 201–203 |
| 693 | i-$C_3H_7$ | H | H | 3-$NO_2$ | 3-$CF_3$-4-$OCHF_2$ | 231–232 |
| 694 | i-$C_3H_7$ | H | H | 3-$NO_2$ | 2,4-$(CH_3)_2$-3-$OCH_3$ | 201–203 |
| 695 | i-$C_3H_7$ | H | H | 3-$NO_2$ | 2-$CH_3$-3-$OCHF_2$ | 200–202 |
| 696 | i-$C_3H_7$ | H | H | 3-$NO_2$ | 2-$CH_3$-4-$OCHF_2$ | 186–188 |
| 697 | i-$C_3H_7$ | H | H | 3-$NO_2$ | 2-$CH_3$-4-$OCH_2CF_3$ | 241–243 |
| 698 | i-$C_3H_7$ | H | H | 3-$NO_2$ | 2-$CH_3$-4-$OCF_2CBrF_2$ | 229–230 |
| 699 | i-$C_3H_7$ | H | H | 3-$NO_2$ | 2-$CH_3$-4-$OCH_2CF_2CHF_2$ | 199–200 |
| 700 | i-$C_3H_7$ | H | H | 3-$NO_2$ | 2-$CH_3$-4-$OCF_2CBrFCF_3$ | 224–226 |
| 701 | i-$C_3H_7$ | H | H | 3-$NO_2$ | 2-$CH_3$-4-$OCH_2CHFOCF_3$ | 208–210 |
| 702 | i-$C_3H_7$ | H | H | 3-$NO_2$ | 3-$OCH_3$-4-$OCHF_2$ | 242–243 |
| 703 | i-$C_3H_7$ | H | H | 3-$NO_2$ | 2-Cl-4-$CF(CF_3)_2$ | 198–200 |
| 704 | i-$C_3H_7$ | H | H | 3-$NO_2$ | 2-Cl-4-$OCF_3$ | 188–190 |
| 705 | i-$C_3H_7$ | H | H | 3-$NO_2$ | 2-Br-4-$OCF_3$ | 202–203 |
| 706 | i-$C_3H_7$ | H | H | 3-$NO_2$ | 2-$CH_3$-4-$NO_2$ | 201–203 |
| 707 | i-$C_3H_7$ | H | H | 3-$NO_2$ | 2-Cl-5-$NO_2$ | 193–195 |
| 708 | i-$C_3H_7$ | H | H | 3-$NO_2$ | 2-$CH_3$-5-$NO_2$ | 197–199 |
| 709 | i-$C_3H_7$ | H | H | 3-$NO_2$ | 2,3-$(CH_3)_2$-4-$NO_2$ | 207–209 |
| 710 | i-$C_3H_7$ | H | H | 3-$NO_2$ | 2-$CH_3$-4-$OCF_3$ | 184–186 |
| 711 | i-$C_3H_7$ | H | H | 3-$NO_2$ | 2-$CH_3$-4-$OCBrF_2$ | 217–218 |
| 712 | i-$C_3H_7$ | H | H | 3-$NO_2$ | 2-$CH_3$-4-$OCF_2CHF_2$ | 205–207 |
| 713 | i-$C_3H_7$ | H | H | 3-$NO_2$ | 2-$CH_3$-3-$OCF_2CHClF$ | 164–166 |
| 714 | i-$C_3H_7$ | H | H | 3-$NO_2$ | 2-$CH_3$-4-$OCF_2CHClF$ | 192–193 |
| 715 | i-$C_3H_7$ | H | H | 3-$NO_2$ | 2-$CH_3$-4-$OCF_2CCl_2F$ | 212–213 |
| 716 | i-$C_3H_7$ | H | H | 3-$NO_2$ | 2-$CH_3$-4-$OCF_2CHFCF_3$ | 198–199 |
| 717 | i-$C_3H_7$ | H | H | 3-$NO_2$ | 2-$CH_3$-3-Cl-4-$OCHF_2$ | 236–238 |
| 718 | i-$C_3H_7$ | H | H | 3-$NO_2$ | 2-$CH_3$-4-$OCF_2CHF_2$-5-Cl | 233–234 |
| 719 | i-$C_3H_7$ | H | H | 3-$NO_2$ | 2-$CH_3$-4-$SCH_3$ | 214–216 |
| 720 | i-$C_3H_7$ | H | H | 3-$NO_2$ | 2,3-$(CH_3)_2$-4-$SCH_3$ | 254–256 |
| 721 | i-$C_3H_7$ | H | H | 3-$NO_2$ | 2-$CH_3$-4-$SC_3H_7$-i | 209–211 |
| 722 | i-$C_3H_7$ | H | H | 3-$NO_2$ | 2-$CH_3$-4-$SCHF_2$ | 225–227 |
| 723 | i-$C_3H_7$ | H | H | 3-$NO_2$ | 2-$CH_3$-4-$N(CH_3)_2$ | 215–217 |
| 724 | i-$C_3H_7$ | H | H | 3-$NO_2$ | 2-$CH_3$-4-(3-$CF_3$-PhO) | 174–175 |
| 725 | i-$C_3H_7$ | H | H | 3-$NO_2$ | 2-$CH_3$-4-($F_5$-PhO) | 242–244 |
| 726 | i-$C_3H_7$ | H | H | 3-$NO_2$ | 2-$CH_3$-4-(2-Cl-4-$CF_3$-PhO) | 191–192 |
| 727 | i-$C_3H_7$ | H | H | 3-$NO_2$ | 2-$CH_3$-4-(4-Cl-PhS) | 165–167 |
| 728 | i-$C_3H_7$ | H | H | 3-$NO_2$ | 2-$CH_3$-4-(5-$CF_3$-2-Pyi-O) | 216–218 |
| 729 | i-$C_3H_7$ | H | H | 3-$NO_2$ | 2-$CH_3$-4-(3-Cl-5-$CF_3$-2-Pyi-O) | 236–238 |
| 730 | i-$C_3H_7$ | H | H | 3-$NO_2$ | 4-(3-Cl-5-$CF_3$-2-Pyi-S) | 190–192 |
| 731 | i-$C_3H_7$ | H | H | 3-$NO_2$ | 2-$CH_3$-4-P=$O(OC_2H_5)_2$ | 128–130 |
| 732 | i-$C_3H_7$ | H | H | 3-$NO_2$ | 2-$CH_3$-4-P=$S(OCH_3)_2$ | 128–130 |
| 733 | i-$C_3H_7$ | H | H | 3-$NO_2$ | -3-$OCH_2$O-4- | 229–231 |
| 734 | i-$C_3H_7$ | H | H | 3-$NO_2$ | 3-$CH_2CH_2CH_2$-4 | 209–211 |
| 735 | i-$C_3H_7$ | H | H | 3-$NO_2$ | 2-$CH_2CH_2CH_2$-3 | 226–228 |
| 736 | i-$C_3H_7$ | H | H | 3-$NO_2$ | 3-N=$C(CF_3)$—NH-4 | 162–164 |
| 737 | i-$C_3H_7$ | H | H | 3-$NO_2$ | 3-N=$C(CF_3)$—$N(CH_3)$-4 | 186–188 |
| 738 | i-$C_3H_7$ | H | H | 5-$NO_2$ | 2-$CH_3$-5-Cl | 226–228 |
| 739 | i-$C_3H_7$ | H | H | 6-$NO_2$ | 2-$CH_3$-5-Cl | 247–249 |
| 740 | i-$C_3H_7$ | H | H | 6-$NO_2$ | 2-Cl-4-$CF_3$ | Crystals |
| 741 | i-$C_3H_7$ | H | H | 6-$NO_2$ | 2-Cl-4-$CF_2CF_2CF_3$ | 192–193 |
| 742 | i-$C_3H_7$ | H | H | 6-$NO_2$ | 2-$CH_3$-4-$CF_3$ | 239–240 |
| 743 | i-$C_3H_7$ | H | H | 6-$NO_2$ | 2-$CH_3$-4-$OCF_2CHFCF_3$ | 252–253 |
| 744 | i-$C_3H_7$ | H | H | 3-CN | 2-$CH_3$-4-Cl | 162–164 |
| 745 | i-$C_3H_7$ | H | H | 6-CN | 2-$CH_3$-4-Cl | Crystals |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 749 | i-$C_3H_7$ | H | H | 3-$CH_3$ | 4-$OCF_3$ | 180–182 |
| 750 | i-$C_3H_7$ | H | H | 3-$CH_3$ | 2-$CH_3$-4-Cl | 169–171 |
| 751 | i-$C_3H_7$ | H | H | 3-$CH_3$ | 2-$CH_3$-4-$OCHF_2$ | 192–193 |
| 752 | i-$C_3H_7$ | H | H | 5-$CH_3$ | 2-$CH_3$-5-Cl | 193–195 |
| 753 | i-$C_3H_7$ | H | H | 6-$C_2H_5$ | 2-$CH_3$-4-Cl | 180–182 |
| 754 | i-$C_3H_7$ | H | H | 3-$CF_3$ | H | 202–204 |
| 755 | i-$C_3H_7$ | H | H | 3-$CF_3$ | 2-$CH_3$-5-Cl | 196–198 |
| 756 | i-$C_3H_7$ | H | H | 3-$CF_3$ | 2-$CH_3$-3-Cl | 216–218 |
| 757 | i-$C_3H_7$ | H | H | 3-$CF_3$ | 2,6-$(C_2H_5)_2$ | 238–239 |
| 758 | i-$C_3H_7$ | H | H | 3-$CF_3$ | 2-$CH_3$-4-Cl | 207–209 |
| 759 | i-$C_3H_7$ | H | H | 3-$CF_3$ | 2-$CH_3$-4-$OCHF_2$ | 212–213 |
| 760 | i-$C_3H_7$ | H | H | 5-$CF_3$ | 2,6-$(C_2H_5)_2$ | 240–241 |
| 761 | i-$C_3H_7$ | H | H | 5-$CF_3$ | 2-$CH_3$-4-Cl | 203–205 |
| 762 | i-$C_3H_7$ | H | H | 5-$CF_3$ | 3-$CF_3$-5-$OCH_3$ | 209–210 |
| 763 | i-$C_3H_7$ | H | H | 5-$CF_3$ | 2-$CH_3$-4-$OCHF_2$ | 196–197 |
| 764 | i-$C_3H_7$ | H | H | 6-$CF_3$ | H | 152–154 |
| 765 | i-$C_3H_7$ | H | H | 6-$CF_3$ | 2-$CH_3$-3-Cl | 158–160 |
| 766 | i-$C_3H_7$ | H | H | 6-$CF_3$ | 2-$CH_3$-5-Cl | 273–275 |
| 767 | i-$C_3H_7$ | H | H | 3-$OCH_3$ | 4-$OCF_3$ | 178–180 |
| 768 | i-$C_3H_7$ | H | H | 3-$OCH_3$ | 2-$CH_3$-4-Br | 214–215 |
| 769 | i-$C_3H_7$ | H | H | 6-$OCH_3$ | 4-$OCF_3$ | 189–190 |
| 770 | i-$C_3H_7$ | H | H | 6-$OCH_3$ | 2-$CH_3$-5-Cl | 155–157 |
| 771 | i-$C_3H_7$ | H | H | 6-$OCH_3$ | 2-$CH_3$-4-Br | 195–197 |
| 772 | i-$C_3H_7$ | H | H | 3-$OCHF_2$ | 2-$CH_3$-4-Cl | 212–213 |
| 773 | i-$C_3H_7$ | H | H | 3-$OCHF_2$ | 2-$CH_3$-5-Cl | 198–200 |
| 774 | i-$C_3H_7$ | H | H | 3-$OCHF_2$ | 2-$CH_3$-4-$OCHF_2$ | 174–175 |
| 775 | i-$C_3H_7$ | H | H | 4-$OCHF_2$ | 2-$CH_3$-5-Cl | 215–217 |
| 776 | i-$C_3H_7$ | H | H | 5-$OCHF_2$ | 2-$CH_3$-5-Cl | 173–175 |
| 777 | i-$C_3H_7$ | H | H | 6-$OCHF_2$ | 2-$CH_3$-4-Cl | 224–226 |
| 778 | i-$C_3H_7$ | H | H | 6-$OCHF_2$ | 2-$CH_3$-5-Cl | 191–193 |
| 779 | i-$C_3H_7$ | H | H | 6-$OCHF_2$ | 2-$CH_3$-4-$OCHF_2$ | 199–200 |
| 780 | i-$C_3H_7$ | H | H | 3-$SCH_3$ | 2-$CH_3$-3-Cl | 191–193 |
| 781 | i-$C_3H_7$ | H | H | 3-$SCH_3$ | 2-$CH_3$-4-Cl | 188–190 |
| 782 | i-$C_3H_7$ | H | H | 3-$SCH_3$ | 2-$CH_3$-4-Br | 185–187 |
| 783 | i-$C_3H_7$ | H | H | 3-$SCH_3$ | 2-$CH_3$-4-$OCHF_2$ | 159–161 |
| 784 | i-$C_3H_7$ | H | H | 6-$SCH_3$ | 2-$CH_3$-4-Br | 201–202 |
| 785 | i-$C_3H_7$ | H | H | 6-$SCH_3$ | 2-$CH_3$-3-Cl | 207–209 |
| 786 | i-$C_3H_7$ | H | H | 6-$SCH_3$ | 2-$CH_3$-4-Cl | 204–206 |
| 787 | i-$C_3H_7$ | H | H | 6-$SCH_3$ | 2-$CH_3$-4-$OCHF_2$ | 212–214 |
| 788 | i-$C_3H_7$ | H | H | 3-$SC_3H_7$-i | 2-$CH_3$-4-Cl | 183–184 |
| 789 | i-$C_3H_7$ | H | H | 6-$SC_3H_7$-i | 2-$CH_3$-4-Cl | 228–229 |
| 790 | i-$C_3H_7$ | H | H | 3-$SOCH_3$ | 2-$CH_3$-4-Br | 125–130 |
| 791 | i-$C_3H_7$ | H | H | 3-$SOCH_3$ | 2-$CH_3$-4-$OCHF_2$ | 215–217 |
| 792 | i-$C_3H_7$ | H | H | 6-$SOCH_3$ | 2-$CH_3$-4-Br | 203–208 |
| 793 | i-$C_3H_7$ | H | H | 3-$SOC_3H_7$-i | 2-$CH_3$-4-Cl | 157–160 |
| 794 | i-$C_3H_7$ | H | H | 6-$SOC_3H_7$-i | 2-$CH_3$-4-Cl | 170–173 |
| 795 | i-$C_3H_7$ | H | H | 3-$SO_2CH_3$ | 2-$CH_3$-4-$OCHF_2$ | 211–213 |
| 796 | i-$C_3H_7$ | H | H | 3-$SO_2C_3H_7$-i | 2-$CH_3$-4-Cl | 240–242 |
| 797 | i-$C_3H_7$ | H | H | 3-$SCH_2CF_3$ | 2-$CH_3$-4-$OCHF_2$ | 184–186 |
| 798 | i-$C_3H_7$ | H | H | 6-$SCH_2CF_3$ | 2-$CH_3$-4-$OCHF_2$ | 239–241 |
| 799 | i-$C_3H_7$ | H | H | 3-$SOCH_2CF_3$ | 2-$CH_3$-4-$OCHF_2$ | 198–200 |
| 800 | i-$C_3H_7$ | H | H | 6-$SOCH_2CF_3$ | 2-$CH_3$-4-$OCHF_2$ | 238–240 |
| 801 | i-$C_3H_7$ | H | H | 6-C≡CH | 2-$CH_3$-4-Cl | 253–255 |
| 802 | i-$C_3H_7$ | H | H | 6-$COOCH_3$ | 2-$CH_3$-4-Cl | 149–151 |
| 803 | i-$C_3H_7$ | H | H | 3-$CONHC_3H_7$-i | 2-$CH_3$-4-Cl | 187–189 |
| 804 | i-$C_3H_7$ | H | H | 6-$CONHC_3H_7$-i | 2-$CH_3$-4-Cl | 191–193 |
| 807 | i-$C_3H_7$ | H | H | 3-Ph | 2-$CH_3$-4-Cl | 228–229 |
| 808 | i-$C_3H_7$ | H | H | 6-Ph | 4-$OCF_3$ | 213–214 |
| 809 | i-$C_3H_7$ | H | H | 6-Ph | 2-$CH_3$-4-Cl | 254–256 |
| 810 | i-$C_3H_7$ | H | H | 3-O-Ph | 2-$CH_3$-4-$OCHF_2$ | 175–177 |
| 811 | i-$C_3H_7$ | H | H | 6-O-Ph | 2-$CH_3$-4-$OCHF_2$ | 194–196 |
| 812 | i-$C_3H_7$ | H | H | 3-(4-Cl-PhO) | 2-$CH_3$-4-Br | 204–206 |
| 813 | i-$C_3H_7$ | H | H | 3-S-Ph | 2-$CH_3$-4-Cl | 204–206 |
| 814 | i-$C_3H_7$ | H | H | 3-S-Ph | 2-$CH_3$-4-Br | 193–194 |
| 815 | i-$C_3H_7$ | H | H | 6-S-Ph | 2-$CH_3$-4-Cl | 211–213 |
| 816 | i-$C_3H_7$ | H | H | 6-S-Ph | 2-$CH_3$-4-Br | 193–194 |
| 817 | i-$C_3H_7$ | H | H | 3-SO-Ph | 2-$CH_3$-4-Cl | 201–203 |
| 818 | i-$C_3H_7$ | H | H | 3-$SO_2$-Ph | 2-$CH_3$-4-Cl | 189–191 |
| 819 | i-$C_3H_7$ | H | H | 3-CH=CH—CH=CH-4 | 2-$CH_3$-4-$OCHF_2$ | 158–160 |
| 820 | i-$C_3H_7$ | H | H | 5-CH=CH—CH=CH-6 | 2-$CH_3$-4-$OCHF_2$ | 154–155 |
| 821 | i-$C_3H_7$ | H | H | 3-CH=CH—CH=CH-4 | 2-$CH_3$-5-Cl | 156–158 |
| 822 | i-$C_3H_7$ | H | H | 4-CH=CH—CH=CH-5 | 2-$CH_3$-5-Cl | 229–231 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 823 | i-$C_3H_7$ | H | H | 5-CH=CH—CH=CH-6 | 2-$CH_3$-5-Cl | 232–234 |
| 824 | i-$C_3H_7$ | $CH_3$ | H | H | 4-$CF_3$ | 178–180 |
| 825 | i-$C_3H_7$ | $CH_3$ | H | 3-$NO_2$ | 2-$CH_3$-4-$OCHF_2$ | 148–149 |
| 826 | i-$C_3H_7$ | $CH_3$ | H | H | 2-$CH_3$-4-Cl | 82–83 |
| 827 | i-$C_3H_7$ | H | $CH_3$ | H | 2-$CH_3$-4-Cl | 165–166 |
| 828 | i-$C_3H_7$ | $CH_2OCH_3$ | H | H | 2-$CH_3$-4-Cl | Oil |
| 829 | n-$C_4H_9$ | H | H | H | 4-$CF_3$ | 171–173 |
| 830 | n-$C_4H_9$ | H | H | 3-$NO_2$ | 2-$CH_3$-5-Cl | 172–174 |
| 831 | i-$C_4H_9$ | H | H | 3-$NO_2$ | 2-$CH_3$-5-Cl | 186–188 |
| 832 | i-$C_4H_9$ | H | H | 3-$NO_2$ | 2-$CH_3$-4-$OCHF_2$ | 192–193 |
| 833 | i-$C_4H_9$ | H | H | H | 4-$CF_3$ | 149–151 |
| 834 | i-$C_4H_9$ | $CH_3$ | H | 6-$NO_2$ | 2-$CH_3$-4-$OCHF_2$ | 135–137 |
| 835 | s-$C_4H_9$ | H | H | H | 4-$CF_3$ | 194–195 |
| 836 | s-$C_4H_9$ | H | H | 3-Cl | 2-$CH_3$-4-$OCHF_2$ | 203–205 |
| 837 | s-$C_4H_9$ | H | H | 6-Cl | 2-$CH_3$-4-$OCHF_2$ | 213–215 |
| 838 | s-$C_4H_9$ | H | H | 3-$NO_2$ | 2-$CH_3$-5-Cl | 205–207 |
| 839 | s-$C_4H_9$ | H | H | 3-$NO_2$ | 2-$CH_3$-4-$OCHF_2$ | 228–229 |
| 840 | t-$C_4H_9$ | H | H | H | H | 237–239 |
| 841 | t-$C_4H_9$ | H | H | H | 2-$CH_3$-5-Cl | 200–202 |
| 842 | t-$C_4H_9$ | H | H | 3-$NO_2$ | 2-$CH_3$-5-Cl | 256–258 |
| 843 | t-$C_4H_9$ | H | H | 3-$NO_2$ | 2-$CH_3$-4-$OCHF_2$ | 172–173 |
| 844 | $CH_2C(CH_3)_3$ | H | H | 3-$NO_2$ | 2-$CH_3$-4-$OCHF_2$ | 226–227 |
| 845 | $CH(C_2H_5)_2$ | H | H | 3-$NO_2$ | 2-$CH_3$-4-$OCHF_2$ | 245–246 |
| 846 | $CH(CH_3)CH(CH_3)_2$ | H | H | 3-$NO_2$ | 2-$CH_3$-4-$OCHF_2$ | 245–247 |
| 847 | n-$C_6H_{17}$ | H | H | 3-$NO_2$ | 2-$CH_3$-5-Cl | 164–166 |
| 848 | c-$C_3H_5$ | H | H | H | 4-$CF_3$ | 195–197 |
| 849 | c-$C_3H_5$ | H | H | 3-Cl | 2-$CH_3$-4-$OCHF_2$ | 156–158 |
| 850 | c-$C_3H_5$ | H | H | 6-Cl | 2-$CH_3$-4-$OCHF_2$ | 179–181 |
| 851 | c-$C_3H_5$ | H | H | 3-$NO_2$ | 2-$CH_3$-5-Cl | 194–196 |
| 852 | c-$C_3H_5$ | H | H | 3-$NO_2$ | 2-$CH_3$-4-$OCHF_2$ | 191–192 |
| 853 | c-$C_4H_7$ | H | H | H | 2-$CH_3$-5-Cl | 205–207 |
| 854 | c-$C_4H_7$ | H | H | 3-$NO_2$ | 2-$CH_3$-5-Cl | 206–208 |
| 855 | c-$C_4H_7$ | H | H | 3-$NO_2$ | 2-$CH_3$-5-F | 199–201 |
| 856 | C-$C_5H_9$ | H | H | 3-$NO_2$ | 2-$CH_3$-4-$OCHF_2$ | 219–220 |
| 857 | c-$C_5H_9$ | H | H | H | 4-$CF_3$ | 208–210 |
| 858 | c-$C_5H_9$ | H | H | 3-$NO_2$ | 2-$CH_3$-5-Cl | 200–202 |
| 859 | c-$C_6H_{11}$ | H | H | 3-$NO_2$ | 2-$CH_3$-5-Cl | 225–227 |
| 860 | $CH_2$—$C_3H_5$-c | H | H | 3-$NO_2$ | 2-$CH_3$-5-F | 190–192 |
| 861 | $CH_2CH_2Cl$ | H | H | 3-$NO_2$ | 2-$CH_3$-5-F | 179–181 |
| 862 | $CH_2CH_2F$ | H | H | 3-$NO_2$ | 2-$CH_3$-5-F | 179–181 |
| 863 | $CH_2CH_2F$ | H | H | 3-$NO_2$ | 2-$CH_3$-4-$OCHF_2$ | 190–191 |
| 864 | $CH_2CF_3$ | H | H | H | 2-$CH_3$-5-Cl | 187–189 |
| 865 | $CH_2CH=CH_2$ | H | H | H | 4-$CF_3$ | 161–163 |
| 866 | $CH_2CH=CH_2$ | H | H | 3-$NO_2$ | 2-$CH_3$-5-Cl | 175–177 |
| 867 | $CH_2CH=CH_2$ | H | H | 3-$NO_2$ | 2-$CH_3$-4-$OCHF_2$ | 194–195 |
| 868 | $CH_2C\equiv CH$ | H | H | H | 4-$CF_3$ | 185–188 |
| 869 | $CH_2C\equiv CH$ | H | H | 3-$NO_2$ | 2-$CH_3$-5-Cl | 191–193 |
| 870 | $CH_2C\equiv CH$ | H | H | 3-$NO_2$ | 2-$CH_3$-4-$OCHF_2$ | 190–191 |
| 871 | $CH_2CH_2OCH_3$ | H | H | 3-$NO_2$ | 2-$CH_3$-5-Cl | 165–167 |
| 872 | $CH_2CH_2OCH_3$ | H | H | 3-$NO_2$ | 2-$CH_3$-4-$OCHF_2$ | 165–167 |
| 873 | $CH(CH_3)CH_2OCH_3$ | H | H | H | 4-$CF_3$ | 252–253 |
| 874 | $CH(CH_3)CH_2OCH_3$ | H | H | 3-$NO_2$ | 2-$CH_3$-4-$OCHF_2$ | 153–155 |
| 875 | $CH_2CH(OC_2H_5)_2$ | H | H | 3-$NO_2$ | 2-$CH_3$-4-$OCHF_2$ | 149–151 |
| 876 | $CH_2$-Ph | H | H | H | 4-$CF_3$ | 148–150 |
| 877 | $CH_2$-Ph | H | H | 3-$NO_2$ | 2-$CH_3$-5-Cl | 196–198 |
| 878 | $CH(CH_3)$-Ph | H | H | 3-$NO_2$ | 2-$CH_3$-5-Cl | 168–170 |
| 879 | $CH(CH_3)$-Ph | H | H | 3-$NO_2$ | 2-$CH_3$-4-$OCHF_2$ | 187–189 |
| 880 | $CH_2CH_2O$-(2,4-$(CH_3)_2$-Ph | H | H | 3-$NO_2$ | 2-$CH_3$-5-Cl | 126–128 |
| 881 | —$CH_2CH_2CH_2CH_2$— | | H | H | 4-$CF_3$ | 170–171 |
| 882 | —$CH_2CH_2CH_2CH_2$— | | H | 6-$NO_2$ | 2-$CH_3$-5-Cl | 157–159 |
| 883 | —$CH_2CH_2CH_2CH_2$— | | H | 6-$NO_2$ | 2-$CH_3$-4-$OCHF_2$ | 163–165 |
| 884 | —$CH_2CH_2OCH_2CH_2$— | | H | H | 4-$CF_3$ | 167–168 |
| 885 | —$CH_2CH_2OCH_2CH_2$— | | H | 6-$NO_2$ | 2-$CH_3$-5-Cl | 192–194 |
| 886 | —$CH_2CH_2OCH_2CH_2$— | | H | 6-$NO_2$ | 2-$CH_3$-4-$OCHF_2$ | 186–188 |
| 887 | —$CH_2CH(CH_3)OCH(CH_3)CH_2$— | | H | 6-$NO_2$ | 3-$CF_3$-5-$OCH_3$ | 164–165 |
| 888 | $CH_2$-3-Pyi | H | H | 3-$NO_2$ | 2-$CH_3$-4-Br | 180–182 |
| 889 | i-$C_3H_7$ | H | H | H | 4-$CF_2CF_3$ | 155–157 |
| 890 | i-$C_3H_7$ | H | H | 3-$NO_2$ | 4-$CF_2CF_3$ | 223–225 |
| 891 | i-$C_3H_7$ | H | H | 3-F | 4-$CF_2CF_3$ | 199–201 |
| 892 | i-$C_3H_7$ | H | H | 6-F | 4-$CF_2CF_3$ | 213–215 |
| 893 | i-$C_3H_7$ | H | H | 3-Cl | 4-$CF_2CF_3$ | 214–216 |
| 894 | i-$C_3H_7$ | H | H | 6-Cl | 4-$CF_2CF_3$ | 225–227 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 895 | i-$C_3H_7$ | H | H | 3-I | 4-$CF_2CF_3$ | 208–210 |
| 896 | i-$C_3H_7$ | H | H | 6-I | 4-$CF_2CF_3$ | 224–226 |
| 897 | i-$C_3H_7$ | H | H | H | 2-$CH_3$-4-$OSO_2$-(4-$CH_3$-Ph) | 135–137 |
| 898 | i-$C_3H_7$ | H | H | 3-$NO_2$ | 2-$CH_3$-4-$OSO_2$-(4-$CH_3$-Ph) | 208–210 |
| 899 | i-$C_3H_7$ | H | H | 3-Cl | 2-$CH_3$-4-$OSO_2$-(4-$CH_3$-Ph) | 187–189 |
| 900 | i-$C_3H_7$ | H | H | 6-Cl | 2-$CH_3$-4-$OSO_2$-(4-$CH_3$-Ph) | 218–220 |
| 901 | i-$C_3H_7$ | H | H | 3-F | 2-F-4-O-(4-$CF_3$-2-Cl-Ph) | 137–139 |
| 902 | i-$C_3H_7$ | H | H | 6-F | 2-F-4-O-(4-$CF_3$-2-Cl-Ph) | 155–157 |
| 903 | i-$C_3H_7$ | H | H | 3-Cl | 2-F-4-O-(4-$CF_3$-2-Cl-Ph) | 119–121 |
| 904 | i-$C_3H_7$ | H | H | 6-Cl | 2-F-4-O-(4-$CF_3$-2-Cl-Ph) | 154–156 |
| 905 | i-$C_3H_7$ | H | H | 3-F | 2-$CH_3$-4-$SCF_2CF_3$ | 140–142 |
| 906 | i-$C_3H_7$ | H | H | 6-F | 2-$CH_3$-4-$SCF_2CF_3$ | 162–164 |
| 907 | i-$C_3H_7$ | H | H | 3-Cl | 2-$CH_3$-4-$SCF_2CF_3$ | 172–173 |
| 908 | i-$C_3H_7$ | H | H | 6-Cl | 2-$CH_3$-4-$SCF_2CF_3$ | 193–195 |
| 909 | i-$C_3H_7$ | H | H | 3-I | 2-$CH_3$-4-$SCF_2CF_3$ | 207–209 |
| 910 | i-$C_3H_7$ | H | H | 6-I | 2-$CH_3$-4-$SCF_2CF_3$ | 196–198 |
| 911 | i-$C_3H_7$ | H | H | 3-Cl | 4-CH=C(Cl)$CF_3$ | 196.3–208.2 |
| 912 | i-$C_3H_7$ | H | H | 6-Cl | 4-CH=C(Cl)$CF_3$ | 202.8–209.4 |
| 913 | i-$C_3H_7$ | H | H | 3-Cl | 4-CH=$CBr_2$ | 209.8–214.8 |
| 914 | i-$C_3H_7$ | H | H | 6-Cl | 4-CH=$CBr_2$ | 207.7–213.9 |
| 915 | i-$C_3H_7$ | H | H | 3-Cl | 4-CH=$CCl_2$ | 120.1 |
| 916 | i-$C_3H_7$ | H | H | 6-Cl | 4-CH=$CCl_2$ | 199.7 |
| 917 | i-$C_3H_7$ | H | H | 3-I | 4-CH=C(Cl)$CF_3$ | 196.6 |
| 918 | i-$C_3H_7$ | H | H | 6-I | 4-CH=C(Cl)$CF_3$ | 203.3 |
| 919 | i-$C_3H_7$ | H | H | 3-I | 2-$C_2H_5$-4-I | 195.5 |
| 920 | i-$C_3H_7$ | H | H | 6-I | 2-$C_2H_5$-4-I | 242.3 |
| 921 | $C_2H_5$ | H | H | H | 2-$C_2H_5$-3-Cl-6-$C_2H_5$ | 171–173 |
| 922 | i-$C_3H_7$ | H | H | H | 2-$C_2H_5$-3-Cl-6-$C_2H_5$ | 185–186 |
| 923 | t-$C_4H_9$ | H | H | H | 2-$C_2H_5$-3-Cl-6-$C_2H_5$ | 166–167 |
| 924 | i-$C_3H_7$ | H | H | 3-Cl | 2-$C_2H_5$-3-Cl-6-$C_2H_5$ | 260–261 |
| 925 | i-$C_3H_7$ | H | H | 3-I | 2-$C_2H_5$-3-Cl-6-$C_2H_5$ | 269–271 |
| 926 | t-$C_4H_9$ | H | H | 3-Cl | 2-$C_2H_5$-3-Cl-6-$C_2H_5$ | 221–222 |
| 927 | t-$C_4H_9$ | H | H | H | 2-$CH_3$-4-Cl | 216–218 |
| 928 | t-$C_4H_9$ | H | H | H | 4-$CF_3$ | 220–221 |
| 929 | t-$C_4H_9$ | H | H | H | 4-$OCF_3$ | 178–179 |
| 930 | t-$C_4H_9$ | H | H | H | 2-$CH_3$-4-$OCF_3$ | 184–185 |
| 931 | t-$C_4H_9$ | H | H | H | 2-$CH_3$-4-$CF_2CF_3$ | 223–224 |
| 932 | t-$C_4H_9$ | H | H | 3-Cl | 2-$CH_3$-4-$CF_2CF_3$ | 219–220 |
| 933 | t-$C_4H_9$ | H | $CH_3$ | H | 4-$OCF_3$ | 155–158 |
| 934 | t-$C_4H_9$ | H | H | 3-Cl | 4-$CF_3$ | 228–229 |
| 935 | t-$C_4H_9$ | H | H | 6-Cl | 4-$CF_3$ | 253–255 |
| 936 | t-$C_4H_9$ | H | H | 3-Cl | 4-$OCF_3$ | 268–270 |
| 937 | t-$C_4H_9$ | H | H | 3-Cl | 2-$CH_3$-4-Cl | 242–244 |
| 938 | t-$C_4H_9$ | H | H | 6-Cl | 2-$CH_3$-4-Cl | 262–264 |
| 939 | t-$C_4H_9$ | H | H | 3-I | 4-$CF_3$ | 268–269 |
| 940 | t-$C_4H_9$ | H | H | 3-I | 4-$OCF_3$ | 263–265 |
| 941 | t-$C_4H_9$ | H | H | 3-I | 2-$CH_3$-4-Cl | 218–220 |
| 942 | t-$C_4H_9$ | H | H | 3-I | 2-$CH_3$-4-$CF_2CF_3$ | 205–207 |
| 943 | t-$C_4H_9$ | H | H | 6-I | 2-$CH_3$-4-$CF_2CF_3$ | 216–217 |
| 944 | t-$C_4H_9$ | H | H | 3-Cl | 2-$CH_3$-4-$OCF_3$ | 260–262 |
| 945 | n-$C_4H_9$ | H | H | 3-I | 2-$CH_3$-4-$CF_2CF_3$ | 173.1–178.5 |
| 946 | n-$C_4H_9$ | H | H | 6-I | 2-$CH_3$-4-$CF_2CF_3$ | 181.8–187.7 |
| 947 | n-$C_5H_{11}$ | H | H | 3-I | 2-$CH_3$-4-$CF_2CF_3$ | 140.2–151.4 |
| 948 | n-$C_5H_{11}$ | H | H | 6-I | 2-$CH_3$-4-$CF_2CF_3$ | 168.7–171.3 |
| 949 | n-$C_6H_{13}$ | H | H | 3-I | 2-$CH_3$-4-$CF_2CF_3$ | 135.5–143.9 |
| 950 | n-$C_6H_{13}$ | H | H | 6-I | 2-$CH_3$-4-$CF_2CF_3$ | 167.1–169.9 |
| 951 | i-$C_3H_7$ | H | H | 3-I | 2-$C_2H_5$-4-I | 254.8–273.8 |
| 952 | i-$C_3H_7$ | H | H | 3-I | 2-n-$C_3H_7$-4-I | 179.7 |
| 953 | i-$C_3H_7$ | H | H | 3-$CH_3$ | 2-$CH_3$-4-$CF_2CF_3$ | 184–186 |
| 954 | i-$C_3H_7$ | H | H | 6-$CH_3$ | 2-$CH_3$-4-$CF_2CF_3$ | 177–179 |
| 955 | t-$C_4H_9$ | H | H | 3-$CH_3$ | 2-$CH_3$-4-$CF_2CF_3$ | 198–200 |
| 956 | t-$C_4H_9$ | H | H | 6-$CH_3$ | 2-$CH_3$-4-$CF_2CF_3$ | 236–237 |
| 957 | t-$C_4H_9$ | H | H | 3-I | 2-$CH_3$-4-$OCF_3$ | 208–210 |
| 958 | t-$C_4H_9$ | H | H | 6-I | 2-$CH_3$-4-$OCF_3$ | 253–255 |
| 959 | n-$C_3H_7$ | H | H | 3-I | 2-$CH_3$-3-Cl | 190–192 |
| 960 | n-$C_3H_7$ | H | H | 6-I | 2-$CH_3$-3-Cl | 159–161 |
| 961 | n-$C_3H_7$ | H | H | 6-I | 2-$C_2H_5$-3-Cl-6-$C_2H_5$ | 225–228 |
| 962 | i-$C_3H_7$ | H | H | 3-$NO_2$ | 4-$OCOCF_3$ | 185–187 |
| 963 | i-$C_3H_7$ | H | H | 3-Cl | 4-$OCOCF_3$ | Paste |
| 964 | i-$C_3H_7$ | H | H | 3-I | 4-$OCOCF_3$ | Paste |
| 965 | i-$C_3H_7$ | H | H | 3-I | 2-i-$C_3H_7$-4-I | 132.5 |
| 966 | i-$C_3H_7$ | H | H | 3-I | 2-n-$C_4H_9$-4-I | 194.2–198.3 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 967 | i-$C_3H_7$ | H | H | 3-I | 2-$CH_3$-4-Br-6-$CH_3$ | 119.1 |
| 968 | i-$C_3H_7$ | H | H | 3-Cl | 4-$CO_2CH(CF_3)_2$ | 168–170 |
| 969 | i-$C_3H_7$ | H | H | 3-I | 4-$CO_2CH(CF_3)_2$ | 193–195 |
| 970 | i-$C_3H_7$ | H | H | 3-$NO_2$ | 4-$CO_2CH(CF_3)_2$ | 215–217 |
| 971 | i-$C_3H_7$ | H | H | 3-Cl | 2-$CH_3$-4-C≡C-(2,4-$Cl_2$-Ph) | 123–125 |
| 972 | i-$C_3H_7$ | H | H | 3-I | 2-$CH_3$-4-C≡C-(2,4-$Cl_2$-Ph) | 138–140 |
| 973 | i-$C_3H_7$ | H | H | 3-Cl | 3-$OCF_2CF_2$-4 | 125–128 |
| 974 | i-$C_3H_7$ | H | H | 3-I | 3-$OCF_2CF_2$-4 | 123–126 |
| 975 | i-$C_3H_7$ | H | H | H | 3-$OCF_2CF_2O$-4 | 152–154 |
| 976 | i-$C_3H_7$ | H | H | 3-$NO_2$ | 3-$OCF_2CF_2O$-4 | 247–248 |
| 977 | i-$C_3H_7$ | H | H | 3-Cl | 3-$OCF_2CF_2O$-4 | 224–226 |
| 978 | i-$C_3H_7$ | H | H | H | 4-$C(CF_3)_2OH$ | 87–89 |
| 979 | i-$C_3H_7$ | H | H | 3-$NO_2$ | 4-$C(CF_3)_2OH$ | 205–207 |
| 980 | i-$C_3H_7$ | H | H | 3-Cl | 4-$C(CF_3)_2OH$ | 187–189 |
| 981 | $CH_2CH_2OCH_3$ | H | H | 3-I | 2-$CH_3$-4-$CF_2CF_3$ | 145.3–151.7 |
| 982 | $CH_2CH_2OCH_3$ | H | H | 6-I | 2-$CH_3$-4-$CF_2CF_3$ | 166.7–169.4 |
| 983 | $CH_2CH_2OC_2H_5$ | H | H | 3-I | 2-$CH_3$-4-$CF_2CF_3$ | 146.5–150.3 |
| 984 | $CH_2CH_2OC_2H_5$ | H | H | 6-I | 2-$CH_3$-4-$CF_2CF_3$ | 157.3–160.4 |
| 985 | $(CH_2)_3OCH_3$ | H | H | 3-I | 2-$CH_3$-4-$CF_2CF_3$ | 151.9–155.8 |
| 986 | $(CH_2)_3OCH_3$ | H | H | 6-I | 2-$CH_3$-4-$CF_2CF_3$ | 156.5–158.8 |
| 987 | $CH_2CH=CH_2$ | H | H | 3-I | 2-$CH_3$-4-$CF_2CF_3$ | 157.5 |
| 988 | $CH_2CH=CH_2$ | H | H | 6-I | 2-$CH_3$-4-$CF_2CF_3$ | 164.6–171.3 |
| 989 | $CH_2C≡CH$ | H | H | 3-I | 2-$CH_3$-4-$CF_2CF_3$ | 153.6–158.4 |
| 990 | $CH_2C≡CH$ | H | H | 6-I | 2-$CH_3$-4-$CF_2CF_3$ | 171.5–178.1 |
| 991 | c-$C_5H_9$ | H | H | 3-I | 2-$CH_3$-4-$CF_2CF_3$ | 212.9 |
| 992 | c-$C_5H_9$ | H | H | 6-I | 2-$CH_3$-4-$CF_2CF_3$ | 205.2 |
| 993 | c-$C_6H_{11}$ | H | H | 3-I | 2-$CH_3$-4-$CF_2CF_3$ | 219.7–224.3 |
| 994 | c-$C_6H_{11}$ | H | H | 6-I | 2-$CH_3$-4-$CF_2CF_3$ | 239.0–244.4 |
| 995 | i-$C_3H_7$ | H | H | H | 4-$SCF_3$ | 182–184 |
| 996 | i-$C_3H_7$ | H | H | 3-$NO_2$ | 4-$SCF_3$ | 228–229 |
| 997 | i-$C_3H_7$ | H | H | 3-Cl | 4-$SCF_3$ | 229–231 |
| 998 | i-$C_3H_7$ | H | H | 3-I | 4-$SCF_3$ | 226–227 |
| 999 | i-$C_3H_7$ | H | H | H | 4-$SOCF_3$ | 175–178 |
| 1000 | i-$C_3H_7$ | H | H | 3-$NO_2$ | 4-$SOCF_3$ | 202–205 |
| 1001 | i-$C_3H_7$ | H | H | 3-Cl | 4-$SOCF_3$ | 242–244 |
| 1002 | i-$C_3H_7$ | H | H | 3-I | 4-$SOCF_3$ | 229–231 |
| 1003 | i-$C_3H_7$ | H | H | 3-I | 3-$OCF_2CF_2O$-4 | 163–165 |
| 1004 | i-$C_3H_7$ | H | H | 3-I | 4-$C(CF_3)_2OH$ | 227–229 |
| 1005 | i-$C_4H_9$ | H | H | 3-I | 2-$CH_3$-4-$CF_2CF_3$ | 200.4–206.8 |
| 1006 | i-$C_4H_9$ | H | H | 6-I | 2-$CH_3$-4-$CF_2CF_3$ | 179.2–181.8 |
| 1007 | s-$C_4H_9$ | H | H | 3-I | 2-$CH_3$-4-$CF_2CF_3$ | 226.0–230.9 |
| 1008 | s-$C_4H_9$ | H | H | 6-I | 2-$CH_3$-4-$CF_2CF_3$ | 216.1–218.0 |
| 1009 | s-$C_5H_{11}$ | H | H | 3-I | 2-$CH_3$-4-$CF_2CF_3$ | 215.3–218.2 |
| 1010 | s-$C_5H_{11}$ | H | H | 6-I | 2-$CH_3$-4-$CF_2CF_3$ | 191.4–210.5 |
| 1011 | $CH(C_2H_5)_2$ | H | H | 3-I | 2-$CH_3$-4-$CF_2CF_3$ | 234.8–236.9 |
| 1012 | $CH(C_2H_5)_2$ | H | H | 6-I | 2-$CH_3$-4-$CF_2CF_3$ | 253.7–255.7 |
| 1013 | $CH(C_2H_5)CH_2O—CH_3$ | H | H | 3-I | 2-$CH_3$-4-$CF_2CF_3$ | 177 |
| 1014 | $CH(C_2H_5)CH_2O—CH_3$ | H | H | 6-I | 2-$CH_3$-4-$CF_2CF_3$ | 198.3–201.0 |
| 1015 | i-$C_5H_{11}$ | H | H | 3-I | 2-$CH_3$-4-$CF_2CF_3$ | 190.0–192.5 |
| 1016 | i-$C_5H_{11}$ | H | H | 6-I | 2-$CH_3$-4-$CF_2CF_3$ | 187.8 |
| 1017 | i-$C_3H_7$ | H | H | 3-I | 2-$C_2H_5$-4-$CF_2CF_3$ | 232.5–235.8 |
| 1018 | t-$C_4H_9$ | H | H | H | 2-$CH_3$-4-$OCHF_2$ | 138–140 |
| 1019 | t-$C_4H_9$ | H | H | 3-Cl | 2-$CH_3$-4-$OCHF_2$ | 206–208 |
| 1020 | t-$C_4H_9$ | H | H | 3-I | 2-$CH_3$-4-$OCHF_2$ | 204–206 |
| 1021 | t-$C_4H_9$ | H | H | H | 2-Cl-4-$OCF_3$ | 162–164 |
| 1022 | t-$C_4H_9$ | H | H | 3-Cl | 2-Cl-4-$OCF_3$ | 189–191 |
| 1023 | t-$C_4H_9$ | H | H | 3-I | 2-Cl-4-$OCF_3$ | 188–190 |
| 1024 | c-$C_3H_5$ | H | H | 3-I | 2-$CH_3$-4-$CF_2CF_3$ | 156.0–165.0 |
| 1025 | c-$C_3H_5$ | H | H | 6-I | 2-$CH_3$-4-$CF_2CF_3$ | 173.2–176.4 |
| 1026 | $CH_2CH(CH_3)—C_2H_5$ | H | H | 3-I | 2-$CH_3$-4-$CF_2CF_3$ | 148.6 |
| 1027 | $CH_2CH(CH_3)—C_2H_5$ | H | H | 6-I | 2-$CH_3$-4-$CF_2CF_3$ | 157.8 |
| 1028 | $CH_2$-c-$C_6H_{11}$ | H | H | 3-I | 2-$CH_3$-4-$CF_2CF_3$ | 186.8–188.7 |
| 1029 | $CH2(4$-t-$C_4H_9$-c-$C_6H_{11})$ | H | H | 3-I | 2-$CH_3$-4-$CF_2CF_3$ | 226.0–231.2 |
| 1030 | $CH2(4$-t-$C_4H_9$-c-$C_6H_{11})$ | H | H | 6-I | 2-$CH_3$-4-$CF_2CF_3$ | 215.4 |
| 1031 | $CH(CH_3)CH_2O—CH_3$ | H | H | 3-I | 2-$CH_3$-4-$CF_2CF_3$ | 187.2–189.9 |
| 1032 | $CH(CH_3)CH_2O—CH_3$ | H | H | 6-I | 2-$CH_3$-4-$CF_2CF_3$ | 169.7–176.1 |
| 1033 | $CH(CH_3)CH—(CH_3)_2$ | H | H | 3-I | 2-$CH_3$-4-$CF_2CF_3$ | 208.3–212.7 |
| 1034 | $CH(CH_3)CH—(CH_3)_2$ | H | H | 6-I | 2-$CH_3$-4-$CF_2CF_3$ | 219.3–223.0 |
| 1035 | $C_2H_5$ | $C_2H_5$ | H | 3-I | 2-$CH_3$-4-$CF_2CF_3$ | 131.3 |
| 1036 | $C_2H_5$ | $C_2H_5$ | H | 6-I | 2-$CH_3$-4-$CF_2CF_3$ | 137 |
| 1037 | t-$C_4H_9$ | H | H | H | 2-$CH_3$-4-$CF(CF_3)_2$ | 172–175 |
| 1038 | t-$C_4H_9$ | H | H | 3-Cl | 2-$CH_3$-4-$CF(CF_3)_2$ | 241–243 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 1039 | t-$C_4H_9$ | H | H | 3-I | 2-$CH_3$-4-CF($CF_3$)$_2$ | 238–240 |
| 1040 | $CH_2CF_3$ | H | H | 3-I | 2-$CH_3$-4-$CF_2CF_3$ | 166.1–175.5 |
| 1041 | $CH_2CF_3$ | H | H | 6-I | 2-$CH_3$-4-$CF_2CF_3$ | 184.7–202.5 |
| 1042 | i-$C_3H_7$ | $CH_3$ | H | 3-I | 2-$CH_3$-4-$CF_2CF_3$ | 201.4 |
| 1043 | i-$C_4H_9$ | $CH_3$ | H | 3-I | 2-$CH_3$-4-$CF_2CF_3$ | 183.5–189.0 |
| 1044 | n-$C_3H_7$ | n-$C_3H_7$ | H | 3-I | 2-$CH_3$-4-$CF_2CF_3$ | 142.6–145.4 |
| 1045 | $CH_2CH=CH_2$ | $CH_2CH=CH_2$ | H | 3-I | 2-$CH_3$-4-$CF_2CF_3$ | 100.2–105.6 |
| 1046 | $CH_2CH_2O$—$C_2H_5$ | $CH_2CH_2O$—$C_2H_5$ | H | 3-I | 2-$CH_3$-4-$CF_2CF_3$ | 84.0–87.3 |
| 1047 | $CH_2CH_2CH_2CH_2$ | | H | 3-I | 2-$CH_3$-4-$CF_2CF_3$ | 172.7–177.3 |
| 1048 | $C_2H_5$ | $C_2H_5$ | H | 3-I | 2-$CH_3$-4-$CF_2CF_3$ | 119.1 |
| 1049 | t-$C_4H_9$ | H | H | H | 2-$CH_3$-4-OCBrF$_2$ | 195–197 |
| 1050 | t-$C_4H_9$ | H | H | 3-Cl | 2-$CH_3$-4-OCBrF$_2$ | 198–200 |
| 1051 | t-$C_4H_9$ | H | H | 3-I | 2-$CH_3$-4-OCBrF$_2$ | 196–198 |
| 1052 | t-$C_4H_9$ | H | H | H | 4-C($CF_3$)$_2$OH | 123–125 |
| 1053 | t-$C_4H_9$ | H | H | 3-Cl | 4-C($CF_3$)$_2$OH | 185–187 |
| 1054 | t-$C_4H_9$ | H | H | 3-I | 4-C($CF_3$)$_2$OH | 203–205 |
| 1055 | i-$C_3H_7$ | H | H | 3-I | 2,4-$F_2$ | 236–237 |
| 1056 | $C_2H_5$ | H | H | 3-I | 2-$CH_3$-4-OCF$_2$—CHF$_2$ | 176–178 |
| 1057 | $C_2H_5$ | H | H | 6-I | 2-$CH_3$-4-OCF$_2$—CHF$_2$ | 207–209 |
| 1058 | n-$C_3H_7$ | H | H | 3-I | 2-$CH_3$-4-OCF$_2$—CHF$_2$ | 185–187 |
| 1059 | n-$C_3H_7$ | H | H | 6-I | 2-$CH_3$-4-OCF$_2$—CHF$_2$ | 215–217 |
| 1060 | t-$C_4H_{11}$ | H | H | H | 2-$CH_3$-4-OCF$_2$—CHF$_2$ | 197–198 |
| 1061 | t-$C_4H_9$ | H | H | 3-Cl | 2-$CH_3$-4-OCF$_2$—CHF$_2$ | 192–194 |
| 1062 | t-$C_4H_9$ | H | H | 3-I | 2-$CH_3$-4-OCF$_2$—CHF$_2$ | 217–218 |
| 1063 | i-$C_3H_7$ | H | H | 3-Cl | 2-$CH_3$-4-O-(3,5-($CH_3O$)$_2$-2-Pym) | 186–188 |
| 1064 | i-$C_3H_7$ | H | H | 3-I | 2-$CH_3$-4-O-(3,5-($CH_3O$)$_2$-2-Pym) | 201–202 |
| 1065 | t-$C_4H_9$ | H | H | H | 3-OCF$_2$CF$_2$O-4 | 156–158 |
| 1066 | t-$C_4H_9$ | H | H | 3-Cl | 3-OCF$_2$CF$_2$O-4 | 240–241 |
| 1067 | t-$C_4H_9$ | H | H | 3-I | 3-OCF$_2$CF$_2$O-4 | 252–253 |
| 1068 | $CH_3$ | $CH_3$ | H | 3-I | 2-$CH_3$-4-$CF_2CF_3$ | 148.7 |
| 1069 | n-$C_3H_7$ | $CH_3$ | H | 3-I | 2-$CH_3$-4-$CF_2CF_3$ | 129.3 |
| 1070 | $CH_2CH_2OCH_2CH_2$ | | H | 3-I | 2-$CH_3$-4-$CF_2CF_3$ | 164.7 |
| 1071 | i-$C_3H_7$ | i-$C_3H_7$ | H | H | 2-$CH_3$-4-$CF_2CF_3$ | 169.1 |
| 1072 | i-$C_3H_7$ | i-$C_3H_7$ | H | 6-I | 2-$CH_3$-4-$CF_2CF_3$ | 201.2 |
| 1073 | $C_2H_5$ | H | H | 3-I | 2-$CH_3$-4-CF($CF_3$)$_2$ | 194–195 |
| 1074 | $C_2H_5$ | H | H | 6-I | 2-$CH_3$-4-CF($CF_3$)$_2$ | 218–220 |
| 1075 | n-$C_3H_7$ | H | H | 3-I | 2-$CH_3$-4-CF($CF_3$)$_2$ | 188–190 |
| 1076 | n-$C_3H_7$ | H | H | 6-I | 2-$CH_3$-4-CF($CF_3$)$_2$ | 201–203 |
| 1077 | i-$C_3H_7$ | H | H | H | 4-SO$_2$CF$_3$ | 184–186 |
| 1078 | i-$C_3H_7$ | H | H | 3-Cl | 4-SO$_2$CF$_3$ | 239–241 |
| 1079 | i-$C_3H_7$ | H | H | 3-I | 4-SO$_2$CF$_3$ | 225–227 |
| 1080 | t-$C_4H_9$ | H | H | 3-I | 4-SO$_2$CF$_3$ | 230–232 |
| 1081 | i-$C_3H_7$ | i-$C_3H_7$ | H | 3-I | 2-$CH_3$-4-$CF_2CF_3$ | Paste |
| 1082 | $CH_2CH_2CH_2CH_2CH_2$ | | H | 3-I | 2-$CH_3$-4-$CF_2CF_3$ | 140.0–146.8 |
| 1083 | $CH_2CH_2CH(CH_3)CH_2$—$CH_2$— | | H | 3-I | 2-$CH_3$-4-$CF_2CF_3$ | 171.4 |
| 1086 | i-$C_3H_7$ | H | H | H | 2-$CH_3$-4-OCF$_2$CF$_2$-Ph | 138–140 |
| 1087 | i-$C_3H_7$ | H | H | 3-Cl | 2-$CH_3$-4-OCF$_2$CF$_2$-Ph | 160–162 |
| 1088 | i-$C_3H_7$ | H | H | 3-I | 2-$CH_3$-4-OCF$_2$CF$_2$-Ph | 209–211 |
| 1089 | i-$C_3H_7$ | H | H | 3-NO$_2$ | 2-$CH_3$-4-OCF$_2$CF$_2$-Ph | 190–192 |
| 1090 | i-$C_3H_7$ | H | H | H | 2-$CH_3$-4-SCH$_2$CH$_2$—CF=CF$_2$ | 190–192 |
| 1091 | i-$C_3H_7$ | H | H | H | 2-$CH_3$-4-SOCH$_2$CH$_2$—CF=CF$_2$ | 149–153 |
| 1092 | i-$C_3H_7$ | H | H | H | 2-$CH_3$-4-SO$_2$CH$_2$—CH$_2$CF=CF$_2$ | 183–185 |
| 1093 | i-$C_3H_7$ | H | H | 3-Cl | 2-$CH_3$-4-SCH$_2$CH$_2$—CF=CF$_2$ | 168–170 |
| 1094 | i-$C_3H_7$ | H | H | 3-Cl | 2-$CH_3$-4-SOCH$_2$CH$_2$—CF=CF$_2$ | 164–167 |
| 1095 | i-$C_3H_7$ | H | H | 3-Cl | 2-$CH_3$-4-SO$_2$CH$_2$—CH$_2$CF=CF$_2$ | 181–183 |
| 1096 | i-$C_3H_7$ | H | H | 3-I | 2-$CH_3$-4-SCH$_2$CH$_2$—CF=CF$_2$ | 193–195 |
| 1097 | i-$C_3H_7$ | H | H | 3-I | 2-$CH_3$-4-SOCH$_2$CH$_2$—CF=CF$_2$ | 182–186 |
| 1098 | i-$C_3H_7$ | H | H | 3-I | 2-$CH_3$-4-SO$_2$CH$_2$—CH$_2$CF=CF$_2$ | 208–210 |
| 1099 | i-$C_3H_7$ | H | H | H | 3-OCF$_2$O-4 | 216–218 |
| 1100 | i-$C_3H_7$ | H | H | 3-NO$_2$ | 3-OCF$_2$O-4 | 227–229 |
| 1101 | i-$C_3H_7$ | H | H | 3-Cl | 3-OCF$_2$O-4 | 243–245 |
| 1102 | i-$C_3H_7$ | H | H | 3-I | 3-OCF$_2$O-4 | 229–231 |
| 1103 | t-$C_4H_9$ | H | H | H | 3-OCF$_2$O-4 | 209–211 |
| 1104 | t-$C_4H_9$ | H | H | 3-Cl | 3-OCF$_2$O-4 | 206–208 |
| 1105 | t-$C_4H_9$ | H | H | 3-I | 3-OCF$_2$O-4 | 228–230 |
| 1106 | i-$C_3H_7$ | H | H | H | 4-SCBrF$_2$ | 175–177 |
| 1107 | i-$C_3H_7$ | H | H | H | 4-SOCBrF$_2$ | 158–161 |
| 1108 | i-$C_3H_7$ | H | H | 3-NO$_2$ | 4-SCBrF$_2$ | 180–182 |
| 1109 | i-$C_3H_7$ | H | H | 3-NO$_2$ | 4-SOCBrF$_2$ | 195–198 |
| 1110 | i-$C_3H_7$ | H | H | 3-Cl | 4-SCBrF$_2$ | 156–158 |
| 1111 | i-$C_3H_7$ | H | H | 3-Cl | 4-SOCBrF$_2$ | 218–220 |
| 1112 | i-$C_3H_7$ | H | H | 3-I | 4-SCBrF$_2$ | 206–208 |

TABLE 1-continued ($Z^1, Z^2 = O$)

| No | $R^1$ | $R^2$ | $R^3$ | Xn | Ym | Physical Properties (melting point: °C) |
|---|---|---|---|---|---|---|
| 1113 | i-$C_3H_7$ | H | H | 3-I | 4-SOCBrF$_2$ | 158–160 |
| 1114 | t-$C_4H_9$ | H | H | 3-Cl | 4-SCBrF$_2$ | 210–212 |
| 1115 | t-$C_4H_9$ | H | H | 3-I | 4-SCBrF$_2$ | 219–220 |
| 1116 | $C_2H_5$ | $C_2H_5$ | H | 3-I | 2-$CH_3$-4-$CF_2CF_3$ | 179.8–183.7 |
| 1117 | $CH_2CH_2CH_2$—$CH_2CH_2CH_2$ | | H | 3-I | 2-$CH_3$-4-$CF_2CF_3$ | 170.7 |
| 1118 | $C_2H_5$ | $C_2H_5$ | H | 3-$NO_2$ | 2-$CH_3$-4-$OCF_3$ | 161.9 |
| 1119 | $C_2H_5$ | $C_2H_5$ | H | 3-$NO_2$ | 2-$CH_3$-4-$CF(CF_3)_2$ | 169.1 |
| 1120 | $CH_3$ | $CH_3$ | $CH_3$ | 3-I | 2-$CH_3$-4-$CF_2CF_3$ | 141.9–146.6 |
| 1121 | i-$C_3H_7$ | $CH_3$ | $CH_3$ | 3-I | 2-$CH_3$-4-$CF_2CF_3$ | Paste |
| 1122 | $C_2H_5$ | $C_2H_5$ | $CH_3$ | 3-I | 2-$CH_3$-4-$CF_2CF_3$ | Paste |
| 1123 | i-$C_3H_7$ | H | H | H | 4-$SCF_3$ | 135–137 |
| 1124 | i-$C_3H_7$ | H | H | 3-$NO_2$ | 4-$SCF_3$ | 187–189 |
| 1125 | i-$C_3H_7$ | H | H | 3-Cl | 4-$SCF_3$ | 192–194 |
| 1126 | i-$C_3H_7$ | H | H | 3-I | 4-$SCF_3$ | 194–196 |
| 1127 | t-$C_4H_9$ | H | H | 3-I | 4-$SCF_3$ | 195–197 |
| 1128 | $C_2H_5$ | $C_2H_5$ | H | 3-I | 4-$SCF_3$ | 173–175 |
| 1129 | $C_2H_5$ | $C_2H_5$ | H | 3-I | 3-$OCF_2O$-4 | 128–130 |
| 1130 | $C_2H_5$ | $C_2H_5$ | H | 3-I | 4-$C(CF_3)_2OH$ | 152–154 |
| 1131 | $C_2H_5$ | $C_2H_5$ | H | 3-$NO_2$ | 2-$CH_3$-4-$OCF_3$ | 178.7–182.6 |
| 1132 | $C_2H_5$ | $C_2H_5$ | H | 3-$NO_2$ | 2-$CH_3$-4-$OCF_2CHF_2$ | 160.8–165.0 |
| 1133 | $C_2H_5$ | $C_2H_5$ | H | 3-$NO_2$ | 2-Cl-4-$CF_2CF_3$ | 91.9–95.2 |
| 1134 | $C_2H_5$ | $C_2H_5$ | H | 3-$NO_2$ | 2-F-4-$CF_2CF_3$ | 162.6–166.8 |
| 1135 | $C_2H_5$ | $C_2H_5$ | H | 3-$NO_2$ | 2-$CH_3$-4-Cl | 188.8–190.8 |
| 1136 | $C_2H_5$ | $C_2H_5$ | H | 3-$NO_2$ | 4-$OCF_3$ | 185.7–187.9 |
| 1137 | $C_2H_5$ | $C_2H_5$ | H | 6-$NO_2$ | 2-$CH_3$-4-$OCF_2CHF_2$ | 111.2 |
| 1138 | $C_2H_5$ | $C_2H_5$ | H | 6-$NO_2$ | 2-$CH_3$-4-Cl | 149.7 |
| 1139 | $C_2H_5$ | $C_2H_5$ | H | 6-$NO_2$ | 4-$OCF_3$ | 173.4 |
| 1140 | $CH_2CH(CH_3)CH_2$—$CH(CH_3)CH_2$ | | H | 6-I | 2-$CH_3$-4-$CF_2CF_3$ | 166.4 |
| 1141 | t-$C_4H_9$ | H | H | 3-I | 2-$CH_3$-4-$CF_3$ | 197–198 |
| 1142 | i-$C_3H_7$ | H | H | 3-I | 3-N=$C(CF_2CF_3)O$-4 | 214–216 |
| 1143 | t-$C_4H_9$ | H | H | 3-I | 3-N=$C(CF_2CF_3)O$-4 | 253–254 |
| 1144 | $C_2H_5$ | $C_2H_5$ | H | 3-I | 2-$CH_3$-4-$CF_3$ | 160–161 |
| 1145 | i-$C_3H_7$ | H | H | H | 3-$OCHFCF_2O$-4 | 102–104 |
| 1146 | i-$C_3H_7$ | H | H | 3-$NO_2$ | 3-$OCHFCF_2O$-4 | 190–192 |
| 1147 | i-$C_3H_7$ | H | H | 3-Cl | 3-$OCHFCF_2O$-4 | 123–125 |
| 1148 | i-$C_3H_7$ | H | H | 3-I | 3-$OCHFCF_2O$-4 | 218–220 |
| 1149 | t-$C_4H_9$ | H | H | H | 3-$OCHFCF_2O$-4 | 165–167 |
| 1150 | t-$C_4H_9$ | H | H | 3-I | 3-$OCHFCF_2O$-4 | 240–241 |
| 1151 | $C_2H_5$ | $C_2H_5$ | H | 3-I | 3-$OCHFCF_2O$-4 | 193–195 |
| 1152 | t-$C_5H_{11}$ | H | H | 3-F | 2-$CH_3$-4-$CF_2CF_3$ | 223.3 |
| 1153 | t-$C_5H_{11}$ | H | H | 3-F | 2-$CH_3$-4-$CF(CF_3)_2$ | 222 |
| 1154 | t-$C_5H_{11}$ | H | H | 3-F | 2-$CH_3$-4-$OCF_3$ | 193.6–195.8 |
| 1155 | t-$C_5H_{11}$ | H | H | 3-F | 2-$CH_3$-4-$OCHF_2$ | 165.5–174.0 |
| 1156 | n-$C_3H_7$ | n-$C_3H_7$ | H | 3-I | 2-$CH_3$-4-$OCF_3$ | 132.2–135.0 |
| 1157 | n-$C_3H_7$ | n-$C_3H_7$ | H | 3-I | 2-$CH_3$-4-$OCHF_2$ | 81.4–87.8 |
| 1158 | n-$C_3H_7$ | n-$C_3H_7$ | H | 3-I | 2-$CH_3$-4-$OCF_2CHF_2$ | 116.3 |
| 1159 | i-$C_3H_7$ | $C_2H_5$ | H | 3-I | 2-$CH_3$-4-$CF_2CF_3$ | 124.4 |
| 1160 | i-$C_3H_7$ | $C_2H_5$ | H | 3-I | 4-$OCF_3$ | 137.3–144.1 |
| 1161 | i-$C_3H_7$ | H | H | 3-I | 3-$OCF_2CHFO$-4 | 161–163 |
| 1162 | i-$C_3H_7$ | H | H | 3-$NO_2$ | 3-$OCF_2CHFO$-4 | 238–240 |
| 1163 | i-$C_3H_7$ | H | H | 3-Cl | 3-$OCF_2CHFO$-4 | 243–245 |
| 1164 | i-$C_3H_7$ | H | H | 3-I | 3-$OCF_2CHFO$-4 | 192–194 |
| 1165 | t-$C_4H_9$ | H | H | H | 3-$OCF_2CHFO$-4 | 205–207 |
| 1166 | t-$C_4H_9$ | H | H | 3-I | 3-$OCF_2CHFO$-4 | 238–240 |
| 1167 | $C_2H_5$ | $C_2H_5$ | H | 3-I | 3-$OCF_2CHFO$-4 | 195–197 |
| 1168 | i-$C_3H_7$ | H | H | 3-I | 2-$CH_3$-4-$SOCF_3$ | 148–152 |
| 1169 | t-$C_4H_9$ | H | H | 3-I | 2-$CH_3$-4-$SOCF_3$ | 165–168 |
| 1173 | i-$C_3H_7$ | H | H | 3-I | 3-N=$C(4$-$CF_3$-Ph$)$-O-4 | 253–255 |
| 1174 | t-$C_4H_9$ | H | H | 3-I | 3-N=$C(4$-$CF_3$-Ph$)$-O-4 | 251–253 |
| 1175 | $C_2H_5$ | $C_2H_5$ | H | 3-I | 3-N=$C(4$-$CF_3$-Ph$)$-O-4 | 231–233 |
| 1176 | i-$C_3H_7$ | H | H | 3-I | 3-O—$C(2$-$CF_3$-Ph$)$=N-4 | 242–244 |
| 1177 | t-$C_4H_9$ | H | H | 3-I | 3-O—$C(2$-$CF_3$-Ph$)$=N-4 | 229–231 |
| 1178 | $C_2H_5$ | $C_2H_5$ | H | 3-I | 3-O—$C(2$-$CF_3$-Ph$)$=N-4 | 203–205 |
| 1179 | $C_2H_5$ | $C_2H_5$ | $C_2H_5$ | 3-I | 2-$CH_3$-4-$CF_2CF_3$ | Paste |
| 1180 | i-$C_3H_7$ | H | H | 3-I | 3-O—$C(CF_2CF_3)$ | 130–132 |
| 1181 | t-$C_4H_9$ | H | H | 3-I | 3-O—$C(CF_2CF_3)$=N-4 | 205–207 |
| 1182 | $C_2H_5$ | $C_2H_5$ | H | 3-I | 3-O—$C(CF_2CF_3)$=N-4 | 188–190 |
| 1183 | i-$C_3H_7$ | H | H | 3-$CF_3$ | 2-$CH_3$-4-$OCF_3$ | 222–224 |
| 1184 | i-$C_3H_7$ | H | H | 3-$CF_3$ | 2-$CH_3$-4-$CF_2CF_3$ | 219–221 |
| 1185 | $C_2H_5$ | $C_2H_5$ | H | 3-$CF_3$ | 2-$CH_3$-4-$OCF_3$ | 192–194 |
| 1186 | $C_2H_5$ | $C_2H_5$ | H | 3-$CF_3$ | 2-$CH_3$-4-$CF_2CF_3$ | 218–220 |
| 1187 | i-$C_3H_7$ | H | H | 3-Cl | 2-F-4-$OCF_3$ | 126–128 |

TABLE 1-continued ($Z^1$, $Z^2$ = O)

| No | $R^1$ | $R^2$ | $R^3$ | Xn | Ym | Physical Properties (melting point: °C. |
|---|---|---|---|---|---|---|
| 1188 | i-$C_3H_7$ | H | H | 3-I | 2-F-4-$OCF_3$ | 220–222 |
| 1189 | t-$C_4H_9$ | H | H | 3-I | 2-F-4-$OCF_3$ | 198–200 |
| 1190 | $C_2H_5$ | $C_2H_5$ | H | 3-I | 2-F-4-$OCF_3$ | 129–131 |
| 1191 | i-$C_3H_7$ | H | H | 3-$OCF_3$ | 2-$CH_3$-4-$CF_2CF_3$ | 190–192 |
| 1192 | t-$C_4H_9$ | H | H | 3-$OCF_3$ | 2-$CH_3$-4-$CF_2CF_3$ | 205–207 |
| 1193 | $C_2H_5$ | $C_2H_5$ | H | 3-$OCF_3$ | 2-$CH_3$-4-$CF_2CF_3$ | 146–148 |
| 1202 | i-$C_3H_7$ | H | H | 4-I | 2-$CH_3$-4-$CF_2CF_3$ | 197–199 |
| 1203 | i-$C_3H_7$ | H | H | 5-I | 2-$CH_3$-4-$CF_2CF_3$ | 201–203 |
| 1204 | i-$C_3H_7$ | H | H | 4-I | 2-$CH_3$-4-$OCHF_2$ | 241–243 |
| 1205 | i-$C_3H_7$ | H | H | 5-I | 2-$CH_3$-4-$OCHF_2$ | 214–216 |
| 1206 | i-$C_3H_7$ | H | H | 3-$CF_3$ | 2-$CH_3$-4-$OCF_2CHF_2$ | 195–197 |
| 1207 | i-$C_3H_7$ | H | H | 3-$CF_3$ | 2-$CH_3$-4-$CF(CF_3)_2$ | 227–229 |
| 1208 | i-$C_3H_7$ | H | H | H | 2-$C_2H_5$-4-$OCF_3$ | 160–162 |
| 1209 | i-$C_3H_7$ | H | H | 3-Cl | 2-$C_2H_5$-4-$OCF_3$ | 205–207 |
| 1210 | i-$C_3H_7$ | H | H | 3-I | 2-$C_2H_5$-4-$OCF_3$ | 241–243 |
| 1211 | t-$C_4H_9$ | H | H | 3-I | 2-$C_2H_5$-4-$OCF_3$ | 224–225 |
| 1212 | $C_2H_5$ | $C_2H_5$ | H | 3-I | 2-$C_2H_5$-4-$OCF_3$ | 141–143 |
| 1221 | i-$C_3H_7$ | H | H | 3,4-$Cl_2$ | 2-$CH_3$-4-$OCF_3$ | 199–200 |
| 1222 | i-$C_3H_7$ | H | H | 3,4-$Cl_2$ | 2-$CH_3$-4-$CF_2CF_3$ | 208–209 |
| 1223 | i-$C_3H_7$ | H | H | 3,4-$Cl_2$ | 2-$CH_3$-4-$CF(CF_3)_2$ | 228–229 |
| 1224 | i-$C_3H_7$ | H | H | 3,5-$Cl_2$ | 2-$CH_3$-4-$OCF_3$ | 228–230 |
| 1225 | i-$C_3H_7$ | H | H | 3,5-$Cl_2$ | 2-$CH_3$-4-$CF_2CF_3$ | 219–220 |
| 1226 | i-$C_3H_7$ | H | H | 3,5-$Cl_2$ | 2-$CH_3$-4-$CF(CF_3)_2$ | 211–212 |
| 1227 | i-$C_3H_7$ | H | H | 3-Cl-4-F | 2-$CH_3$-4-$OCF_3$ | 184–186 |
| 1228 | i-$C_3H_7$ | H | H | 3-Cl-4-F | 2-$CH_3$-4-$CF_2CF_3$ | 178–180 |
| 1229 | i-$C_3H_7$ | H | H | 3-Cl-4-F | 2-$CH_3$-4-$CF(CF_3)_2$ | 200–201 |
| 1230 | t-$C_4H_9$ | H | H | 3-$CF_3$ | 2-$CH_3$-4-$OCF_3$ | 209–210 |
| 1231 | t-$C_4H_9$ | H | H | 3-$CF_3$ | 2-$CH_3$-4-$CF_2CF_3$ | 210–211 |
| 1232 | t-$C_4H_9$ | H | H | 3-$CF_3$ | 2-$CH_3$-4-$CF(CF_3)_2$ | 242–243 |
| 1233 | i-$C_3H_7$ | H | H | 3-OCF | 2-$CH_3$-4-$OCF_3$ | 219–220 |
| 1234 | t-$C_4H_9$ | H | H | 3-$OCF_3$ | 2-$CH_3$-4-$OCF_3$ | 222–223 |
| 1235 | $C_2H_5$ | $C_2H_5$ | H | 3-$OCF_3$ | 2-$CH_3$-4-$OCF_3$ | 125–126 |
| 1236 | i-$C_3H_7$ | H | H | 3-$OCF_3$ | 2-$CH_3$-4-$CF(CF_3)_2$ | 235–236 |
| 1237 | t-$C_4H_9$ | H | H | 3-$OCF_3$ | 2-$CH_3$-4-$CF(CF_3)_2$ | 220–222 |
| 1238 | $C_2H_5$ | $C_2H_5$ | H | 3-$OCF_3$ | 2-$CH_3$-4-$CF(CF_3)_2$ | 156–157 |
| 1245 | i-$C_3H_7$ | H | H | 3-CN | 2-$CH_3$-4-$CF_2CF_3$ | 168–170 |
| 1246 | i-$C_3H_7$ | H | H | 4-I | 2-$CH_3$-4-$OCF_3$ | 238–240 |
| 1247 | i-$C_3H_7$ | H | H | 5-I | 2-$CH_3$-4-$OCF_3$ | 205–206 |
| 1248 | i-$C_3H_7$ | H | H | 4-I | 2-$CH_3$-4-$OCF_2CHF_2$ | 222–223 |
| 1249 | i-$C_3H_7$ | H | H | 5-I | 2-$CH_3$-4-$OCF_2CHF_2$ | 203–204 |
| 1250 | i-$C_3H_7$ | H | H | 4-I | 2-$CH_3$-4-$CF(CF_3)_2$ | 215–216 |
| 1251 | i-$C_3H_7$ | H | H | 5-I | 2-$CH_3$-4-$CF(CF_3)_2$ | 216–217 |
| 1256 | i-$C_3H_7$ | H | H | 3-Cl-4-F | 2-$CH_3$-4-$CF_2CF_3$ | 235–236 |
| 1257 | t-$C_4H_9$ | H | H | 3-Cl-4-F | 2-$CH_3$-4-$CF_2CF_3$ | 225–226 |
| 1258 | $C_2H_5$ | $C_2H_5$ | H | 3-Cl-4-F | 2-$CH_3$-4-$CF_2CF_3$ | 155–156 |
| 1259 | i-$C_3H_7$ | H | H | 3-Cl-4-F | 2-$CH_3$-4-$OCF_3$ | 229–231 |
| 1260 | t-$C_4H_9$ | H | H | 3-Cl-4-F | 2-$CH_3$-4-$OCF_3$ | 237–238 |
| 1261 | $C_2H_5$ | $C_2H_5$ | H | 3-Cl-4-F | 2-$CH_3$-4-$OCF_3$ | 140–141 |
| 1262 | i-$C_3H_7$ | H | H | 3-Cl-4-F | 2-$CH_3$-4-$CF(CF_3)_2$ | 264–265 |
| 1263 | t-$C_4H_9$ | H | H | 3-Cl-4-F | 2-$CH_3$-4-$CF(CF_3)_2$ | 253–154 |
| 1264 | $C_2H_5$ | $C_2H_5$ | H | 3-Cl-4-F | 2-$CH_3$-4-$CF(CF_3)_2$ | 158–159 |
| 1266 | i-$C_3H_7$ | H | H | 3,4-$Br_2$ | 2-$CH_3$-4-$CF_2CF_3$ | 162–164 |
| 1277 | i-$C_3H_7$ | H | H | 4-Cl | 2-$CH_3$-4-$CF_2CF_3$ | 185–186 |
| 1278 | t-$C_4H_9$ | H | H | 4-Cl | 2-$CH_3$-4-$CF_2CF_3$ | 206–207 |
| 1280 | $C_2H_5$ | $C_2H_5$ | H | 4-Cl | 2-$CH_3$-4-$CF_2CF_3$ | 163–164 |
| 1281 | $C_2H_5$ | $C_2H_5$ | H | 4-Cl-6-I | 2-$CH_3$-4-$CF_2CF_3$ | 193–194 |
| 1283 | i-$C_3H_7$ | H | H | 3,4-$F_2$ | 2-$CH_3$-4-$OCF_3$ | 194–195 |
| 1284 | t-$C_4H_9$ | H | H | 3,4-$F_2$ | 2-$CH_3$-4-$OCF_3$ | 216–217 |
| 1285 | $C_2H_5$ | $C_2H_5$ | H | 3,4-$F_2$ | 2-$CH_3$-4-$OCF_3$ | 156–157 |
| 1287 | i-$C_3H_7$ | H | H | 4,5-$F_2$ | 2-$CH_3$-4-$OCF_3$ | 195–196 |
| 1288 | t-$C_4H_9$ | H | H | 4,5-$F_2$ | 2-$CH_3$-4-$OCF_3$ | 223–224 |
| 1290 | i-$C_3H_7$ | H | H | 3-I | 2-$CH_3$-4-OC—($CF_2CF_3$)=C—($CF_3$)$_2$ | 226–227 |
| 1291 | i-$C_3H_7$ | H | H | 3-Cl | 2-$CH_3$-4-OC—($CF_2CF_3$)=C—($CF_3$)$_2$ | 204–205 |
| 1292 | i-$C_3H_7$ | H | H | 3-I | 2-$CH_3$-4-OC—($OCH_3$)=C—($CF_3$)$_2$ | 198–199 |
| 1293 | i-$C_3H_7$ | H | H | 3-Cl | 2-$CH_3$-4-OC—($OCH_3$)=C—($CF_3$)$_2$ | 179–180 |
| 1294 | $CH(CH_3)CH_2OH$ | H | H | H | 2-$CH_3$-4-$C_2F_5$ | 73–74 |
| 1295 | i-$C_3H_7$ | H | H | 6-Cl | 2-$OCH_3$-5-Ph | 120 |
| 1296 | i-$C_3H_7$ | H | H | 3-Cl | 2-$OCH_3$-5-Ph | 195 |
| 1297 | n-$C_3H_7$ | H | H | 6-Cl | 2-$OCH_3$-5-Ph | 200 |
| 1298 | $CH(CH_3)CH_2OH$ | H | H | 3-Cl | 2-$CH_3$-4-$C_2F_5$ | 195 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 1299 | $CH(C_2H_5)CH_2OH$ | H | H | H | $2\text{-}CH_3\text{-}4\text{-}C_2F_5$ | 78 |
| 1300 | $CH(CH_3)CH_2OH$ | H | H | 3-I | $2\text{-}CH_3\text{-}4\text{-}C_2F_5$ | 98–99 |
| 1301 | $i\text{-}C_3H_7$ | H | H | 3-Cl | $2\text{-}CH_3\text{-}4\text{-}C{\equiv}C\text{-}C_4H_9\text{-}t$ | 210 |
| 1302 | $i\text{-}C_3H_7$ | H | H | 6-Cl | $2\text{-}CH_3\text{-}4\text{-}C{\equiv}C\text{-}C_4H_9\text{-}t$ | 205 |
| 1303 | $n\text{-}C_3H_7$ | H | H | 3-I | $2\text{-}CH_3\text{-}4\text{-}C_2F_5$ | 200 |
| 1304 | $n\text{-}C_3H_7$ | H | H | 6-I | $2\text{-}CH_3\text{-}4\text{-}C_2F_5$ | 195 |
| 1305 | $i\text{-}C_3H_7$ | H | H | 3-I | $2\text{-}CH_3\text{-}4\text{-}C{\equiv}C\text{-}C_4H_9\text{-}t$ | 205 |
| 1306 | $i\text{-}C_3H_7$ | H | H | 6-I | $2\text{-}CH_3\text{-}4\text{-}C{\equiv}C\text{-}C_4H_9\text{-}t$ | 170 |
| 1307 | $CH_2\text{-}Ph$ | H | H | 3-Cl | $2\text{-}CH_3\text{-}4\text{-}C_2F_5$ | 175 |
| 1308 | $CH_2\text{-}Ph$ | H | H | 6-Cl | $2\text{-}CH_3\text{-}4\text{-}C_2F_5$ | 175 |
| 1309 | $CH_2\text{-}(2\text{-}Cl\text{-}Ph)$ | H | H | 3-Cl | $2\text{-}CH_3\text{-}4\text{-}C_2F_5$ | 170 |
| 1310 | $CH_2\text{-}(2\text{-}Cl\text{-}Ph)$ | H | H | 6-Cl | $2\text{-}CH_3\text{-}4\text{-}C_2F_5$ | 210 |
| 1311 | $CH_3$ | H | H | 3-I | $2\text{-}CH_3\text{-}4\text{-}C_2F_5$ | 190 |
| 1312 | $CH_3$ | H | H | 6-I | $2\text{-}CH_3\text{-}4\text{-}C_2F_5$ | 200 |
| 1313 | $C_2H_5$ | H | H | 3-I | $2\text{-}CH_3\text{-}4\text{-}C_2F_5$ | 182 |
| 1314 | $C_2H_5$ | H | H | 6-I | $2\text{-}CH_3\text{-}4\text{-}C_2F_5$ | 205 |
| 1315 | $CH_2CH(OH)CH_3$ | H | H | 3-Cl | $2\text{-}CH_3\text{-}4\text{-}C_2F_5$ | 187 |
| 1316 | $CH(C_2H_5)CH_2OH$ | H | H | 3-Cl | $2\text{-}CH_3\text{-}4\text{-}C_2F_5$ | 208 |
| 1317 | $C(CH_3)_2CH_2OH$ | H | H | 3-Cl | $2\text{-}CH_3\text{-}4\text{-}C_2F_5$ | 181–182 |
| 1318 | $CH_2CH(OH)C_2H_5$ | H | H | 3-Cl | $2\text{-}CH_3\text{-}4\text{-}C_2F_5$ | 171–172 |
| 1319 | $CH_2CH_2\text{-}Ph$ | H | H | 3-Cl | $2\text{-}CH_3\text{-}4\text{-}C_2F_5$ | 150 |
| 1320 | $CH_2CH_2\text{-}Ph$ | H | H | 6-Cl | $2\text{-}CH_3\text{-}4\text{-}C_2F_5$ | 190 |
| 1321 | $CH(CH_3)\text{-}Ph$ | H | H | 3-Cl | $2\text{-}CH_3\text{-}4\text{-}C_2F_5$ | 160 |
| 1322 | $CH(CH_3)\text{-}Ph$ | H | H | 6-Cl | $2\text{-}CH_3\text{-}4\text{-}C_2F_5$ | 190 |
| 1323 | $i\text{-}C_3H_7$ | H | H | 3-Cl | $2\text{-}CH_3\text{-}4\text{-}CH_2CH_2C(CH_3)_3$ | 220 |
| 1324 | $i\text{-}C_3H_7$ | H | H | 6-Cl | $2\text{-}CH_3\text{-}4\text{-}CH_2CH_2C(CH_3)_3$ | 205 |
| 1325 | $i\text{-}C_3H_7$ | H | H | 3-Cl | $2\text{-}CH_3\text{-}4\text{-}C{\equiv}C\text{-}Ph$ | 215 |
| 1326 | $i\text{-}C_3H_7$ | H | H | 6-Cl | $2\text{-}CH_3\text{-}4\text{-}C{\equiv}C\text{-}Ph$ | 230 |
| 1327 | $O\text{-}n\text{-}C_3H_7$ | H | H | 3-Cl | $2\text{-}CH_3\text{-}4\text{-}C_2F_5$ | 165 |
| 1328 | $O\text{-}n\text{-}C_3H_7$ | H | H | 6-Cl | $2\text{-}CH_3\text{-}4\text{-}C_2F_5$ | 150 |
| 1329 | $O\text{-}CH_2CH{=}CHCl$ (E) | H | H | 3-Cl | $2\text{-}CH_3\text{-}4\text{-}C_2F_5$ | 150 |
| 1330 | $i\text{-}C_3H_7$ | H | H | 3-Cl | $2\text{-}CH_3\text{-}4\text{-}CN$ | 230 |
| 1331 | $(CH_2)_3\text{-}Ph$ | H | H | 3-Cl | $2\text{-}CH_3\text{-}4\text{-}C_2F_5$ | 112 |
| 1332 | $(CH_2)_3\text{-}Ph$ | H | H | 6-Cl | $2\text{-}CH_3\text{-}4\text{-}C_2F_5$ | 105 |
| 1333 | $CH_2(4\text{-}Cl\text{-}Ph)$ | H | H | 3-Cl | $2\text{-}CH_3\text{-}4\text{-}C_2F_5$ | 198 |
| 1334 | $CH_2(4\text{-}Cl\text{-}Ph)$ | H | H | 6-Cl | $2\text{-}CH_3\text{-}4\text{-}C_2F_5$ | 156 |
| 1335 | $CH_2(3\text{-}Cl\text{-}Ph)$ | H | H | 3-Cl | $2\text{-}CH_3\text{-}4\text{-}C_2F_5$ | 168 |
| 1336 | $CH_2(3\text{-}Cl\text{-}Ph)$ | H | H | 6-Cl | $2\text{-}CH_3\text{-}4\text{-}C_2F_5$ | 177 |
| 1337 | $CH_2(2\text{-}CH_3\text{-}Ph)$ | H | H | 3-Cl | $2\text{-}CH_3\text{-}4\text{-}C_2F_5$ | 152 |
| 1338 | $CH_2(2\text{-}CH_3\text{-}Ph)$ | H | H | 6-Cl | $2\text{-}CH_3\text{-}4\text{-}C_2F_5$ | 147 |
| 1339 | $CH_2(3\text{-}CH_3\text{-}Ph)$ | H | H | 3-Cl | $2\text{-}CH_3\text{-}4\text{-}C_2F_5$ | Crystals |
| 1340 | $CH_2(3\text{-}CH_3\text{-}Ph)$ | H | H | 6-Cl | $2\text{-}CH_3\text{-}4\text{-}C_2F_5$ | 173 |
| 1341 | $CH_2(4\text{-}CH_3\text{-}Ph)$ | H | H | 3-Cl | $2\text{-}CH_3\text{-}4\text{-}C_2F_5$ | 175 |
| 1342 | $CH_2(4\text{-}CH_3\text{-}Ph)$ | H | H | 6-Cl | $2\text{-}CH_3\text{-}4\text{-}C_2F_5$ | Crystals |
| 1343 | $CH_2(2\text{-}CH_3O\text{-}Ph)$ | H | H | 3-Cl | $2\text{-}CH_3\text{-}4\text{-}C_2F_5$ | Crystals |
| 1344 | $CH_2(2\text{-}CH_3O\text{-}Ph)$ | H | H | 6-Cl | $2\text{-}CH_3\text{-}4\text{-}C_2F_5$ | 176 |
| 1345 | $CH_2(3\text{-}CH_3O\text{-}Ph)$ | H | H | 3-Cl | $2\text{-}CH_3\text{-}4\text{-}C_2F_5$ | 73 |
| 1346 | $CH_2(3\text{-}CH_3O\text{-}Ph)$ | H | H | 6-Cl | $2\text{-}CH_3\text{-}4\text{-}C_2F_5$ | 86 |
| 1347 | $CH_2(4\text{-}CH_3O\text{-}Ph)$ | H | H | 3-Cl | $2\text{-}CH_3\text{-}4\text{-}C_2F_5$ | 169 |
| 1348 | $CH_2(4\text{-}CH_3O\text{-}Ph)$ | H | H | 6-Cl | $2\text{-}CH_3\text{-}4\text{-}C_2F_5$ | 168 |
| 1349 | $CH_2(2,4\text{-}Cl_2\text{-}Ph)$ | H | H | 3-Cl | $2\text{-}CH_3\text{-}4\text{-}C_2F_5$ | 169 |
| 1350 | $CH_2(2,4\text{-}Cl_2\text{-}Ph)$ | H | H | 6-Cl | $2\text{-}CH_3\text{-}4\text{-}C_2F_5$ | 205 |
| 1351 | $CH_2(3,4\text{-}Cl_2\text{-}Ph)$ | H | H | 3-Cl | $2\text{-}CH_3\text{-}4\text{-}C_2F_5$ | 179 |
| 1352 | $CH_2(3,4\text{-}Cl_2\text{-}Ph)$ | H | H | 6-Cl | $2\text{-}CH_3\text{-}4\text{-}C_2F_5$ | 192 |
| 1353 | $CH_2(2,3\text{-}Cl_2\text{-}Ph)$ | H | H | 3-Cl | $2\text{-}CH_3\text{-}4\text{-}C_2F_5$ | 179 |
| 1354 | $CH_2(2,3\text{-}Cl_2\text{-}Ph)$ | H | H | 6-Cl | $2\text{-}CH_3\text{-}4\text{-}C_2F_5$ | 208 |
| 1355 | $CH_2\text{-}2\text{-}Pyi$ | H | H | 3-Cl | $2\text{-}CH_3\text{-}4\text{-}C_2F_5$ | 143 |
| 1356 | $(CH_2)_2(2\text{-}Cl\text{-}Ph)$ | H | H | 3-Cl | $2\text{-}CH_3\text{-}4\text{-}C_2F_5$ | 141 |
| 1357 | $(CH_2)_2(2\text{-}Cl\text{-}Ph)$ | H | H | 6-Cl | $2\text{-}CH_3\text{-}4\text{-}C_2F_5$ | Paste |
| 1358 | $(CH_2)_2(3\text{-}Cl\text{-}Ph)$ | H | H | 3-Cl | $2\text{-}CH_3\text{-}4\text{-}C_2F_5$ | 117 |
| 1359 | $(CH_2)_2(3\text{-}Cl\text{-}Ph)$ | H | H | 6-Cl | $2\text{-}CH_3\text{-}4\text{-}C_2F_5$ | Paste |
| 1360 | $(CH_2)_2(4\text{-}Cl\text{-}Ph)$ | H | H | 3-Cl | $2\text{-}CH_3\text{-}4\text{-}C_2F_5$ | 118 |
| 1361 | $(CH_2)_2(4\text{-}Cl\text{-}Ph)$ | H | H | 6-Cl | $2\text{-}CH_3\text{-}4\text{-}C_2F_5$ | 138 |
| 1362 | $CH(CH_3)(2\text{-}Cl\text{-}Ph)$ | H | H | 3-Cl | $2\text{-}CH_3\text{-}4\text{-}C_2F_5$ | Paste |
| 1363 | $CH(CH_3)(2\text{-}Cl\text{-}Ph)$ | H | H | 6-Cl | $2\text{-}CH_3\text{-}4\text{-}C_2F_5$ | 197 |
| 1364 | $CH(CH_3)(3\text{-}Cl\text{-}Ph)$ | H | H | 3-Cl | $2\text{-}CH_3\text{-}4\text{-}C_2F_5$ | 100 |
| 1365 | $CH(CH_3)(3\text{-}Cl\text{-}Ph)$ | H | H | 6-Cl | $2\text{-}CH_3\text{-}4\text{-}C_2F_5$ | Crystals |
| 1366 | $CH(CH_3)(4\text{-}Cl\text{-}Ph)$ | H | H | 3-Cl | $2\text{-}CH_3\text{-}4\text{-}C_2F_5$ | 195 |
| 1367 | $CH(CH_3)(4\text{-}Cl\text{-}Ph)$ | H | H | 6-Cl | $2\text{-}CH_3\text{-}4\text{-}C_2F_5$ | Paste |
| 1368 | $(CH_2)_2O(2\text{-}Cl\text{-}Ph)$ | H | H | 3-Cl | $2\text{-}CH_3\text{-}4\text{-}C_2F_5$ | 162 |
| 1369 | $(CH_2)_2O(2\text{-}Cl\text{-}Ph)$ | H | H | 6-Cl | $2\text{-}CH_3\text{-}4\text{-}C_2F_5$ | 160 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 1370 | (CH$_2$)$_2$O(3-Cl-Ph) | H | H | 3-Cl | 2-CH$_3$-4-C$_2$F$_5$ | 115 |
| 1371 | (CH$_2$)$_2$O(3-Cl-Ph) | H | H | 6-Cl | 2-CH$_3$-4-C$_2$F$_5$ | 172 |
| 1372 | (CH$_2$)$_2$O(4-Cl-Ph) | H | H | 3-Cl | 2-CH$_3$-4-C$_2$F$_5$ | 185 |
| 1373 | (CH$_2$)$_2$O(4-Cl-Ph) | H | H | 6-Cl | 2-CH$_3$-4-C$_2$F$_5$ | 148 |
| 1374 | (CH$_2$)$_2$O-Ph | H | H | 3-Cl | 2-CH$_3$-4-C$_2$F$_5$ | 154 |
| 1375 | (CH$_2$)$_2$O-Ph | H | H | 6-Cl | 2-CH$_3$-4-C$_2$F$_5$ | 183 |
| 1376 | (CH$_2$)$_2$NH-Ph | H | H | 3-Cl | 2-CH$_3$-4-C$_2$F$_5$ | 104 |
| 1377 | (CH$_2$)$_2$NH-Ph | H | H | 6-Cl | 2-CH$_3$-4-C$_2$F$_5$ | Paste |
| 1378 | CH(CH$_3$)CH$_2$OH | H | H | 6-Cl | 2-CH$_3$-4-C$_2$F$_5$ | 192 |
| 1379 | CH(Ph)CH$_2$OH | H | H | H | 2-CH$_3$-4-C$_2$F$_5$ | 100–101 |
| 1380 | CH(4-t-C$_4$H$_9$-Ph)-CH$_2$OH | H | H | H | 2-CH$_3$-4-C$_2$F$_5$ | 107–108 |
| 1381 | C(CH$_3$)$_2$CH$_2$OH | H | H | H | 2-CH$_3$-4-C$_2$F$_5$ | 227 |
| 1382 | i-C$_3$H$_7$ | H | H | 3-Cl | 2-F-4-C$_2$F$_5$ | 190 |
| 1383 | i-C$_3$H$_7$ | H | H | 3-Cl | 2-Cl-4-C$_2$F$_5$ | 180 |
| 1384 | i-C$_3$H$_7$ | H | H | 3-Cl | 2-CF$_3$-4-C$_2$F$_5$ | 235 |
| 1385 | i-C$_3$H$_7$ | H | H | 3-I | 2-F-4-C$_2$F$_5$ | 190 |
| 1386 | i-C$_3$H$_7$ | H | H | 3-I | 2-Cl-4-C$_2$F$_5$ | 200 |
| 1387 | i-C$_3$H$_7$ | H | H | 3-I | 2-CF$_3$-4-C$_2$F$_5$ | 255 |
| 1388 | i-C$_3$H$_7$ | H | H | 3-I | 2-OCH$_3$-4-C$_2$F$_5$ | 152 |
| 1389 | i-C$_3$H$_7$ | H | H | 3-I | 2-CH$_3$-4-CN | 215 |
| 1390 | 2-Fur | H | H | 3-Cl | 2-CH$_3$-4-C$_2$F$_5$ | 178 |
| 1391 | 2-Fur | H | H | 6-Cl | 2-CH$_3$-4-C$_2$F$_5$ | 149 |
| 1392 | 2-TetFur | H | H | 3-Cl | 2-CH$_3$-4-C$_2$F$_5$ | 153 |
| 1393 | 2-TetFur | H | H | 6-Cl | 2-CH$_3$-4-C$_2$F$_5$ | 130 |
| 1394 | CH$_2$-4-Pyi | H | H | 3-Cl | 2-CH$_3$-4-C$_2$F$_5$ | 88 |
| 1395 | CH$_2$-4-Pyi | H | H | 6-Cl | 2-CH$_3$-4-C$_2$F$_5$ | Paste |
| 1396 | (CH$_2$)$_3$OH | H | H | H | 2-CH$_3$-4-C$_2$F$_5$ | 83–84 |
| 1397 | (CH$_2$)$_2$OH | H | H | H | 2-CH$_3$-4-C$_2$F$_5$ | 136 |
| 1398 | CH$_2$CH(OH)CH$_2$Ph | H | H | H | 2-CH$_3$-4-C$_2$F$_5$ | 77–78 |
| 1399 | (CH$_2$)$_3$OH | H | H | 3-Cl | 2-CH$_3$-4-C$_2$F$_5$ | 188 |
| 1400 | CH$_2$-Ph | H | H | 3-I | 2-CH$_3$-4-C$_2$F$_5$ | 172 |
| 1401 | CH$_2$-Ph | H | H | 6-I | 2-CH$_3$-4-C$_2$F$_5$ | 212 |
| 1402 | CH$_2$(2-Cl-Ph) | H | H | 3-I | 2-CH$_3$-4-C$_2$F$_5$ | 136 |
| 1403 | CH$_2$(2-Cl-Ph) | H | H | 6-I | 2-CH$_3$-4-C$_2$F$_5$ | 214 |
| 1404 | CH$_2$(2-CH$_3$-Ph) | H | H | 3-I | 2-CH$_3$-4-C$_2$F$_5$ | 100 |
| 1405 | CH$_2$(2-CH$_3$-Ph) | H | H | 6-I | 2-CH$_3$-4-C$_2$F$_5$ | 185 |
| 1406 | CH$_2$-Ph | CH$_3$ | H | 3-Cl | 2-CH$_3$-4-C$_2$F$_5$ | Paste |
| 1407 | CH$_2$-Ph | CH$_2$-Ph | H | 3-Cl | 2-CH$_3$-4-C$_2$F$_5$ | 136 |
| 1408 | CH$_2$-Ph | CH$_2$-Ph | H | 6-Cl | 2-CH$_3$-4-C$_2$F$_5$ | Paste |
| 1409 | i-C$_3$H$_7$ | H | H | 3-I | 2-C$_2$F$_5$-4-Br | 250 |
| 1410 | i-C$_3$H$_7$ | H | H | 3-I | 2-C$_2$F$_5$-4-C$_2$F$_5$ | 245 |
| 1411 | CH$_2$C≡CH | H | H | H | 2-CH$_3$-4-C$_2$F$_5$ | 133–135 |
| 1412 | CH(4-Ph-Ph)CH$_2$—OH | H | H | 3-Cl | 2-CH$_3$-4-C$_2$F$_5$ | 112 |
| 1414 | C(CH$_3$)$_2$C≡CH | H | H | H | 2-CH$_3$-4-C$_2$F$_5$ | 207 |
| 1415 | C(CH$_3$)$_2$CH$_2$OH | H | H | 6-Cl | 2-CH$_3$-4-C$_2$F$_5$ | 231 |
| 1416 | CH(4-Cl-Ph)CH$_2$—OH | H | H | 6-Cl | 2-CH$_3$-4-C$_2$F$_5$ | 225 |
| 1417 | C(CH$_3$)$_2$-Ph | H | H | 3-Cl | 2-CH$_3$-4-C$_2$F$_5$ | 190 |
| 1418 | C(CH$_3$)$_2$CH$_2$-Ph | H | H | 3-Cl | 2-CH$_3$-4-C$_2$F$_5$ | 192 |
| 1419 | CH$_2$-3-Pyi | H | H | 3-Cl | 2-CH$_3$-4-C$_2$F$_5$ | Paste |
| 1420 | CH$_2$-3-Pyi | H | H | 6-Cl | 2-CH$_3$-4-C$_2$F$_5$ | Paste |
| 1421 | CH$_2$-Ph | H | H | 3-Cl | 2-CH$_3$-4-OCHF$_2$ | 187 |
| 1422 | CH$_2$-Ph | H | H | 6-Cl | 2-CH$_3$-4-OCHF$_2$ | 198 |
| 1423 | CH$_2$-(2-Cl-Ph) | H | H | 3-Cl | 2-CH$_3$-4-OCHF$_2$ | 178 |
| 1424 | CH$_2$-(2-Cl-Ph) | H | H | 6-Cl | 2-CH$_3$-4-OCHF$_2$ | 192 |
| 1425 | CH$_2$-(2-CH$_3$-Ph) | H | H | 3-Cl | 2-CH$_3$-4-OCHF$_2$ | 183 |
| 1426 | CH$_2$-(2-CH$_3$-Ph) | H | H | 6-Cl | 2-CH$_3$-4-OCHF$_2$ | 192 |
| 1427 | t-C$_4$H$_9$ | H | H | 3-I | 2-F-4-C$_2$F$_5$ | 220 |
| 1428 | t-C$_4$H$_9$ | H | H | 3-I | 2-Cl-4-C$_2$F$_5$ | 187 |
| 1429 | t-C$_4$H$_9$ | H | H | 3-I | 2-CF$_3$-4-C$_2$F$_5$ | 240 |
| 1430 | CH$_2$-Ph | H | H | 3-I | 2-CH$_3$-4-OCHF$_2$ | 176 |
| 1431 | CH$_2$-Ph | H | H | 6-I | 2-CH$_3$-4-OCHF$_2$ | 196 |
| 1432 | CH$_2$-(2-Cl-Ph) | H | H | 3-I | 2-CH$_3$-4-OCHF$_2$ | 189 |
| 1433 | CH$_2$-(2-Cl-Ph) | H | H | 6-I | 2-CH$_3$-4-OCHF$_2$ | 227 |
| 1434 | CH$_2$-(2-CH$_3$-Ph) | H | H | 3-I | 2-CH$_3$-4-OCHF$_2$ | 215 |
| 1435 | CH$_2$-(2-CH$_3$-Ph) | H | H | 6-I | 2-CH$_3$-4-OCHF$_2$ | 209 |
| 1436 | CH$_2$-Ph | CH$_3$ | H | 6-Cl | 2-CH$_3$-4-C$_2$F$_5$ | Paste |
| 1437 | CH$_2$-Ph | CH$_3$ | H | 3-Cl | 2-CH$_3$-4-OCHF$_2$ | Paste |
| 1438 | CH$_2$-Ph | CH$_3$ | H | 3-I | 2-CH$_3$-4-C$_2$F$_5$ | 175 |
| 1439 | CH$_2$-Ph | CH$_3$ | H | 6-I | 2-CH$_3$-4-C$_2$F$_5$ | Paste |
| 1440 | CH$_2$-Ph | CH$_3$ | H | 3-I | 2-CH$_3$-4-OCHF$_2$ | Paste |
| 1441 | CH(C$_2$H$_5$)CH$_2$OH | H | H | 6-Cl | 2-CH$_3$-4-C$_2$F$_5$ | 213 |
| 1442 | (R)-C*H(Ph)-CH$_2$OH | H | H | 3-Cl | 2-CH$_3$-4-C$_2$F$_5$ | 105–107 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 1443 | (R)-C*H(Ph)-CH$_2$OH | H | H | 6-Cl | 2-CH$_3$-4-C$_2$F$_5$ | 145–146 |
| 1445 | (S)-C*H(CH$_3$)—CH$_2$OH | H | H | 3-Cl | 2-CH$_3$-4-C$_2$F$_5$ | 93–95 |
| 1446 | (s)-C*H(CH$_3$)—CH$_2$OH | H | H | 6-Cl | 2-CH$_3$-4-C$_2$F$_5$ | 93–95 |
| 1447 | t-C$_4$H$_9$ | H | H | 3-Cl | 4-C$_2$F$_5$ | 275 |
| 1448 | t-C$_4$H$_9$ | H | H | 3-Cl | 2-F-4-C$_2$F$_5$ | 225 |
| 1449 | t-C$_4$H$_9$ | H | H | 3-Cl | 2-Cl-4-C$_2$F$_5$ | 200 |
| 1450 | n-C$_3$H$_7$ | H | H | 3-I | 2-CH$_3$-4-OCHF$_2$ | 181 |
| 1451 | n-C$_3$H$_7$ | H | H | 6-I | 2-CH$_3$-4-OCHF$_2$ | 233 |
| 1452 | c-C$_3$H$_5$ | H | H | 3-I | 2-CH$_3$-4-OCHF$_2$ | 182 |
| 1453 | c-C$_3$H$_5$ | H | H | 6-I | 2-CH$_3$-4-OCHF$_2$ | 231 |
| 1454 | s-C$_4$H$_9$ | H | H | 3-I | 2-CH$_3$-4-OCHF$_2$ | 225 |
| 1455 | s-C$_4$H$_9$ | H | H | 6-I | 2-CH$_3$-4-OCHF$_2$ | 244 |
| 1456 | CH$_2$C≡CH | H | H | 3-I | 2-CH$_3$-4-OCHF$_2$ | 196 |
| 1457 | CH$_2$-Ph | C$_2$H$_5$ | H | 3-Cl | 2-CH$_3$-4-C$_2$F$_5$ | Paste |
| 1458 | (R)-C*H(CH$_3$)-Ph | H | H | 3-Cl | 2-CH$_3$-4-OCHF$_2$ | 136 |
| 1459 | (S)-C*H(CH$_3$)-Ph | H | H | 3-Cl | 2-CH$_3$-4-OCHF$_2$ | 136 |
| 1460 | (R)-C*H(CH$_3$)—CH$_2$OH | H | H | 3-Cl | 2-CH$_3$-4-C$_2$F$_5$ | 94–95 |
| 1461 | (R)-C*H(CH$_3$)—CH$_2$OH | H | H | 6-Cl | 2-CH$_3$-4-C$_2$F$_5$ | 94–95 |
| 1464 | C(CH$_3$)$_2$CH$_2$OH | H | H | 3-I | 2-CH$_3$-4-C$_2$F$_5$ | 118 |
| 1465 | CH(CH$_3$)CH$_2$OH | H | H | 6-I | 2-CH$_3$-4-C$_2$F$_5$ | 130–131 |
| 1466 | C(CH$_3$)$_2$C≡CH | H | H | 3-Cl | 2-CH$_3$-4-C$_2$F$_5$ | 210–211 |
| 1467 | C(CH$_3$)$_2$C≡CH | H | H | 6-Cl | 2-CH$_3$-4-C$_2$F$_5$ | 230 |
| 1468 | CH$_2$(2-F-Ph) | H | H | 3-Cl | 2-CH$_3$-4-C$_2$F$_5$ | 187 |
| 1469 | CH$_2$(2-F-Ph) | H | H | 6-Cl | 2-CH$_3$-4-C$_2$F$_5$ | 165 |
| 1470 | CH$_2$-Ph | H | H | 3-F | 2-CH$_3$-4-C$_2$F$_5$ | 158 |
| 1471 | CH$_2$-Ph | H | H | 6-F | 2-CH$_3$-4-C$_2$F$_5$ | 134 |
| 1472 | s-C$_4$H$_9$ | H | H | 3-I | 2-F-4-C$_2$F$_5$ | 200 |
| 1473 | s-C$_4$H$_9$ | H | H | 3-I | 2-Cl-4-C$_2$F$_5$ | 205 |
| 1474 | i-C$_3$H$_7$ | H | H | 3-I | 2-F-4-n-C$_3$F$_7$ | 165 |
| 1475 | t-C$_4$H$_9$ | H | H | 3-I | 2-C$_2$H$_5$-4-C$_2$F$_5$ | 235 |
| 1476 | CH$_2$CH(OH)Ph | H | H | 3-Cl | 2-CH$_3$-4-C$_2$F$_5$ | 108 |
| 1477 | CH$_2$CH(OH)Ph | H | H | 6-Cl | 2-CH$_3$-4-C$_2$F$_5$ | 105 |
| 1478 | C(CH$_3$)$_2$C≡CH | H | H | 3-Cl | 2-CH$_3$-4-C$_2$F$_5$ | 105 |
| 1479 | C(CH$_3$)$_2$C≡C-2-Thi | H | H | 3-Cl | 2-CH$_3$-4-C$_2$F$_5$ | 110 |
| 1480 | C(CH$_3$)$_2$C≡C-Ph | H | H | 6-Cl | 2-CH$_3$-4-C$_2$F$_5$ | 194 |
| 1481 | (R)-C*H(CH$_3$)—CH$_2$OH | H | H | 3-I | 2-CH$_3$-4-C$_2$F$_5$ | 103–105 |
| 1482 | (S)-C*H(CH$_3$)—CH$_2$OH | H | H | 3-I | 2-CH$_3$-4-C$_2$F$_5$ | 103–105 |
| 1483 | (R)-C*H(CH$_3$)—CH$_2$OH | H | H | 6-I | 2-CH$_3$-4-C$_2$F$_5$ | 173–174 |
| 1484 | C(CH$_3$)$_2$(4-Cl-Ph) | H | H | 3-Cl | 2-CH$_3$-4-C$_2$F$_5$ | 218 |
| 1485 | C(CH$_3$)$_2$(3-Cl-Ph) | H | H | 3-Cl | 2-CH$_3$-4-C$_2$F$_5$ | 128 |
| 1486 | CH$_2$-Ph | H | H | 3-Cl | 2-F-4-C$_2$F$_5$ | 162 |
| 1487 | CH$_2$-Ph | H | H | 3-Cl | 2-Cl-4-C$_2$F$_5$ | 153 |
| 1488 | C$_2$H$_5$ | H | H | 3-Cl | 2-F-4-C$_2$F$_5$ | 135 |
| 1489 | C$_2$H$_5$ | H | H | 3-Cl | 2-Cl-4-C$_2$F$_5$ | 125 |
| 1490 | C$_2$H$_5$ | H | H | 3-Cl | 2-F-4-n-C$_3$F$_7$ | 128 |
| 1491 | n-C$_3$H$_7$ | H | H | 3-Cl | 2-F-4-C$_2$F$_5$ | 153 |
| 1492 | n-C$_3$H$_7$ | H | H | 3-Cl | 2-Cl-4-C$_2$F$_5$ | 147 |
| 1493 | n-C$_3$H$_7$ | H | H | 3-Cl | 2-F-4-n-C$_3$F$_7$ | 142 |
| 1494 | i-C$_3$H$_7$ | H | H | 3-Cl | 2-F-4-n-C$_3$F$_7$ | 142 |
| 1495 | i-C$_3$H$_7$ | H | H | 3-Cl | 2-C$_2$H$_5$-4-C$_2$F$_5$ | 213 |
| 1496 | t-C$_4$H$_9$ | H | H | 3-Cl | 2-F-4-n-C$_3$F$_7$ | 172 |
| 1497 | t-C$_4$H$_9$ | H | H | 3-Cl | 2-C$_2$H$_5$-4-C$_2$F$_5$ | 194 |
| 1498 | s-C$_4$H$_9$ | H | H | 3-Cl | 2-F-4-C$_2$F$_5$ | 209 |
| 1499 | s-C$_4$H$_9$ | H | H | 3-Cl | 2-Cl-4-C$_2$F$_5$ | 194 |
| 1500 | s-C$_4$H$_9$ | H | H | 3-Cl | 2-F-4-n-C$_3$F$_7$ | 182 |
| 1501 | s-C$_4$H$_9$ | H | H | 3-Cl | 2-C$_2$H$_5$-4-C$_2$F$_5$ | 212 |
| 1502 | C$_2$H$_5$ | H | H | 3-I | 2-F-4-C$_2$F$_5$ | 135 |
| 1503 | C$_2$H$_5$ | H | H | 3-I | 2-Cl-4-C$_2$F$_5$ | 155 |
| 1504 | t-C$_4$H$_9$ | H | H | 3-I | 2-F-4-n-C$_3$F$_7$ | 180 |
| 1505 | t-C$_4$H$_9$ | H | H | 3-F | 2-CH$_3$-4-C$_2$F$_5$ | 220 |
| 1506 | t-C$_4$H$_9$ | H | H | 3-F | 2-CH$_3$-4-OCHF$_2$ | 186 |
| 1507 | t-C$_4$H$_9$ | H | H | 3-F | 2-F-4-C$_2$F$_5$ | 214 |
| 1508 | t-C$_4$H$_9$ | H | H | 3-F | 2-Cl-4-C$_2$F$_5$ | 222 |
| 1509 | t-C$_4$H$_9$ | H | H | 3-F | 2-F-4-n-C$_3$F$_7$ | 179 |
| 1510 | C$_2$H$_5$ | H | H | 3-F | 2-F-4-C$_2$F$_5$ | 125 |
| 1511 | C$_2$H$_5$ | H | H | 6-F | 2-F-4-C$_2$F$_5$ | 155 |
| 1512 | n-C$_3$H$_7$ | H | H | 3-F | 2-F-4-C$_2$F$_5$ | 130 |
| 1513 | n-C$_3$H$_7$ | H | H | 6-F | 2-F-4-C$_2$F$_5$ | 170 |
| 1514 | i-C$_3$H$_7$ | H | H | 3-F | 2-F-4-C$_2$F$_5$ | 190 |
| 1515 | i-C$_3$H$_7$ | H | H | 6-F | 2-F-4-C$_2$F$_5$ | 180 |
| 1516 | i-C$_3$H$_7$ | H | H | 3-F | 2-Cl-4-C$_2$F$_5$ | 210 |
| 1517 | i-C$_3$H$_7$ | H | H | 6-F | 2-Cl-4-C$_2$F$_5$ | 160 |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 1518 | (s)-C*H(CH$_3$)—CH$_2$OH | H | H | 6-I | 2-CH$_3$-4-C$_2$F$_5$ | 173–174 |
| 1519 | C(CH$_3$)$_2$CH$_2$OH | H | H | 3-I | 2-CH$_3$-4-OCF$_3$ | 205 |
| 1520 | C(CH$_3$)$_2$CH$_2$OH | H | H | 6-I | 2-CH$_3$-4-OCF$_3$ | 248 |
| 1521 | i-C$_3$H$_7$ | H | H | 3-I | 2-CH$_3$-4-(4-CF$_3$O-Ph) | 247–250 |
| 1522 | i-C$_3$H$_7$ | H | H | 3-I | 2-CH$_3$-4-(4-CF$_3$-Ph) | 243–246 |
| 1523 | CH$_2$(2-CF$_3$-Ph) | H | H | 3-Cl | 2-CH$_3$-4-C$_2$F$_5$ | 183 |
| 1524 | n-C$_3$H$_7$ | H | H | 3-I | 2-F-4-n-C$_3$F$_7$ | 145 |
| 1525 | C$_2$H$_5$ | C$_2$H$_5$ | H | 3-F | 2-CH$_3$-4-C$_2$F$_5$ | 135 |
| 1526 | C$_2$H$_5$ | C$_2$H$_5$ | H | 3-F | 2-CH$_3$-4-i-C$_3$F$_7$ | 150 |
| 1527 | C$_2$H$_5$ | C$_2$H$_5$ | H | 3-F | 2-CH$_3$-4-OCF$_3$ | 125 |
| 1528 | C$_2$H$_5$ | C$_2$H$_5$ | H | 3-F | 2-CH$_3$-4-OCHF$_2$ | 110 |
| 1529 | C$_2$H$_5$ | C$_2$H$_5$ | H | 3-F | 2-CH$_3$-4-OCF$_2$CHF$_2$ | 155 |
| 1530 | C$_2$H$_5$ | C$_2$H$_5$ | H | 3-F | 2-F-4-C$_2$F$_5$ | 130 |
| 1531 | C$_2$H$_5$ | C$_2$H$_5$ | H | 3-F | 2-Cl-4-C$_2$F$_5$ | 110 |
| 1532 | C$_2$H$_5$ | C$_2$H$_5$ | H | 3-I | 2-CH$_3$-4-i-C$_3$F$_7$ | 142 |
| 1533 | C$_2$H$_5$ | C$_2$H$_5$ | H | 3-I | 2-CH$_3$-4-OCF$_3$ | 142 |
| 1534 | C$_2$H$_5$ | C$_2$H$_5$ | H | 3-I | 4-OCF$_3$ | 142 |
| 1535 | C$_2$H$_5$ | C$_2$H$_5$ | H | 3-Cl | 2-CH$_3$-4-C$_2$F$_5$ | 150 |
| 1536 | C$_2$H$_5$ | C$_2$H$_5$ | H | 3-Cl | 2-CH$_3$-4-OCF$_3$ | 123 |
| 1537 | C$_2$H$_5$ | C$_2$H$_5$ | H | 3-Cl | 2-CH$_3$-4-i-C$_3$F$_7$ | 147 |
| 1538 | C$_2$H$_5$ | C$_2$H$_5$ | H | 3-Cl | 2-CH$_3$-4-OCHF$_2$ | 92 |
| 1539 | C$_2$H$_5$ | C$_2$H$_5$ | H | 3-Cl | 2-CH$_3$-4-OCF$_2$CHF$_2$ | 135 |
| 1540 | C$_2$H$_5$ | C$_2$H$_5$ | H | 3-Cl | 2-Cl-4-C$_2$F$_5$ | 110 |
| 1541 | C$_2$H$_5$ | C$_2$H$_5$ | H | 3-Cl | 2-F-4-C$_2$F$_5$ | 113 |
| 1542 | C$_2$H$_5$ | C$_2$H$_5$ | H | 3-Cl | 2-CH$_3$—Cl | 142 |
| 1543 | C$_2$H$_5$ | C$_2$H$_5$ | H | 3-Cl | 2-C$_2$H$_5$-4-C$_2$F$_5$ | 101 |
| 1544 | C$_2$H$_5$ | C$_2$H$_5$ | H | 3-Cl | 4-OCF$_3$ | 138 |
| 1545 | C$_2$H$_5$ | C$_2$H$_5$ | H | 3-Cl | 4-CF$_3$ | 188 |
| 1546 | C$_2$H$_5$ | C$_2$H$_5$ | H | 3-F | 2-CH$_3$-4-Cl | 135 |
| 1547 | C$_2$H$_5$ | C$_2$H$_5$ | H | 3-F | 4-CF$_3$ | 175 |
| 1548 | C$_2$H$_5$ | C$_2$H$_5$ | H | 3-F | 4-OCF$_3$ | 155 |
| 1549 | C$_2$H$_5$ | C$_2$H$_5$ | H | 3-F | 2-C$_2$H$_5$-4-C$_2$F$_5$ | 80 |
| 1550 | C$_2$H$_5$ | C$_2$H$_5$ | H | 3-NO$_2$ | 2-CH$_3$-4-C$_2$F$_5$ | 185 |
| 1551 | C$_2$H$_5$ | C$_2$H$_5$ | H | 6-NO$_2$ | 2-CH$_3$-4-C$_2$F$_5$ | 145 |
| 1552 | t-C$_4$H$_9$ | H | H | 3-I | 3-CH$_3$-4-C$_2$F$_5$ | 215 |
| 1553 | CH$_2$-Ph | CH$_3$ | CH$_3$ | 3-Cl | 2-CH$_3$-4-C$_2$F$_5$ | Paste |
| 1554 | CH(CH$_3$)-Ph | H | CH$_3$ | 3-Cl | 2-CH$_3$-4-C$_2$F$_5$ | Paste |
| 1555 | C$_2$H$_5$ | C$_2$H$_5$ | H | 3-I | 2-CH$_3$-4-OCHF$_2$ | 138–139 |
| 1556 | C$_2$H$_5$ | C$_2$H$_5$ | H | 3-I | 2-CH$_3$-4-OCF$_2$CHF$_2$ | 136 |
| 1557 | C$_2$H$_5$ | C$_2$H$_5$ | H | 3-I | 2-CH$_3$-4-Cl | 179 |
| 1558 | C$_2$H$_5$ | C$_2$H$_5$ | H | 3-I | 4-CF$_3$ | 187 |
| 1559 | C$_2$H$_5$ | C$_2$H$_5$ | H | 3-I | 2-C$_2$H$_5$-4-C$_2$F$_5$ | 106 |
| 1560 | C$_2$H$_5$ | C$_2$H$_5$ | H | 3-I | 2-Cl-4-C$_2$F$_5$ | 103–105 |
| 1561 | C$_2$H$_5$ | C$_2$H$_5$ | H | 3-I | 2-CH$_3$-4-C$_2$F$_5$ | 115 |
| 1562 | t-C$_4$H$_9$ | H | H | 3-I | 2-Br-4-C$_2$F$_5$ | 185 |
| 1563 | i-C$_3$H$_7$ | H | H | 3-I | 3-CH$_3$-4-C$_2$F$_5$ | 240 |
| 1564 | i-C$_3$H$_7$ | H | H | H | 4-O-(2-Pym) | 246 |
| 1565 | C(CH$_3$)$_2$—CH$_2$CH$_3$ | H | H | 3-I | 2-CH$_3$-4-C$_2$F$_5$ | 193 |
| 1566 | C(CH$_3$)$_2$—CH$_2$CH$_3$ | H | H | 3-I | 2-CH$_3$-4-OCF$_3$ | 180 |
| 1567 | C(CH$_3$)$_2$CH$_2$CH$_3$ | H | H | 3-I | | 178–179 |
| 1568 | C(CH$_3$)$_2$CH$_2$CH$_3$ | H | H | 3-I | 2-CH$_3$-4-OCHF$_2$ | 176–177 |
| 1569 | C(CH$_3$)$_2$CH═CH$_2$ | H | H | 3-Cl | 2-CH$_3$-4-C$_2$F$_5$ | 223–224 |
| 1570 | C(CH$_3$)$_2$CH≡C-(4-CH$_3$-Ph) | H | H | 3-Cl | 2-CH$_3$-4-C$_2$F$_5$ | 92–93 |
| 1571 | C(CH$_3$)$_2$CH≡C-(2,4-Cl$_2$-Ph) | H | H | 3-Cl | 2-CH$_3$-4-C$_2$F$_5$ | 96–97 |
| 1572 | C(CH$_3$)$_2$CH≡C-(4-CH$_3$O-Ph) | H | H | 3-Cl | 2-CH$_3$-4-C$_2$F$_5$ | 88–89 |
| 1573 | n-C$_3$H$_7$ | C$_2$H$_5$ | H | 3-I | 2-CH$_3$-4-C$_2$F$_5$ | 93 |
| 1574 | n-C$_3$H$_7$ | C$_2$H$_5$ | H | 3-I | 2-CH$_3$-4-OCF$_3$ | 109 |
| 1575 | n-C$_3$H$_7$ | C$_2$H$_5$ | H | 3-I | 2-CH$_3$-4-OCHF$_2$ | 102 |
| 1576 | CH$_2$(4-CF$_3$O-Ph) | H | H | 3-Cl | 2-CH$_3$-4-C$_2$F$_5$ | 172 |
| 1577 | CH$_2$(4-CF$_3$O-Ph) | H | H | 6-Cl | 2-CH$_3$-4-C$_2$F$_5$ | 193 |
| 1578 | CH$_2$(3-Cl-Ph) | CH$_3$ | H | 3-Cl | 2-CH$_3$-4-C$_2$F$_5$ | Paste |
| 1579 | CH$_2$(2-F-Ph) | CH$_3$ | H | 3-Cl | 2-CH$_3$-4-C$_2$F$_5$ | 115 |
| 1580 | i-C$_3$H$_7$ | H | H | 3-I | 2-Br-4-C$_2$F$_5$ | 190 |
| 1581 | n-C$_3$H$_7$ | C$_2$H$_5$ | H | 3-F | 2-CH$_3$-4-C$_2$F$_5$ | 120 |
| 1582 | n-C$_3$H$_7$ | C$_2$H$_5$ | H | 3-F | 4-OCF$_3$ | 115 |
| 1583 | n-C$_3$H$_7$ | C$_2$H$_5$ | H | 3-F | 4-OCHF$_2$ | 85 |
| 1584 | n-C$_3$H$_7$ | C$_2$H$_5$ | H | 3-F | 2-Cl-4-C$_2$F$_5$ | 75 |
| 1585 | C(CH$_3$)$_2$CH≡C-(4-CF$_3$-Ph) | H | H | 3-Cl | 2-CH$_3$-4-C$_2$F$_5$ | 102–103 |
| 1586 | C(CH$_3$)$_2$CH≡C-(2,6-Cl$_2$-Ph) | H | H | 3-Cl | 2-CH$_3$-4-C$_2$F$_5$ | 115–117 |
| 1587 | C(CH$_3$)$_2$CH≡C-2-Pyi | H | H | 3-Cl | 2-CH$_3$-4-C$_2$F$_5$ | 169 |
| 1588 | C(CH$_3$)$_2$CH≡CH | H | H | 3-Cl | 2-CH$_3$-4-OCHF$_2$ | 191–192 |
| 1589 | C(CH$_3$)$_2$CH═CH$_2$ | H | H | 6-Cl | 2-CH$_3$-4-C$_2$F$_5$ | 242 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 1590 | $C(CH_3)_2CH\equiv C$-3-Pyi | H | H | 3-Cl | 2-$CH_3$-4-$C_2F_5$ | 134–135 |
| 1591 | i-$C_3H_7$ | H | H | H | 2-$CH_3$-4-(2,6-($CH_3O)_2$-Ph) | 165 |
| 1592 | i-$C_3H_7$ | H | H | H | 2-$CH_3$-4-(3,5-($CH_3O)_2$-Ph) | 150 |
| 1593 | $C_2H_5$ | $C_2H_5$ | H | H | 2-$CH_3$-4-(3,5-($CH_3O)_2$-Ph) | Paste |
| 1594 | i-$C_3H_7$ | H | H | 3-Cl | 2-F-4-($OCF_2O$)-5 | 195 |
| 1595 | i-$C_3H_7$ | H | H | 3-I | 2-F-4-($OCF_2O$)-5 | 208 |
| 1596 | t-$C_4H_9$ | H | H | 3-I | 2-F-4-($OCF_2O$)-5 | 202 |
| 1597 | i-$C_3H_7$ | H | H | 3-Cl | 2-$CH_3$-4-($OCHFCF_2$—O)-5 | 211 |
| 1598 | i-$C_3H_7$ | H | H | 3-I | 2-$CH_3$-4-($OCHFCF_2$—O)-5) | 212 |
| 1599 | t-$C_4H_9$ | H | H | 3-I | 2-$CH_3$-4-($OCHFCF_2$—O)-5 | 217 |
| 1600 | i-$C_3H_7$ | H | H | 3-I | 2-Cl-4-($OCHFCF_2$—O)-5 | 210 |
| 1601 | i-$C_3H_7$ | H | H | 3-I | 2-Cl-4-($OCF_2CHF$—O)-5 | 214 |
| 1602 | $C(CH_3)_2C\equiv CH$ | H | H | 3-Cl | 2-$CH_3$-4-$OCF_3$ | 178–180 |
| 1603 | $C(CH_3)_2CHBr$—$CH_2Br$ | H | H | 3-Cl | 2-$CH_3$-4-$C_2F_5$ | 130–131 |
| 1604 | $C(CH_3)_2CH=CH$-Ph(E) | H | H | 3-Cl | 2-$CH_3$-4-$C_2F_5$ | 90–93 |
| 1605 | $C(CH_3)_2CH_2Br$ | H | H | 3-I | 2-$CH_3$-4-$OCF_3$ | 139–141 |
| 1606 | (S)-$C*H$—($CH_3$)—$CH_2Br$ | H | H | 3-I | 2-$CH_3$-4-$C_2F_5$ | 105–107 |
| 1607 | (R)-$C*H$—($CH_3$)—$CH_2Br$ | H | H | 3-I | 2-$CH_3$-4-$C_2F_5$ | 105–107 |
| 1608 | i-$C_3H_7$ | H | H | 3-I | 3-Cl-4-$C_2F_5$ | 145 |
| 1609 | t-$C_4H_9$ | H | H | 3-I | 3-Cl-4-$C_2F_5$ | 260 |
| 1610 | i-$C_3H_7$ | H | H | 3-I | 2-$CH_3$-4-$C_2F_5$-5-$CH_3$ | 210 |
| 1611 | t-$C_4H_9$ | H | H | 3-I | 2-$CH_3$-4-$C_2F_5$-5-$CH_3$ | 215 |
| 1612 | i-$C_3H_7$ | H | H | 3-I | 2,3-($CH_3)_2$-4-$C_2F_5$ | 210 |
| 1613 | t-$C_4H_9$ | H | H | 3-I | 2,3-($CH_3)_2$-4-$C_2F_5$ | 220 |
| 1614 | $C_2H_5$ | $C_2H_5$ | H | 3-I | 2-$CH_3$-4-(4-F-Ph) | 130–133 |
| 1615 | $C_2H_5$ | $C_2H_5$ | H | 3-I | 2-$CH_3$-4-(4-Cl-Ph) | 173–175 |
| 1616 | i-$C_3H_7$ | H | H | H | 2-$CH_3$-4-O-(2-Thz) | 149 |
| 1617 | i-$C_3H_7$ | H | H | 3-I | Mixture of 2-$CH_3$-4-(4-(2-$CH_3$-Thz)) and 2-$CH_3$-5-(4-(2-$CH_3$-Thz)) (1:1) | 235 |
| 1618 | i-$C_3H_7$ | H | H | 3-I | 2-$CH_3$-4-O-(2-Pym) | 239 |
| 1619 | $C_2H_5$ | $C_2H_5$ | H | 3-I | 2-$CH_3$-4-(4-$CF_3$-Ph) | 112–115 |
| 1620 | i-$C_3H_7$ | H | H | 3-I | 4-$CF_2CF_2O$-5 | 239 |
| 1621 | i-$C_3H_7$ | H | H | 3-Cl | 4-$CF_2CF_2O$-5 | 243 |
| 1622 | i-$C_3H_7$ | H | H | 3-I | 2-Cl-4-$OCF_2O$-5 | 226 |
| 1623 | i-$C_3H_7$ | H | H | 3-Cl | 2-Cl-4-$OCF_2O$-5 | 223 |
| 1624 | t-$C_4H_9$ | H | H | 3-I | 2-Cl-4-$OCF_2O$-5 | 221 |
| 1625 | i-$C_3H_7$ | H | H | 3-I | 2-Cl-4-$OCF_2CF_2O$ | 241 |
| 1626 | i-$C_3H_7$ | H | H | 3-I | 2-Cl-3-$OCF_2CF_2O$-4 | 219 |
| 1627 | $C(CH_3)_2CH_2Cl$ | H | H | 3-I | 2-$CH_3$-4-$OCF_3$ | 160 |
| 1628 | $C(CH_3)_2C\equiv C$-3-Thi | H | H | 3-Cl | 2-$CH_3$-4-$C_2F_5$ | 78–80 |
| 1629 | $C(CH_3)_2C\equiv CH$ | H | H | 3-I | 2-$CH_3$-4-$C_2F_5$ | 187–188 |
| 1630 | i-$C_3H_7$ | H | H | 3-I | 2-$CH_3$-4-(3,5-($CH_3O)_2$-Ph) | 199 |
| 1631 | i-$C_3H_7$ | H | H | H | 3-$OCH_2O$-4 | 195 |
| 1632 | i-$C_3H_7$ | H | H | H | 2-F-4-Cl | 177 |
| 1633 | $C(CH_3)_2C\equiv C$-(4-$CF_3O$-Ph) | H | H | 3-Cl | 2-$CH_3$-4-$C_2F_5$ | 92–93 |
| 1634 | $C(CH_3)_2C\equiv CH$ | H | H | 3-I | 2-$CH_3$-4-$OCF_3$ | 188–189 |
| 1635 | $C(CH_3)_2C\equiv CH$ | H | H | 3-I | 2-$CH_3$-4-$OCHF_2$ | 175–176 |
| 1636 | i-$C_3H_7$ | H | H | 3-I | 4-N=(n-$C_3F_7$)C—O-5 | 182 |
| 1637 | i-$C_3H_7$ | H | H | 3-I | 4-O—C(n-$C_3F_7$)=N-5 | 250 |
| 1638 | i-$C_3H_7$ | H | H | 3-Cl | 4-O—C(n-$C_3F_7$)=N-5 | 168 |
| 1639 | t-$C_4H_9$ | H | H | 3-I | 4-O—C(n-$C_3F_7$)=N-5 | 248 |
| 1640 | i-$C_3H_7$ | H | H | 3-I | 2,3-($CH_3)_2$-4-$C_2F_5$ | 195 |
| 1641 | i-$C_3H_7$ | H | H | 3-I | 2-$CH_3$-4-OC($CF_3$)=N-5 | 229 |
| 1642 | i-$C_3H_7$ | H | H | 3-Cl | 2-Cl-3-$OCF_2CF_2O$-4 | 188 |
| 1643 | i-$C_3H_7$ | H | H | 3-Cl | 2-Cl-4-$OCF_2CF_2O$-5 | 203 |
| 1644 | t-$C_4H_9$ | H | H | 3-I | 2-Cl-3-$OCF_2CF_2O$-4 | 189 |
| 1645 | t-$C_4H_9$ | H | H | 3-I | 2-Cl-4-$OCF_2CF_2O$-5 | 234 |
| 1646 | $C(CH_3)_2CH_2Cl$ | H | H | 3-I | 2-$CH_3$-4-$C_2F_5$ | 168–169 |
| 1647 | $C(CH_3)_2CH_2Br$ | H | H | 3-I | 2-$CH_3$-4-$C_2F_5$ | 167–168 |
| 1648 | $C(CH_3)_2C\equiv C$-Naph | H | H | 3-I | 2-$CH_3$-4-$C_2F_5$ | 90 |
| 1649 | $C(CH_3)_2C\equiv C$-(5-Br-2-Pyi) | H | H | 3-Cl | 2-$CH_3$-4-$C_2F_5$ | 105–106 |
| 1650 | $C(CH_3)_2C\equiv C$-(2,4-$F_2$-Ph) | H | H | 3-Cl | 2-$CH_3$-4-$C_2F_5$ | 103–105 |
| 1651 | (S)-$C*H(CH_3)$—$CH_2F$ | H | H | 3-Cl | 2-$CH_3$-4-$C_2F_5$ | 135 |
| 1652 | (S)-$C*H$—($CH_3$)—$CH_2Br$ | H | H | 3-Cl | 2-$CH_3$-4-$C_2F_5$ | 193–198 |
| 1653 | i-$C_3H_7$ | H | H | 3-I | 2-$CH_3$-4-$C_2F_5$-5-Cl | 210 |
| 1654 | t-$C_4H_9$ | H | H | 3-I | 2-$CH_3$-4-$C_2F_5$-5-Cl | 200 |
| 1655 | i-$C_3H_7$ | H | H | 3-I | 2-$CH_3$-4-$C_2F_5$-5-$CH_3$ | 190 |
| 1656 | t-$C_4H_9$ | H | H | 3-I | 2-$CH_3$-4-$C_2F_5$-5-$CH_3$ | 195 |
| 1657 | i-$C_3H_7$ | H | H | H | 3-(2-$CH_3$-4-Thz) | 211 |
| 1658 | i-$C_3H_7$ | H | H | 3-I | 3-(2-$CF_3$-4-Thz) | 122 |
| 1659 | i-$C_3H_7$ | H | H | 3-I | 3-(2-$CH_3$-4-Oxa) | 102 |

TABLE 1-continued ($Z^1, Z^2 = O$)

| No | $R^1$ | $R^2$ | $R^3$ | Xn | Ym | Physical Properties (melting point: °C. |
|---|---|---|---|---|---|---|
| 1660 | i-$C_3H_7$ | H | H | 3-I | 2-I-4-OCF$_2$O-5 | 252 |
| 1661 | i-$C_3H_7$ | H | H | 3-Cl | 2-CH$_3$-4-OCF$_2$O-5 | 218 |
| 1662 | t-$C_4H_9$ | H | H | 3-I | 2-CH$_3$O-4-$C_2F_5$ | 135 |
| 1663 | i-$C_3H_7$ | H | H | 3-I | 2-CH$_3$-4-i-$C_3F_7$-5-F | 235 |
| 1664 | t-$C_4H_9$ | H | H | 3-I | 2-CH$_3$-4-i-$C_3F_7$-5-F | 230 |
| 1665 | i-$C_3H_7$ | H | H | 3-I | 2-CH$_3$-4-i-$C_3F_7$-5-Cl | 210 |
| 1666 | i-$C_3H_7$ | H | H | 3-I | 2-CH$_3$-4-CF$_2$CF$_2$O-5 | 198 |
| 1667 | i-$C_3H_7$ | H | H | 3-I | 2-CH$_3$-4-i-$C_3F_7$ | 270 |
| 1668 | t-$C_4H_9$ | H | H | 3-I | 2-CH$_3$-4-i-$C_3F_7$ | 290 |
| 1669 | i-$C_3H_7$ | H | H | 3-I | 2-F-4-i-$C_3F_7$ | 205 |
| 1670 | t-$C_4H_9$ | H | H | 3-I | 2-F-4-i-$C_3F_7$ | 210 |
| 1671 | i-$C_3H_7$ | H | H | 3-I | 2-SCH$_3$-4-i-$C_3F_7$ | 205 |
| 1672 | t-$C_4H_9$ | H | H | 3-I | 2-SCH$_3$-4-i-$C_3F_7$ | 205 |
| 1673 | i-$C_3H_7$ | H | H | 3-I | 2,4-(CH$_3$)$_2$-4-i-$C_3F_7$ | 240 |
| 1674 | t-$C_4H_9$ | H | H | 3-I | 2,4-(CH$_3$)$_2$-4-i-$C_3F_7$ | 245 |
| 1675 | i-$C_3H_7$ | H | H | 3-I | 4-(2-CH$_3$-4-Thz) | 217 |
| 1676 | i-$C_3H_7$ | H | H | 3-I | 4-(2-CH$_3$-4-Oxa) | 212 |
| 1677 | i-$C_3H_7$ | H | H | 3-I | 4-(2-i-$C_3H_7$-4-Thz) | 199 |
| 1678 | i-$C_3H_7$ | H | H | 3-NO$_2$ | 4-(2-CH$_3$-4-Thz) | 230 |
| 1679 | i-$C_3H_7$ | H | H | 3-I | 2-Cl-3-OCF$_2$CHFO-4 | 188 |
| 1680 | i-$C_3H_7$ | H | H | 3-I | 2-Cl-3-OCHFCF$_2$O-4 | 191 |
| 1681 | i-$C_3H_7$ | H | H | 3-I | Mixture of 2-Cl-3-OCHFCF$_2$O-4-5-Cl and 2-Cl-3-OCHFCF$_2$O-4-6-Cl (1:1) | 199 |
| 1682 | i-$C_3H_7$ | H | H | 3-I | 2-Cl-3-N=C(CF$_3$)—O-4 | 265 |
| 1683 | t-$C_4H_9$ | H | H | 3-I | 2-Cl-3-N=C(CF$_3$)—O-4 | 259 |
| 1684 | i-$C_3H_7$ | H | H | 3-I | 2-Br-4-OCF$_2$CHFO-5 | 185 |
| 1685 | i-$C_3H_7$ | H | H | 3-I | Mixture of 2,3-Br$_2$-4-OCF$_2$CHFO-5; 2,5-Br$_2$-3-OCF$_2$CHFO-4; and 2,6-Br$_2$-3-OCF$_2$CHFO-4(1:1:1) | 250 |
| 1686 | i-$C_3H_7$ | H | H | 3-I | Mixture of 2,3-Br$_2$-4-OCHFCF$_2$O-5; 2,5-Br$_2$-3-CF$_2$CHFO-4; and 2,6-Br$_2$-3-OCF$_2$CHFO-4(1:1:1) | 228 |
| 1689 | i-$C_3H_7$ | H | H | 3-I | 2,3-(CH$_3$)$_2$-4-i-$C_3F_7$ | 270 |
| 1690 | t-$C_4H_9$ | H | H | 3-I | 2,3-(CH$_3$)$_2$-4-i-$C_3F_7$ | 280 |
| 1691 | i-$C_3H_7$ | H | H | 3-I | 2-i-$C_3H_7$-4-i-$C_3F_7$ | 240 |
| 1692 | t-$C_4H_9$ | H | H | 3-I | 2-i-$C_3H_7$-4-i-$C_3F_7$ | 245 |
| 1693 | i-$C_3H_7$ | H | H | 3-I | 2-OC$_2H_5$-4-i-$C_3F_7$ | 195 |
| 1694 | t-$C_4H_9$ | H | H | 3-I | 2-OC$_2H_5$-4-i-$C_3F_7$ | 210 |
| 1695 | i-$C_3H_7$ | H | H | 3-I | 3-F-4-i-$C_3F_7$ | 265 |
| 1696 | t-$C_4H_9$ | H | H | 3-I | 3-F-4-i-$C_3F_7$ | 285 |
| 1697 | i-$C_3H_7$ | H | H | 3-I | 3-Cl-4-i-$C_3F_7$ | 295 |
| 1698 | i-$C_3H_7$ | H | H | 3-I | 2-Br-4-i-$C_3F_7$-5-CH$_3$ | 240 |
| 1699 | i-$C_3H_7$ | H | H | 3-I | 2-Br-4-i-$C_3F_7$ | 240 |
| 1700 | i-$C_3H_7$ | H | H | 3-I | 2-SCH$_3$-4-$C_2F_5$ | 200 |
| 1703 | i-$C_3H_7$ | H | H | 3-I | 4-(2-c-$C_3H_5$-4-Thz) | 198 |
| 1714 | i-$C_3H_7$ | H | H | 3-I | 2-$C_2H_5$-4-i-$C_3F_7$ | 220 |
| 1715 | i-$C_3H_7$ | H | H | 3-I | 2-OCH$_3$-4-i-$C_3F_7$ | 190 |
| 1716 | i-$C_3H_7$ | H | H | 3-I | 2,6(CH$_3$)$_2$-4-i-$C_3F_7$ | 275 |
| 1717 | i-$C_3H_7$ | H | H | 3-I | 2,6-(CH$_3$)$_2$-4-$C_2F_5$ | 250 |
| 1722 | i-$C_3H_7$ | H | H | 3-I | 2-Cl-4-i-$C_3F_7$ | 220 |
| 1723 | t-$C_4H_9$ | H | H | 3-I | 2-Cl-4-i-$C_3F_7$ | 210 |
| 1726 | i-$C_3H_7$ | H | H | 3-I | 2-(CH$_2$)$_4$-3-4-i-$C_3F_7$ | 260 |
| 1727 | t-$C_4H_9$ | H | H | 3-I | 2-(CH$_2$)$_4$-3-4-i-$C_3F_7$ | 272 |
| 1732 | i-$C_3H_7$ | H | H | 3-I | 2-Cl-3-OCF$_2$CF$_2$O-4 | 245 |
| 1733 | i-$C_3H_7$ | H | H | 3-I | 2-Cl-3-OCHFCF$_2$O-4 | 190 |
| 1737 | i-$C_3H_7$ | H | H | 3-I | 4-C(CH$_3$)=NOCH$_3$ | 190 |
| 1742 | i-$C_3H_7$ | H | H | 3-I | 2-OCF$_2$O-3 | 190 |
| 1743 | i-$C_3H_7$ | H | H | 3-I | 2-OCF$_2$O-3-6-Cl | 213 |
| 1744 | i-$C_3H_7$ | H | H | 3-I | 2-OCF$_2$O-3-4-Cl | 202 |
| 1745 | i-$C_3H_7$ | H | H | 3-I | 2-OCF$_2$O-3-4,6-Cl$_2$ | 228 |
| 1746 | i-$C_3H_7$ | H | H | 3-I | 2-OCF$_2$O-3-4-i-$C_3F_7$ | 175 |
| 1747 | t-$C_4H_9$ | H | H | 3-I | 2-OCF$_2$O-3-4-Cl | 235 |
| 1748 | t-$C_4H_9$ | H | H | 3-I | 2-OCF$_2$O-3-4,6-Cl$_2$ | 243 |
| 1749 | i-$C_3H_7$ | H | H | 3-I | 4-C(CH$_3$)=NOCH$_2$-Ph | 205 |
| 1750 | i-$C_3H_7$ | H | H | 3-I | 4-C(CH$_3$)=NOCH$_2$—C=CH$_2$ | Decomp. |
| 1751 | CH$_3$ | CH$_3$ | H | H | 2-CH$_3$-4-Cl | 149 |
| 1752 | $C_2H_5$ | $C_2H_5$ | H | H | 2-CH$_3$-4-Cl | 172 |
| 1753 | n-$C_3H_7$ | n-$C_3H_7$ | H | H | 2-CH$_3$-4-Cl | 126 |
| 1762 | i-$C_3H_7$ | H | H | 3-I | 3-C(i-$C_3F_7$)=NN-(i-$C_3F_7$)-4 | Paste |
| 1763 | i-$C_3H_7$ | H | H | 3-I | 4-i-$C_3H_7$-2-N=CH—S-3 | 200 |

TABLE 1-continued ($Z^1$, $Z^2$ = O)

| No | $R^1$ | $R^2$ | $R^3$ | Xn | Ym | Physical Properties (melting point: °C) |
|---|---|---|---|---|---|---|
| 1764 | i-$C_3H_7$ | H | H | 3-I | 3-S—C(i-$C_3H_7$)=N-4 | 218 |
| 1765 | i-$C_3H_7$ | H | H | 3-I | 4-(2-$CF_3$-4-Thz) | 105 |
| 1766 | i-$C_3H_7$ | H | H | 3-I | 3-$SCH_3$-4-i-$C_3F_7$ | 160 |
| 1767 | i-$C_3H_7$ | H | H | 3-I | 2-Ph-4-i-$C_3F_7$ | 240 |
| 1768 | i-$C_3H_7$ | H | H | 3-I | 2-OPh-4-i-$C_3F_7$ | 180 |
| 1769 | i-$C_3H_7$ | H | H | 3-I | 2-$OCH_3$-4-i-$C_3F_7$ | 265 |
| 1770 | $(CH_2)_2$-3-Pyi | H | H | 3-I | 2-$CH_3$-4-i-$C_3F_7$ | Amorphous |
| 1771 | $(CH_2)_2$-3-Pyi | H | H | 6-I | 2-$CH_3$-4-i-$C_3F_7$ | Amorphous |
| 1772 | $(CH_2)_2$-3-Pyi | H | H | 3-I | 2-$CH_3$-4-$OCF_3$ | 169–173 |
| 1773 | $CH(CH_3)$-2-Pyi | H | H | 3-I | 2-$CH_3$-4-i-$C_3F_7$ | Amorphous |
| 1774 | $CH(CH_3)$-2-Pyi | H | H | 6-I | 2-$CH_3$-4-i-$C_3F_7$ | Amorphous |
| 1775 | $CH(CH_3)$-2-Pyi | H | H | 3-I | 2-$CH_3$-4-$OCF_3$ | 158–161 |
| 1776 | $CH(CH_3)$-2-Pyi | H | H | 6-I | 2-$CH_3$-4-$OCF_3$ | 213–216 |
| 1777 | $CH(CH_3)$-2-Pyi | H | H | 3-I | 2-$CH_3$-4-$C_2F_5$ | 149–152 |
| 1778 | $CH(CH_3)$-2-Pyi | H | H | 6-I | 2-$CH_3$-4-$C_2F_5$ | 194–196 |
| 1780 | N(Ph)$COCF_3$ | H | H | 3-I | 2-$CH_3$-4-$C_2F_5$ | 239–241 |
| 1799 | $CH(CH_3)$-2-Fur | H | H | 3-I | 2-$CH_3$-4-i-$C_3F_7$ | 191 |
| 1800 | $CH(CH_3)$-2-Thi | H | H | 3-I | 2-$CH_3$-4-i-$C_3F_7$ | 159 |
| 1801 | i-$C_3H_7$ | H | H | 3-$CF_3$ | 2-$CH_3$-4-$C_2F_5$ | 210–212 |
| 1802 | i-$C_3H_7$ | H | H | 3-Cl-6-$CF_3S$ | 2-$CH_3$-4-$C_2F_5$ | 236–237 |
| 1803 | i-$C_3H_7$ | H | H | 3-$CF_3S$O | 2-$CH_3$-4-$C_2F_5$ | 186–187 |
| 1804 | i-$C_3H_7$ | H | H | 3-$CF_3$SO | 2-$CH_3$-4-$C_2F_5$ | 206–208 |
| 1805 | i-$C_3H_7$ | H | H | 3-$CF_3$SO | 2-$CH_3$-4-i-$C_3F_7$ | 211–213 |
| 1815 | i-$C_3H_7$ | H | H | 3-I | 2-$CH_3$-4-s-$C_4F_9$ | 190 |
| 1816 | i-$C_3H_7$ | H | H | 3-I | 2-OH-4-i-$C_3F_7$ | 155 |
| 1824 | i-$C_3H_7$ | H | H | 3-I | 2-N=C($CF_3$)O-3-4-i-$C_3F_7$ | 132 |
| 1825 | i-$C_3H_7$ | H | H | 3-I | 2-N=C($CF_3$)O-3 | 145 |
| 1826 | t-$C_4H_9$ | H | H | 3-I | 2-N=C($CF_3$)O-3-4-i-$C_3F_7$ | 110 |
| 1827 | t-$C_4H_9$ | H | H | 3-I | 2-N=C($CF_3$)O-3 | 120 |
| 1829 | $(CH_2)_2$NH—$CO_2C_2H_5$ | H | H | 3-I | 2-$CH_3$-4-i-$C_3F_7$ | 155 |
| 1830 | $(CH_2)_2$NH$CO_2CH_2$Ph | H | H | 3-I | 2-$CH_3$-4-$C_2F_5$ | 155 |
| 1831 | $(CH_2)_2$CH=$CF_2$ | H | H | 3-I | 2-$CH_3$-4-$C_2F_5$ | 180 |
| 1838 | i-$C_3H_7$ | H | H | H | 2-$CH_3$-4-$OCF_2CF_3$ | |
| 1839 | i-$C_3H_7$ | H | H | 3-$NO_2$ | 2-$CH_3$-4-$OCF_2CF_3$ | |
| 1840 | i-$C_3H_7$ | H | H | 3-F | 2-$CH_3$-4-$OCF_2CF_3$ | |
| 1841 | i-$C_3H_7$ | H | H | 3-Cl | 2-$CH_3$-4-$OCF_2CF_3$ | |
| 1842 | i-$C_3H_7$ | H | H | 3-Br | 2-$CH_3$-4-$OCF_2CF_3$ | |
| 1843 | i-$C_3H_7$ | H | H | 3-Cl-4-F | 2-$CH_3$-4-$OCF_2CF_3$ | |
| 1844 | i-$C_3H_7$ | H | H | 3,4-$Cl_2$ | 2-$CH_3$-4-$OCF_2CF_3$ | |
| 1845 | i-$C_3H_7$ | H | H | 3-I | 4-$OCF_2CF_3$ | |
| 1846 | i-$C_3H_7$ | H | H | 3-I | 2-Cl-4-$OCF_2CF_3$ | |
| 1847 | i-$C_3H_7$ | H | H | 3-I | 2-$CH_3$-4-$OCF_2CF_3$ | |
| 1848 | t-$C_4H_9$ | H | H | 3-I | 2-$CH_3$-4-$OCF_2CF_3$ | |
| 1849 | $C_2H_5$ | $C_2H_5$ | H | 3-I | 2-$CH_3$-4-$OCF_2CF_3$ | |
| 1850 | i-$C_3H_7$ | H | H | 3-I | 2-$C_2H_5$-4-$OCF_2CF_3$ | |
| 1851 | i-$C_3H_7$ | H | H | H | 2-$CH_3$-4-O-n-$C_3F_7$ | |
| 1852 | i-$C_3H_7$ | H | H | 3-$NO_2$ | 2-$CH_3$-4-O-n-$C_3F_7$ | |
| 1853 | i-$C_3H_7$ | H | H | 3-F | 2-$CH_3$-4-O-n-$C_3F_7$ | |
| 1854 | i-$C_3H_7$ | H | H | 3-Cl | 2-$CH_3$-4-O-n-$C_3F_7$ | |
| 1855 | i-$C_3H_7$ | H | H | 3-Br | 2-$CH_3$-4-O-n-$C_3F_7$ | |
| 1856 | t-$C_4H_9$ | H | H | 3-Cl-4-F | 2-$CH_3$-4-O-n-$C_3F_7$ | |
| 1857 | $C_2H_5$ | $C_2H_5$ | H | 3,4-$Cl_2$ | 2-$CH_3$-4-O-n-$C_3F_7$ | |
| 1858 | i-$C_3H_7$ | H | H | 3-I | 4-O-n-$C_3F_7$ | |
| 1859 | i-$C_3H_7$ | H | H | 3-I | 2-Cl-4-O-n-$C_3F_7$ | |
| 1860 | i-$C_3H_7$ | H | H | 3-I | 2-$CH_3$-4-O-n-$C_3F_7$ | |
| 1861 | t-$C_4H_9$ | H | H | 3-I | 2-$CH_3$-4-O-n-$C_3F_7$ | |
| 1862 | $C_2H_5$ | $C_2H_5$ | H | 3-I | 2-$CH_3$-4-O-n-$C_3F_7$ | |
| 1863 | i-$C_3H_7$ | H | H | 3-I | 2-$C_2H_5$-4-$OCF_2CF_3$ | |
| 1864 | i-$C_3H_7$ | H | H | 3-I | 2-$CH_3$-4-C≡C-t-$C_4F_9$ | |
| 1865 | i-$C_3H_7$ | H | H | 3-L | 2-$CH_3$-4-C≡C-$CF_3$ | |
| 1866 | i-$C_3H_7$ | H | H | 3-I | 2-$CH_3$-4-C≡C-i-$C_3F_7$ | |
| 1867 | i-$C_3H_7$ | H | H | 3-I | 2-$CH_3$-4-CF=$CF_2$ | |
| 1868 | i-$C_3H_7$ | H | H | 3-I | 2-$CH_3$-4-CF=$CFCF_3$ | |
| 1869 | i-$C_3H_7$ | H | H | 3-I | 2-$CH_3$-4-C($CF_3$)=$CF_2$ | |
| 1870 | i-$C_3H_7$ | H | H | 3-I | 2-$CH_3$-4-$COCH_3$ | |
| 1871 | i-$C_3H_7$ | H | H | 3-I | 2-$CH_3$-4-$COCF_3$ | 195 |
| 1872 | i-$C_3H_7$ | H | H | 3-I | 2-$CH_3$-4-$COC_2F_5$ | |
| 1873 | i-$C_3H_7$ | H | H | 3-I | 2-$CH_3$-4-COCF$(CH_3)_2$ | |
| 1874 | i-$C_3H_7$ | H | H | 3-I | 2-$CH_3$-4-$COOCH_3$ | 217 |
| 1875 | i-$C_3H_7$ | H | H | 3-I | 2-$CH_3$-4-$COOC_2H_5$ | |
| 1876 | i-$C_3H_7$ | H | H | 3-I | 2-$CH_3$-4-C($CH_3$)=$NOCH_3$ | 218 |
| 1877 | i-$C_3H_7$ | H | H | 3-I | 2-$CH_3$-4-C($CH_3$)=$NOC_2H_5$ | |

TABLE 1-continued ($Z^1$, $Z^2$ = O)

| No | $R^1$ | $R^2$ | $R^3$ | Xn | Ym | Physical Properties (melting point: °C. |
|---|---|---|---|---|---|---|
| 1878 | i-$C_3H_7$ | H | H | 3-I | 2-$CH_3$-4-C($CH_3$)=NO—$CH_2$CH=$CH_2$ | |
| 1879 | i-$C_3H_7$ | H | H | 3-I | 2-$CH_3$-4-C($CH_3$)=NO—$CH_2$C≡CH | |
| 1880 | i-$C_3H_7$ | H | H | 3-I | 2-$CH_3$-4-C($CH_3$)=NO$CH_2$-Ph | |
| 1881 | i-$C_3H_7$ | H | H | 3-I | 2-$CH_3$-4-$CH_2$OH | |
| 1882 | i-$C_3H_7$ | H | H | 3-I | 4-CH(OH)$CH_3$ | |
| 1883 | i-$C_3H_7$ | H | H | 3-I | 2-$CH_3$-4-CH(OH)$CH_3$ | |
| 1884 | i-$C_3H_7$ | H | H | 3-I | 2-$CH_3$-4-$CH_2$ON=C($CH_3$)$_2$ | |
| 1885 | i-$C_3H_7$ | H | H | 3-I | 2-$CH_3$-4-$CH_2$ON=C(Ph)-i-$C_3H_7$ | |
| 1886 | i-$C_3H_7$ | H | H | 3-I | 2-O$CH_2$O-3-4-i-$C_3F_7$ | |
| 1887 | i-$C_3H_7$ | H | H | 3-I | 2-O$CH_2$$CH_2$O-3-4-i-$C_3F_7$ | |
| 1888 | i-$C_3H_7$ | H | H | 3-I | 2-O$CF_2$$CF_2$O-3-4-i-$C_3F_7$ | |
| 1889 | i-$C_3H_7$ | H | H | 3-I | 2-O$CF_2$CHFO-3-4-i-$C_3F_7$ | |
| 1890 | i-$C_3H_7$ | H | H | 3-I | 2-OCHF$CF_2$O-3-4-i-$C_3F_7$ | |
| 1891 | i-$C_3H_7$ | H | H | 3-I | 2-S$CH_2$S-3-4-i-$C_3F_7$ | |
| 1892 | i-$C_3H_7$ | H | H | 3-I | 2-S$CF_2$S-3-4-i-$C_3F_7$ | |
| 1893 | i-$C_3H_7$ | H | H | 3-I | 2-S$CH_2$$CH_2$S-3-4-i-$C_3F_7$ | |
| 1894 | i-$C_3H_7$ | H | H | 3-I | 2-S$CF_2$$CF_2$S-3-4-i-$C_3F_7$ | |
| 1895 | i-$C_3H_7$ | H | H | 3-I | 2-$CH_2$O$CH_2$-3-4-i-$C_3F_7$ | |
| 1896 | i-$C_3H_7$ | H | H | 3-I | 2-$CH_2$S$CH_2$-3-4-i-$C_3F_7$ | |
| 1897 | i-$C_3H_7$ | H | H | 3-I | 2-$CF_2$O$CF_2$-3-4-i-$C_3F_7$ | |
| 1898 | i-$C_3H_7$ | H | H | 3-I | 2-$CF_2$S$CF_2$-3-4-i-$C_3F_7$ | |
| 1899 | i-$C_3H_7$ | H | H | 3-Br | 2-$CH_3$-4-i-$C_3F_7$ | |
| 1900 | i-$C_3H_7$ | H | H | 3-Br-4-Cl | 2-$CH_3$-4-i-$C_3F_7$ | |
| 1901 | i-$C_3H_7$ | H | H | 3-I-4-F | 2-$CH_3$-4-i-$C_3F_7$ | |
| 1902 | i-$C_3H_7$ | H | H | 3-I-4-Cl | 2-$CH_3$-4-i-$C_3F_7$ | |
| 1903 | i-$C_3H_7$ | H | H | 3-I-4-$CF_3$ | 2-$CH_3$-4-i-$C_3F_7$ | |
| 1904 | i-$C_3H_7$ | H | H | 3-I-4-O$CH_3$ | 2-$CH_3$-4-i-$C_3F_7$ | |
| 1905 | i-$C_3H_7$ | H | H | 3-I-4-Br | 2-$CH_3$-4-i-$C_3F_7$ | |
| 1906 | i-$C_3H_7$ | H | H | 3-Cl-4-$CF_3$ | 2-$CH_3$-4-i-$C_3F_7$ | |
| 1907 | i-$C_3H_7$ | H | H | 3-$CF_3$-4-Cl | 2-$CH_3$-4-i-$C_3F_7$ | |
| 1908 | i-$C_3H_7$ | H | H | 3-$CF_3$-4-F | 2-$CH_3$-4-i-$C_3F_7$ | |
| 1909 | i-$C_3H_7$ | H | H | 3-$CF_3$-4-O$CH_3$ | 2-$CH_3$-4-i-$C_3F_7$ | |
| 1910 | i-$C_3H_7$ | H | H | 3-N=CH—CH=CH-4 | 2-$CH_3$-4-i-$C_3F_7$ | |
| 1911 | i-$C_3H_7$ | H | H | 3-O$CH_2$O-4 | 2-$CH_3$-4-i-$C_3F_7$ | |
| 1912 | i-$C_3H_7$ | H | H | 3-O$CH_2$O-4 | 2-$CH_3$-4-$C_2F_5$ | |
| 1913 | i-$C_3H_7$ | H | H | 3-O$CH_2$O-4 | 2-$CH_3$-4-O$CF_3$ | |
| 1914 | i-$C_3H_7$ | H | H | 3-O$CF_2$O-4 | 2-$CH_3$-4-i-$C_3F_7$ | |
| 1915 | i-$C_3H_7$ | H | H | 3-O$CF_2$O-4 | 2-$CH_3$-4-$C_2F_5$ | |
| 1916 | i-$C_3H_7$ | H | H | 3-O$CF_2$O-4 | 2-$CH_3$-4-O$CF_3$ | |
| 1917 | i-$C_3H_7$ | H | H | 3-O$CH_2$$CH_2$O-4 | 2-$CH_3$-4-i-$C_3F_7$ | |
| 1918 | i-$C_3H_7$ | H | H | 3-O$CF_2$$CF_2$O-4 | 2-$CH_3$-4-i-$C_3F_7$ | |
| 1919 | i-$C_3H_7$ | H | H | 3-OCHF$CF_2$O-4 | 2-$CH_3$-4-i-$C_3F_7$ | |
| 1920 | i-$C_3H_7$ | H | H | 3-O$CF_2$CHFO-4 | 2-$CH_3$-4-i-$C_3F_7$ | |
| 1921 | i-$C_3H_7$ | H | H | 3-O$CH_2$$CH_2$-4 | 2-$CH_3$-4-i-$C_3F_7$ | |
| 1922 | i-$C_3H_7$ | H | H | 3-$CH_2$$CH_2$O-4 | 2-$CH_3$-4-i-$C_3F_7$ | |
| 1923 | i-$C_3H_7$ | H | H | 3-O$CF_2$$CF_2$-4 | 2-$CH_3$-4-i-$C_3F_7$ | |
| 1924 | i-$C_3H_7$ | H | H | 3-$CF_2$$CF_2$O-4 | 2-$CH_3$-4-i-$C_3F_7$ | |
| 1925 | i-$C_3H_7$ | H | H | 3-SO$CH_3$ | 2-$CH_3$-4-i-$C_3F_7$ | |
| 1926 | i-$C_3H_7$ | H | H | 3-$SO_2$$CH_3$ | 2-$CH_3$-4-i-$C_3F_7$ | |
| 1927 | i-$C_3H_7$ | H | H | 3-$CF_3$S | 2-$CH_3$-4-i-$C_3F_7$ | 222–223 |
| 1928 | i-$C_3H_7$ | H | H | 6-$CF_3$S | 2-$CH_3$-4-i-$C_3F_7$ | 219–221 |
| 1929 | t-$C_4H_9$ | H | H | 3-$CF_3$S | 2-$CH_3$-4-i-$C_3F_7$ | 231 |
| 1930 | t-$C_4H_9$ | H | H | 6-$CF_3$S | 2-$CH_3$-4-i-$C_3F_7$ | 245–247 |
| 1931 | t-$C_4H_9$ | H | H | 3-$CF_3$$SO_2$ | 2-$CH_3$-4-i-$C_3F_7$ | |
| 1932 | t-$C_4H_9$ | H | H | 3-$CF_3$$SO_2$ | 2-$CH_3$-4-$C_2F_5$ | |
| 1933 | t-$C_4H_9$ | H | H | 3-$CF_3$$SO_2$ | 2-$CH_3$-4-O$CF_3$ | |
| 1934 | $C_2H_5$ | $C_2H_5$ | H | 3-$CF_3$$SO_2$ | 2-$CH_3$-4-i-$C_3F_7$ | |
| 1935 | $C_2H_5$ | $C_2H_5$ | H | 3-CONH$CH_3$ | 2-$CH_3$-4-i-$C_3F_7$ | |
| 1936 | $C_2H_5$ | $C_2H_5$ | H | 3-CON($CH_3$)$_2$ | 2-$CH_3$-4-i-$C_3F_7$ | |
| 1937 | $C_2H_5$ | $C_2H_5$ | H | 3-CO$CH_3$ | 2-$CH_3$-4-i-$C_3F_7$ | |
| 1938 | $C_2H_5$ | $C_2H_5$ | H | 3-CO$C_2H_5$ | 2-$CH_3$-4-i-$C_3F_7$ | |
| 1939 | $C_2H_5$ | $C_2H_5$ | H | 3-C($CH_3$)=NO$CH_3$ | 2-$CH_3$-4-i-$C_3F_7$ | |
| 1940 | $C_2H_5$ | $C_2H_5$ | H | 3-C($CH_3$)=NO—$C_2H_5$ | 2-$CH_3$-4-i-$C_3F_7$ | |
| 1941 | i-$C_3H_7$ | H | H | 3-C≡CH | 2-$CH_3$-4-$C_2F_5$ | |
| 1942 | i-$C_3H_7$ | H | H | 3-C≡CH | 2-$CH_3$-4-i-$C_3F_7$ | |
| 1943 | i-$C_3H_7$ | H | H | 3-C≡C-t-$C_4H_9$ | 2-$CH_3$-4-$C_2F_5$ | 195–202 |
| 1944 | i-$C_3H_7$ | H | H | 3-C≡C-t-$C_4H_9$ | 2-$CH_3$-4-i-$C_3F_7$ | |
| 1945 | i-$C_3H_7$ | H | H | 3-C≡C-Ph | 2-$CH_3$-4-$C_2F_5$ | 179–183 |
| 1946 | i-$C_3H_7$ | H | H | 3-C≡C-Ph | 2-$CH_3$-4-i-$C_3F_7$ | |
| 1947 | i-$C_3H_7$ | H | H | 3-C≡C—$CF_3$ | 2-$CH_3$-4-$C_2F_5$ | |

TABLE 1-continued ($Z^1$, $Z^2$ = O)

| No | $R^1$ | $R^2$ | $R^3$ | Xn | Ym | Physical Properties (melting point: °C.) |
|---|---|---|---|---|---|---|
| 1948 | i-$C_3H_7$ | H | H | 3-C≡C—$CF_3$ | 2-$CH_3$-4-i-$C_3F_7$ | |
| 1949 | i-$C_3H_7$ | H | H | 3-$C_2F_5$ | 2-$CH_3$-4-$C_2F_5$ | |
| 1950 | t-$C_4H_9$ | H | H | 3-$C_2F_5$ | 2-$CH_3$-4-$C_2F_5$ | |
| 1951 | $C_2H_5$ | $C_2H_5$ | H | 3-$C_2F_5$ | 2-$CH_3$-4-$C_2F_5$ | |
| 1952 | i-$C_3H_7$ | H | H | 3-$C_2F_5$ | 2-$CH_3$-4-i-$C_3F_7$ | |
| 1953 | t-$C_4H_9$ | H | H | 3-$C_2F_5$ | 2-$CH_3$-4-i-$C_3F_7$ | |
| 1954 | $C_2H_5$ | $C_2H_5$ | H | 3-$C_2F_5$ | 2-$CH_3$-4-i-$C_3F_7$ | |
| 1955 | i-$C_3H_7$ | SN-(n-$C_4H_9$)$_2$ | H | 3-I | 2-$CH_3$-4-i-$C_3F_7$ | |
| 1956 | i-$C_3H_7$ | $SO_2CH_3$ | H | 3-I | 2-$CH_3$-4-i-$C_3F_7$ | |
| 1957 | i-$C_3H_7$ | CN | H | 3-I | 2-$CH_3$-4-i-$C_3F_7$ | |
| 1958 | i-$C_3H_7$ | $COOCH_3$ | H | 3-I | 2-$CH_3$-4-i-$C_3F_7$ | |
| 1959 | i-$C_3H_7$ | $COOC_2H_5$ | H | 3-I | 2-$CH_3$-4-i-$C_3F_7$ | |
| 1960 | i-$C_3H_7$ | $COCH_3$ | H | 3-I | 2-$CH_3$-4-i-$C_3F_7$ | |
| 1961 | i-$C_3H_7$ | $COC_2H_5$ | H | 3-I | 2-$CH_3$-4-i-$C_3F_7$ | |
| 1962 | i-$C_3H_7$ | CO-Ph | H | 3-I | 2-$CH_3$-4-i-$C_3F_7$ | |
| 1963 | i-$C_3H_7$ | $NHCOCH_3$ | H | 3-I | 2-$CH_3$-4-i-$C_3F_7$ | |
| 1964 | $C_2H_5$ | $C_2H_5$ | SN(n-$C_4H_9$)$_2$ | 3-I | 2-$CH_3$-4-i-$C_3F_7$ | |
| 1965 | $C_2H_5$ | $C_2H_5$ | $SO_2CH_3$ | 3-I | 2-$CH_3$-4-i-$C_3F_7$ | |
| 1966 | $C_2H_5$ | $C_2H_5$ | CN | 3-I | 2-$CH_3$-4-i-$C_3F_7$ | |
| 1967 | $C_2H_5$ | $C_2H_5$ | $COOCH_3$ | 3-I | 2-$CH_3$-4-i-$C_3F_7$ | |
| 1968 | $C_2H_5$ | $C_2H_5$ | $COOC_2H_5$ | 3-I | 2-$CH_3$-4-i-$C_3F_7$ | |
| 1969 | $C_2H_5$ | $C_2H_5$ | $COCH_3$ | 3-I | 2-$CH_3$-4-i-$C_3F_7$ | |
| 1970 | $C_2H_5$ | $C_2H_5$ | $COC_2H_5$ | 3-I | 2-$CH_3$-4-i-$C_3F_7$ | Amorphous |
| 1971 | $C_2H_5$ | $C_2H_5$ | COPh | 3-I | 2-$CH_3$-4-i-$C_3F_7$ | |
| 1972 | $C_2H_5$ | $C_2H_5$ | $NHCOCH_3$ | 3-I | 2-$CH_3$-4-i-$C_3F_7$ | |
| 1973 | ($CH_2$)$_2$COO-13 $CH_3$ | H | H | 3-I | 2-$CH_3$-4-i-$C_3F_7$ | |
| 1974 | ($CH_2$)$_2$COO—$CH_3$ | H | H | 3-I | 2-$CH_3$-4-$C_2F_5$ | |
| 1975 | ($CH_2$)$_2$COO—$C_2H_5$ | H | H | 3-I | 2-$CH_3$-4-i-$C_3F_7$ | 133.2 |
| 1976 | ($CH_2$)$_2$COO—$C_2H_5$ | H | H | 3-I | 2-$CH_3$-4-$C_2F_5$ | |
| 1977 | ($CH_2$)$_2$COO—$C_2H_5$ | H | H | 6-I | 2-$CH_3$-4-$C_2F_5$ | 163.5 |
| 1978 | $CH(CH_3)CH_2$—$COOCH_3$ | H | H | 3-I | 2-$CH_3$-4-i-$C_3F_7$ | |
| 1979 | $CH(CH_3)CH_2COOC_2H_5$ | H | H | 3-I | 2-$CH_3$-4-i-$C_3F_7$ | |
| 1980 | $CH(CH_3)CH_2COO$-i-$C_3H_7$ | H | H | 3-I | 2-$CH_3$-4-i-$C_3F_7$ | |
| 1981 | ($CH_2$)$_2$$CONHCH_3$ | H | H | 3-I | 2-$CH_3$-4-i-$C_3F_7$ | |
| 1982 | ($CH_2$)$_2$$CONHC_2H_5$ | H | H | 3-I | 2-$CH_3$-4-i-$C_3F_7$ | |
| 1983 | $CH(CH_3)CH_2CONHCH_3$ | H | H | 3-I | 2-$CH_3$-4-i-$C_3F_7$ | |
| 1984 | $CH(CH_3)CH_2CONHC_2H_5$ | H | H | 3-I | 2-$CH_3$-4-i-$C_3F_7$ | |
| 1985 | $CH(CH_3)CH_2CONH$-i-$C_3H_7$ | H | H | 3-I | 2-$CH_3$-4-i-$C_3F_7$ | |
| 1986 | $CH(CH_3)CH_2CON$—($CH_3$)$_2$ | H | H | 3-I | 2-$CH_3$-4-i-$C_3F_7$ | |
| 1987 | $CH(CH_3)CH_2CON$—($C_2H_5$)$_2$ | H | H | 3-I | 2-$CH_3$-4-i-$C_3F_7$ | |
| 1988 | ($CH_2$)$_2$$NHCOOCH_3$ | H | H | 3-I | 2-$CH_3$-4-$C_2F_5$ | |
| 1989 | ($CH_2$)$_2$$NHCOOCH_3$ | H | H | 3-I | 2-$CH_3$-4-i-$C_3F_7$ | |
| 1990 | ($CH_2$)$_2$$NHCOOC_2H_5$ | H | H | 3-I | 2-$CH_3$-4-$C_2F_5$ | 145 |
| 1991 | ($CH_2$)$_2$$NHCOOC_2H_5$ | H | H | 3-I | 2-$CH_3$-4-$OCF_3$ | 210 |
| 1992 | $CH(CH_3)CH_2NHCOOCH_3$ | H | H | 3-I | 2-$CH_3$-4-i-$C_3F_7$ | |
| 1993 | $CH(CH_3)CH_2NHCOO$—$C_2H_5$ | H | H | 3-I | 2-$CH_3$-4-i-$C_3F_7$ | |
| 1994 | ($CH_2$)$_2$P($CH_3$)$_2$ | H | H | 3-I | 2-$CH_3$-4-i-$C_3F_7$ | |
| 1995 | $CH(CH_3)P(C_2H_5)_2$ | H | H | 3-I | 2-$CH_3$-4-i-$C_3F_7$ | |
| 1996 | ($CH_2$)$_2$P(Ph)$_2$ | H | H | 3-I | 2-$CH_3$-4-i-$C_3F_7$ | |
| 1997 | $CH(CH_3)CH_2P(CH_3)_2$ | H | H | 3-I | 2-$CH_3$-4-i-$C_3F_7$ | |
| 1998 | $CH(CH_3)CH_2P(C_2H_5)_2$ | H | H | 3-I | 2-$CH_3$-4-i-$C_3F_7$ | |
| 1999 | $CH(CH_3)CH_2P(Ph)_2$ | H | H | 3-I | 2-$CH_3$-4-i-$C_3F_7$ | |
| 2000 | $CH(CH_3)(CH_2)_2P$—($CH_3$)$_2$ | H | H | 3-I | 2-$CH_3$-4-i-$C_3F_7$ | |
| 2001 | $CH(CH_3)(CH_2)_3P$—($CH_3$)$_2$ | H | H | 3-I | 2-$CH_3$-4-i-$C_3F_7$ | |
| 2002 | ($CH_2$)$_2$PO($CH_3$)$_2$ | H | H | 3-I | 2-$CH_3$-4-i-$C_3F_7$ | |
| 2003 | ($CH_2$)$_2$PO(O$C_2H_5$)$_2$ | H | H | 3-I | 2-$CH_3$-4-i-$C_3F_7$ | Amorphous |
| 2004 | $CH(CH_3)CH_2PO(OCH_3)_2$ | H | H | 3-I | 2-$CH_3$-4-i-$C_3F_7$ | |
| 2005 | ($CH_2$)$_2$OPO(O$CH_3$)$_2$ | H | H | 3-I | 2-$CH_3$-4-i-$C_3F_7$ | |
| 2006 | $CH(CH_3)CH_2PS(OCH_3)_2$ | H | H | 3-I | 2-$CH_3$-4-i-$C_3F_7$ | |
| 2007 | $CH(CH_3)CH_2PS$—(O$C_2H_5$)$_2$ | H | H | 3-I | 2-$CH_3$-4-i-$C_3F_7$ | |
| 2008 | ($CH_2$)$_2$OPO(O$C_2H_5$)$_2$ | H | H | 3-I | 2-$CH_3$-4-i-$C_3F_7$ | |
| 2009 | $CH(CH_3)CH_2OPO$—(O$CH_3$)$_2$ | H | H | 3-I | 2-$CH_3$-4-i-$C_3F_7$ | |
| 2010 | $CH(CH_3)CH_2OPO$—(O$C_2H_5$)$_2$ | H | H | 3-I | 2-$CH_3$-4-i-$C_3F_7$ | |
| 2011 | ($CH_2$)$_2$OPS(O$CH_3$)$_2$ | H | H | 3-I | 2-$CH_3$-4-i-$C_3F_7$ | |
| 2012 | ($CH_2$)$_2$OPS(O$C_2H_5$)$_2$ | H | H | 3-I | 2-$CH_3$-4-i-$C_3F_7$ | |
| 2013 | $CH(CH_3)CH_2OPS$—(O$CH_3$)$_2$ | H | H | 3-I | 2-$CH_3$-4-i-$C_3F_7$ | |
| 2014 | $CH(CH_3)CH_2OPS$—(O$C_2H_5$)$_2$ | H | H | 3-I | 2-$CH_3$-4-i-$C_3F_7$ | |
| 2015 | $CH(CH_3)$-2-Pyi-N-Oxide | H | H | 3-I | 2-$CH_3$-4-$C_2F_5$ | 198–205 |
| 2016 | $CH(CH_3)$-2-Pyi-N-Oxide | H | H | 3-I | 2-$CH_3$-4-i-$C_3F_7$ | 208–210 |
| 2017 | i-$C_3H_7$ | H | H | 3-I | 2-$CH_3$-4-C($CF_3$)=$NOCH_3$ | |

TABLE 1-continued ($Z^1$, $Z^2$ = O)

| No | $R^1$ | $R^2$ | $R^3$ | Xn | Ym | Physical Properties (melting point: °C. |
|---|---|---|---|---|---|---|
| 2018 | i-$C_3H_7$ | H | H | 3-I | 2-$CH_3$-4-C($CF_3$)=NO$CH_2$Ph | |
| 2019 | i-$C_3H_7$ | H | H | 3-I | 2-NCHCHCHCH-3-4-i-$C_3F_7$ | 180 |
| 2020 | i-$C_3H_7$ | H | H | 3-I | 2-n-$C_3H_7$-4-i-$C_3F_7$ | 225 |
| 2021 | i-$C_3H_7$ | H | H | 3-I | 2-O-(2-Pyi)-4-i-$C_3F_7$ | 158.3–159.8 |

The abbreviations in Table 1 stand for the following substituents:
Ph: phenyl group,
c-: alicyclic hydrocarbon group,
Pyi: pyridyl group,
Pym: pyrimidinyl group,
Fur: furyl group,
TetFur: tetrahydrofuryl group,
Thi: thienyl group,
Thz: thiazolyl group,
Naph: naphthyl group,
Oxa: oxazolyl group,
C*: asymmetric carbon atom

TABLE 2

| No | $R^1$ | $R^2$ | $R^3$ | Xn | Ym | $Z^1$ | $Z^2$ | Physical Properties (melting point: °C. |
|---|---|---|---|---|---|---|---|---|
| S-1 | i-$C_3H_7$ | H | H | 3-Cl | 2-$CH_3$-4-$CF_2CF_3$ | S | O | 162–164 |
| S-2 | t-$C_4H_9$ | H | H | 3-Cl | 2-$CH_3$-4-$CF_2CF_3$ | S | O | 141–143 |
| S-3 | c-$C_3H_5$ | H | H | 3-Cl | 2-$CH_3$-4-$CF_2CF_3$ | S | O | 138–139 |
| S-4 | $C_2H_5$ | $C_2H_5$ | H | 3-Cl | 2-$CH_3$-4-$CF_2CF_3$ | S | O | 184–186 |
| S-5 | i-$C_3H_7$ | H | H | H | 2-$CH_3$-4-Cl | S | O | 168–170 |
| S-6 | i-$C_3H_7$ | H | H | H | 2-$CH_3$-4-Cl | O | S | |
| S-7 | i-$C_3H_7$ | H | H | 3-I | 2-$CH_3$-4-i-$C_3H_7$ | O | S | |
| S-8 | i-$C_3H_7$ | H | H | H | 2-$CH_3$-4-i-$C_3H_7$ | S | S | |
| S-9 | i-$C_3H_7$ | H | H | 3-I | 2-$CH_3$-4-i-$C_3H_7$ | S | S | |

The $^1$H-NMR data of the compounds obtained as paste (physical properties) are given in Table 3 below.

TABLE 3

| No. | $^1$H—NMR[$CDCl_3$/TMS, δ values (ppm)] |
|---|---|
| 1122 | 1.2–1.4(m.6H), 2.4–2.5(m.3H), 3.1–3.9(m.7H), 6.6–7.9(m.6H) |
| 1218 | 1.3(d.3H), 2.3(s.3H), 2.9–3.2(m.2H), 4.4(m.1H), 6.2(d.1H), 7.1–7.5(m.3H), 7.8(d.1H), 8.0(d.1H), 8.4(d.1H), 8.5(s.1H). |

The fluorine-containing aniline compound of the general formula (ST-I) of the present invention is useful as an intermediate of a medicine, agrochemical, chemical product etc., particularly, is useful as a starting material of the phthalic acid diamide derivative of the general formula (I) of the present invention. That is, the fluorine-containing aniline compound of the general formula (ST-I) is useful as an aniline of the general formula (IV) in the Production processes 1, 3, 5 and 6 as illustrated above. The fluorine-containing aniline compound of the general formula (ST-I) of the present invention can be produced, for example, by any of the following production processes.

Production process 8

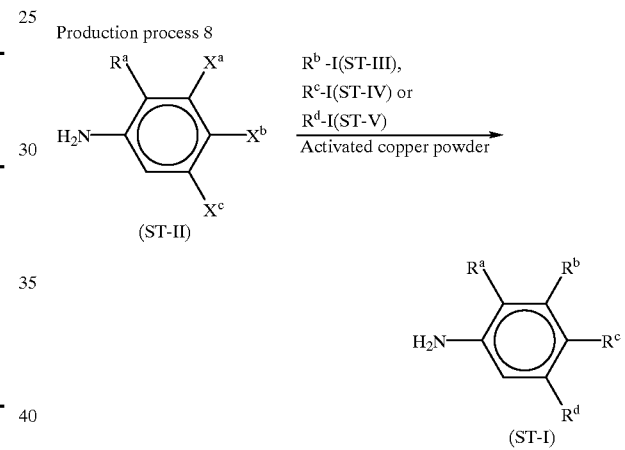

wherein each of $X^a$, $X^b$ and $x^c$ is a hydrogen atom, an iodine atom or a bromine atom, provided that at least one of $X^a$, $X^b$ and $X^c$ is not a hydrogen atom, and $R^a$, $R^b$, $R^c$ and $R^d$ are as defined above.

A fluorine-containing aniline compound of the general formula (ST-I) can be produced by reacting an aniline derivative of the general formula (ST-II) with a perfluoroalkyl iodide of the general formula (ST-III), general formula (ST-IV) or general formula (ST-V) in the presence of activated copper powder and an inert solvent.

Usually, the amount of each of the perfluoroalkyl iodide of the general formula (ST-III), (ST-IV) or (ST-V) and the activated copper powder used may be properly chosen in the range of 1 to 5 times the amount of the aniline derivative of the general formula (ST-II).

As the inert solvent used in the reaction, any solvent may be used so long as it does not remarkably inhibit the progress of the reaction. There can be used, for example, aprotic polar solvents such as N,N-dimethylformamide (DMF), dimethyl sulfoxide (DMSO), etc. The reaction temperature may be properly chosen in the range of room temperature to 200° C.

After completion of the reaction, the desired compound is isolated from the reaction mixture containing the desired compound by a conventional method and can, if necessary, be purified by silica gel chromatography, distillation, recrystallization, etc.

The reaction can be carried out by the method described in Bull. Chem. Soc. Jpn., 65, 2141–2144 (1992).

Production process 9

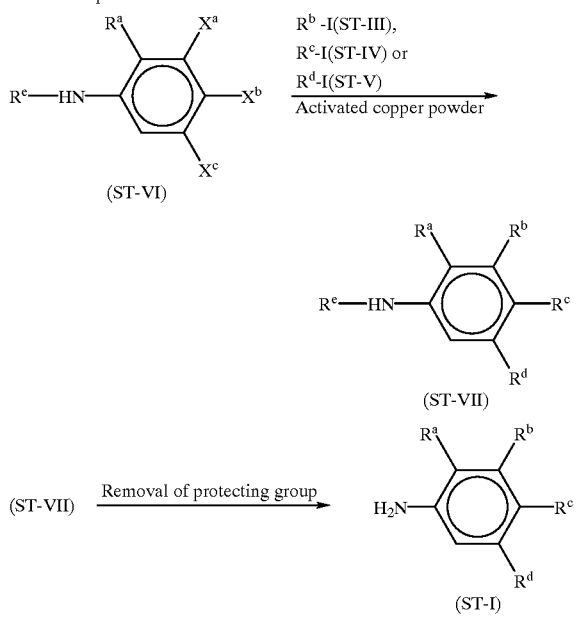

wherein $R^a$, $R^b$, $R^c$, $R^d$, $X^a$, $X^b$ and $X^c$ are as defined above, and $R^e$ is a protecting group such as an acyl group.

A fluorine-containing aniline compound of the general formula (ST-I) can be produced by reacting an acylaniline derivative of the general formula (ST-VI) with a perfluoroalkyl iodide of the general formula (ST-III), general formula (ST-IV) or general formula (ST-V) in the presence of activated copper powder and an inert solvent to obtain an acylaniline derivative of the general formula (ST-VII), and deacylating the acylaniline derivative (ST-VII) after or without isolation.

① General formula (ST-VI)→general formula (ST-VII)

This reaction can be carried out according to production process 8.

② General formula (ST-VII)→general formula (ST-I)

This reaction is usually carried out under acidic conditions. In the reaction, for example, an aqueous mineral acid solution such as a 5 to 35% aqueous hydrochloric acid solution is used as an acid. If necessary, there may be used together therewith alcohols such as methanol, ethanol, etc., and inert solvents such as tetrahydrofuran (THF), acetonitrile, etc. The reaction temperature may be chosen in the range of room temperature to the boiling point of the solvent used. The desired compound can be produced by carrying out the similar workup as in production process 8.

Production process 10

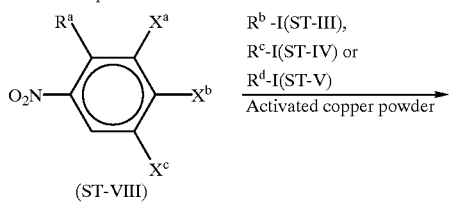

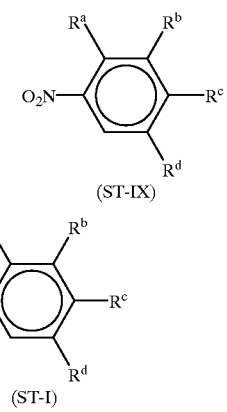

wherein $R^a$, $R^b$, $R^c$, $R^d$, $X^a$, $X^b$ and $X^c$ are as defined above.

A fluorine-containing aniline compound of the general formula (ST-I) can be produced by reacting a nitrobenzene derivative of the general formula (ST-VIII) with a perfluoroalkyl iodide of the general formula (ST-III), general formula (ST-IV) or general formula (ST-V) in the presence of activated copper powder and an inert solvent to obtain a nitrobenzene derivative of the general formula (ST-IX), and reducing the nitrobenzene derivative (ST-IX) after or without isolation.

① General formula (ST-VIII) general formula (ST-IX)

This reaction can be carried out according to production process 8.

② General formula (ST-IX)→general formula (ST-I)

Usually, the desired compound can be produced by subjecting the nitrobenzene derivative (ST-IX) to catalytic hydrogenation in an alcohol solvent in the presence of a catalyst such as 5% palladium carbon (proportion: 1 to 5% by weight), or reducing the nitro-benzene derivative (ST-IX) with an aqueous hydrochloric acid solution containing stannous chloride, in a solvent such as ethanol.

The reaction ② can be carried out according to the method described in Journal of Chemical Society of Japan, 1973, 2351.

Typical examples of the fluorine-containing aniline compound of the general formula (ST-I) of the present invention are given in Table 4 but they are not intended in any way to limit the scope of the present invention.

General formula (ST-I)

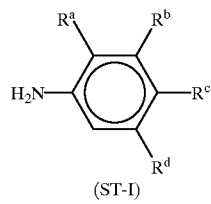

TABLE 4

| No. | $R^a$ | $R^b$ | $R^c$ | $R^d$ | Physical property or $^1$H—NMR (δ, ppm) |
|---|---|---|---|---|---|
| ST-1 | CH$_3$ | H | H | C$_2$F$_5$ | 2.21(s, 3H), 3.84(br, 2H), 6.86(s, 1H), 6.91(d, 1H), 7.15(d, 1H) |

TABLE 4-continued

| No. | $R^a$ | $R^b$ | $R^c$ | $R^d$ | Physical property or $^1$H—NMR ($\delta$, ppm) |
|---|---|---|---|---|---|
| ST-2 | $CH_3$ | H | H | $i\text{-}C_3F_7$ | |
| ST-3 | $CH_3$ | H | $C_2F_5$ | H | b.p. 95–105° C./ 10 mmHg |
| ST-4 | $CH_3$ | H | $i\text{-}C_3F_7$ | H | b.p. 100–110° C./ 10 mmHg |
| ST-5 | $CH_3$ | H | $n\text{-}C_3F_7$ | H | 2.20(s, 3H), 3.9(br, 2H), 6.70(d, 1H), 7.22–7.27(m, 2H). |
| ST-6 | $CH_3$ | H | $n\text{-}C_4F_9$ | H | 2.19(s, 3H), 4.2(br, 2H), 6.70(d, 1H), 7.20–7.26(m, 2H). |
| ST-7 | $CH_3$ | H | $CF(CF_3)$ —$C_2F_5$ | H | |
| ST-8 | $CH_3$ | $C_2F_5$ | H | H | 2.22(s, 3H), 3.83(br, 2H), 6.86(d, 1H), 6.99(d, 1H), 7.12(t, 1H). |
| ST-9 | $CH_3$ | $i\text{-}C_3F_7$ | H | H | |
| ST-10 | F | H | $i\text{-}C_3F_7$ | H | |
| ST-11 | Cl | H | $C_2F_5$ | H | 4.4(br, 2H), 6.8(d, 1H), 7.27(dd, 1H), 7.47(d, 1H). |
| ST-12 | Cl | H | $i\text{-}C_3F_7$ | H | 4.5(br, 2H), 7.41(s, 1H), 7.81(d, 1H), 8.05(d, 1H). |
| ST-13 | Cl | H | $n\text{-}C_3F_7$ | H | 4.1(br, 2H), 6.83(d, 1H), 7.24(d, 1H), 7.43(s, 1H). |
| ST-14 | Br | H | $C_2F_5$ | H | |
| ST-15 | $OCH_3$ | H | $C_2F_5$ | H | 3.85(br, 2H), 3.93(s, 3H), 6.72(d, 1H), 6.92(s, 1H), 7.03(d, 1H). |
| ST-16 | $OCH_3$ | H | $i\text{-}C_3F_7$ | H | |
| ST-17 | $OC_2H_5$ | H | $i\text{-}C_3F_7$ | H | |
| ST-18 | $C_2H_5$ | H | $C_2F_5$ | H | 1.29(t, 3H), 2.52(q, 2H), 3.95(br, 2H), 6.8(d, 1H), 7.2–7.26(m, 2H). |
| ST-19 | $C_2H_5$ | H | $i\text{-}C_3F_7$ | H | |
| ST-20 | $i\text{-}C_3F_7$ | H | $i\text{-}C_3F_7$ | H | |
| ST-21 | $n\text{-}C_4H_9$ | H | $C_2F_5$ | H | 0.9(t, 3H), 1.4(q, 2H), 1.6(q, 2H), 2.5(t, 2H), 3.95(br, 2H), 6.69(d, 2H), 7.19–7.21(m, 2H). |
| ST-22 | $CF_3$ | H | $C_2F_5$ | H | 4.52(br, 2H), 6.81(d, 1H), 7.48(d, 1H), 7.63(br, 1H). |
| ST-23 | $CF_3$ | H | $i\text{-}C_3F_7$ | H | |

Agricultural and horticultural insecticides containing the phthalic acid diamide derivative of the general formula (I) of the present invention as an active ingredient are suitable for controlling various insect pests such as agricultural insect pests, forest insect pests, horticultural insect pests, stored grain insect pests, sanitary insect pests, nematodes, etc., which are injurious to paddy rice, fruit trees, vegetables, other crops, flowers and ornamental plants, etc. They have a marked insecticidal effect, for example, on LEPIDOPTERA including summer fruit tortrix (*Adoxophyes orana fasciata*), smaller tea tortrix (*Adoxophyes sp.*), Manchurian fruit moth (*Grapholita inopinata*), oriental fruit moth (*Grapholita molesta*), soybean pod border (*Leguminivora glycinivorella*), mulberry leafroller (*Olethreutes mori*), tea leafroller (*Caloptilia thevivora*), Caloptilia sp. (*Calopilia zachrysa*), apple leafminer (*Phyllonorycter ringoniella*), pear barkminer (*Spulerrina astaurota*), common white (*Piers rapae crucivora*), tabacco budworm (*Heliothis sp.*), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tabacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnip aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), San Jose scale (*Comstockaspis perniciosa*), arrowhead scale (*Unaspis vanonensis*), etc.; COLEOPTERA including soybean beetle (*Anomala rufocuprea*), Japanese beetle (*Popillia japonica*), tabacco beetle (*Lasioderma serricorne*), powderpost beetle (*Lyctus brunneus*), twenty-eight-spotted ladybird (*Epilachna vigintiotopunctata*), adzuki bean weevile (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica sp.*), etc.; DIPTERA including melon fly (*Dacus(Zeugodacus) cucurbitae*), oriental fruit fly (*Dacus(Bactrocera) dorsalis*), rice leafminer (*Agnomyza oryzae*), onion maggot (*Delia antiqua*), seedcorn maggot (*Delia platura*), soybean pod gall midge (*Asphondylia sp.*), muscid fly (*Musca domestica*), house mosquito (*Culex pipiens pipiens*), etc.; and TYLENCHIDA including root-lesion nematode (*Pratylenchus sp.*), coffer root-lesion nematode (*Pratylenchus coffeae*), potato cyst nematode (*Globodera rostochiensis*), root-knot nematode (*Meloidogyne sp.*), citrus nematode (*Tylenchulus semipenetrans*), Aphelenchus sp. (*Aphelenchus avenae*), chrysanthemum foliar (*Aphelenchoides ritzemabosi*), etc.

The agricultural and horticultural insecticide containing the phthalic acid diamide derivative of the general formula (I) of the present invention as an active ingredient has a marked insecticidal effect on the above-exemplified insect pests, sanitary insect pests, and/or nematodes, which are injurious to paddy field crops, upland crops, fruit trees, vegetables, other crops, flowers and ornament plants, and the like. Therefore, the desired effect of the agricultural and horticultural insecticide of the present invention can be obtained by applying the insecticide to the paddy field water, stalks and leaves of fruit trees, vegetables, other crops, flowers and ornament plants, soil, etc. at a season at which the insect pests, sanitary pests or nematodes are expected to appear, before their appearance or at the time when their appearance is confirmed.

In general, the agricultural and horticultural insecticide of the present invention is used after being prepared into conveniently usable forms according to an ordinary manner for preparation of agrochemicals.

That is, the phthalic acid diamide derivative of the general formula (I) and, optionally, an adjuvant are blended with a suitable inert carrier in a proper proportion and prepared into a suitable preparation form such as a suspension, emulsifiable concentrate, soluble concentrate, wettable powder, granules, dust or tablets through dissolution, dispersion, suspension, mixing, impregnation, adsorption or sticking.

The inert carrier used in this invention may be either solid or liquid. As the solid carrier, there can be exemplified soybean flour, cereal flour, wood flour, bark flour, saw dust, powdered tobacco stalks, powdered walnut shells, bran, powdered cellulose, extraction residues of vegetables, powdered synthetic polymers or resins, clays (e.g. kaolin, bentonite, and acid clay), talcs (e.g. talc and pyrophyllite), silica powders or flakes (e.g. diatomaceous earth, silica sand, mica and white carbon, i.e. synthetic, high-dispersion silicic acid, also called finely divided hydrated silica or hydrated silicic acid, some of commercially available products contain calcium silicate as the major component), activated carbon, powdered sulfur, powdered pumice, calcined diatomaceous earth, ground brick, fly ash, sand, calcium carbonate powder, calcium phosphate powder and other inorganic or mineral powders, chemical fertilizers (e.g. ammonium sulfate, ammonium phosphate, ammonium nitrate, urea and ammonium chloride), and compost. These carriers may be used alone or as a mixture thereof.

The liquid carrier is that which itself has solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, Cellosolve, dipropyl ether and tetrahydrofuran; aliphatic hydrocarbons such as kerosene and mineral oils; aromatic hydrocarbons such as benzene, toluene, xylene, solvent naphtha and alkylnaphthalenes; halogenated hydrocarbons such as dichloroethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan mono-laurate, polyoxyethylene sorbitan monooleate, alkylarylsulfonates, naphthalenesulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicon oils may also be used as a defoaming agent.

The content of the active ingredient may be varied as required. In dusts or granules, the suitable content thereof is from 0.01 to 50% by weight. In emulsifiable concentrates or flowable wettable powders, it is also from 0.01 to 50% by weight.

The agricultural and horticultural insecticide of the present invention is used to control a variety of insect pests in the following manner. That is, it is applied to a crop on which the insect pests are expected to appear or a site where the appearance of the insect pests is undesirable, as it is or after being properly diluted with or suspended in water or the like, in an amount effective for control of the insect pests.

The applying dosage of the agricultural and horticultural insecticide of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.1 g to 10 kg (in terms of the active ingredient) per 10 ares depending upon purposes.

The agricultural and horticultural insecticide of the present invention may be used in admixture with other agricultural and horticultural disease or pest controllers in order to expand both spectrum of controllable diseases and insect pest species and the period of time when effective applications are possible or to reduce the dosage.

Typical examples of the present invention are described below, but they should not be construed as limiting the scope of the invention.

EXAMPLES

Example 1

(1-1) Production of 3-chloro-N-[4-(1,1,2,2-tetrafluoroethoxy) -2 -methylphenyl]phthalimide In 10 ml of acetic acid were dissolved 0.55 g of 3-chlorophthalic anhydride and 0.67 g of 4-(1,1,2,2-tetrafluoroethoxy)-2-methylaniline, and the reaction was carried out with heating under reflux for 3 hours. After completion of the reaction, the solvent was distilled off under reduced pressure and the resulting residue was washed with an ether-hexane mixed solvent to obtain 1.1 g of the desired compound.

Physical property: m.p. 121–122° C. Yield: 95%.

(1-2) Production of 3-chloro-$N^1$-[4-(1,1,2,2-tetrafluoroethoxy)-2-methylphenyl]-$N^2$-isopropylphthalic acid diamide (compound No. 141) and 6-chloro-$N^1$-[4-(1,1,2,2-tetrafluoroethoxy)-2-methylphenyl]-$N^2$-isopropylphthalic acid diamide (compound No. 239)

In 10 ml of dioxane was dissolved 1.1 g of 3-chloro-N-[4-(1,1,2,2-tetrafluoroethoxy)-2-methylphenyl]-phthalimide, followed by adding thereto 0.5 g of isopropylamine, and the reaction was carried out at 80+ C. for 3 hours. After completion of the reaction, the solvent was distilled off under reduced pressure and the resulting residue was purified by a silica gel column chromatography using a hexane/ethyl acetate (2/1) mixed solvent as an eluent, to obtain 0.4 g of the desired compound (compound No. 141) having an Rf value of 0.5 to 0.7 and 0.5 g of the other desired compound (compound No. 239) having an Rf value of 0.2 to 0.4.

Compound No. 141:

Physical property: m.p. 202–204° C.

Yield: 31%.

Compound No. 239:

Physical property: m.p. 199–201° C.

Yield: 39%.

Example 2

(2-1) Production of N-(4-trifluoromethoxyphenyl)-3-nitrophthalimide

In 50 ml of acetic acid were dissolved 5.97 g of 3-nitrophthalic anhydride and 5.31 g of 4-trifluoromethoxyaniline, and the reaction was carried out with heating under reflux for 3 hours. After completion of the reaction, the solvent was distilled off under reduced pressure and the resulting residue was washed with an ether-hexane mixed solvent to obtain 10.2 g of the desired compound.

Physical property: m.p. 149–150° C.
Yield: 97%.

(2-2) Production of 3-amino-N-(4-trifluoromethoxyphenyl)phthalimide

In a pressure vessel were placed 10.0 g of N-(4-trifluoromethoxyphenyl)-3-nitrophthalimide, 100 ml of acetic acid and 0.5 g of 5% palladium carbon, and catalytic reduction with hydrogen was carried out at a hydrogen pressure of 5 kg/cm$^2$. After completion of the reaction, the catalyst was filtered off and the filtrate was concentrated under reduced pressure. The resulting residue was washed with an ether-hexane mixed solvent to obtain 9.0 g of the desired compound.

Physical property: m.p. 161–162° C.
Yield: 98%.

(2-3) Production of 3-bromo-N-(4-trifluoromethoxyphenyl)phthalimide

In 20 ml of acetic acid was dissolved 1.6 g of 3-amino-N-(4-trifluoromethoxyphenyl)phthalimide, and a solution of 0.35 g of sodium nitrite in 5 ml of concentrated sulfuric acid was added dropwise while maintaining the temperature at 150° C. or lower. The resulting mixture was stirred at 15° C. or lower for another 20 minutes to obtain a diazonium salt. The diazonium salt was slowly added to a mixture of a solution of 0.86 g of cuprous bromide in 50 ml of hydrobromic acid and 10 ml of toluene which was maintained at 80° C. The resulting mixture was stirred until foaming ceased. After completion of the reaction, the organic layer was washed with an aqueous sodium thiosulfate solution and an aqueous sodium chloride solution, dried over anhydrous magnesium sulfate, and then distilled under reduced pressure to remove the solvent, and the resulting residue was purified by a silica gel chromatography to obtain 1.3 g of the desired compound.

Physical property: m.p. 117–1180° C. Yield: 67%.

(2-4) Production of 3-bromo-N$^1$-(4-trifluoromethoxyphenyl)-N$^2$-isopropylphthalic acid diamide (compound No. 262) and 6-bromo-N$^1$-(4-trifluoromethoxyphenyl)-N$^2$-isopropylphthalic acid diamide (compound No. 302)

From 1.3 g of 3-bromo-N-(4-trifluoromethoxyphenyl)phthalimide, 0.5 g of the desired compound (compound No. 262) and 0.7 g of the other desired compound (compound No. 302) were obtained in the same manner as in Example 1-2.

Compound No. 262:
Physical property: m.p. 208–210° C.
Yield: 33%.

Compound No. 302:
Physical property: m.p. 210–212° C.
Yield: 47%.

Example 3

(3-1) Production of N-(4-difluoromethoxy-2-methylphenyl)-3-nitrophthalimide

In 100 ml of acetic acid were dissolved 5.8 g of 3-nitrophthalic anhydride and 5.2 g of 4-difluoromethoxy-2-methylaniline, and the reaction was carried out with heating under reflux for 3 hours. After completion of the reaction, the solvent was distilled off under reduced pressure and the resulting residue was washed with an ether-hexane mixed solvent to obtain 10.2 g of the desired compound.

Physical property: m.p. 163–164° C. Yield: 98%.

(3-2) Production of N$^1$-(4-difluoromethoxy-2-methylphenyl)-N$^2$-isopropyl-3-nitrophthalic acid diamide (compound No. 696)

In 100 ml of dioxane was dissolved 10 g of N-(4-difluoromethoxy-2-methylphenyl)-3-nitrophthalimide, followed by adding thereto 2.5 g of isopropylamine, and the reaction was carried out for 3 hours. After completion of the reaction, the solvent was distilled off under reduced pressure and the resulting residue was washed with ether to obtain 4.0 g of the desired compound.

Physical property: m.p. 148–149° C. Yield: 86%.

(3-3) Production of 3-amino-N$^1$-(4-difluoromethoxy-2-methylphenyl)-N$^2$-isopropylphthalic acid diamide In a pressure vessel were placed 5 g of N$^1$-(4-difluoromethoxy-2-methylphenyl)-N$^2$-isopropyl-3-nitrophthalic acid diamide, 50 ml of acetic acid and 0.25 g of 5% palladium carbon, and catalytic reduction with hydrogen was carried out at a hydrogen pressure of 5 kg/cm$^2$. After completion of the reaction, the catalyst was filtered off and the filtrate was concentrated under reduced pressure. The resulting residue was washed with an ether-hexane mixed solvent to obtain 4.0 g of the desired compound.

Physical property: m.p. 148–149° C. Yield: 86%.

(3-4) Production of N$^1$-(4-difluoromethoxy-2-methylphenyl)-3-iodo-N$^2$-isopropylphthalic acid diamide (compound No. 387)

In 20 ml of acetic acid was dissolved 1.89 g of 3-amino-N$^1$-(4-difluoromethoxy-2-methylphenyl)-N$^2$-isopropylphthalic acid diamide, and 1.5 g of concentrated sulfuric acid was added under ice-cooling. While maintaining the resulting solution at 15° C. or lower, a solution of 0.35 g of sodium nitrite in 0.5 ml of water was added dropwise. The resulting solution was stirred at 150° C. or lower for another 20 minutes to obtain a diazonium salt. The diazonium salt was slowly added to a mixture of 50 ml of an aqueous solution containing 1.0 g of potassium iodide and 50 ml of chloroform which was maintained at 40° C. The resulting mixture was stirred until foaming ceased. After completion of the reaction, the organic layer was washed with an aqueous sodium thiosulfate solution and an aqueous sodium chloride solution, dried over anhydrous magnesium sulfate, and then distilled under reduced pressure to remove the solvent, and the resulting residue was purified by a silica gel chromatography to obtain 0.8 g of the desired compound.

Physical property: m.p. 207–209° C. Yield: 33%.

Example 4

(4-1) Production of 3-iodo-2-N-isopropyl-phthalamic acid

A solution of 0.67 g of isopropylamine in 5 ml of acetonitrile was added dropwise to a solution of 1.37 g of 3-iodophthalic anhydride in 10 ml of acetonitrile under ice-cooling, and the reaction was carried out with stirring at room temperature for another 5 hours. After completion of the reaction, the crystals formed in the reaction solution were collected by filtration and washed with a small volume of acetonitrile to obtain 1.45 g of the desired compound.

Yield: 87%. $^1$H-NMR [CDCl$_3$/TMS, δ values (ppm)] 1.23(6H, d), 4.35(1H, m), 5.80(1H, d), 6.85(1H, broad), 7.07(1H, t), 7.93(1H, d), 7.96(1H, d).

(4-2) Production of 6-iodo-N-isopropyl-phthalic acid isoimide

In 10 ml of toluene was dissolved 0.45 g of 3-iodo-2-N-isopropyl-phthalamic acid, followed by adding thereto 0.85 g of trifluoroacetic anhydride, and the reaction was carried out with stirring for 30 minutes. After completion of the reaction, the solvent was distilled off under reduced pressure to obtain 0.43 g of the desired compound as a crude product. The obtained desired compound was used in the subsequent reaction without purification.

Physical property: m.p. 87.5–88.5° C.

(4-3) Production of 3-iodo-$N^1$-(4-pentafluoroethyl-2-methylphenyl)-$N^2$-isopropyl-phthalic acid diamide (compound No. 372)

In 10 ml of tetrahydrofuran was dissolved 0.43 g of the 6-iodo-N-isopropyl-phthalic acid isoimide obtained in 4-2, followed by adding thereto 0.30 g of 4-pentafluoroethyl-2-methylaniline, and the reaction was carried out with stirring for 1 hour. After completion of the reaction, the solvent was removed from the reaction solution by distillation under reduced pressure, and the resulting residue was washed with ether-n-hexane to obtain 0.70 g of the desired compound.

Physical property: m.p. 195–196° C. Yield: 95%.

Example 5

(5-1) Production of ethyl 6-nitro-N-(4-chloro-2-methylphenyl)-phthalamate

In 30 ml of tetrahydrofuran was dissolved 1.29 g of 3-nitro-2-ethoxycarbonylbenzoyl chloride, followed by adding thereto 0.71 g of 4-chloro-2-methylaniline and 0.56 g of triethylamine, and the reaction was carried out with stirring for 30 minutes. After completion of the reaction, the reaction solution containing the desired compound was poured into water and the desired compound was extracted with ethyl acetate. The extracted solution was dried over anhydrous magnesium sulfate and distilled under reduced pressure to remove the solvent, and the resulting residue was purified by a silica gel column chromatography to obtain 1.7 g of the desired compound.

Physical property: m.p. 164–165° C. Yield: 94%.

(5-2) Production of 3-nitro-$N^1$-(4-chloro-2-methylphenyl)-$N^2$-isopropyl-phthalic acid diamide (compound No. 664)

In 20 ml of dioxane was dissolved 1.7 g of ethyl 6-nitro-N-(4-chloro-2-methylphenyl)-phthalamate, followed by adding thereto 1.5 g of isopropylamine, and the reaction was carried out with stirring at 80° C. for 1 hour. After completion of the reaction, the solvent was removed from the reaction solution containing the desired compound, by distillation under reduced pressure, and the resulting residue was purified by a silica gel column chromatography to obtain 1.5 g of the desired compound.

Physical property: m.p. 202–204° C. Yield: 85%.

Example 6

(6-1) Production of N-isopropyl-3,4-dichlorophthalamic acid

In 30 ml of tetrahydrofuran was dissolved 2.32 g of N-isopropyl-3,4-dichlorobenzamide, and 21 ml of s-BuLi (0.96 M/L) was slowly added while maintaining the temperature at –70° C. The resulting mixture was stirred at –70° C. for 30 minutes, after which the cooling bath was removed. An excess of carbon dioxide was introduced into the reaction solution, and the thus treated solution was stirred at room temperature for 30 minutes to carry out the reaction.

After completion of the reaction, the reaction solution was poured into water and acidified with diluted hydrochloric acid, and the desired compound was extracted with ethyl acetate. The extracted solution was dried over anhydrous magnesium sulfate and distilled under reduced pressure to remove the solvent, and the crystals thus obtained were washed with an ether-hexane mixed solvent to obtain 2.4 g of the desired compound.

Physical property: m.p. 155–156° C. Yield: 86.9%.

(6-2) Production of N-isopropyl-3,4-dichlorophthalic acid isoimide

In 10 ml of toluene was dissolved 0.41 g of N-isopropyl-3,4-dichlorophthalamic acid, followed by adding thereto 0.42 g of trifluoroacetic anhydride, and the reaction was carried out with stirring at room temperature for 30 minutes. After completion of the reaction, the solvent was distilled off under reduced pressure to obtain 0.39 g of the desired compound as a crude product. The obtained desired compound was used in the subsequent reaction without purification.

(6-3) Production of 3,4-dichloro-$N^1$-(4-pentafluoroethyl-2-methylphenyl)-$N^2$-isopropylphthalic acid diamide (compound No. 1222)

In 10 ml of acetonitrile was dissolved 0.39 g of N-isopropyl-3,4-dichlorophthalic acid isoimide, followed by adding thereto 0.34 g of 4-pentafluoroethyl-2-methylaniline, and the reaction was carried out with stirring for 2 hours. After completion of the reaction, the reaction solution was maintained at 0° C. for 10 minutes and the crystals precipitated were collected by filtration and washed with hexane to obtain 0.61 g of the desired compound.

Physical property: m.p. 208–209° C. Yield: 84.1%.

Example 7

Production of 3-chloro-2-isopropylaminothiocarbonyl-N-(pentafluoroethyl-2-methylphenyl)benzamide (compound No. S-1)

In 20 ml of tetrahydrofuran was dissolved 1.06 g of N-(pentafluoroethyl-2-methylphenyl)-3-chlorobenzamide, and 7 ml of s-BuLi (0.96 M/L) was slowly added while maintaining the temperature at –70° C. The resulting mixture was stirred at –70° C. for 30 minutes, after which the cooling bath was removed. A solution of 0.33 g of isopropyl isothiocyanate in 5 ml of tetrahydrofuran was poured into the reaction solution, and the resulting solution was stirred at room temperature for 30 minutes to carry out the reaction.

After completion of the reaction, the reaction solution was poured into water and acidified with diluted hydrochloric acid, and the desired compound was extracted with ethyl acetate. The extracted solution was dried over anhydrous magnesium sulfate and distilled under reduced pressure to remove the solvent, and the crystals thus obtained were washed with an ether-hexane mixed solvent to obtain 1.2 g of the desired compound.

Physical property: m.p. 162–164° C. Yield: 86%.

Example 8

Production of 2-methyl-4-pentafluoroethylaniline (compound No. ST-3)

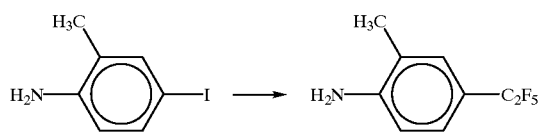

In an autoclave were placed 11.7 g (0.05 mole) of 2-methyl-4-iodoaniline, 6.4 g of copper powder, 18.5 g of iodopentafluoroethane and 100 ml of DMSO, and the reaction was carried out with stirring for 6 hours while maintaining the internal temperature at 120° C. After completion of the reaction, the reaction mixture was cooled to room temperature, poured into 500 ml of ice water, and thoroughly stirred. Then, the insoluble materials were removed and the desired compound was extracted with 300 ml of ethyl acetate. The extract solution was washed with water, dried over anhydrous sodium sulfate and then concentrated, after which the residue was purified by vacuum distillation to obtain 9.8 g of the desired compound.

Physical property: b.p. 95–105° C./10 mmHg. Yield: 87%.

Example 9

(9-1). Production of 2-ethyl-4-pentafluoroethylacetanilide

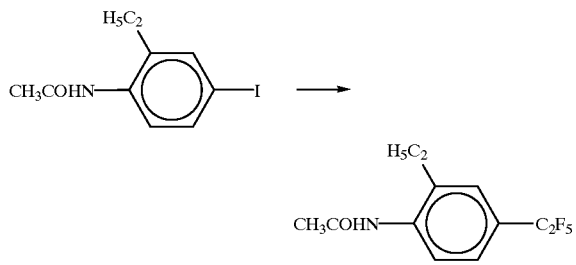

In an autoclave were placed 4.0 g (0.0138 mole) of 2-ethyl-4-iodoacetanilide, 1.8 g of copper powder, 5.1 g of iodopentafluoroethane and 40 ml of DMSO, and the reaction was carried out with stirring for 6 hours while maintaining the internal temperature at 120° C. After completion of the reaction, the reaction mixture was cooled to room temperature, poured into 200 ml of ice water, and thoroughly stirred. Then, the insoluble materials were removed and the desired compound was extracted with 200 ml of ethyl acetate. The extract solution was washed with water, dried over anhydrous sodium sulfate and then concentrated, after which the residue was purified by a silica gel column chromatography to obtain 0.7 g (yield: 18%) of the desired compound.

(9-2). Production of 2-ethyl-4-pentafluoroethylaniline (compound No. ST-18)

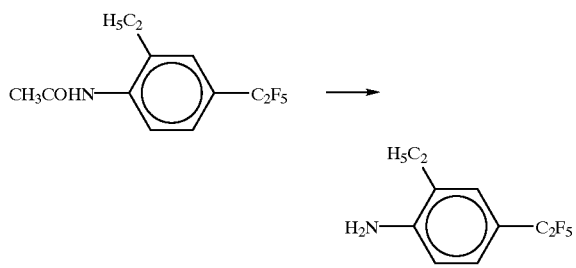

To 10 ml of a 6N aqueous hydrochloric acid solution was added 0.6 g (2.1 mmoles) of 2-ethyl-4-pentafluoroethylacetanilide, and the reaction was carried out with heating under reflux for 2 hours. After completion of the reaction, the reaction solution was ice-cooled and then neutralized with a 10% aqueous sodium hydroxide solution, and the desired compound was extracted with ethyl acetate. The extract solution was washed with water, dried over anhydrous sodium sulfate and then concentrated under reduced pressure to obtain 0.4 g of the desired compound.

Physical property: $^1$H-NMR (δ, ppm); 1.29(t, 3H), 2.52(q, 2H), 3.95(br, 2H), 6.8(d, 1H), 7.2–7.26(m, 2H). Yield: 80%.

Example 10

Production of 2-chloro-4-pentafluoroethylaniline (compound No. ST-11)

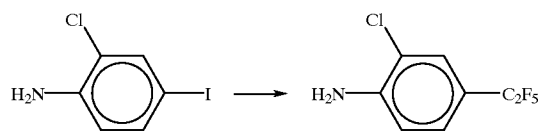

In an autoclave were placed 5.0 g (19.7 mmoles) of 2-chloro-4-iodoaniline, 2.8 g of copper powder, 10.0 g of iodopentafluoroethane and 50 ml of DMF, and the reaction was carried out with stirring for 20 hours while maintaining the internal temperature at 135° C. After completion of the reaction, the reaction mixture was cooled to room temperature, poured into 200 ml of ice water, and thoroughly stirred. Then, the insoluble materials were removed and the desired compound was extracted with 200 ml of ethyl acetate. The extract solution was washed with water, dried over anhydrous sodium sulfate and then concentrated, after which the residue was purified by a silica gel column chromatography to obtain 4.2 g of the desired compound.

Physical property: $^1$H-NMR (δ, ppm); 4.4(br, 2H), 6.8(d, 1H), 7.27(dd, 1H), 7.47(d, 1H). Yield: 87%.

Example 11

Production of 2-trifluoromethyl-4-pentafluoroethylaniline (compound No. ST-22)

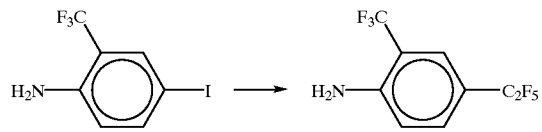

In an autoclave were placed 6.0 g (20.9 moles) of 2-trifluoro-4-iodoaniline, 2.8 g of copper powder, 11.1 g of iodopentafluoroethane and 40 ml of DMF, and the reaction was carried out with stirring for 7 hours while maintaining the internal temperature at 135° C. After completion of the reaction, the reaction mixture was cooled to room temperature, poured into 200 ml of ice water, and thoroughly stirred. Then, the insoluble materials were removed and the desired compound was extracted with 200 ml of ethyl acetate. The extract solution was washed with water, dried over anhydrous sodium sulfate and then concentrated, after which the residue was purified by a silica gel column chromatography to obtain 3.9 g of the desired compound.

Physical property: $^1$H-NMR (δ, ppm); 4.52(br, 2H), 6.81 (d, 1H), 7.27(dd, 1H), 7.48(d, 1H), 7.63(br, 1H). Yield: 67%.

Example 12

(12-1). Production of 2-methyl-4-(heptafluoropropan-2-yl)-nitrobenzene

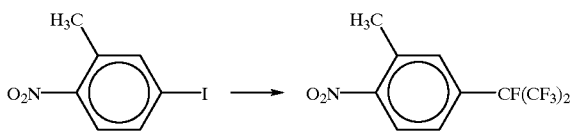

In an autoclave were placed 12.0 g (0.0456 mole) of 4-iodo-2-methylnitrobenzene, 11.6 g of copper powder, 40 g of 2-iodoheptafluoropropane and 200 ml of DMF, and the reaction was carried out with stirring for 6 hours while maintaining the internal temperature at 140° C. After completion of the reaction, the reaction mixture was cooled to room temperature, poured into 600 ml of ice water, and thoroughly stirred. Then, the insoluble materials were removed and the desired compound was extracted with 300 ml of hexane. The extract solution was washed with water, dried over anhydrous sodium sulfate and then concentrated, after which the residue was purified by vacuum distillation to obtain 11.4 g of the desired compound.

Physical property: b.p. 120–125° C./10 mmHg. Yield: 82%.

(12-2). Production of 2-methyl-4-(heptafluoropropan-2-yl)-aniline (compound No. ST-4)

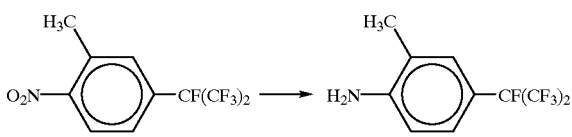

In 60 ml of ethanol was dissolved 11.4 g (0.0374 mole) of 2-methyl-4-(heptafluoropropan-2-yl)-nitrobenzene, and a solution of 29.5 g of $SnCl_2 \cdot 2H_2O$ in 40 ml of hydrochloric acid was added dropwise thereto under ice-cooling over a period of 30 minutes. After completion of the dropwise addition, the reaction was carried out at room temperature for 2 hours. After completion of the reaction, the reaction solution was poured into 200 ml of ice water and neutralized with a 40% aqueous sodium hydroxide solution under ice-cooling. Then, a 40% aqueous sodium hydroxide solution was further added thereto until a homogeneous solution was obtained, and the desired compound was extracted with 100 ml of ether. The extract solution was washed with water, dried over anhydrous sodium sulfate and then concentrated, after which the residue was purified by vacuum distillation to obtain 9.8 g of the desired compound.

Physical property: b.p. 100–110° C./10 mmHg. Yield: 95%.

Example 13

Production of 3-bromo-$N^1$-(4-nonafluorobutyl-2-methylphenyl)-$N^2$-isopropyl-phthalic acid diamide (Compound No. 281)

In 10 ml of tetrahydrofuran was dissolved 0.54 g of 6-bromo-N-isopropyl-phthalic acid isoimide, followed by adding thereto 0.30 g of 2-methyl-4-nonafluorobutylaniline, and the reaction was carried out with stirring for 1 hour. After completion of the reaction, the solvent was removed from the reaction solution by distillation under reduced pressure, and the resulting residue was washed with ether-n-hexane to obtain 1.1 g of the desired compound.

Physical property: m.p. 190–191° C. Yield 94%.

Typical preparation examples and test examples of the present invention are described below but they should not be construed as limiting the scope of the invention.

In the preparation examples, parts are all by weight.

Formulation Example 1

| | |
|---|---|
| Each compound listed in Table 1 | 50 parts |
| Xylene | 40 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Table 1 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Table 1 | 5 parts |
| Mixed powder of bentonite and clay | 90 parts |
| Calcium lignin sulfonate | 5 parts |

Granules were prepared by mixing the above ingredients uniformly, and kneading the resulting mixture together with a suitable amount of water, followed by granulation and drying.

Formulation Example 4

| | |
|---|---|
| Each compound listed in Table 1 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal effect on diamondback moth (*Plutella xylostella*)

Adult diamondback moths were released and allowed to oviposit on a Chinese cabbage seedling. Two days after the release, the seedling having eggs deposited thereon was immersed for about 30 seconds in a liquid chemical prepared by diluting a preparation containing each compound listed in Table 1 as an active ingredient to adjust the concentration to 500 ppm. After air-drying, it was allowed to stand in a room thermostated at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality (\%)} = \frac{\begin{bmatrix}\text{Number of}\\\text{hatched insects}\\\text{in untreated group}\end{bmatrix} - \begin{bmatrix}\text{Number of}\\\text{hatched insects}\\\text{in treated group}\end{bmatrix}}{\begin{bmatrix}\text{Number of}\\\text{hatched insects}\\\text{in untreated group}\end{bmatrix}} \times 100$$

Criterion:

| Effect | Mortality (%) |
|---|---|
| A | 100 |
| B | 99–90 |
| C | 89–80 |
| D | 79–50 |

The results obtained are shown in Table 5.

Test Example 2

Insecticidal effect on common cutworm (*Spodoptera Litura*)

A piece of cabbage leaf (cultivar; Shikidori) was immersed for about 30 seconds in a liquid chemical prepared by diluting a preparation containing each compound listed in Table 1 as an active ingredient to adjust the concentration to 500 ppm. After air-drying, it was placed in a plastic Petri dish with a diameter of 9 cm and inoculated with second-instar larvae of common cutworm, after which the dish was closed and then allowed to stand in a room thermostated at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality (\%)} = \frac{\begin{bmatrix}\text{Number of}\\\text{alive larvae in}\\\text{untreated group}\end{bmatrix} - \begin{bmatrix}\text{Number of}\\\text{alive larvae in}\\\text{treated group}\end{bmatrix}}{\begin{bmatrix}\text{Number of}\\\text{alive larvae in}\\\text{untreated group}\end{bmatrix}} \times 100$$

The results obtained are shown in Table 5.

Test Example 3

Insecticidal effect on rice leafroller (*Cnaphalocrocis medinalis*)

The lamina of a rice plant at the 6 to 8 leaf stage was immersed for about 30 seconds in a liquid chemical prepared by diluting a preparation containing each compound listed in Table 1 as an active ingredient to adjust the concentration to 500 ppm. After air-drying, the lamina was placed in a plastic Petri dish with a diameter of 9 cm whose bottom had been covered with a wetted filter paper. The lamina was inoculated with third-instar larvae of rice leafroller, after which the dish was allowed to stand in a room thermostated at 25° C. and having a humidity of 70%. Four days after the inoculation, the dead and alive were counted and the insecticidal effect was judged according to the criterion shown in Test Example 1. The test was carried out with triplicate groups of 10 insects.

The results obtained are shown in Table 5.

TABLE 5

| No | Test Example 1 | Test Example 2 | Test Example 3 |
|---|---|---|---|
| 1 | D | D | A |
| 2 | A | C | |
| 3 | C | | |
| 4 | A | | D |
| 7 | A | | |
| 8 | A | A | A |
| 9 | A | | A |
| 10 | A | D | D |
| 11 | A | C | C |
| 12 | A | D | |
| 13 | D | | D |
| 14 | A | | |
| 15 | A | | A |
| 16 | A | | |
| 17 | A | | D |
| 18 | D | | A |
| 20 | A | | |
| 22 | A | D | |
| 23 | A | | D |
| 24 | A | | D |
| 25 | A | | A |
| 26 | A | | D |
| 27 | A | A | C |
| 28 | | | A |
| 29 | A | B | A |
| 30 | A | A | A |
| 31 | A | | |
| 32 | A | | |
| 33 | A | | |
| 34 | A | C | |
| 37 | A | | |
| 41 | A | | A |
| 42 | A | D | A |
| 43 | B | D | |
| 44 | | | A |
| 45 | A | | A |
| 46 | A | | B |
| 47 | A | D | A |
| 48 | A | B | A |
| 49 | A | A | A |
| 50 | A | A | A |
| 51 | A | | A |
| 52 | A | A | A |
| 53 | A | | A |
| 55 | A | B | A |
| 56 | A | A | A |
| 58 | A | A | A |
| 59 | A | | |
| 60 | A | A | A |
| 61 | A | B | A |
| 62 | A | A | A |
| 63 | A | B | A |
| 64 | A | B | A |
| 65 | A | A | A |
| 66 | A | A | B |
| 67 | A | A | A |
| 68 | A | | |
| 69 | A | | A |
| 70 | A | | A |
| 71 | | | D |
| 73 | A | | |
| 74 | A | | |
| 75 | A | | A |
| 76 | C | | B |
| 77 | A | C | A |
| 78 | A | A | A |
| 79 | A | A | D |
| 81 | | | A |
| 83 | A | A | A |
| 84 | A | | |
| 86 | B | | B |
| 87 | A | | A |

TABLE 5-continued

| No | Test Example 1 | Test Example 2 | Test Example 3 |
|---|---|---|---|
| 88 | A | | |
| 89 | A | B | A |
| 90 | A | A | B |
| 91 | A | A | A |
| 92 | A | | |
| 93 | A | A | A |
| 98 | A | | C |
| 99 | A | | A |
| 100 | A | A | A |
| 101 | A | | |
| 102 | A | D | A |
| 103 | A | C | A |
| 109 | A | A | C |
| 110 | A | | A |
| 111 | A | C | B |
| 112 | A | A | A |
| 113 | A | B | A |
| 114 | A | A | A |
| 115 | A | C | A |
| 116 | A | D | A |
| 117 | A | A | A |
| 118 | A | A | A |
| 119 | A | A | A |
| 120 | A | D | A |
| 121 | A | A | A |
| 122 | A | A | A |
| 123 | A | | A |
| 124 | A | A | A |
| 125 | A | B | A |
| 126 | A | A | A |
| 127 | A | A | A |
| 128 | A | D | A |
| 129 | A | A | A |
| 130 | A | A | A |
| 132 | A | A | A |
| 133 | A | A | A |
| 134 | A | | A |
| 135 | A | A | A |
| 136 | A | A | A |
| 137 | A | | A |
| 138 | A | A | A |
| 139 | A | A | A |
| 140 | A | A | A |
| 141 | A | A | A |
| 142 | A | A | B |
| 143 | A | A | A |
| 144 | A | A | A |
| 145 | A | A | A |
| 146 | A | A | A |
| 147 | A | C | |
| 148 | A | A | A |
| 149 | A | A | A |
| 150 | A | A | A |
| 151 | A | | |
| 152 | A | A | A |
| 153 | A | | D |
| 157 | A | A | A |
| 158 | A | A | A |
| 159 | A | A | A |
| 161 | A | D | A |
| 162 | A | A | B |
| 163 | A | A | A |
| 164 | A | A | A |
| 165 | A | B | C |
| 167 | A | A | A |
| 168 | A | | |
| 169 | A | D | |
| 170 | A | D | B |
| 171 | A | | D |
| 172 | A | A | D |
| 173 | A | D | D |
| 174 | A | | |
| 175 | A | | |
| 176 | A | D | A |
| 177 | A | A | A |
| 178 | A | | A |
| 179 | A | | |
| 180 | A | A | A |
| 181 | | A | |
| 183 | A | B | |
| 185 | A | | |
| 186 | D | | |
| 187 | A | | D |
| 188 | D | | D |
| 189 | A | | |
| 190 | A | | |
| 191 | A | | A |
| 192 | A | | |
| 193 | A | D | |
| 194 | A | | |
| 195 | A | | |
| 196 | A | | D |
| 197 | A | A | A |
| 198 | A | C | A |
| 199 | A | | |
| 200 | A | | A |
| 201 | A | B | A |
| 202 | A | | |
| 203 | A | | |
| 206 | A | | A |
| 207 | A | | |
| 208 | A | | |
| 209 | A | | B |
| 210 | A | | D |
| 211 | A | | A |
| 212 | A | D | A |
| 213 | A | A | A |
| 214 | A | A | A |
| 215 | A | D | |
| 216 | A | | A |
| 217 | A | | A |
| 218 | A | | C |
| 219 | A | D | A |
| 220 | A | | A |
| 221 | A | A | A |
| 222 | A | B | A |
| 223 | A | A | A |
| 225 | A | B | A |
| 226 | A | | A |
| 227 | A | | |
| 228 | | B | A |
| 229 | A | D | A |
| 230 | A | C | A |
| 231 | | B | A |
| 232 | A | | |
| 233 | A | | |
| 234 | A | | A |
| 235 | A | | A |
| 236 | A | A | A |
| 237 | A | | A |
| 238 | A | | A |
| 239 | A | A | A |
| 240 | A | | |
| 241 | A | B | A |
| 242 | A | B | A |
| 243 | A | A | B |
| 244 | A | C | |
| 245 | A | D | |
| 246 | A | B | B |
| 248 | A | C | |
| 249 | A | D | A |
| 250 | A | | D |
| 251 | A | | A |
| 252 | A | | |
| 253 | A | A | C |
| 254 | A | A | |
| 255 | A | | A |
| 256 | A | | |
| 257 | A | | B |
| 258 | A | | A |
| 259 | A | | D |
| 261 | A | A | D |

TABLE 5-continued

| No | Test Example 1 | Test Example 2 | Test Example 3 |
|---|---|---|---|
| 262 | A | A | D |
| 263 | A |   | A |
| 264 | — | D | A |
| 265 | A |   |   |
| 266 | A | A | A |
| 267 | A | A | A |
| 268 | A | A | A |
| 269 | A | A | A |
| 270 | A | A | A |
| 271 | A | A | A |
| 272 | A | A | A |
| 273 | A | D | D |
| 274 | A | A | A |
| 275 | A | D | A |
| 276 | A | A | A |
| 277 | A | A | A |
| 278 | A | A | A |
| 279 | A | A | A |
| 281 | A | A | A |
| 282 | A | A | A |
| 283 | A | A | A |
| 284 | A | A | A |
| 285 | A | D | A |
| 286 | A | A | A |
| 287 | A | A | A |
| 288 | A | A | A |
| 289 | A | A | A |
| 290 | A | A | A |
| 291 | A | A | A |
| 292 | A | A | A |
| 293 | A | A | A |
| 294 | A | A | A |
| 295 | D |   |   |
| 296 | A | A | A |
| 297 | A | A | B |
| 298 | A | A | A |
| 299 | A | A | A |
| 300 | A |   | A |
| 301 | A | A | D |
| 302 | A |   | D |
| 303 | A |   | D |
| 304 | A |   |   |
| 305 | A | A | A |
| 306 | A | A | A |
| 307 | A |   | D |
| 308 | A |   |   |
| 309 | A | A |   |
| 310 | A |   |   |
| 311 | A |   | D |
| 312 | A | A | A |
| 313 | A | A | A |
| 314 | A |   | A |
| 315 | A |   | A |
| 316 | A | A | A |
| 318 | A | B | A |
| 319 | A | B | B |
| 320 | A |   | D |
| 321 | A | A |   |
| 322 | A |   | B |
| 323 | A | C | A |
| 324 | A |   | A |
| 325 | A | A | A |
| 326 | A |   | A |
| 327 | A |   | A |
| 328 | A | A | A |
| 329 | A | A | A |
| 330 | A |   | A |
| 332 | A |   | A |
| 333 | A |   | D |
| 334 | A | C | C |
| 335 | A |   | B |
| 336 | A |   | D |
| 337 | A |   | A |
| 338 | A | B | A |
| 339 | A | B | A |
| 340 | A |   | A |
| 341 | A |   | A |
| 342 | A |   |   |
| 343 | A |   |   |
| 345 | A | B | A |
| 346 | A | C | A |
| 347 | A | B | C |
| 348 | A |   | A |
| 349 |   |   | A |
| 350 | A | A | A |
| 351 | A | A | A |
| 352 |   |   | A |
| 353 | A | A | A |
| 354 | A | A | A |
| 355 | A | C | A |
| 356 | A | A | A |
| 360 | A | D | A |
| 361 | A | A | A |
| 362 | A | A | A |
| 363 | A | A | A |
| 364 | A | A | D |
| 365 | A | A | A |
| 366 | A | A | A |
| 367 | A | A | A |
| 368 | A | A | A |
| 369 | A | A | A |
| 370 | A | A | A |
| 371 | A | A | A |
| 372 | A | A | A |
| 373 | A | A | A |
| 374 | A | A | A |
| 375 | A | A | A |
| 376 | A |   | A |
| 377 | A |   | A |
| 378 | A | D | A |
| 379 | A | A | A |
| 380 | A | A | A |
| 381 | A | A | A |
| 382 | A | B | A |
| 383 | A |   | A |
| 384 | A |   | C |
| 385 | A | B | A |
| 386 | A | A | A |
| 387 | A | A | A |
| 388 | A | A | B |
| 389 | A | A | A |
| 390 | A | A | A |
| 391 | A | A | A |
| 392 | A | A | A |
| 393 | A | A | A |
| 394 | A | A | A |
| 395 | A | A | A |
| 396 | A | A | A |
| 397 | A | A | A |
| 398 | A |   |   |
| 399 | A | A | A |
| 400 | A | D | A |
| 402 | A |   |   |
| 403 | A | B | A |
| 404 | A | A | A |
| 406 | A | A | A |
| 407 | A | A | A |
| 408 | A | B | A |
| 409 | A | A | A |
| 410 | A | A | A |
| 411 | A |   | A |
| 412 | A |   | C |
| 413 | A |   | C |
| 414 | A |   | A |
| 415 |   |   | A |
| 416 | A | A | A |
| 417 | A | A | A |
| 418 |   |   | A |
| 419 | A | A | A |
| 420 | A |   | D |
| 421 | A | B | A |
| 422 | A |   |   |

TABLE 5-continued

| No | Test Example 1 | Test Example 2 | Test Example 3 |
|---|---|---|---|
| 424 | A | A | |
| 427 | A | | D |
| 428 | A | | |
| 429 | A | D | |
| 430 | A | D | D |
| 431 | A | A | |
| 432 | A | | A |
| 433 | A | | A |
| 434 | A | | |
| 435 | A | B | A |
| 436 | A | B | A |
| 437 | A | C | A |
| 438 | A | B | A |
| 439 | A | A | A |
| 440 | A | C | B |
| 441 | A | | B |
| 442 | A | | |
| 443 | A | | D |
| 444 | A | | A |
| 445 | | B | A |
| 446 | A | A | A |
| 447 | A | B | C |
| 448 | A | | A |
| 449 | A | | |
| 450 | A | | C |
| 451 | A | A | |
| 452 | A | A | A |
| 453 | A | D | A |
| 454 | A | A | A |
| 455 | A | B | A |
| 456 | A | | A |
| 457 | A | A | B |
| 458 | A | | |
| 459 | A | | |
| 460 | A | B | |
| 461 | A | | |
| 462 | A | | |
| 463 | A | | |
| 464 | A | | A |
| 465 | A | | |
| 466 | A | | A |
| 467 | A | | A |
| 468 | A | A | B |
| 469 | A | A | D |
| 470 | A | C | C |
| 471 | A | A | A |
| 472 | A | | B |
| 473 | A | A | A |
| 474 | A | B | A |
| 475 | A | | D |
| 476 | A | A | A |
| 477 | A | | C |
| 478 | A | | |
| 479 | A | | A |
| 480 | A | B | A |
| 488 | A | A | A |
| 489 | A | A | A |
| 490 | A | A | A |
| 491 | A | A | A |
| 492 | A | A | A |
| 493 | A | A | A |
| 494 | A | | A |
| 495 | A | A | A |
| 496 | A | A | A |
| 498 | A | A | A |
| 499 | A | A | A |
| 500 | A | B | A |
| 501 | A | A | A |
| 502 | A | A | A |
| 503 | A | B | A |
| 504 | A | A | A |
| 505 | A | A | A |
| 506 | A | | |
| 507 | A | B | A |
| 508 | A | B | A |
| 509 | A | A | A |
| 510 | A | B | A |
| 511 | A | A | A |
| 512 | A | A | A |
| 513 | A | A | A |
| 514 | A | A | A |
| 515 | A | | C |
| 516 | A | A | A |
| 517 | A | A | A |
| 518 | A | | B |
| 519 | A | A | A |
| 520 | A | | |
| 521 | A | A | A |
| 522 | A | D | A |
| 523 | A | A | A |
| 524 | A | A | A |
| 526 | A | A | |
| 527 | A | A | A |
| 528 | A | | A |
| 529 | A | D | A |
| 530 | A | | D |
| 531 | A | | A |
| 532 | A | | A |
| 533 | A | A | A |
| 534 | A | | A |
| 535 | A | A | |
| 536 | | | A |
| 537 | A | | |
| 538 | A | A | A |
| 539 | A | | |
| 540 | A | | |
| 543 | A | | A |
| 544 | A | | A |
| 545 | A | | A |
| 546 | A | | A |
| 547 | A | A | D |
| 548 | A | A | A |
| 549 | A | A | D |
| 550 | A | C | A |
| 551 | A | | A |
| 552 | A | | B |
| 553 | A | C | A |
| 554 | A | | A |
| 555 | A | | B |
| 557 | A | C | B |
| 558 | A | A | A |
| 559 | A | | |
| 560 | A | | |
| 561 | A | C | A |
| 562 | A | | A |
| 563 | A | | A |
| 564 | A | | B |
| 565 | A | | A |
| 566 | A | | B |
| 567 | A | D | D |
| 568 | A | C | A |
| 569 | A | A | A |
| 570 | A | A | |
| 571 | A | C | |
| 573 | A | | |
| 575 | A | | A |
| 576 | A | | C |
| 577 | A | | A |
| 579 | A | A | A |
| 580 | A | | A |
| 581 | A | B | A |
| 582 | A | | A |
| 584 | A | D | |
| 585 | A | | A |
| 586 | A | | D |
| 587 | A | | |
| 588 | A | | |
| 589 | A | | A |
| 590 | A | | |
| 591 | A | D | |
| 592 | A | | |
| 593 | A | | |

TABLE 5-continued

| No | Test Example 1 | Test Example 2 | Test Example 3 |
|---|---|---|---|
| 594 | A | | |
| 595 | A | A | A |
| 596 | D | | D |
| 597 | B | | |
| 598 | A | | |
| 599 | A | D | A |
| 600 | A | | |
| 601 | A | | |
| 602 | A | | A |
| 603 | B | | C |
| 604 | A | | D |
| 605 | | | C |
| 606 | A | D | A |
| 607 | A | A | A |
| 608 | A | | |
| 609 | A | B | A |
| 610 | A | A | C |
| 611 | A | | A |
| 612 | A | | D |
| 613 | A | | |
| 614 | A | | |
| 615 | A | | |
| 616 | A | | D |
| 617 | A | A | A |
| 618 | A | A | A |
| 619 | A | A | A |
| 621 | A | | |
| 622 | A | | |
| 623 | A | | A |
| 624 | A | | |
| 625 | A | D | D |
| 626 | A | | |
| 628 | A | B | A |
| 633 | A | D | |
| 634 | A | | D |
| 635 | A | D | |
| 636 | A | D | A |
| 637 | A | | |
| 638 | B | | |
| 639 | A | | |
| 640 | A | | |
| 641 | D | D | |
| 642 | A | | |
| 643 | A | | A |
| 644 | A | A | |
| 645 | A | | |
| 646 | A | D | |
| 647 | A | | B |
| 648 | A | D | A |
| 649 | A | | C |
| 650 | A | | |
| 652 | A | | |
| 653 | A | | |
| 654 | | D | |
| 656 | A | | A |
| 657 | D | | |
| 658 | A | | |
| 659 | A | | |
| 660 | A | | A |
| 661 | B | | D |
| 662 | A | | |
| 663 | A | A | D |
| 664 | A | A | |
| 665 | A | A | B |
| 666 | A | | D |
| 667 | A | A | A |
| 668 | A | | |
| 669 | A | D | A |
| 670 | A | | D |
| 671 | A | | D |
| 672 | A | | |
| 673 | A | D | D |
| 674 | A | D | A |
| 675 | A | A | A |
| 676 | A | C | A |
| 677 | A | | |
| 678 | A | | |
| 679 | A | | A |
| 680 | A | | D |
| 681 | A | A | A |
| 682 | A | | A |
| 683 | A | A | A |
| 684 | A | A | A |
| 686 | A | A | A |
| 687 | A | D | D |
| 688 | A | | A |
| 689 | A | D | A |
| 690 | A | | A |
| 691 | A | D | C |
| 692 | A | D | |
| 693 | A | A | |
| 694 | A | | A |
| 695 | A | A | A |
| 696 | A | A | A |
| 697 | A | | A |
| 698 | A | B | A |
| 699 | A | A | D |
| 700 | A | A | A |
| 701 | A | A | A |
| 703 | A | A | A |
| 704 | A | | A |
| 705 | A | D | A |
| 706 | A | A | |
| 708 | D | | |
| 709 | A | A | |
| 710 | A | C | A |
| 711 | A | C | A |
| 712 | A | A | A |
| 713 | A | B | D |
| 714 | A | A | A |
| 715 | A | A | A |
| 716 | A | A | A |
| 717 | A | | A |
| 718 | A | | A |
| 719 | A | D | |
| 720 | A | | |
| 721 | A | | |
| 722 | A | | A |
| 723 | D | | D |
| 724 | A | | B |
| 725 | A | A | |
| 727 | A | B | A |
| 728 | A | | A |
| 729 | A | | A |
| 732 | A | | |
| 733 | A | | |
| 735 | | | D |
| 737 | A | | |
| 738 | D | | |
| 740 | A | | A |
| 741 | A | A | A |
| 742 | A | | |
| 743 | D | | |
| 744 | C | | |
| 745 | D | | |
| 749 | A | | |
| 750 | A | | A |
| 751 | A | | A |
| 752 | A | | |
| 753 | A | A | D |
| 755 | A | | A |
| 758 | | | A |
| 759 | | | D |
| 765 | | | A |
| 766 | A | | |
| 767 | A | C | A |
| 768 | A | B | A |
| 769 | A | | D |
| 770 | A | A | A |
| 771 | A | | C |
| 772 | A | | A |
| 773 | A | | A |

TABLE 5-continued

| No | Test Example 1 | Test Example 2 | Test Example 3 |
|---|---|---|---|
| 774 | A |   | A |
| 776 | B |   | D |
| 777 | A |   | D |
| 778 | A |   | A |
| 780 | A | A | A |
| 781 | A | A | A |
| 782 | A |   | A |
| 783 | A | A | A |
| 785 |   | A |   |
| 788 | C |   | C |
| 790 |   |   | A |
| 791 | A |   | A |
| 793 | A |   |   |
| 795 | A | B | A |
| 796 | A |   |   |
| 797 | A |   | C |
| 798 |   |   | A |
| 799 | A |   | A |
| 800 |   |   | C |
| 801 | A | A | D |
| 802 | D |   |   |
| 803 | A |   | A |
| 808 | A |   |   |
| 819 | A | B | A |
| 821 | A |   | A |
| 822 | D |   | D |
| 824 | A |   |   |
| 825 | A |   |   |
| 826 | A |   | A |
| 827 | A |   |   |
| 830 | C |   |   |
| 831 | D | D |   |
| 832 | A |   |   |
| 833 | A |   | D |
| 835 | A |   |   |
| 836 | A |   | A |
| 837 | A |   |   |
| 838 | A | C | A |
| 839 | A |   | C |
| 840 | A |   | D |
| 841 | A | D |   |
| 842 | A | A | D |
| 845 | A |   |   |
| 846 | A |   |   |
| 847 |   | D |   |
| 848 | A |   |   |
| 849 | A | B | A |
| 850 | A |   | A |
| 851 | A | D | A |
| 852 | A |   | D |
| 854 | A |   |   |
| 855 | A |   |   |
| 856 | A |   | D |
| 858 | C | A |   |
| 859 | D |   |   |
| 860 | A |   |   |
| 861 | A |   |   |
| 862 | A | D | D |
| 863 | A |   | B |
| 864 | A |   |   |
| 865 | A |   |   |
| 866 | D |   |   |
| 867 | A |   | C |
| 869 | A | D |   |
| 870 | A |   |   |
| 871 | A |   |   |
| 872 | A |   | C |
| 874 | A | C | A |
| 875 | A |   |   |
| 878 | C |   |   |
| 879 | A |   | A |
| 880 |   | D |   |
| 881 | A | D |   |
| 888 | D |   |   |
| 889 | A |   | A |
| 890 | A | A | A |
| 891 | A | A | A |
| 892 | A |   | A |
| 893 | A | A | A |
| 894 | A | A | A |
| 895 | A | A | A |
| 901 | A | D | A |
| 902 | A |   |   |
| 903 | A | A | A |
| 904 | A |   |   |
| 905 | A | A | A |
| 906 | A | D | A |
| 907 | A | A | A |
| 908 | A | D | A |
| 909 | A | A | A |
| 910 |   |   | A |
| 911 | A |   | D |
| 912 | A |   |   |
| 913 | A |   |   |
| 914 | A |   |   |
| 915 | A | A | A |
| 916 | A |   |   |
| 917 | A | A | A |
| 918 | A |   |   |
| 919 | A |   |   |
| 920 | A |   |   |
| 924 | A |   |   |
| 925 | A |   | A |
| 927 | A | A | A |
| 928 | A |   | A |
| 929 | A | A | A |
| 930 | A | A | A |
| 931 | A | A | A |
| 932 | A | A | A |
| 933 | A | A | A |
| 934 | A | A | A |
| 935 | A | A | A |
| 936 | A | A | A |
| 937 | A | A | A |
| 938 | A | A |   |
| 939 | A | A | A |
| 940 | A | A | A |
| 941 | A | A | A |
| 942 | A | A | A |
| 943 | A | C | A |
| 944 | A | A | A |
| 945 | A | A | A |
| 946 | A |   | A |
| 947 | A | A | A |
| 949 | A | A | A |
| 950 |   |   | C |
| 951 | A | A | A |
| 952 | A |   | A |
| 953 | A | A | A |
| 954 | A |   | A |
| 955 | A | A | A |
| 956 | A |   | A |
| 957 | A | A | A |
| 958 | A |   | A |
| 959 | A |   | A |
| 965 | A | C |   |
| 966 | A |   | B |
| 971 | A | A | A |
| 972 |   | A |   |
| 973 | A | A | A |
| 974 | A | A | A |
| 975 | A |   | A |
| 976 | A | A | A |
| 977 | A | A | A |
| 978 | A | C | A |
| 979 | A | A | A |
| 980 | A | A | A |
| 981 | A | A | A |
| 982 | A |   | C |
| 983 | A | A | A |
| 984 | A |   |   |
| 985 | A | A | A |

TABLE 5-continued

| No | Test Example 1 | Test Example 2 | Test Example 3 |
|---|---|---|---|
| 986 | A | | A |
| 987 | A | A | A |
| 988 | A | | |
| 989 | A | A | A |
| 990 | A | | A |
| 991 | A | A | A |
| 992 | A | | |
| 993 | A | | A |
| 995 | A | | A |
| 996 | A | A | A |
| 997 | A | A | A |
| 998 | A | A | A |
| 999 | A | | A |
| 1000 | A | D | A |
| 1001 | A | A | A |
| 1002 | A | A | A |
| 1003 | A | A | A |
| 1004 | A | A | A |
| 1005 | A | A | A |
| 1006 | A | | |
| 1007 | A | A | A |
| 1008 | A | | A |
| 1009 | A | A | A |
| 1010 | A | | A |
| 1011 | A | A | A |
| 1013 | A | A | A |
| 1014 | A | | A |
| 1015 | A | D | A |
| 1016 | | | A |
| 1017 | A | A | A |
| 1018 | A | D | A |
| 1019 | A | A | A |
| 1020 | A | A | A |
| 1021 | A | | A |
| 1022 | A | A | A |
| 1023 | A | A | A |
| 1024 | A | A | A |
| 1025 | A | | |
| 1026 | A | | A |
| 1027 | | | A |
| 1028 | A | A | A |
| 1031 | A | A | A |
| 1032 | A | | A |
| 1033 | A | A | A |
| 1034 | A | | |
| 1035 | A | A | A |
| 1036 | A | | A |
| 1037 | A | A | A |
| 1038 | A | A | A |
| 1039 | A | A | A |
| 1040 | A | A | A |
| 1041 | A | A | A |
| 1042 | A | A | A |
| 1043 | A | | A |
| 1044 | A | A | A |
| 1045 | A | A | A |
| 1046 | A | A | A |
| 1047 | A | | A |
| 1048 | A | | A |
| 1049 | A | A | A |
| 1050 | A | A | A |
| 1051 | A | A | A |
| 1052 | A | A | |
| 1053 | A | A | A |
| 1054 | A | A | A |
| 1055 | A | A | A |
| 1056 | A | A | A |
| 1057 | A | | A |
| 1058 | A | A | A |
| 1059 | A | | |
| 1060 | A | A | A |
| 1061 | A | A | A |
| 1062 | A | A | A |
| 1063 | | | A |
| 1064 | A | | A |
| 1065 | A | | |
| 1066 | A | C | A |
| 1067 | A | A | A |
| 1068 | A | A | A |
| 1069 | A | A | A |
| 1070 | A | A | A |
| 1071 | A | C | A |
| 1072 | | | A |
| 1073 | A | A | A |
| 1074 | A | A | A |
| 1075 | A | A | A |
| 1076 | A | | A |
| 1077 | A | | A |
| 1078 | A | A | A |
| 1079 | A | A | A |
| 1080 | A | A | A |
| 1081 | A | A | A |
| 1082 | A | | |
| 1083 | A | | |
| 1086 | A | | A |
| 1087 | A | A | A |
| 1088 | A | | A |
| 1089 | A | | A |
| 1099 | A | | A |
| 1100 | A | C | A |
| 1101 | A | C | A |
| 1102 | A | A | A |
| 1103 | A | | A |
| 1104 | A | A | A |
| 1105 | A | A | A |
| 1106 | A | | A |
| 1107 | A | | A |
| 1108 | A | | A |
| 1109 | A | | A |
| 1110 | A | C | A |
| 1111 | A | | A |
| 1112 | A | A | A |
| 1113 | A | A | A |
| 1114 | A | A | A |
| 1115 | A | A | A |
| 1116 | A | A | A |
| 1117 | A | A | A |
| 1118 | A | A | A |
| 1119 | A | A | A |
| 1120 | A | A | A |
| 1121 | A | A | A |
| 1122 | A | A | A |
| 1123 | A | A | A |
| 1124 | A | A | A |
| 1125 | A | A | A |
| 1126 | A | A | A |
| 1127 | A | A | A |
| 1128 | A | A | A |
| 1129 | A | A | A |
| 1130 | A | A | A |
| 1131 | A | A | A |
| 1132 | A | | A |
| 1133 | A | | A |
| 1134 | A | | A |
| 1135 | A | | A |
| 1136 | A | | A |
| 1137 | A | | |
| 1138 | | | A |
| 1139 | A | | |
| 1140 | | | A |
| 1141 | A | A | A |
| 1142 | A | A | A |
| 1143 | A | C | A |
| 1144 | A | A | A |
| 1145 | A | | A |
| 1146 | A | C | A |
| 1147 | A | A | A |
| 1148 | A | A | A |
| 1149 | A | | A |
| 1150 | A | A | A |
| 1151 | A | A | A |
| 1152 | A | A | A |

TABLE 5-continued

| No | Test Example 1 | Test Example 2 | Test Example 3 |
|---|---|---|---|
| 1153 | A | A | A |
| 1154 | A | C | A |
| 1155 | A |   | A |
| 1156 | A | A | A |
| 1157 | A |   | A |
| 1158 | A | D | A |
| 1159 | A | A | A |
| 1160 | A | A | A |
| 1161 | A | D | A |
| 1162 | A | A | A |
| 1163 | A | A | A |
| 1164 | A | A | A |
| 1165 | A | A | A |
| 1166 | A | A |   |
| 1167 | A | A | A |
| 1168 | A | A | A |
| 1169 | A | A | A |
| 1173 | A | A | A |
| 1174 | A | A | A |
| 1175 | A |   |   |
| 1178 | A |   |   |
| 1179 | A | A | — |
| 1180 | A |   | — |
| 1181 | A |   | — |
| 1182 | A |   | — |
| 1183 | A | A | — |
| 1184 | A | A | — |
| 1185 | A | C | — |
| 1186 | A | A | — |
| 1187 | A | A | — |
| 1188 | A | A | — |
| 1189 | A | A | — |
| 1190 | A | A | A |
| 1191 | A | A | A |
| 1192 | A | A | A |
| 1193 | A | A | A |
| 1202 | A | A | A |
| 1203 | A | D | A |
| 1204 | A | A | A |
| 1205 | A |   | A |
| 1206 | A | A | A |
| 1207 | A | A | A |
| 1208 | A |   | A |
| 1209 | A | D | A |
| 1210 | A | A | A |
| 1211 | A | A | A |
| 1212 | A | A | A |
| 1221 | A | A | A |
| 1222 | A | A | A |
| 1223 | A | A | A |
| 1224 |   |   | B |
| 1225 |   |   | A |
| 1226 |   |   | A |
| 1227 | A | A | A |
| 1228 | A | A | A |
| 1229 | A | A | A |
| 1230 | A | A | A |
| 1231 | A | A | A |
| 1232 | A | A | A |
| 1233 | A | A | — |
| 1234 | A | A | — |
| 1235 | A | D | — |
| 1236 | A | A | — |
| 1237 | A | A | — |
| 1238 | A |   | — |
| 1245 | A | A | — |
| 1246 | A | A | A |
| 1247 | C |   |   |
| 1248 | A | A | A |
| 1249 | A |   |   |
| 1250 | A | A | A |
| 1251 | A | A | A |
| 1256 | A | A | — |
| 1257 | A | A | — |
| 1258 | A | A | — |
| 1259 | A |   | — |
| 1260 | A |   | — |
| 1261 | A | A | — |
| 1262 | A | A | A |
| 1263 | A | A | A |
| 1264 | A | A | A |
| 1266 | A |   | A |
| 1277 | A | A | A |
| 1278 | A | A | A |
| 1280 | A | A | A |
| 1281 | A |   | A |
| 1283 | A | — | — |
| 1284 | A | — | A |
| 1285 | A | — | A |
| 1287 | A | A | A |
| 1288 | A |   |   |
| 1291 | A |   |   |
| 1293 |   |   | A |
| 1294 | A | A | A |
| 1295 | A | A | A |
| 1296 | A | A | A |
| 1297 | A | A | A |
| 1298 | A | A | A |
| 1299 | A | A | A |
| 1300 | A | A | A |
| 1301 | A |   | A |
| 1303 | A | A | A |
| 1304 | A |   | A |
| 1305 | A | A | A |
| 1306 |   |   | A |
| 1307 | A | A | A |
| 1308 |   |   | C |
| 1309 | A | A | A |
| 1310 |   |   | B |
| 1311 | A | A | A |
| 1312 | A |   | A |
| 1313 | A | A | A |
| 1314 | A | A | A |
| 1315 | A | A | A |
| 1316 | A | A | A |
| 1317 | A | C | A |
| 1318 | A |   | A |
| 1319 | A | — | — |
| 1321 | A | — | A |
| 1322 | A |   |   |
| 1323 | A |   | A |
| 1325 | A |   | A |
| 1327 | A |   |   |
| 1328 | A |   |   |
| 1330 | A | A | A |
| 1331 | A |   | A |
| 1332 | A |   |   |
| 1333 | A |   | A |
| 1335 | A | C | A |
| 1337 | A |   | A |
| 1338 | A |   |   |
| 1339 | A |   | A |
| 1340 | A |   | A |
| 1341 | A |   |   |
| 1342 | A |   |   |
| 1343 | A |   | A |
| 1345 | A |   |   |
| 1346 | A |   |   |
| 1347 | A |   |   |
| 1348 | A |   |   |
| 1349 | A |   |   |
| 1350 |   |   | A |
| 1351 | A |   | A |
| 1352 | A |   | A |
| 1353 | A | A | A |
| 1355 | A | A | A |
| 1356 | A |   |   |
| 1358 | A |   | C |
| 1360 | A |   | C |
| 1361 |   |   | A |
| 1362 | A | A | A |
| 1363 | A |   |   |

TABLE 5-continued

| No | Test Example 1 | Test Example 2 | Test Example 3 |
|---|---|---|---|
| 1364 | A | A | A |
| 1365 | A | | |
| 1366 | A | A | A |
| 1367 | A | | |
| 1368 | A | | |
| 1370 | A | | A |
| 1372 | A | | |
| 1373 | A | | |
| 1374 | A | | |
| 1376 | A | | |
| 1379 | A | | |
| 1381 | A | | C |
| 1382 | A | A | A |
| 1383 | A | A | A |
| 1384 | A | A | A |
| 1385 | A | A | A |
| 1386 | A | A | A |
| 1387 | A | A | A |
| 1388 | A | D | A |
| 1389 | A | A | A |
| 1390 | A | | A |
| 1392 | A | | A |
| 1393 | A | | A |
| 1394 | A | | A |
| 1395 | A | | |
| 1398 | A | | |
| 1399 | A | A | A |
| 1400 | A | A | A |
| 1401 | A | | |
| 1402 | A | A | A |
| 1404 | A | C | A |
| 1406 | A | A | A |
| 1409 | A | | A |
| 1410 | A | | A |
| 1411 | A | | A |
| 1412 | A | | |
| 1414 | A | A | A |
| 1415 | A | | A |
| 1416 | | | A |
| 1417 | A | A | A |
| 1418 | A | A | A |
| 1419 | A | | A |
| 1420 | A | | A |
| 1421 | A | | |
| 1423 | A | | |
| 1424 | | A | A |
| 1427 | A | A | A |
| 1428 | A | A | A |
| 1429 | A | A | A |
| 1430 | A | D | A |
| 1431 | A | | |
| 1432 | | | A |
| 1434 | A | | |
| 1436 | A | A | A |
| 1438 | A | A | A |
| 1439 | A | | C |
| 1440 | A | | |
| 1441 | A | | A |
| 1442 | A | | |
| 1443 | A | | |
| 1445 | A | A | A |
| 1446 | A | | |
| 1447 | A | A | A |
| 1448 | A | A | A |
| 1449 | A | A | A |
| 1450 | A | A | A |
| 1451 | A | | |
| 1452 | A | A | A |
| 1453 | A | | |
| 1454 | A | A | A |
| 1456 | A | | A |
| 1457 | A | | A |
| 1458 | A | A | A |
| 1459 | A | A | |
| 1460 | A | C | A |
| 1461 | A | | A |
| 1464 | A | A | A |
| 1465 | A | | A |
| 1466 | A | A | A |
| 1467 | A | A | A |
| 1468 | A | C | A |
| 1469 | A | | |
| 1470 | A | | A |
| 1472 | A | A | A |
| 1473 | A | A | A |
| 1474 | A | A | A |
| 1475 | A | A | A |
| 1476 | A | | |
| 1478 | A | A | A |
| 1479 | A | A | A |
| 1480 | | | A |
| 1481 | A | A | A |
| 1482 | A | A | A |
| 1484 | A | A | A |
| 1485 | A | A | A |
| 1486 | A | A | |
| 1487 | A | A | |
| 1488 | A | | A |
| 1489 | A | A | A |
| 1490 | A | | A |
| 1491 | A | A | A |
| 1492 | A | | A |
| 1493 | A | | A |
| 1494 | A | A | A |
| 1495 | A | A | A |
| 1496 | A | A | A |
| 1497 | A | A | A |
| 1498 | A | A | A |
| 1499 | A | A | A |
| 1500 | A | A | A |
| 1501 | A | A | A |
| 1502 | A | A | A |
| 1503 | A | C | A |
| 1504 | A | A | A |
| 1505 | A | A | A |
| 1506 | A | A | A |
| 1507 | A | A | A |
| 1508 | A | C | A |
| 1509 | A | C | A |
| 1510 | A | | A |
| 1511 | A | | |
| 1512 | A | A | A |
| 1513 | A | | |
| 1514 | A | | A |
| 1515 | A | | |
| 1516 | A | A | A |
| 1517 | A | | A |
| 1518 | A | | |
| 1519 | A | | A |
| 1520 | | | A |
| 1521 | A | | |
| 1522 | A | A | A |
| 1523 | A | | A |
| 1524 | A | A | A |
| 1525 | A | A | A |
| 1526 | A | A | A |
| 1527 | A | | A |
| 1528 | A | | A |
| 1529 | A | | A |
| 1530 | A | | A |
| 1531 | A | A | A |
| 1532 | A | A | A |
| 1533 | A | A | A |
| 1534 | A | A | A |
| 1535 | A | A | A |
| 1536 | A | A | A |
| 1537 | A | A | A |
| 1538 | A | A | A |
| 1539 | A | A | A |
| 1540 | A | A | A |
| 1541 | A | A | A |
| 1542 | A | D | A |

TABLE 5-continued

| No | Test Example 1 | Test Example 2 | Test Example 3 |
|---|---|---|---|
| 1543 | A | A | A |
| 1544 | A | A | A |
| 1545 | A | D | A |
| 1546 | A | C | A |
| 1547 | A |   | A |
| 1548 | A |   | A |
| 1549 | A | D | A |
| 1550 | A | A | A |
| 1551 | A | D | A |
| 1552 | A | A | A |
| 1553 | A |   | A |
| 1554 | A | A |   |
| 1555 | A |   | A |
| 1556 | A | A | A |
| 1557 | A | A | A |
| 1558 | A | C | A |
| 1559 | A | A | A |
| 1560 | A | A | A |
| 1561 | A | A | A |
| 1562 | A | A | A |
| 1563 | A | A | A |
| 1565 | A | A | A |
| 1566 | A | A | A |
| 1567 | A | A | A |
| 1568 | A | A | A |
| 1569 | A | A | A |
| 1570 |   |   | A |
| 1571 | A | A | A |
| 1572 | A | A | A |
| 1573 | A | A | A |
| 1574 | A | A | A |
| 1575 | A |   | A |
| 1576 | A | D | A |
| 1577 | A |   |   |
| 1578 | A |   | A |
| 1579 | A |   |   |
| 1580 | A | A | A |
| 1581 | A | A | A |
| 1582 | A |   | A |
| 1583 | A |   | A |
| 1584 | A |   | A |
| 1585 | A | A | A |
| 1586 | A | C | A |
| 1587 | A | A | A |
| 1588 | A |   | A |
| 1589 | A |   | A |
| 1590 | A | A | A |
| 1594 | A | A | — |
| 1595 | A | A | — |
| 1596 | A | A | — |
| 1597 | A | A | — |
| 1598 | A | A | — |
| 1599 | A | A | — |
| 1600 | A | A | — |
| 1601 | A | A | — |
| 1602 | A | A | A |
| 1603 | A | A | A |
| 1604 | A | A | A |
| 1605 | A | C | — |
| 1606 | A | A | — |
| 1607 | A | A | — |
| 1608 | A | A | — |
| 1609 | A | A | — |
| 1610 | A | A | — |
| 1611 | A |   | — |
| 1612 | A | A | — |
| 1613 | A | A | — |
| 1614 | A | C | A |
| 1615 | A | A | A |
| 1617 | A |   | A |
| 1618 | A | C | A |
| 1619 | A | A | — |
| 1620 | A |   | A |
| 1622 | A | A | A |
| 1623 | A | C | A |
| 1624 | A | D | A |
| 1625 | A | A | A |
| 1626 | A |   | A |
| 1627 | A | A | A |
| 1628 | A | A | A |
| 1629 | A | A | A |
| 1632 | A |   | A |
| 1633 | A | A | A |
| 1634 | A | A | A |
| 1635 | A | A | A |
| 1636 | A | D | A |
| 1637 | A | A | A |
| 1638 | A | A | A |
| 1639 | A | A | A |
| 1640 | A | A | A |
| 1641 | A |   | A |
| 1642 | A | A | A |
| 1643 | A |   | A |
| 1644 | A | A | A |
| 1645 | A | A | A |
| 1646 | A | A | A |
| 1647 | A | A | A |
| 1648 | A | A | A |
| 1649 | A | A | A |
| 1650 | A | A | A |
| 1651 | A | A | A |
| 1652 | A | A | A |
| 1653 | A | A | A |
| 1654 | A | A | A |
| 1655 | A | A | A |
| 1656 | A | A | A |
| 1658 | A |   |   |
| 1659 | A |   | A |
| 1660 | A | A | — |
| 1661 | A |   | — |
| 1662 | A | A | — |
| 1663 | A | A | — |
| 1664 | A | A | — |
| 1665 | A | A | — |
| 1666 | A | A | — |
| 1667 | A | A | — |
| 1668 | A | A | — |
| 1669 | A | A | — |
| 1670 | A | A | — |
| 1671 | A | A | — |
| 1672 | A | A | — |
| 1673 | A |   | — |
| 1674 | A | A | — |
| 1679 | A | A | A |
| 1680 | A | A | A |
| 1681 | A | A | A |
| 1682 | A | A | — |
| 1683 | A |   | — |
| 1684 | A | A | — |
| 1685 | A | A | — |
| 1686 | A | A | — |
| 1689 | A | A | — |
| 1690 | A | A | — |
| 1691 | A | A | — |
| 1692 | A |   | — |
| 1693 | A | A | — |
| 1694 | A |   | — |
| 1695 | A | A | — |
| 1696 | A | A | — |
| 1697 | A | A | — |
| 1698 | A |   | — |
| 1699 | A | A | — |
| 1700 | A | D | — |
| 1714 | A | A | A |
| 1715 | A | A | A |
| 1716 | A | A | A |
| 1717 | A | A | A |
| 1722 | A | A | A |
| 1723 | A | A | A |
| 1726 | A |   | A |
| 1727 | A |   | A |
| 1732 | A | A | A |

TABLE 5-continued

| No | Test Example 1 | Test Example 2 | Test Example 3 |
|---|---|---|---|
| 1733 | A | A | A |
| 1737 | A | C | A |
| 1742 | A |   | A |
| 1743 | A |   | A |
| 1747 | A | C |   |
| 1748 | A |   | A |
| 1750 | A |   | A |
| 1752 | A |   | A |
| 1763 | A |   | A |
| 1764 | A | A | A |
| 1765 | A | A | A |
| 1766 | A | A | A |
| 1767 | A |   |   |
| 1768 | A |   | A |
| 1770 | A | — | A |
| 1772 | A | — | A |
| 1773 | A | A | A |
| 1774 | A | — | A |
| 1775 | A | — | A |
| 1776 | A | — | A |
| 1777 | A | A | A |
| 1778 | A | — | A |
| 1799 | A | A | A |
| 1800 | A | A | A |
| 1801 | A | A | A |
| 1802 | A |   |   |
| 1803 | A | A | A |
| 1804 | A |   |   |
| 1805 | A |   |   |

In Table 5, "—" means that test is not conducted.

What is claimed is:

1. A phthalic acid diamide derivative represented by the general formula (I),

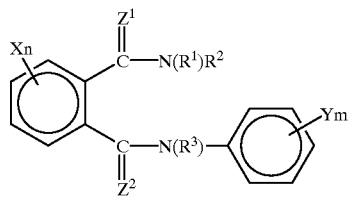

(I)

wherein $R^1$, $R^2$ and $R^3$ may be the same or different, and are each a hydrogen atom, a cyano group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group or a group of the formula —$A^1$—$Q_l$ (wherein $A^1$ is —O—, —S—, —$SO_2$—, —C(=O)—, a group of the formula —N(R )— (wherein $R^4$ is a $C_1$–$C_6$ alkylcarbonyl group, a halo-$C_1$–$C_6$ alkylcarbonyl group, a $C_1$–$C_6$ alkoxycarbonyl group, a phenylcarbonyl group, or a substituted phenylcarbonyl group having at least one substituent which may be the same or different, and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different), a $C_1$–$C_8$ alkylene group, a $C_3$–$C_6$ alkenylene group or a $C_3$–$C_6$ alkynylene group;

(1) when $A^1$ is —O— or a group of the formula —N($R^4$)— (wherein $R^4$ is the same as defined above), then Q is a hydrogen atom, a $C_1$$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkyl sulfonyl group, a mono-$C_1$–$C_6$ alkylamino group and a di-$C_1$–$C_6$ alkylamino group which may be the same or different, a phenyl-$C_1$–$C_4$ alkyl group or a substituted phenyl-$C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

(2) when $A^1$ is —S—, —$SO_2$— or —C(=O)—, then Q is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_1$–$C_6$ alkoxy group, a mono-$C_1$–$C_6$ alkylamino group, a di-$C_1$–$C_6$ alkylamino group which may be the same or different, a $C_1$–$C_6$ alkoxycarbonylamino group, a $C_1$–$C_6$ alkoxycarbonyl-$C_1$–$C_6$ alkylamino group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylamino group, a substituted phenylamino group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or a pyrazolyl group), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (3) when $A^1$ is a $C_1$–$C_8$ alkylene group, a $C_3$–$C_6$ alkenylene group or a $C_3$–$C_6$ alkynylene group, then Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$Z^3$—$R^5$ (wherein $Z^3$ is —O—, —S—, —SO—, —$SO_2$— or a group of the formula —$N(R^6)$— (wherein $R^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^5$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different);

l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

X may be the same or different, and is a hydrogen atom, a halogen atom, a cyano group, a nitro group, a $C_3$–$C_6$ cycloalkyl group, a halo-$C_3$–$C_6$ cycloalkyl group, a phenyl group, a substituted phenyl group having at least one substituents which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^2$—$R^7$ (wherein $A^2$ is —O—, —S—, —SO—, —$SO_2$—, —C(=O)—, —C(=$NOR^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl-$C_1$–$C_4$ alkyl group, or a substituted phenyl-$C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —$SO_2$—, then $R^7$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group, a di-$C_1$–$C_6$ alkoxyphosphoryl group which may be the same or different, a di-$C_1$–$C_6$ alkoxythiophosphoryl group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^3$—$R^9$ (wherein $A^3$ is —C(=O)—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_3$–$C_6$ alkynylene group, or a halo-$C_3$–$C_6$ alkynylene group, (i) when $A^3$ is —C(=O)— or —$SO_2$—, then $R^9$ is a $C_1$–$C_6$ alkyl group, a halo-$C_1$–$C_6$ alkyl group, a $C_1$–$C_6$ alkoxy group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (ii) when $A^3$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_3$–$C_6$ alkynylene group or a halo-$C_3$–$C_6$ alkynylene group, then $R^9$ is a hydrogen atom, a halogen atom, a cyano group, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^4$—$R^{10}$ (wherein $A^4$ is —O—, —S—, —SO—, —$SO_2$—, —C(=O)—, or a group of the formula —N($R^{11}$)— (wherein $R^{11}$ is a hydrogen atom, a $C_1$–$C_6$ alkyl group, a halo-$C_1$–$C_6$ alkyl group, a $C_3$–$C_6$ alkenyl group, a $C_3$–$C_6$ alkynyl group, a $C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^{10}$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different));

(2) when $A^2$ is —C(=O)— or a group of the formula —C(=NOR$^8$)— (wherein $R^8$ is the same as defined above), then R is a $C_1$–$C_6$ alkyl group, a halo $C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylamino group, a substituted phenylamino group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having one or more substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulf inyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^5$—$R^{12}$ (wherein $A^5$ is —O—, —S—, —SO—, —$SO_2$— or a group of the formula —N($R^{13}$)— (wherein $R^{13}$ is a hydrogen atom, a $C_1$–$C_6$ alkyl group, a halo-$C_1$–$C_6$ alkyl group, a $C_2$–$C_6$ alkenyl group, a $C_2$–$C_6$ alkynyl group, a $C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^{12}$ is a hydrogen atom, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituents which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^6$—$R^{14}$ (wherein $A^6$ is —C(=O)—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(i) when $A^6$ is —C(=O)— or —$SO_2$—, then $R^{14}$ is a $C_1$–$C_6$ alkyl group, a halo-$C_1$–$C_6$ alkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

(ii) when $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^{14}$ is a hydrogen atom, a halogen atom, a cyano group, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a $C_1$–$C_6$ alkylcarbonyl group, a halo-$C_1$–$C_6$ alkylcarbonyl group, a $C_1$–$C_6$ alkoxycarbonyl group, a phenyl group, a substituted phenyl group having at least one substituent which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenoxy group, a substituted phenoxy group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylthio group, a substituted phenylthio group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$-alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different)));

n is an integer of 1 to 4;

further, X may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), by combining together with the adjacent carbon atoms in the phenyl ring, and said condensed ring may have at least one substituents, which may be the same or different, and selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), and a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

Y is the same or different, and is a hydrogen atom, a halogen atom, a cyano group, a nitro group, a $C_3$–$C_6$ cycloalkyl group, a halo-$C_3$–$C_6$ cycloalkyl group, a di-$C_1$–$C_6$ alkoxyphosphoryl group which may be the same or different, a di-$C_1$–$C_6$ alkoxythiophosphoryl group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —A$^2$—R$^7$ (wherein A$^2$ and R$^7$ are the same as defined above);

m is an integer of 1 to 5;

further, Y may form a condensed ring (the condensed ring is the same as defined above), by combining together with the adjacent carbon atoms in the phenyl ring, said condensed ring may have at least one substituents, which may be the same or different, and selected from the group consisting of a halogen atom, a cyano group, a nitro group, a C$_1$–C$_6$ alkyl group, a halo-C$_1$–C$_6$ alkyl group, a C$_2$–C$_6$ alkenyl group, a halo-C$_2$–C$_6$ alkenyl group, a C$_2$–C$_6$ alkynyl group, a halo-C$_2$–C$_6$ alkynyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a mono-C$_1$–C$_6$ alkylamino group, a di-C$_1$–C$_6$ alkylamino group which may be the same or different, a phenyl group, a substituted phenyl group having at least one substituent which may be the same or different and is selected from the group consisting of a halogen atom, a cyano group, a nitro group, a C$_1$–C$_6$ alkyl group, a halo-C$_1$–C$_6$ alkyl group, a C$_2$–C$_6$ alkenyl group, a halo-C$_2$–C$_6$ alkenyl group, a C$_2$–C$_6$ alkynyl group, a halo-C$_2$–C$_6$ alkynyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a mono-C$_1$–C$_6$ alkylamino group and a di-C$_1$–C$_6$ alkylamino group which may be the same or different, a naphthyl group, a substituted naphthyl group having at least one substituent which may be the same or different and is selected from the group consisting of a halogen atom, a cyano group, a nitro group, a C$_1$–C$_6$ alkyl group, a halo-C$_1$–C$_6$ alkyl group, a C$_2$–C$_6$ alkenyl group, a halo-C$_2$–C$_6$ alkenyl group, a C$_2$–C$_6$ alkynyl group, a halo-C$_2$–C$_6$ alkynyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a mono-C$_1$–C$_6$ alkylamino group and a di-C$_1$–C$_6$ alkylamino group which may be the same or different, a heterocyclic group (which is the same as defined above), and a substituted heterocyclic group (wherein said heterocyclic group is the same as defined above) having at lease one substituent which may be the same or different and is selected from the group consisting of a halogen atom, a cyano group, a nitro group, a C$_1$–C$_6$ alkyl group, a halo-C$_1$–C$_6$ alkyl group, a C$_2$–C$_6$ alkenyl group, a halo-C$_2$–C$_6$ alkenyl group, a C$_2$–C$_6$ alkynyl group, a halo-C$_2$–C$_6$ alkynyl group, a C$_1$–C$_6$ alkoxy group, a halo-C$_1$–C$_6$ alkoxy group, a C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a mono-C$_1$–C$_6$ alkylamino group and a di-C$_1$–C$_6$ alkylamino group which may be the same or different;

Z$^1$ and Z$^2$ are each represents an oxygen atom or a sulfur atom; provided that, (1) when X, R$^1$ and R$^3$ are hydrogen atoms at the same time; m is an integer of 2; Y at 2-position is a fluorine atom and Y at 3-position is a chlorine atom; then R$^2$ is not ethyl group, isopropyl group, cyclohexyl group, 2-propenyl group, methylthiopropyl group and a-methylbenzyl group, (2) when X and R$^3$ are hydrogen atoms at the same time; m is an integer of 2; Y at 2-position is a fluorine atom and Y at 3-position is a chlorine atom; then the 4 to 7 membered ring by combining R$^1$ and R$^2$ to each other, in which the ring may contain the same or different 1 to 3 hetero atoms selected from the group consisting of oxygen atom, sulfur atom and nitrogen atom is not morpholino group, (3) when X, R$^1$ and R$^3$ are hydrogen atoms at the same time; and R$^2$ is 1,2,2-trimethylpropyl group; then Y is not a hydrogen atom, (4) when X, R$^1$ and R$^3$ are hydrogen atoms at the same time; R$^2$ is 2,2-dimethylpropyl group; and m is an integer of 1; then Y is not 2-ethoxy group, and (5) when X, R$^1$ and R$^3$ are hydrogen atoms at the same time; and R$^2$ is tert-butyl group group; and m is an integer of 1; then Y is not 4-chlorine atom, 2-nitro group, 4-nitro group, 3-methoxy group, 4-methoxy group and 2,6-dimethyl groups.

2. The phthalic acid diamide derivative according to claim 1, wherein R$^1$, R$^1$ and R$^3$ may be the same or different, and are each a hydrogen atom, a C$_3$–C$_6$ cycloalkyl group, a halo-C$_3$–C$_6$ cycloalkyl group, or a group of the formula —A$^1$—Q$_l$ (wherein A$^1$ is a C$_1$–C$_8$ alkylene group, a C$_3$–C$_6$ alkenylene group or a C$_3$–C$_6$ alkynylene group; and Q is a hydrogen atom, a halogen atom, a cyano group, a nitro group, a halo-C$_1$–C$_6$ alkyl group, a C$_3$–C$_6$ cycloalkyl group, a halo-C$_3$–C$_6$ cycloalkyl group, a C$_1$–C$_6$ alkoxycarbonyl group, a di-C$_1$–C$_6$ alkoxyphosphoryl group which may be the same or different, a di-C$_1$–C$_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulf inyl group, a C$_1$–C$_6$ alkylsulfonyl group and a halo-C$_1$–C$_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, or a group of the formula —Z$^3$—R$^5$ (wherein Z$^3$ is —O—, —S—, —SO—, —SO$_2$— or a group of the formula —N(R$^6$)— (wherein R$^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and $R^5$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4);

$R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

X may be the same or different, and is a hydrogen atom, a halogen atom, a cyano group, a nitro group, a $C_3$–$C_6$ cycloalkyl group, a halo-$C_3$–$C_6$ cycloalkyl group, a phenyl group, a substituted phenyl group having at least one substituents which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, and a halo-$C_1$–$C_6$ alkylsulfonyl group, or a group of the formula —$A^2$—$R^7$ (wherein $A^2$ is —O—, —S—, —SO—, —$SO_2$, —C(=O)—, —C(=$NOR^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl-$C_1$–$C_4$ alkyl group, or a substituted phenyl-$C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —$SO_2$—, then $R^7$ is a halo-$C_3$–$C_6$ cycloalkyl group, a halo-$C_3$–$C_6$ cycloalkenyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^3$—$R^9$ (wherein $A^3$ is a $C_1$–$C_6$ alkylene group, a halo-C alkylene group, a $C_3$–$C_6$ alkenylene group, a halo-$C_3$–$C_6$ alkenylene group, a $C_3$–$C_6$ alkynylene group or a halo-$C_3$–$C_6$ alkynylene group; $R^9$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^4$—$R^{10}$ (wherein $A^4$ is —O—, —S—, —SO—, —$SO_2$— or —C(=O)—, and $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group));

(2) when $A^2$ is —C(=O)— or a group of the formula —C(=$NOR^8$)— (wherein $R^8$ is the same as defined the above), then $R^7$ is a $C_1$–$C_6$ alkyl group, a halo $C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenylamino group, a substituted phenylamino group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, and a halo-$C_1$–$C_6$ alkylsulfonyl group, a heterocyclic group (which is the same as defined the above), or a substituted heterocyclic group (wherein the heterocyclic group is the same as defined the above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^5$—$R^{12}$ (wherein $A^5$ is —O—, —S—, —SO— or —$SO_2$—; and $R^{12}$ is a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, or a halo-$C_3$–$C_6$ alkynylene group; and $R^{14}$ is a hydrogen atom, a halogen atom, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenoxy group, a substituted phenoxy group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenylthio group, a substituted phenylthio group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$-alkylsulfonyl group, a heterocyclic group (which is the same as defined the above), or a substituted heterocyclic group (wherein the heterocyclic ring is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group)));

n is an integer of 1 to 4;

further, X may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), by combining together with the adjacent carbon atoms in the phenyl ring, said condensed ring may have at least one substituent, which may be the same or different, and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

Y is the same or different, and is a hydrogen atom, a halogen atom, a cyano group, a nitro group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^2$—$R^7$ (wherein $A^2$ and $R^7$ are the same as defined above);

m is an integer of 1 to 5;

further, Y may form a condensed ring (the same as defined above), by combining together with the adjacent carbon atoms in the phenyl ring, said condensed ring may have at least one substituent, which may be the same or different, and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), and a substituted heterocyclic group (wherein said heterocyclic group is the same as defined the above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; and $Z^1$ and $Z^2$ are each represents an oxygen atom or a sulfur atom.

3. The phthalic acid diamide derivative according to claim 2, represented by the general formula (I-1),

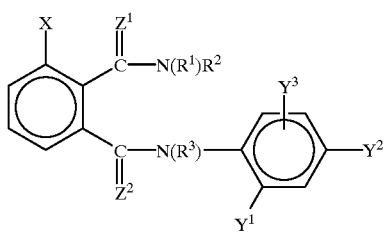
(I-1)

{wherein, $R^1$, $R^2$ and $R^3$ may be the same or different, and are each a hydrogen atom, a $C_3$–$C_6$ cycloalkyl group, a halo-$C_3$–$C_6$ cycloalkyl group or a group of the formula —$A^1$—$Q_l$ (wherein, $A^1$ is a $C_1$–$C_8$ alkylene group, a $C_3$–$C_6$ alkenylene group or a $C_3$–$C_6$ alkynylene group; Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$Z^3$—$R^5$ (wherein $Z^3$ is —O—, —S—, —SO—, —$SO_2$— or a group of the formula —N($R^6$)— (wherein $R^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and $R^5$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic ring is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

X is a hydrogen atom or a nitro group;

$Y^1$ and $Y^3$ may be the same or different and are each a hydrogen atom, a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a phenoxy group, a substituted phenoxy group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a pyridyloxy group, a substituted pyridyloxy group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group;

$Y^2$ is a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^2$—$R^7$ (wherein $A^2$ is —O—, —S—, —SO—, —$SO_2$—, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group and, (1) when $A^2$ is —O—, —S—, —SO— or —$SO_2$—, then $R^7$ is a halo-$C_3$–$C_6$ cycloalkyl group, a halo-$C_3$–$C_6$ cycloalkenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined above), a substituted heterocyclic group (wherein the heterocyclic ring is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^3$—$R^9$ (wherein $A^3$ is a halo-$C_1$–$C_6$ alkylene group, a halo-$C_3$–$C_6$ alkenylene group, a $C_3$–$C_6$ alkynylene group or a halo-$C_3$–$C_6$ alkynylene group; and $R^9$ is a hydrogen atom, a halogen atom, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group or a group of the formula —$A^4$—$R^{10}$ (wherein $A^4$ is —O—, —S— or —$SO_2$—; and $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined above), a substituted heterocyclic group (wherein the heterocyclic ring is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group));

(2) when $A^2$ is a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^5$—$R^{12}$ (wherein $A^5$ is —O—, —S—, —SO— or —$SO_2$—; and $R^{12}$ is a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group; or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group; and $R^{14}$ is a hydrogen atom, a halogen atom, a halo-$C_3$–$C_6$ cycloalkyl group, a halo-$C_1$–$C_6$ alkoxy group, a halo-$C_1$–$C_6$ alkylthio group, a halo-$C_1$–$C_6$ alkylsulfinyl group, a halo-$C_1$–$C_6$ alkylsulfonyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenoxy group, a substituted phenoxy group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenylthio group, a substituted phenylthio group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$-alkylsulfonyl group, a heterocyclic group (which is the same as defined the above), or a substituted heterocyclic group (wherein the heterocyclic group is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group))); further, $Y^1$ and $Y^2$ may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole) by combining to each other together with the adjacent $Y^3$, said condensed ring may have at least one substituent, which is the same or different, selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; and $Z^1$ and $Z^2$ are each an oxygen atom or a sulfur atom}.

4. The phthalic acid diamide derivative according to claim 2, represented by the general formula (I-2),

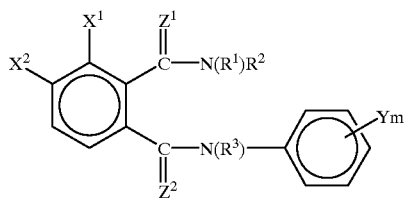

(I-2)

{wherein, $R^1$, $R^2$ and $R^3$ may be the same or different, and are each a hydrogen atom, a $C_3$–$C_6$ cycloalkyl group, a halo-$C_3$–$C_6$ cycloalkyl group or a group of the formula —$A^1$—$Q_l$ (wherein, $A^1$ is a $C_1$–$C_8$ alkylene group, a $C_3$–$C_6$ alkenylene group or a $C_3$–$C_6$ alkynylene group; Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$Z^3$—$R^5$ (wherein $Z^3$ is —O—, —S—, —SO—, —$SO_2$— or a group of the formula —N($R^6$)— (wherein $R^6$ is a hydrogen atom, a $C_1$–$C_6$ alkylcarbonyl group a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and $R^5$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo-$C_1$–$C_6$ alkylcarbonyl group and a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

$X^1$ and $X^2$ may be the same or different and are each a halogen atom, a cyano group, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; further, $X^1$ and $X^2$ may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole) by combining to each other, and said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkyl sulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

Y is the same or different, and are each a hydrogen atom, a halogen atom, a cyano group, a nitro group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of —$A^2$—$R^7$ (wherein $A^2$ is —O—, —S—, —SO—, —$SO_2$—, —C(=O)—, —C(=$NOR^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl-$C_1$–$C_4$ alkyl group, or a substituted phenyl-$C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —$SO_2$—, then R is a halo-$C_3$–$C_6$ cycloalkyl group, a halo-$C_3$–$C_6$ cycloalkenyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^3$—$R^9$ (wherein $A^3$ is a $C_1$–$C_6$ alkylene group, a halo-$C_1$–$C_6$ alkylene group, a $C_3$–$C_6$ alkenylene group, a halo-$C_3$–$C_6$ alkenylene group, a $C_3$–$C_6$ alkynylene group or a halo-$C_3$–$C_6$ alkynylene group; $R^9$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkyl-sulfonyl group and a halo-$C_1$–$C_6$ alkylsulfonyl group, or a group of the formula —$A^4$—$R^{10}$ (wherein $A^4$ is —O—, —S—, —SO—, —$SO_2$— or —C(=O)—, and $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group));

(2) when $A^2$ is —C(=O)— or a group of the formula —C(=$NOR^8$)— (wherein $R^8$ is the same as defined the above), then $R^7$ is a $C_1$–$C_6$ alkyl group, a halo $C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenylamino group, a substituted phenylamino group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, and a halo-$C_1$–$C_6$ alkylsulfonyl group, a heterocyclic group (which is the same as defined the above), or a substituted heterocyclic group (wherein the heterocyclic group is the same as defined the above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^5$—$R^{12}$ (wherein $A^5$ is —O—, —S—, —SO— or —$SO_2$—; and $R^{12}$ is a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, or a halo-$C_3$–$C_6$ alkynylene group; and $R^{14}$ is a hydrogen atom, a halogen atom, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenoxy group, a substituted phenoxy group having at least one substituent which may be the same or different and is selected from the group consisting of a halogen a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenylthio group, a substituted phenylthio group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$-alkylsulfonyl group, a heterocyclic group (which is the same as defined the above), or a substituted heterocyclic group (wherein the heterocyclic ring is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group))); and m is an integer of 1 to 5;

further, Y may form a condensed ring (which is the same as defined above) by combining together with the adjacent carbon atoms in the phenyl ring, said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_3$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_3$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$Z^1$ and $Z^2$ are each an oxygen atom or a sulfur atom}.

5. The phthalic acid diamide derivative according to claim 4, represented by the general formula (I-3),

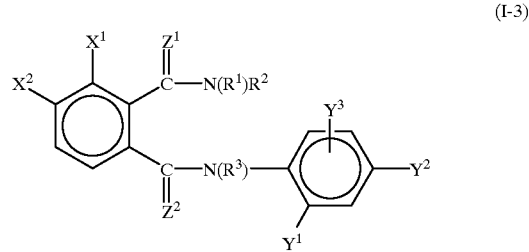

(I-3)

{wherein, $R^1$, $R^2$ and $R^3$ may be the same or different, and are each a hydrogen atom, a $C_3$–$C_6$ cycloalkyl group, a halo-$C_3$–$C_6$ cycloalkyl group or a group of the formula —$A^1$—$Q_l$ (wherein, $A^1$ is a $C_1$–$C_8$ alkylene group, a $C_3$–$C_6$ alkenylene group or a $C_3$–$C_6$ alkynylene group; Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$Z^3$—$R^5$ (wherein $Z^3$ is —O—, —S—, —SO—, —$SO_2$— or a group of the formula —N($R^6$)— (wherein $R^6$ is a hydrogen atom, a $C_1$–$C_6$ alkylcarbonyl group a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group,); and $R^5$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_1$–$C_6$ cycloalkyl group, a halo-$C_3$–$C_6$ cycloalkyl group, a $C_1$–$C_6$ alkylcarbonyl group, a halo-$C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

$X^1$ and $X^2$ may be the same or different and are each a halogen atom, a cyano group, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; further, $X^1$ and $X^2$ may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole) by combining to each other, and said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$Y^2$ and $Y^3$ may be the same or different, and are each a hydrogen atom, a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a phenoxy group, a substituted phenoxy group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a pyridyloxy group, or a substituted pyridyloxy group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, $Y^2$ is a hydrogen atom, a halogen atom, a halo-$C_3$–$C_6$ cycloalkyl group or a group of the formula —$A^2$—$R^7$ (wherein $A^2$ —O—, —S—, —SO—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, or a halo-$C_3$–$C_6$ alkynylene group, and (1) when $A^2$ is —O—, —S—, —SO— or —$SO^2$— then $R^7$ is a halo-$C_3$–$C_6$ cycloalkyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a $C_1$–$C_6$ alkylsulfinyl group and a halo-$C_1$–$C_6$ alkylsulfonyl group, a substituted pyridyloxy group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^3$—$R^9$ (wherein $A^3$ is a halo-$C_1$–$C_6$ alkylene group, or a halo-$C_3$–$C_6$ alkenylene group; and $R^9$ is a hydrogen atom, a halogen atom, a halo-$C_3$–$C_6$ cycloalkyl group, a phenyl group, a substituted phenyl group having at least one substituent, which is the same or different and is selected from the group consisting of a halogen atom a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^4$—$R^{10}$ (wherein $A^4$ is —O—, —S—, —SO— or —$SO_2$—; $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, or a substituted phenyl group having at least one substituent, which is the same or different and is selected from the group consisting of a halogen atom a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group)), (2) when $A^2$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, a halo-$C_3$–$C_6$ alkynylene group, then $R^7$ is a hydrogen atom, a halogen atom, a halo-$C_3$–$C_6$ cycloalkyl group, a phenyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^5$—$R^{12}$ (wherein $A^5$ is —O—, —S—, —SO— or —$SO_2$—; and $R^{12}$ is a $C_3$–$C_6$ cycloalkyl group, a halo-$C_3$–$C_6$ cycloalkyl group, a phenyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group; and $R^{14}$ is a hydrogen atom, a halogen atom, a halo-$C_3$–$C_6$ cycloalkyl group, a halo-$C_1$–$C_6$ alkoxy group, a halo-$C_1$–$C_6$ alkylthio group, a halo-$C_1$–$C_6$ alkylsulfinyl group, a halo-$C_1$–$C_6$ alkylsulfonyl group, a phenyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenoxy group, a substituted phenoxy group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenylthio group, or a substituted phenylthio group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group));

further, $Y^1$ and $Y^2$ may form a condensed ring (the condensed ring is the same as defined above) by combining to each other together with $Y^3$, and said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, and a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$Z^1$ and $Z^2$ are each an oxygen atom or a sulfur atom}.

6. An agricultural and horticultural insecticides, which is characterized by containing, as the effective ingredient, a phthalic acid diamide derivative represented by the general formula (I),

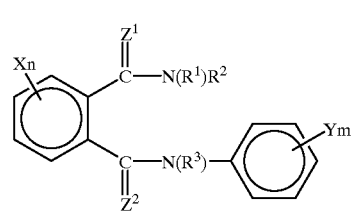

(I)

wherein $R^1$, $R^2$ and $R^3$ may be the same or different, and are each a hydrogen atom, a cyano group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group or a group of the formula —$A^1$—$Q_l$ (wherein $A^1$ is —O—, —S—, —$SO_2$—, —C(=O)—, a group of the formula —N($R^4$)— (wherein $R^4$ is a $C_1$–$C_6$ alkylcarbonyl group, a halo-$C_1$–$C_6$ alkylcarbonyl group, a $C_1$–$C_6$ alkoxycarbonyl group, a phenylcarbonyl group, or a substituted phenylcarbonyl group having at least one substituent which may be the same or different, and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different), a $C_1$–$C_8$ alkylene group, a $C_3$–$C_6$ alkenylene group or a $C_3$–$C_6$ alkynylene group;

(1) when $A^1$ is —O— or a group of the formula —N($R^4$)— (wherein $R^4$ is the same as defined above), then Q is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkyl sulfonyl group, a mono-$C_1$–$C_6$ alkylamino group and a di-$C_1$–$C_6$ alkylamino group which may be the same or different, a phenyl-$C_1$–$C_4$ alkyl group or a substituted phenyl-$C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

(2) when $A^1$ is —S—, —$SO_2$— or —C(=O)—, then Q is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_1$–$C_6$ alkoxy group, a mono-$C_1$–$C_6$ alkylamino group, a di-$C_1$–$C_6$ alkylamino group which may be the same or different, a $C_1$–$C_6$ alkoxycarbonylamino group, a $C_1$–$C_6$ alkoxycarbonyl-$C_1$–$C_6$ alkylamino group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylamino group, a substituted phenylamino group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_3$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or a pyrazolyl group), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_3$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (3) when $A^1$ is a $C_1$–$C_6$ alkylene group, a $C_3$–$C_6$ alkenylene group or a $C_3$–$C_6$ alkynylene group, then Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$Z^3$—$R^5$ (wherein $Z^3$ is —O—, —S—, —SO—, —$SO_2$ or a group of the formula —N($R^6$)— (wherein $R^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^5$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_2$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different);

l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

X may be the same or different, and is a hydrogen atom, a halogen atom, a cyano group, a nitro group, a $C_3$–$C_6$ cycloalkyl group, a halo-$C_3$–$C_6$ cycloalkyl group, a phenyl group, a substituted phenyl group having at least one substituents which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^2$—$R^7$ (wherein $A^2$ is —O—, —S—, —SO—, —$SO_2$—, —C(=O)—, —C(=$NOR^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl–$C_1$–$C_4$ alkyl group, or a substituted phenyl-$C_1$–$C_4$ alkyl group having at least one substituent, in the phenyl ring, which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —$SO_2$—, then $R^7$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group, a di-$C_1$–$C_6$ alkoxyphosphoryl group which may be the same or different, a di-$C_1$–$C_6$ alkoxythiophosphoryl group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-C –$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^3$—$R^9$ (wherein $A^3$ is —C(=O)—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_3$–$C_6$ alkynylene group, or a halo-$C_3$–$C_6$ alkynylene group, (i) when $A^3$ is —C(=O)— or —$SO_2$—, then $R^9$ is a $C_1$–$C_6$ alkyl group, a halo-$C_1$–$C_6$ alkyl group, a $C_1$–$C_6$ alkoxy group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (ii) when $A^3$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_3$–$C_6$ alkynylene group or a halo-$C_3$–$C_6$ alkynylene group, then $R^9$ is a hydrogen atom, a halogen atom, a cyano group, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^4$—$R^{10}$ (wherein $A^4$ is —O—, —S—, —SO—, —$SO_2$—, —C(=O)—, or a group of the formula —N($R^{11}$)— (wherein $R^{11}$ is a hydrogen atom, a $C_1$–$C_6$ alkyl group, a halo-$C_1$–$C_6$ alkyl group, a $C_3$–$C_6$ alkenyl group, a $C_3$–$C_6$ alkynyl group, a $C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^{10}$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_3$–$C_6$ cycloalkenyl group, a halo-$C_3$–$C_6$ cycloalkenyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different));

(2) when $A^2$ is —C(=O)— or a group of the formula —C(=NOR$^8$)— (wherein R$^8$ is the same as defined above), then R$^7$ is a $C_1$–$C_6$ alkyl group, a halo $C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylamino group, a substituted phenylamino group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having one or more substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then R$^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^5$—R$^{12}$ (wherein $A^5$ is —O—, —S—, —SO—, —SO$_2$— or a group of the formula —N(R$^{13}$)— (wherein R$^{13}$ is a hydrogen atom, a $C_1$–$C_6$ alkyl group, a halo-$C_1$–$C_6$ alkyl group, a $C_2$–$C_6$ alkenyl group, a $C_2$–$C_6$ alkynyl group, a $C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituents which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different); and $R^{12}$ is a hydrogen atom, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), a substituted heterocyclic group (wherein the heterocyclic group is the same as defined above) having at least one substituents which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^6$—$R^{14}$ (wherein $A^6$ is —C(=O)—, —$SO_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(i) when $A^6$ is —C(=O)— or —$SO_2$—, then $R^{14}$ is a $C_1$–$C_6$ alkyl group, a halo-$C_1$–$C_6$ alkyl group, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined the above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

(ii) when $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^{14}$ is a hydrogen atom, a halogen atom, a cyano group, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a $C_1$–$C_6$ alkylcarbonyl group, a halo-$C_1$–$C_6$ alkylcarbonyl group, a $C_1$–$C_6$ alkoxycarbonyl group, a phenyl group, a substituted phenyl group having at least one substituent which may be the same or different and are selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenoxy group, a substituted phenoxy group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a phenylthio group, a substituted phenylthio group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$-alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_3$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a alkylthio group, a halo-$C_1$–$C_6$ alkylthio group, a $C_1$–$C_6$ $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), or a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different)));

n is an integer of 1 to 4;

further, X may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), by combining together with the adjacent carbon atoms in the phenyl ring, and said condensed ring may have at least one substituents, which may be the same or different, and selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), and a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

Y is the same or different, and is a hydrogen atom, a halogen atom, a cyano group, a nitro group, a $C_3$–$C_6$ cycloalkyl group, a halo-$C_3$–$C_6$ cycloalkyl group, a di-$C_1$–$C_6$ alkoxyphosphoryl group which may be the same or different, a di-$C_1$–$C_6$ alkoxythiophosphoryl group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined the above), a substituted heterocyclic group (wherein the heterocyclic group is the same as defined above) having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, or a group of the formula —$A^2$—$R^7$ (wherein $A^2$ and $R^7$ are the same as defined above);

m is an integer of 1 to 5;

further, Y may form a condensed ring (the condensed ring is the same as defined above), by combining together with the adjacent carbon atoms in the phenyl ring, said condensed ring may have at least one substituents, which may be the same or different, and selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a naphthyl group, a substituted naphthyl group having at least one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different, a heterocyclic group (which is the same as defined above), and a substituted heterocyclic group (wherein said heterocyclic group is the same as defined above) having at lease one substituent which may be the same or different and is selected from the group consisting of a halogen atom, a cyano group, a nitro group, a $C_1$–$C_6$ alkyl group, a halo-$C_1$–$C_6$ alkyl group, a $C_2$–$C_6$ alkenyl group, a halo-$C_2$–$C_6$ alkenyl group, a $C_2$–$C_6$ alkynyl group, a halo-$C_2$–$C_6$ alkynyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a mono-$C_1$–$C_6$ alkylamino group and a di-$C_1$–$C_6$ alkylamino group which may be the same or different;

$Z^1$ and $Z^2$ are each represents an oxygen atom or a sulfur atom.

7. The agricultural and horticultural insecticides according to claim 6, wherein $R^1$, $R^2$ and $R^3$ may be the same or different, and are each a hydrogen atom, a $C_3$–$C_6$ cycloalkyl group, a halo-$C_3$–$C_6$ cycloalkyl group, or a group of the formula —$A^1$—$Q_l$ (wherein $A^1$ is a $C_1$–$C_8$ alkylene group, a $C_3$–$C_6$ alkenylene group or a $C_3$–$C_6$ alkynylene group; and Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$Z^3$— $R^5$ (wherein $Z^3$ is —O—, —S—, —SO—, —SO$_2$— or a group of the formula —N($R^6$)— (wherein $R^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group,); and $R^5$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4);

$R_1$ and $R_2$ may form a 4 to 7 membered ring by combining to each other, in which the ring may contain the same or different 1 to 3 hetero atoms selected from the group consisting of oxygen atom, sulfur atom and nitrogen atom;

X may be the same or different, and is a hydrogen atom, a halogen atom, a cyano group, a nitro group, a $C_3$–$C_6$ cycloalkyl group, a halo-$C_3$–$C_6$ cycloalkyl group, a phenyl group, a substituted phenyl group having at least one substituents which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, and a halo-$C_1$–$C_6$ alkylsulfonyl group, or a group of the formula —$A^2$— $R^7$ (wherein $A^2$ is —O—, —S—, —SO—, —SO$_2$—, —C(=O)—, —C(=NOR$^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl-$C_1$–$C_4$ alkyl group, or a substituted phenyl-$C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —$SO_2$—, then $R^7$ is a halo-$C_3$–$C_6$ cycloalkyl group, a halo-$C_3$–$C_6$ cycloalkenyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^3$—$R^9$ (wherein $A^3$ is a $C_1$–$C_6$ alkylene group, a halo-$C_1$–$C_6$ alkylene group, a $C_3$–$C_6$ alkenylene group, a halo-$C_3$–$C_6$ alkenylene group, a $C_3$–$C_6$ alkynylene group or a halo-$C_3$–$C_6$ alkynylene group; $R^9$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^4$—$R^{10}$ (wherein $A^4$ is —O—, —S—, —SO—, —$SO_2$— or —C(=O)—, and $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group));

(2) when $A^2$ is —C(=O)— or a group of the formula —C(=$NOR^8$)— (wherein $R^8$ is the same as defined the above), then $R^7$ is a $C_1$–$C_6$ alkyl group, a halo-$C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_3$–$C_6$ alkylamino group which may be the same or different, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenylamino group, a substituted phenylamino group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, and a halo-$C_1$–$C_6$ alkylsulfonyl group, a heterocyclic group (which is the same as defined the above), or a substituted heterocyclic group (wherein the heterocyclic group is the same as defined the above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_{1-6}$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^5$—$R^{12}$ (wherein $A^5$ is —O—, —S—, —SO— or —SO$_2$—; and R$^{12}$ is a C$_3$–C$_6$ cycloalkyl group, a halo-C$_3$–C$_6$ cycloalkyl group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, or a group of the formula —A$^6$—R$^{14}$ (wherein A$^6$ is a C$_1$–C$_6$ alkylene group, a halo-C$_1$–C$_6$ alkylene group, a C$_2$–C$_6$ alkenylene group, a halo-C$_2$–C$_6$ alkenylene group, a C$_2$–C$_6$ alkynylene group, or a halo-C$_3$–C$_6$ alkynylene group; and R$^{14}$ is a hydrogen atom, a halogen atom, a C$_3$–C$_6$ cycloalkyl group, a halo-C$_3$–C$_6$ cycloalkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a phenoxy group, a substituted phenoxy group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a phenylthio group, a substituted phenylthio group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$-alkylsulfonyl group, a heterocyclic group (which is the same as defined the above), or a substituted heterocyclic group (wherein the heterocyclic ring is the same as defined above) having at least one substituent which may be the same or different and is selected from the-group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C –C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group)));

n is an integer of 1 to 4;

further, X may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole), by combining together with the adjacent carbon atoms in the phenyl ring, said condensed ring may have at least one substituent, which may be the same or different, and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group;

Y is the same or different, and is a hydrogen atom, a halogen atom, a cyano group, a nitro group, a halo-C$_3$–C$_6$ cycloalkyl group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, or a group of the formula —A$^2$—R$^7$ (wherein A$^2$ and R$^7$ are the same as defined above);

m is an integer of 1 to 5;

further, Y may form a condensed ring (the same as defined above), by combining together with the adjacent carbon atoms in the phenyl ring, said condensed ring may have at least one substituent, which may be the same or different, and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), and a substituted heterocyclic group (wherein said heterocyclic group is the same as defined the above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; and $Z^1$ and $Z^2$ are each represents an oxygen atom or a sulfur atom.

8. The agricultural and horticultural insecticides according to claim 7, containing as the effective ingredient, a phthalic acid diamide derivative represented by the general formula (I-1),

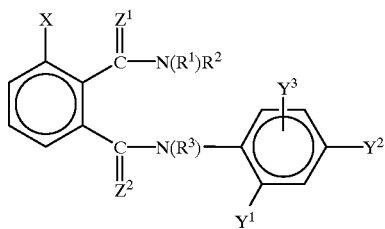

(I-1)

{wherein, $R^1$, $R^2$ and R may be the same or different, and are each a hydrogen atom, a $C_3$–$C_6$ cycloalkyl group, a halo-$C_3$–$C_6$ cycloalkyl group or a group of the formula —$A^1$—$Q_l$ (wherein, $A^1$ is a $C_1$–$C_8$ alkylene group, a $C_3$–$C_6$ alkenylene group or a $C_3$–$C_6$ alkynylene group; Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$Z^3$—$R^5$ (wherein $Z^3$ is —O—, —S—, —SO—, —SO$_2$— or a group of the formula —N($R^6$)— (wherein $R^6$ is a hydrogen atom, a $C_1$–$C_6$ alkylcarbonyl group, a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and $R^5$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo $C_1$–$C_6$ alkylcarbonyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic ring is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

X is a hydrogen atom or a nitro group;

$Y^1$ and $Y^3$ may be the same or different and are each a hydrogen atom, a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a phenoxy group, a substituted phenoxy group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a pyridyloxy group, a substituted pyridyloxy group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group;

$Y^2$ is a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A_2$—$R^7$ (wherein A is —O—, —S—, —SO—, —$SO_2$—, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group and, (1) when $A^2$ is —O—, —S—, —SO— or —$SO_2$—, then $R^7$ is a halo-$C_3$–$C_6$ cycloalkyl group, a halo-$C_3$–$C_6$ cycloalkenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined above), a substituted heterocyclic group (wherein the heterocyclic ring is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^3$—$R^9$ (wherein $A^3$ is a halo-$C_1$–$C_6$ alkylene group, a halo-$C_3$–$C_6$ alkenylene group, a $C_3$–$C_6$ alkynylene group or a halo-$C_3$–$C_6$ alkynylene group; and $R^9$ is a hydrogen atom, a halogen atom, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group or a group of the formula —$A^4$—$R^{10}$ (wherein $A^4$ is —O—, —S— or —$SO_2$—; and $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined above), a substituted heterocyclic group (wherein the heterocyclic ring is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group));

(2) when $A^2$ is a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^5$—$R^{12}$ (wherein $A^5$ is —O—, —S—, —SO— or —$SO_2$—; and $R^{12}$ is a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group; or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group; and $R^{14}$ is a hydrogen atom, a halogen atom, a halo-$C_3$–$C_6$ cycloalkyl group, a halo-$C_1$–$C_6$ alkoxy group, a halo-$C_1$–$C_6$ alkylthio group, a halo-$C_1$–$C_6$ alkylsulfinyl group, a halo-$C_1$–$C_6$ alkylsulfonyl group, a phenyl group, a substituted phenyl group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenoxy group, a substituted phenoxy group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenylthio group, a substituted phenylthio group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$-alkylsulfonyl group, a heterocyclic group (which is the same as defined the above), or a substituted heterocyclic group (wherein the heterocyclic group is the same as defined above) having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group))); further, $Y^1$ and $Y^2$ may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole) by combining to each other together with the adjacent $Y^3$, said condensed ring may have at least one substituent, which is the same or different, selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; and $Z^1$ and $Z^2$ are each an oxygen atom or a sulfur atom}.

9. The agricultural and horticultural insecticides according to claim 7, containing as the active ingredient, a phthalic acid diamide derivative represented by the general formula (I-2),

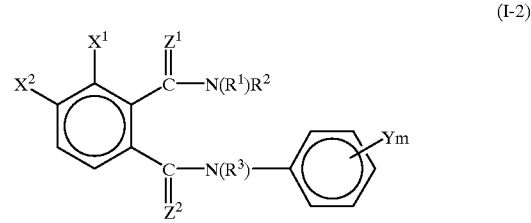

(I-2)

{wherein, $R^1$, $R^2$ and $R^3$ may be the same or different, and are each a hydrogen atom, a $C_3$–$C_6$ cycloalkyl group, a halo-$C_3$–$C_6$ cycloalkyl group or a group of the formula —$A^1$—$Q_l$ (wherein, $A^1$ is a $C_1$–$C_8$ alkylene group, a $C_3$–$C_6$ alkenylene group or a $C_3$–$C_6$ alkynylene group; Q is a hydrogen atom, a halogen atom, a cyano group, a nitro group, a halo-$C_1$–$C_6$ alkyl group, a $C_3$–$C_6$ cycloalkyl group, a halo-$C_3$–$C_6$ cycloalkyl group, a $C_1$–$C_6$ alkoxycarbonyl group, a di-$C_1$–$C_6$ alkoxyphosphoryl group which may be the same or different, a di-$C_1$–$C_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$Z^3$—$R^5$ (wherein $Z^3$ is —O—, —S—, —SO—, —$SO_2$— or a group of the formula —$N(R^6)$— (wherein $R^6$ is a hydrogen atom, a $C_1$–$C_6$ alkylcarbonyl group a halo-$C_1$–$C_6$ alkylcarbonyl group, a $C_1$–$C_6$ alkoxycarbonyl group, a phenylcarbonyl group, a substituted phenylcarbonyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkoxycarbonyl group, or a substituted phenyl $C_1$–$C_4$ alkoxycarbonyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and $R^5$ is a hydrogen atom, a $C_1$–$C_6$ alkyl group, a halo $C_1$–$C_6$ alkyl group, a $C_3$–$C_6$ alkenyl group, a halo-$C_3$–$C_6$ alkenyl group, a $C_3$–$C_6$ alkynyl group, a halo-$C_3$–$C_6$ alkynyl group, a $C_3$–$C_6$ cycloalkyl group, a halo-$C_3$–$C_6$ cycloalkyl group, a $C_1$–$C_6$ alkylcarbonyl group, a halo-$C_1$–$C_6$ alkylcarbonyl group and a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenyl $C_1$–$C_4$ alkyl group, a substituted phenyl $C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), or a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group); and l is an integer of 1 to 4); further, $R^1$ and $R^2$ may form a 4 to 7 membered ring by combining to each other, in which the ring may contain the same or different 1 to 3 hetero atoms selected from the group consisting of oxygen atom, sulfur atom and nitrogen atom;

$X^1$ and $X^2$ may be the same or different and are each a halogen atom, a cyano group, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group; further, $X^1$ and $X^2$ may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole) by combining to each other, and said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkyl sulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

Y is the same or different, and are each a hydrogen atom, a halogen atom, a cyano group, a nitro group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of —$A^2$—$R^7$ (wherein $A^2$ is —O—, —S—, —SO—, —$SO_2$—, —C(=O)—, —C(=$NOR^8$)— (wherein $R^8$ is a hydrogen atom, a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ alkynyl group, a $C_3$–$C_6$ cycloalkyl group, a phenyl-$C_1$–$C_4$ alkyl group, or a substituted phenyl-$C_1$–$C_4$ alkyl group having at least one substituent, in the phenyl ring, which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group), a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group or a halo-$C_3$–$C_6$ alkynylene group;

(1) when $A^2$ is —O—, —S—, —SO— or —SO$_2$—, then $R^7$ is a halo-$C_3$–$C_6$ cycloalkyl group, a halo-$C_3$–$C_6$ cycloalkenyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^3$—$R^9$ (wherein $A^3$ is a $C_1$–$C_6$ alkylene group, a halo-$C_1$–$C_6$ alkylene group, a $C_3$–$C_6$ alkenylene group, a halo-$C_3$–$C_6$ alkenylene group, a $C_3$–$C_6$ alkynylene group or a halo-$C_3$–$C_6$ alkynylene group; $R^9$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^4$—$R^{10}$ (wherein $A^4$ is —O—, —S—, —SO—, —SO$_2$— or —C(=O)—, and $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo–$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), or a substituted heterocyclic group (wherein the heterocyclic group is the same as defined above) having at least one substituent which may be the same or different and is selected from the group consisting of a halogen atom, a $C_1$–$C_6$ alkyl group, a halo–$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group));

(2) when $A^2$ is —C(=O)— or a group of the formula —C(=NOR$^8$)— (wherein $R^8$ is the same as defined the above), then $R^7$ is a $C_1$–$C_6$ alkyl group, a halo $C_1$–$C_6$ alkyl group, a $C_2$–$C_6$ alkenyl group, a halo-$C_2$–$C_6$ alkenyl group, a $C_3$–$C_6$ cycloalkyl group, a halo-$C_3$–$C_6$ cycloalkyl group, a $C_1$–$C_6$ alkoxy group, a $C_1$–$C_6$ alkylthio group, a mono-$C_1$–$C_6$ alkylamino group, a di-$C_1$–$C_6$ alkylamino group which may be the same or different, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenylamino group, a substituted phenylamino group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, and a halo-$C_1$–$C_6$ alkylsulfonyl group, a heterocyclic group (which is the same as defined the above), or a substituted heterocyclic group (wherein the heterocyclic group is the same as defined the above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, (3) when $A^2$ is a $C_1$–$C_6$ alkylene group, a halo-$C_1$–$C_6$ alkylene group, $C_2$–$C_6$ alkenylene group, a halo-$C_2$–$C_6$ alkenylene group, a $C_2$–$C_6$ alkynylene group or a halo-$C_3$–$C_6$ alkynylene group, then $R^7$ is a hydrogen atom, a halogen atom, a $C_3$–$C_6$ cycloalkyl group, a halo-$C_3$–$C_6$ cycloalkyl group, a $C_1$–$C_6$ alkoxycarbonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^5$—$R^{12}$ (wherein $A^5$ is —O—, —S—, —SO— or —$SO_2$—; and $R^{12}$ is a $C_3$–$C_6$ cycloalkyl group, a halo-$C_3$–$C_6$ cycloalkyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined the above), a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, or a halo-$C_3$–$C_6$ alkynylene group; and $R^{14}$ is a hydrogen atom, a halogen atom, a $C_3$–$C_6$ cycloalkyl group, a halo-$C_3$–$C_6$ cycloalkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a phenoxy group, a substituted phenoxy group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfonyl group and a halo-$C_1$–$C_6$ alkylsulfonyl group, a phenylthio group, a substituted phenylthio group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$-alkylsulfonyl group, a heterocyclic group (which is the same as defined the above), or a substituted heterocyclic group (wherein the heterocyclic ring is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group))); and m is an integer of 1 to 5;

further, Y may form a condensed ring (which is the same as defined above) by combining together with the adjacent carbon atoms in the phenyl ring, said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, a substituted phenyl group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$Z^1$ and $Z^2$ are each an oxygen atom or a sulfur atom}.

10. The agricultural and horticultural insecticides according to claim 9, containing as the effective ingredient, a phthalic acid diamide derivative represented by the general formula (I-3),

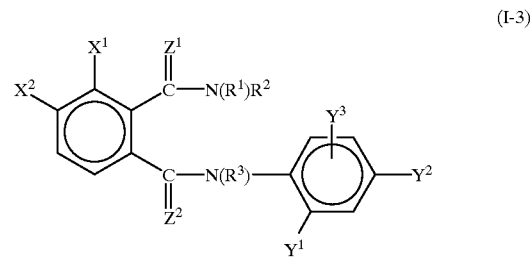

(I-3)

{wherein, $R^1$, $R^2$ and $R^3$ may be the same or different, and are each a hydrogen atom, a $C_3$–$C_6$ cycloalkyl group, a halo-$C_3$–$C_6$ cycloalkyl group or a group of the formula —A$^1$—Q$_i$ (wherein, A$^1$ is a C$_1$–C$_6$ alkylene group, a C$_3$–C$_6$ alkenylene group or a C$_3$–C$_6$ alkynylene group; Q is a hydrogen atom, a halogen atom, a cyano group, a nitro group, a halo-C$_1$–C$_6$ alkyl group, a C$_3$–C$_6$ cycloalkyl group, a halo-C$_3$–C$_6$ cycloalkyl group, a C$_1$–C$_6$ alkoxycarbonyl group, a di-C$_1$–C$_6$ alkoxyphosphoryl group which may be the same or different, a di-C$_1$–C$_6$ alkoxythiophosphoryl group which may be the same or different, a diphenylphosphino group, a diphenylphosphono group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a heterocyclic group (which means pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group or pyrazolyl group), a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and halo-C$_1$–C$_6$ alkylsulfonyl group, or a group of the formula —Z$^3$—R$^5$ (wherein Z$^3$ is —O—, —S—, —SO—, —SO$_2$— or a group of the formula —N(R$^6$)— (wherein R$^6$ is a hydrogen atom, a C$_1$–C$_6$ alkylcarbonyl group a halo-C$_1$–C$_6$ alkylcarbonyl group, a C$_1$–C$_6$ alkoxycarbonyl group, a phenylcarbonyl group, a substituted phenylcarbonyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a phenyl C$_1$–C$_4$ alkoxycarbonyl group, or a substituted phenyl C$_1$–C$_4$ alkoxycarbonyl group having at least one substituent, in the phenyl ring, which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group); and R$^5$ is a hydrogen atom, a C$_1$–C$_6$ alkyl group, a halo-C$_1$–C$_6$ alkyl group, a C$_3$–C$_6$ alkenyl group, a halo-C$_3$–C$_6$ alkenyl group, a C$_3$–C$_6$ alkynyl group, a halo-C$_3$–C$_6$ alkynyl group, a C$_3$–C$_6$ cycloalkyl group, a halo-C$_3$–C$_6$ cycloalkyl group, a C$_1$–C$_6$ alkylcarbonyl group, a halo-C$_1$–C$_6$ alkylcarbonyl group, a C$_1$–C$_6$ alkoxycarbonyl group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a phenyl C$_1$–C$_4$ alkyl group, a substituted phenyl C$_1$–C$_4$ alkyl group having at least one substituent, in the phenyl ring, which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a heterocyclic group (which is the same as defined above), or a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group); and i is an integer of 1 to 4); further, R$^1$ and R$^2$ may form a 4 to 7 membered ring by combining to each other, in which the ring may contain the same or different 1 to 3 hetero atoms selected from the group consisting of oxygen atom, sulfur atom and nitrogen atom;

X$^1$ and X$^2$ may be the same or different and are each a halogen atom, a cyano group, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group; further, X$^1$ and X$^2$ may form a condensed ring (which means naphthalene, tetrahydronaphthalene, indene, indane, quinoline, quinazoline, chroman, isochroman, indole, indoline, benzodioxane, benzodioxole, benzofuran, dihydrobenzofuran, benzothiophene, dihydrobenzothiophene, benzoxazole, benzothiazole, benzimidazole or indazole) by combining to each other, and said condensed ring may have at least one substituent, which is the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group, a halo-C$_1$–C$_6$ alkylsulfonyl group, a phenyl group, a substituted phenyl group having at least one substituent which may be the same or different and is selected from the group consisting of a halogen atom, a C$_1$–C$_6$ alkyl group, a halo-C$_1$–C$_6$ alkyl group, a C$_1$–C$_6$ alkoxy group, a halo-C$_1$–C$_6$ alkoxy group, a C$_1$–C$_6$ alkylthio group, a halo-C$_1$–C$_6$ alkylthio group, a C$_1$–C$_6$ alkylsulfinyl group, a halo-C$_1$–C$_6$ alkylsulfinyl group, a C$_1$–C$_6$ alkylsulfonyl group and a halo-C$_1$–C$_6$ alkylsulfonyl group, a heterocyclic group (which is the same as defined above), and a substituted heterocyclic group (wherein the heterocyclic group is the same as defined above) having at least one substituent which may be the same or different and is selected from the group consisting of a halogen atom, a C$_1$–C$_6$ alkyl group, a halo-C$_1$–C$_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group;

$Y^1$ and $Y^3$ may be the same or different, and are each a hydrogen atom, a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a phenoxy group, a substituted phenoxy group having at least one substituent which may be the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group and a halo-$C_1$–$C_6$ alkylsulfonyl group, a pyridyloxy group, or a substituted pyridyloxy group having at least one substituent which may be the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, $Y^2$ is a hydrogen atom, a halogen atom, a halo-$C_3$–$C_6$ cycloalkyl group or a group of the formula —$A^2$—$R^7$ (wherein $A^2$ —O—, —S—, —SO—, —SO$_2$—, a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, or a halo-$C_3$–$C_6$ alkynylene group, and (1) when $A^2$ is —O—, —S—, —SO— or —SO$_2$-, then $R^7$ is a halo-$C_3$–$C_6$ cycloalkyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a $C_1$–$C_6$ alkylsulfinyl group and a halo-$C_1$–$C_6$ alkylsulfonyl group, a substituted pyridyloxy group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^3$—$R^9$ (wherein $A^3$ is a halo-$C_1$–$C_6$ alkylene group, or a halo-$C_3$–$C_6$ alkenylene group; and $R^9$ is a hydrogen atom, a halogen atom, a halo-$C_3$–$C_6$ cycloalkyl group, a phenyl group, a substituted phenyl group having at least one substituent, which is the same or different and is selected from the group consisting of a halogen atom a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^4$—$R^{10}$ (wherein $A^4$ is —O—, —S—, —SO— or —SO$_2$—; $R^{10}$ is a $C_1$–$C_6$ alkyl group, a halo-$C_1$–$C_6$ alkyl group, a $C_3$–$C_6$ alkenyl group, a halo-$C_3$–$C_6$ alkenyl group, a $C_3$–$C_6$ cycloalkyl group, a halo-$C_3$–$C_6$ cycloalkyl group, a phenyl group, or a substituted phenyl group having at least one substituent, which is the same or different and is selected from the group consisting of a halogen atom a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group)), (2) when $A^2$ is a $C_1$–$C_6$ alkylene group, a halo-$C_1$–$C_6$ alkylene group, a $C_2$–$C_6$ alkenylene group, a halo-$C_2$–$C_6$ alkenylene group, a $C_2$–$C_6$ alkynylene group, a halo-$C_3$–$C_6$ alkynylene group, then $R^7$ is a hydrogen atom, a halogen atom, a halo-$C_3$–$C_6$ cycloalkyl group, a phenyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^5$—$R^{12}$ (wherein $A^5$ is —O—, —S—, —SO— or —S$_2$—; and $R^{12}$ is a $C_3$–$C_6$ cycloalkyl group, a halo-$C_3$–$C_6$ cycloalkyl group, a phenyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, or a group of the formula —$A^6$—$R^{14}$ (wherein $A^6$ is a $C_1$–$C_6$ alkylene group, a halo-$C_1$–$C_6$ alkylene group, a $C_2$–$C_6$ alkenylene group, a halo-$C_2$–$C_6$ alkenylene group; and $R^{14}$ is a hydrogen atom, a halogen atom, a halo-$C_3$–$C_6$ cycloalkyl group, a halo-$C_1$–$C_6$ alkoxy group, a halo-$C_1$–$C_6$ alkylthio group, a halo-$C_1$–$C_6$ alkylsulfinyl group, a halo-$C_1$–$C_6$ alkylsulfonyl group, a phenyl group, a substituted phenyl group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenoxy group, a substituted phenoxy group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group, a phenylthio group, or a substituted phenylthio group having at least one substituent, which is the same or different and is selected from the group consisting of a halogen atom, a halo-$C_1$–$C_6$ alkyl group, a halo-$C_1$–$C_6$ alkoxy group, a halo-$C_1$–$C_6$ alkylthio group, a halo-$C_1$–$C_6$ alkylsulfinyl group and a halo-$C_1$–$C_6$ alkylsulfonyl group));

further, $Y^1$ and $Y^2$ may form a condensed ring (the condensed ring is the same as defined above) by combining to each other together with $Y^3$, and said condensed ring may have at least one substituent, which is the same or different and is selected from the group consisting of a halogen atom, a $C_1$–$C_6$ alkyl group, a halo-$C_1$–$C_6$ alkyl group, a $C_1$–$C_6$ alkoxy group, a halo-$C_1$–$C_6$ alkoxy group, a $C_1$–$C_6$ alkylthio group, a halo-$C_1$–$C_6$ alkylthio group, a $C_1$–$C_6$ alkylsulfinyl group, a halo-$C_1$–$C_6$ alkylsulfinyl group, a $C_1$–$C_6$ alkylsulfonyl group, a halo-$C_1$–$C_6$ alkylsulfonyl group, a phenyl group, and a substituted phenyl group having at least one substituent which may be the same or different and is selected from the group consisting of a halogen atom, a $C_1-C_6$ alkyl group, a halo-$C_1-C_6$ alkyl group, a $C_1-C_6$ alkoxy group, a halo-$C_1-C_6$ alkoxy group, a $C_1-C_6$ alkylthio group, a halo-$C_1-C_6$ alkylthio group, a $C_1-C_6$ alkylsulfinyl group, a halo-$C_1-C_6$ alkylsulfinyl group, a $C_1-C_6$ alkylsulfonyl group and a halo-$C_1-C_6$ alkylsulfonyl group;

$Z^1$ and $Z^2$ are each an oxygen atom or a sulfur atom}.

11. A method for controlling undesirable insect pests for a useful crop, characterized by treating an objective crop with an effective amount of the agricultural and horticultural insecticides according to claim 6.

12. A phthalic acid diamide derivative represented by the general formula (I')

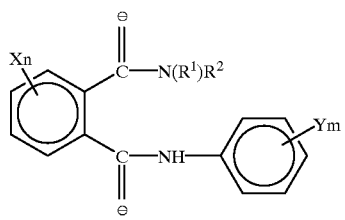

(1')

wherein $R^1$ and $R^2$ may be the same or different, and are each a hydrogen atom, or a group of the formula —$A^1$—$Q_l$ (wherein $A^1$ is a $C_1-C_8$ alkylene group or a $C_3-C_6$ alkynylene group; Q is a hydrogen atom, a halogen atom, a phenyl group, a pyridyl group or a pyridine-N-oxide group; and l is an integer of 1 to 3);

X may be same or different, and is a hydrogen atom, a halogen atom, a cyano group, a nitro group or a group of the formula —$A^2$—$R^7$ (wherein $A^2$ is —O—, —SO— or a halo-$C_1-C_6$ alkylene group; and (1) when $A^2$ is —O— or —SO—, then $R^7$ is a halo $C_1-C_6$alkyl group;

(2) when $A^2$ is a halo $C_1-C_6$ alkylene group, then $R^7$ is a halogen atom);

n is an integer of 1 to 4;

further, X may form bezodioxole by combining together with the adjacent carbon atom in the phenyl ring;

θ is 0;

Y is the same or different, and is a hydrogen atom, a halogen atom, a substituted phenyl group having at least one halo $C_1-C_6$ alkyl group as substituents or a group of the formula —$A^2$—$R^7$ (wherein $A^2$ is —O—, —S—, —SO—, a $C_1-C_6$ alkylene group or a halo $C_1-C_6$ alkylene group;

(1) when $A^2$ is —O—, —S— or —SO—, then $R^7$ is a $C_1-C_6$ alkyl group, a halo $C_1-C_6$ alkyl group, a halo $C_1-C_6$ alkoxy halo $C_1-C_6$ alkyl group, a substituted phenyl group having at least one halogen atom as substituents, a substituted pyridyl group having at least one substituents which may be the same or different and are selected from the group consisting of a halogen atom and a halo $C_1-C_6$ alkyl group as substituents, (2) when $A^2$ is a $C_1-C_6$ alkylene group or a halo-$C_1-C_6$ alkylene group, then $R^7$ a hydrogen atom or a halogen atom);

m is an integer of 1 to 5;

further, Y may form benzoxazole, dihydrobenzofuran, benzodioxane or benzothiazole, by combining together with the adjacent carbon atoms in the phenyl ring, said condensed ring may have at least one substituents, which may be the same or different, and selected from the group consisting of a halogen atom, a halo-$C_1-C_6$ alkyl group and a substituted phenyl group having at least one halo $C_1-C_6$ alkyl group as substituents.

13. The phthalic acid diamide derivative according to claim 12, wherein $R^1$ and $R^2$ may be the same or different, and are each hydrogen atom, ethyl group, i-propyl group, butyl group, t-butyl group, 2,2,2-trifluoroethyl group, 1-methyl-1-phenylethyl group, 1,1-dimethyl propyl group, 1,1-dimethylpropyl-3-(2-pyridyl)-2-yna group, 2-chloro-1, 1-dimethylethyl group or 2-(2-pyridine-N-oxide)ethyl group;

X may be the same or different, and is hydrogen atom, iodine atom, chlorine atom, fluorine atom, cyano group, nitro group, trifluoromethyl group, trifluoromethoxy group or trifluorosulfinyl group n is an integer of 1 to 4;

further, X may form bezodioxole by combining together with the adjacent carbon atom in the phenyl ring;

Y is the same or different, and is hydrogen atom, iodine atom, chlorine atom, fluorine atom, methyl group, i-propyl group, methoxy group, pentafluoroethyl group, trifluoromethyl group, heptafluoro-i-propyl group, heptafluoropropyl group, trifluoromethoxy group, diluoromethoxy group, 1,1,2,2-tetrafluoroethoxy group, 1,1,2,3,3,3-hexafluoroethoxy group, 2-(heptafluoropropyloxy)-1,1,2-trifluoroethoxy group, 4-trifluorophenyl group, 2-(3-chloro-5-trifluoromethyl)pyridyloxy group, methythio group, 4-chlorophenylthio group, pentalfuoroethythio group, trifluoromethylthio group, trifluoromethylsulfinyl group, m is an integer of 1 to 5;

further, Y may form (4-trifluorophenyl)-benzoxazole, tetrafluorobenzofuran, tetrafluorobenzodioxane or 7-heptafluoro-i-propylbenzothiazole, by combining together with the adjacent carbon atoms in the phenyl ring.

14. Agricultural and horticultural insecticides, which are characterized by containing, as the effective ingredient, a phthalic acid diamide derivative according to claim 12 or 13.

15. A method for controlling undesirable insect pests for a useful crop, characterized by treating an objective crop with an effective amount of the agricultural and horticultural insecticides according to claim 14.

16. A phthalic acid diamide derivative represented by the general formula (I)

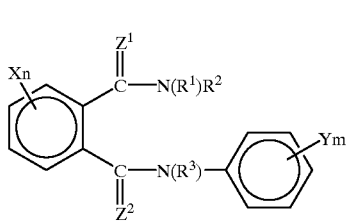

(I)

wherein $R^1$, $R^2$ and $R^3$ may be same or different, and are each a hydrogen atom, a $C_3-C_6$ cycloalkyl group or a group of the formula —$A^1$—$Q_l$ (wherein $A^1$ is —C(=O)—, a $C_1-C_8$ alkylene group, a $C_3-C_6$ alkenylene group or a $C_3-C_6$ alkynylene group;

(1) when $A^1$ is —C(=O)—, then Q is a $C_1$–$C_6$ alkyl group;
(2) when $A^1$ is a $C_1$–$C_8$ alkylene group, a $C_3$–$C_6$ alkenylene group or a $C_3$–$C_6$ alkynylene group, then Q is a hydrogen atom; a halogen atom; a halo-$C_1$–$C_6$ alkyl group; a $C_3$–$C_6$ cycloalkyl group; a $C_1$–$C_6$ alkoxycarbonyl group; a di-$C_1$–$C_6$ alkoxyphosphoryl group in which the alkoxy groups may be the same or different; a phenyl group; a substituted phenyl group having at least one substituent which may be the same or different and selected from the group consisting of a halogen atom, a $C_1$–$C_6$ alkyl group and a $C_1$–$C_6$ alkoxy group; a naphtyl group; a pyridyl group; a pyridine-N-oxide group; a furyl group; a tetrahydrofuryl group; a thienyl group; a substituted pyridyl group having at least one substituent which may be the same or different and selected from the group consisting of a halogen atom; or a group of the formula —$Z^3$—$R^3$ (wherein $Z^3$ is —O— or a group of the formula —N($R^6$)— (wherein $R^6$ is a hydrogen atom, a $C_1$–$C_6$ alkoxylcarbonyl group or a phenyl $C_1$–$C_4$ alkoxycarbonyl group) and $R^5$ is a hydrogen atom, a $C_1$–$C_6$alkyl group, $C_1$–$C_6$ alkoxycarbonyl group, a phenyl group or a substituted phenyl group having at least one substituent which may be the same or different and selected from the group consisting of a halogen atom); and l is an integer of 1 to 3); further, $R^1$ and $R^2$ may form a 4 to 7 membered ring by combining to each other, in which the ring may contain 1 to 3 oxygen atoms;

X may be same or different, and is a halogen atom, a cyano group, a nitro group or a group of the formula —$A^2$—$R^7$ (wherein $A^2$ is —O—, —S—, —SO—, —$SO_2$—, a $C_1$–$C_6$ alkylene group, a halo-$C_1$–$C_6$alkylene group or a $C_2$–$C_6$alkynylene group; and (1) when $A^2$ is —O—, —S—, —SO— or —$SO_2$—, then $R^7$ is a $C_1$–$C_6$ alkyl group or a halo $C_1$–$C_6$ alkyl group;
(2) when A2 is a $C_1$–$C_6$alkylene group, a halo $C_1$–$C_6$ alkylene group or a $C_2$–$C_6$ alkynylene group, then $R^7$ is a hydrogen atom, a halogen atom or a phenyl group);

n is an integer of 0 to 4;

further, X may form benzodioxole by combining together with the adjacent carbon atom in the phenyl ring;

Y is the same or different, and is a halogen atom; a cyano group; a nitro group; a phenyl group; a substituted phenyl group having at least one substituent which may be the same or different and is selected from the group consisting of a halogen atom and a halo $C_1$–$C_6$alkyl group; or a group of the formula —$A^2$—$R^7$ (wherein $A^2$ is —O—, —S—, —SO—, —$SO_2$—, —C(=O)—, a $C_1$–$C_6$alkylene group, a halo $C_1$–$C_6$alkylene group, a halo $C_2$–$C_6$alkenylene group or a $C_2$–$C_6$ alkynylene group;

(1) when $A^2$ is —O—, —S—, —SO— or —$SO_2$, then $R^7$ is a $C_1$–$C_6$ alkyl group; a halo $C_1$–$C_6$alkyl group; a halo $C_3$–$C_6$alkenyl group; a phenyl group; a substituted phenyl group having at least one substituent which may be the same or different and selected from the group consisting of a halogen atom and a halo $C_1$–$C_6$ alkyl group; a substituted pyridyl group having at least one substituents which may be the same or different and selected from the group consisting of a halogen atom and a halo $C_1$–$C_6$ alkyl group; or a group of the formula $A^3$—$R^9$ (wherein $A^3$ is a $C_1$–$C_6$ alkylene group or a halo $C_1$–$C_6$ alkylene group and $R^9$ is a phenyl group or a group of the formula -$A^4$-$R^{10}$ (wherein $A^4$ is —O— and $R^{10}$ is a $C_1$–$C_6$alkyl group or a halo $C_1$–$C_6$alkyl group));
(2) when $A^2$is —C(=O)—, then $R^7$ is a $C_1$–$C_6$ alkyl group;
(3) when $A^2$is a $C_1$–$C_6$ alkylene group, a halo-$C_1$–$C_6$ alkylene group or a halo $C_2$–$C_6$alkenylene group, then $R^7$is a hydrogen atom, a halogen atom or a group of the formula $A^5$—$R^{12}$ (wherein $A^5$ is —O— and $R^{12}$ is a hydrogen atom);

m is an integer of 0 to 5;

further, Y may form benzoxazole, benzimidazole, benzodioxole, dihydrobenzofuran, benzodioxane, benzothiazole or tetrahydronaphthalene, by combining together with the adjacent carbon atoms in the phenyl ring, said condensed ring may have at least one substituents, which may be the same or different, and selected from the group consisting of a halogen atom, a $C_1$–$C_6$ alkyl group, a halo $C_1$–$C_6$ alkyl group and a phenyl group; and $Z^1$ and $Z^2$ each represents an oxygen atom.

17. A phthalic acid diamide derivative represented by the general formula (I)

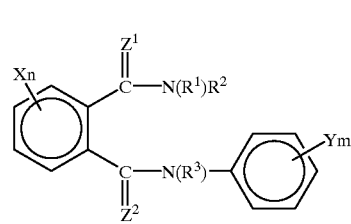

(I)

wherein $R^1$ and $R^2$ may be same or different, and are each a hydrogen atom, a $C_3$–$C_6$ cycloalkyl group or a group of the formula —$A_1$—$Q_1$ (wherein $A^1$ is a $C_1$–$C_8$ alkylene group, a $C_3$–$C_6$ alkenylene group or a $C_3$–$C_6$ alkynylene group; and Q is a hydrogen atom; a halogen atom; a halo-$C_1$–$C_6$ alkyl group; a $C_3$–$C_6$ cycloalkyl group; a alkoxycarbonyl group; a di-$C_1$–$C_6$ alkoxyphosphoryl group in which the alkoxy groups may be the same or different; a phenyl group; a substituted phenyl group having at least one substituent which may be the same or different and selected from the group consisting of a halogen atom, a $C_1$–$C_6$ alkyl group and a $C_1$–$C_6$ alkoxy group; a naphtyl group; a pyridyl group; a pyridine-N-oxide group; a furyl group; a tetrahydrofuryl group; a thienyl group; a substituted pyridyl group having at least one substituent which may be the same or different and selected from the group consisting of a halogen atom; or a group of the formula —$Z^3$—$R^5$ (wherein $Z^3$ is —O— or a group of the formula —N($R^6$)— (wherein $R^6$ is a hydrogen atom, a $C_1$–$C_6$ alkoxylcarbonyl group or a phenyl $C_1$–$C_4$alkoxycarbonyl group) and $R^5$is a hydrogen atom, a $C_1$–$C_6$ alkyl group, $C_1$–$C_6$ alkoxycarbonyl group, a phenyl group or a substituted phenyl group having at least one substituent which may be the same or different and selected from the group consisting of a halogen atom); and l is an integer of 1 to 3; further, $R^1$ and $R^2$ may form a 4 to 7 membered ring by combining to each other, in which the ring may contain 1 to 3 oxygen atoms;

$R^3$ is a hydrogen atom, a $C_1$–$C_6$ alkyl group or a group of the formula —$A^1$—Q (wherein $A^1$ is —C(=O)— and Q is a $C_1$–$C_6$ alkyl group);

X may be same or different, and is a halogen atom, a cyano group, a nitro group or a group of the formula —$A^2$—$R^7$ (wherein $A^2$ is —O—, —S—, —SO—, —$SO_2$—, a $C_1$-$C_6$ alkylene group, a halo-$C_1$-$C_6$ alkylene group or a $C_2$-$C_6$ alkynylene group; and
- (1) when $A^2$ is —O—, —S—, —SO— or —$SO_2$—, then $R^7$ is a $C_1$-$C_6$ alkyl group or a halo $C_1$-$C_6$alkyl group;
- (2) when $A^2$ is a $C_1$-$C_6$ alkylene group, a halo $C_1$-$C_6$ alkylene group or a $C_2$-$C_6$ alkynylene group, then $R^7$ is a hydrogen atom, a halogen atom or a phenyl group);

n is an integer of 0 to 4;

further, X may form benzodioxole by combining together with the adjacent carbon atom in the phenyl ring;

Y is the same or different, and is a halogen atom; a cyano group; a nitro group; a phenyl group; a substituted phenyl group having at least one substituent which may be the same or different and selected from the group consisting of a halogen atom and a halo $C_1$-$C_6$ alkyl group; or a group of the formula —$A^2$—$R^7$(wherein $A^2$ is —O—, —S—, —SO—, —$SO_2$—, —C(=O)—, a $C_0$-$C_6$ alkylene group, a halo $C_1$-$C_6$ alkylene group, a halo $C_2$-$C_6$ alkenylene group or a $C_2$-$C_6$ alkynylene group;
- (1) when $A^2$ is —O—, —S—, —SO— or —$SO_2$—, then $R^7$is a $C_1$-$C_6$ alkyl group; a halo $C_1$-$C_6$ alkyl group; a halo $C_3$-$C_6$ alkenyl group; a phenyl group; a substituted phenyl group having at least one substituent which may be the same or different and is selected from the group consisting of a halogen atom and a halo $C_1$-$C_6$ alkyl group; a substituted pyridyl group having at least one substituents which may be the same or different and selected from the group consisting of a halogen atom and a halo $C_1$-$C_6$ alkyl group; or a group of the formula $A^3$—$R^9$ (wherein $A^3$ is a $C_1$-$C_6$ alkylene group or a halo $C_1$-$C_6$ alkylene group and $R^9$ is a phenyl group or a group of the formula —$A^4$—$R^{10}$ (wherein $A^4$ is —O— and $R^{10}$ is a $C_1$-$C_6$ alkyl group or a halo $C_1$-$C_6$ alkyl group));
- (2) when $A^2$ is —C(=O)—, then $R^7$ is a $C_1$-$C_6$alkyl group;
- (3) when $A^2$ is a $C_1$-$C_6$ alkylene group, a halo-$C_1$-$C_6$ alkylene group or a halo $C_2$-$C_6$ alkenylene group, then $R^7$ is a hydrogen atom, a halogen atom or a group of the formula —$A^5$—$R^{12}$ (wherein $A^5$ is —O— and $R^{12}$ is a hydrogen atom);

m is an integer of 0 to 5; further, Y may form benzoxazole, benzimidazole, benzodioxole, dihydrobenzofuran, benzodioxane, benzothiazole or tetrahydronaphthalene, by combining together with the adjacent carbon atoms in the phenyl ring, said condensed ring may have at least one substituents, which may be the same or different, and selected from the group consisting of a halogen atom, a $C_1$-$C_6$ alkyl group, a halo $C_1$-$C_6$ alkyl group and a phenyl group; and $Z^1$ and $Z^2$ are each represents an oxygen atom.

18. An agricultural and horticultural insecticides, which is characterized by containing, as the effective ingredient, a phthalic acid diamide derivative according to claim 16 or 17.

19. A method for controlling undesirable insect pests for a useful crop, characterized by treating an objective crop with an effective amount of the agricultural and horticultural insecticides according to claim 18.

* * * * *